(12) United States Patent
Block, III et al.

(10) Patent No.: US 9,874,285 B2
(45) Date of Patent: Jan. 23, 2018

(54) ORGAN ON CHIP INTEGRATION AND APPLICATIONS OF THE SAME

(71) Applicant: Vanderbilt University, Nashville, TN (US)

(72) Inventors: Frank E. Block, III, Nashville, TN (US); Philip C. Samson, Nashville, TN (US); Erik M. Werner, Nashville, TN (US); Dmitry A. Markov, Nashville, TN (US); Ronald S. Reiserer, Nashville, TN (US); Jennifer R. Mckenzie, Antioch, TN (US); David E. Cliffel, Nashville, TN (US); William J. Matloff, Paradise Valley, AZ (US); Frank E. Block, Jr., Nashville, TN (US); Joseph R. Scherrer, Nashville, TN (US); W. Hunter Tidwell, Nashville, TN (US); John P. Wikswo, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 89 days.

(21) Appl. No.: 14/646,300

(22) PCT Filed: Nov. 20, 2013

(86) PCT No.: PCT/US2013/071026
§ 371 (c)(1),
(2) Date: May 20, 2015

(87) PCT Pub. No.: WO2014/081840
PCT Pub. Date: May 30, 2014

(65) Prior Publication Data
US 2015/0298123 A1    Oct. 22, 2015

Related U.S. Application Data

(63) Continuation of application No. PCT/US2012/068771, filed on Dec. 10, 2012, and a
(Continued)

(51) Int. Cl.
*F16K 11/16* (2006.01)
*C12M 1/34* (2006.01)
(Continued)

(52) U.S. Cl.
CPC ........ *F16K 11/163* (2013.01); *B01L 3/50273* (2013.01); *C12M 21/08* (2013.01);
(Continued)

(58) Field of Classification Search
CPC ....... B01L 2200/028; B01L 2200/0684; B01L 2200/10; B01L 2200/18; B01L 2300/0819;
(Continued)

(56) References Cited

U.S. PATENT DOCUMENTS

2006/0194273 A1    8/2006  Thomas
2008/0144185 A1*   6/2008  Wang ................. G02B 3/14
                                              359/665
(Continued)

FOREIGN PATENT DOCUMENTS

WO    2012/048261 A2    4/2012

OTHER PUBLICATIONS

Korean Intellectual Property Office (ISR/KR), "International Search Report for PCT/US2013/071026", Korea, dated Mar. 13, 2014.

*Primary Examiner* — Michael L Hobbs
(74) *Attorney, Agent, or Firm* — Locke Lord LLP; Tim Tingkang Xia, Esq.

(57) ABSTRACT

A platform for cultivation, maintenance, and/or analysis of one or more bio-objects includes one or more integrated
(Continued)

bio-object microfluidics modules. Each integrated bio-object microfluidics module is configured to cultivate, maintain, analyze and/or mimic functionalities of a respective bio-object, and includes one or more on-chip pumps; a plurality of fluidic switches; and a microfluidic chip in fluid communication with the one or more on-chip pumps and the plurality of fluidic switches, having at least one chamber for accommodating the bio-object and a plurality of fluidic paths connecting the at least one chamber, the one or more on-chip pumps and the plurality of fluidic switches, and a power and control unit adapted for selectively and individually controlling the one or more on-chip pumps and the plurality of fluidic switches for performing bio-object microfluidics functions.

19 Claims, 92 Drawing Sheets

Related U.S. Application Data continuation-in-part of application No. 13/877,925, filed as application No. PCT/US2011/055432 on Oct. 7, 2011.

(60) Provisional application No. 61/729,149, filed on Nov. 21, 2012, provisional application No. 61/808,455, filed on Apr. 4, 2013, provisional application No. 61/822,081, filed on May 10, 2013, provisional application No. 61/569,145, filed on Dec. 9, 2011, provisional application No. 61/697,204, filed on Sep. 5, 2012, provisional application No. 61/717,441, filed on Oct. 23, 2012, provisional application No. 61/390,982, filed on Oct. 7, 2010.

(51) Int. Cl.
*F04B 43/12* (2006.01)
*B01L 3/00* (2006.01)
*C12M 3/00* (2006.01)
*C12M 3/06* (2006.01)
*C12M 1/00* (2006.01)

(52) U.S. Cl.
CPC ............ *C12M 23/16* (2013.01); *C12M 23/44* (2013.01); *C12M 23/52* (2013.01); *C12M 29/00* (2013.01); *C12M 29/10* (2013.01); *C12M 29/20* (2013.01); *F04B 43/12* (2013.01); *F04B 43/1269* (2013.01); *F04B 43/1292* (2013.01); *B01L 2200/028* (2013.01); *B01L 2200/0684* (2013.01); *B01L 2200/10* (2013.01); *B01L 2200/18* (2013.01); *B01L 2300/0819* (2013.01); *B01L 2300/0867* (2013.01); *B01L 2300/123* (2013.01); *B01L 2400/0644* (2013.01)

(58) Field of Classification Search
CPC ....... B01L 2300/0867; B01L 2300/123; B01L 2400/0644; B01L 3/50273; C12M 21/08; C12M 23/16; C12M 23/44; C12M 23/52; C12M 29/00; C12M 29/10; C12M 29/20; F04B 43/12; F04B 43/1269; F04B 43/1292; F16K 11/163
See application file for complete search history.

(56) References Cited

U.S. PATENT DOCUMENTS

| | | |
|---|---|---|
| 2010/0248258 A1 | 9/2010 | Lee et al. |
| 2011/0086382 A1 | 4/2011 | Marx |
| 2011/0098597 A1 | 4/2011 | Wu et al. |
| 2011/0256574 A1* | 10/2011 | Zhang .............. B01L 3/502761 435/29 |

* cited by examiner

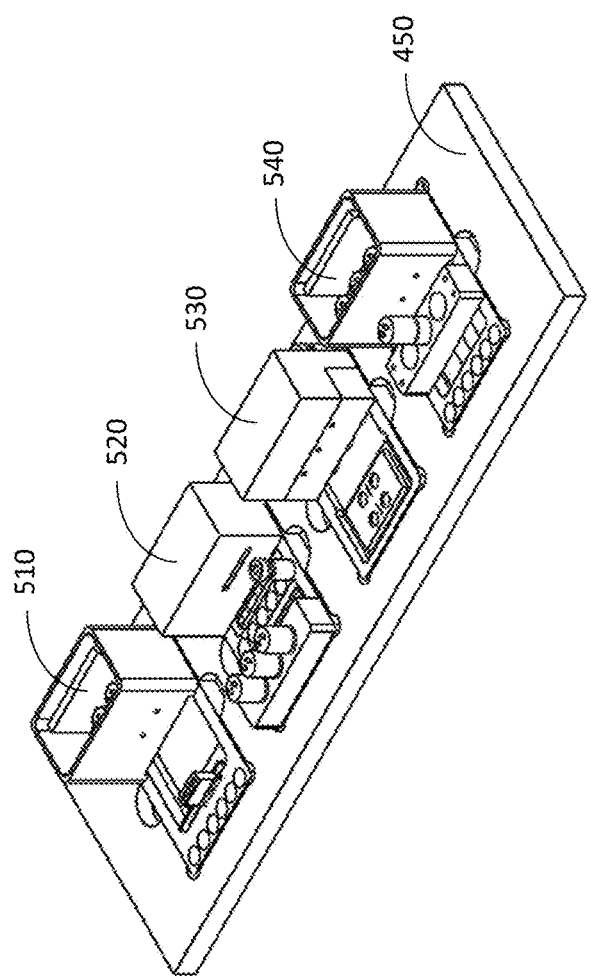
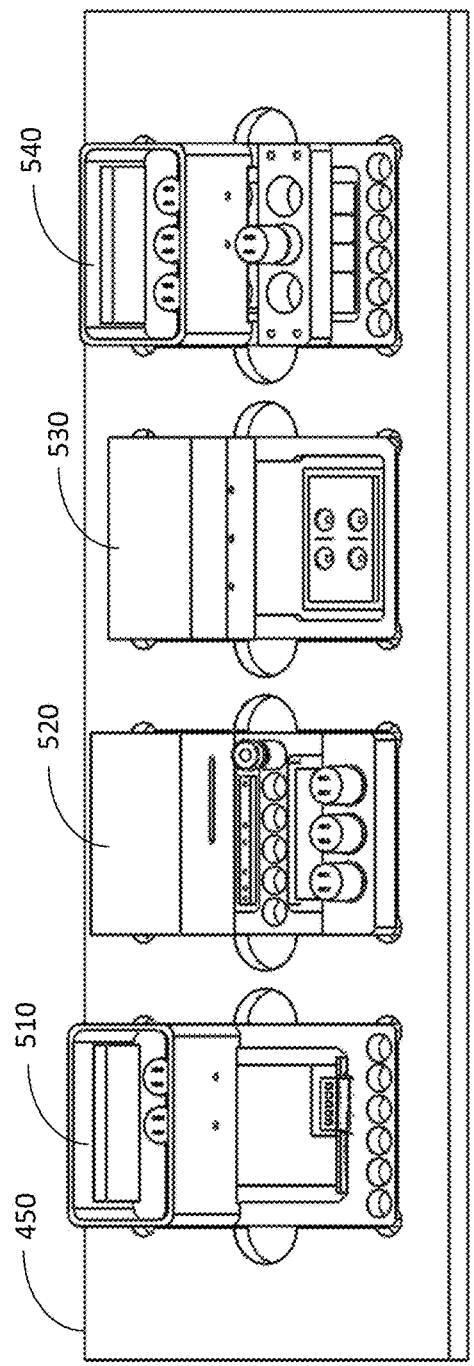
FIG. 6A
FIG. 6B

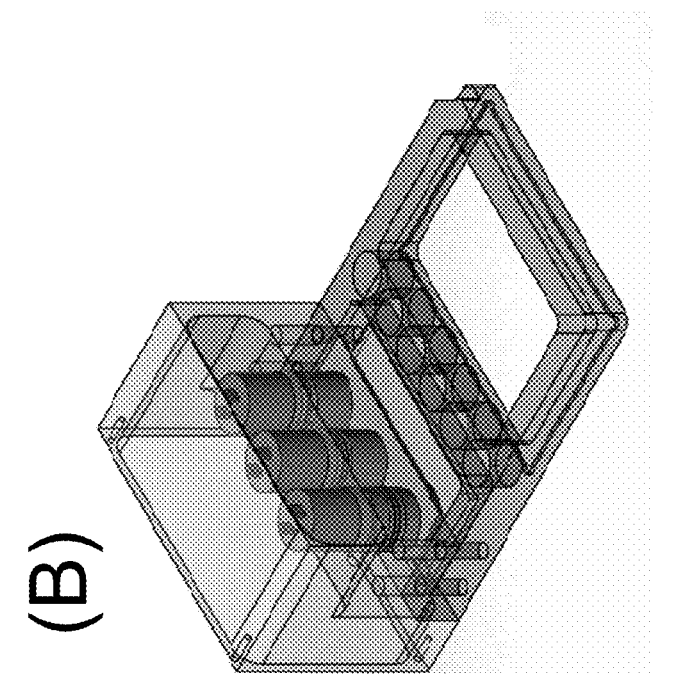
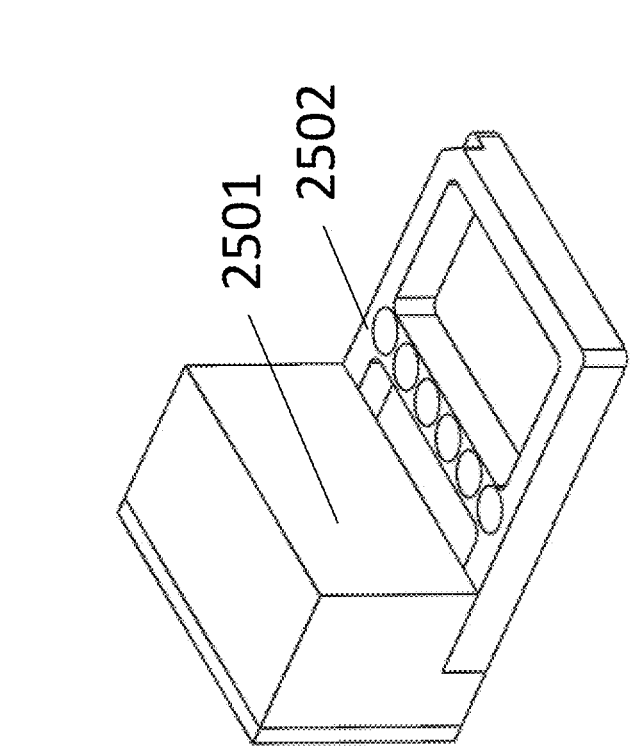
FIG. 25

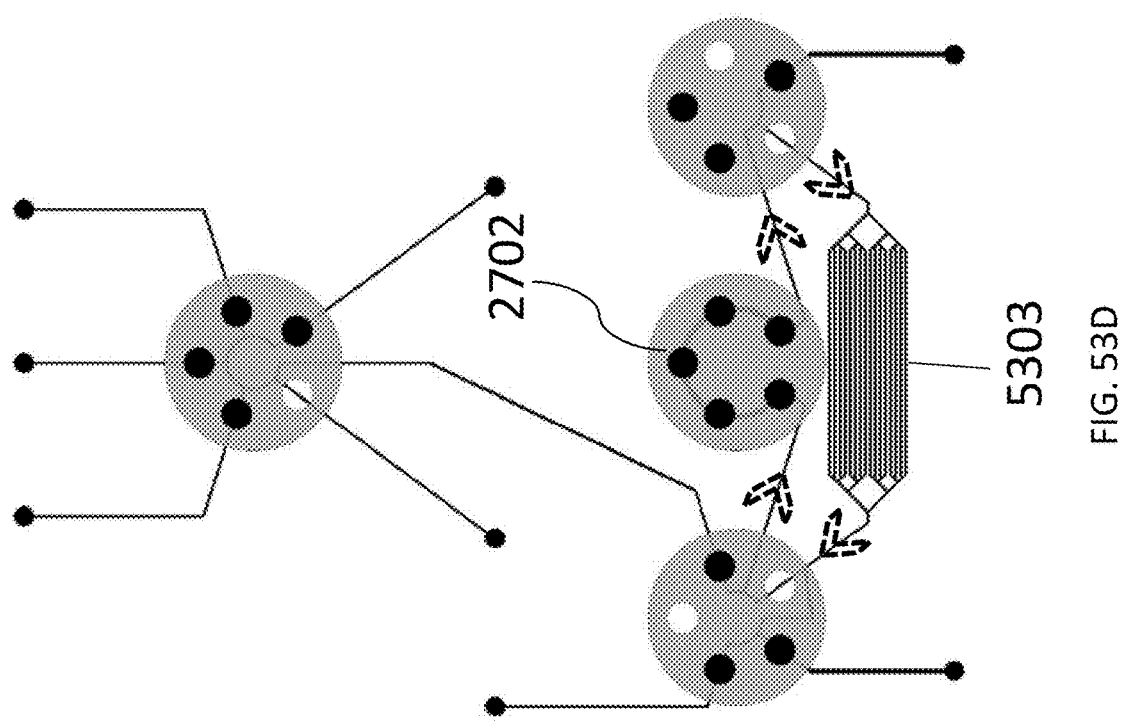

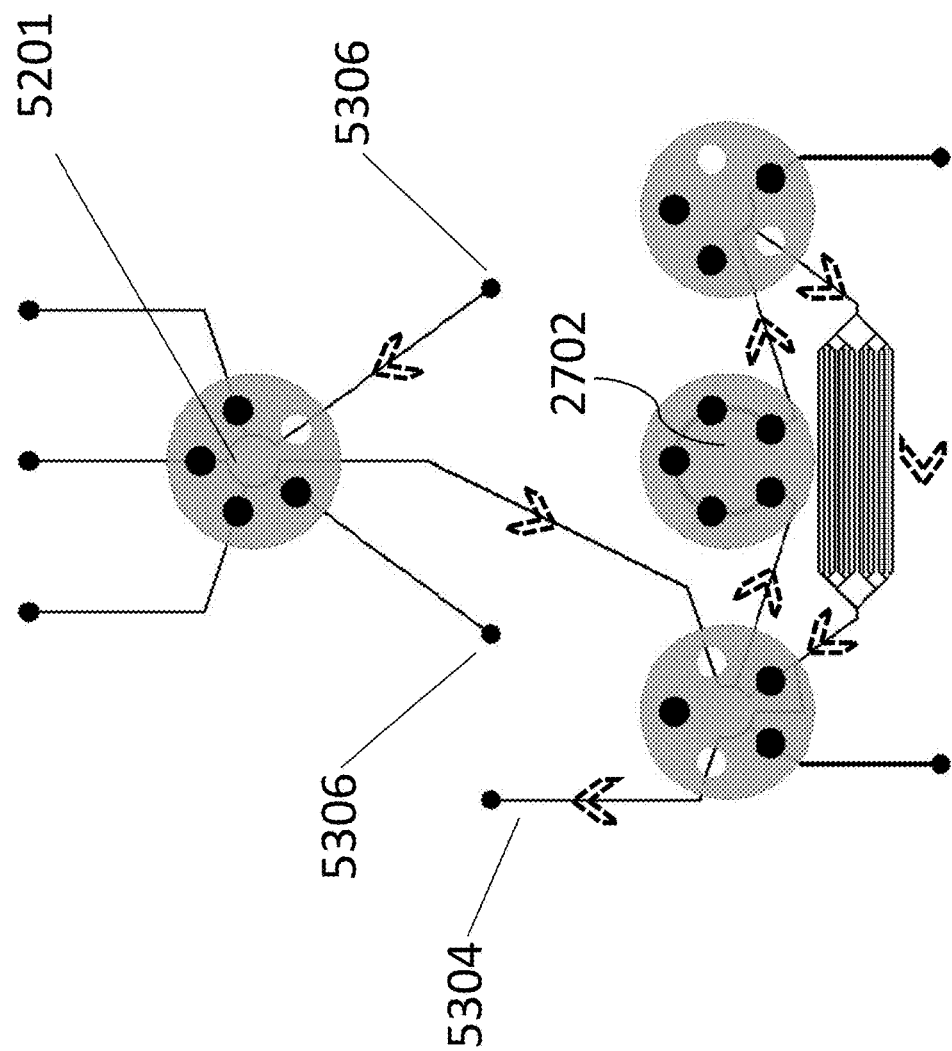

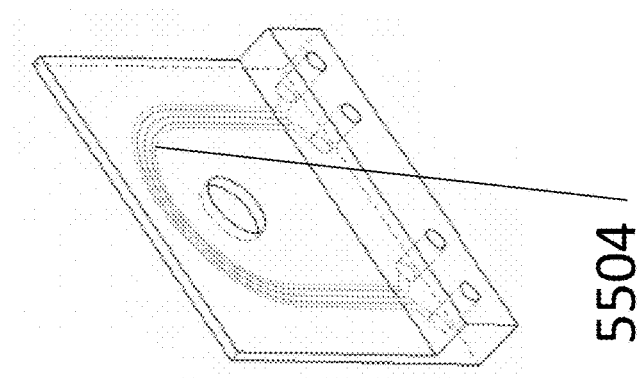
FIG. 55C
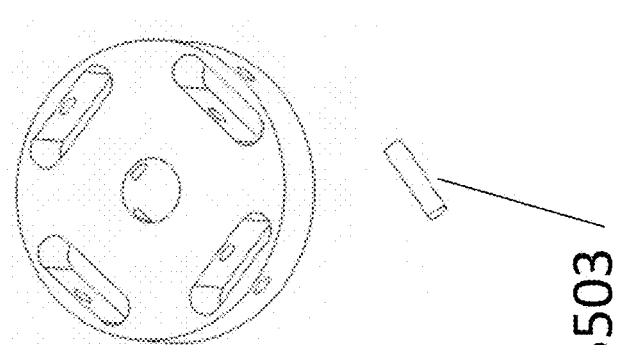
FIG. 55B
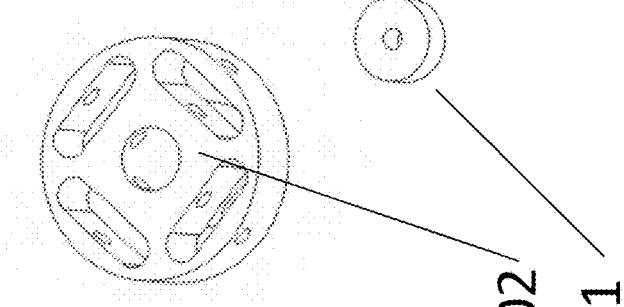
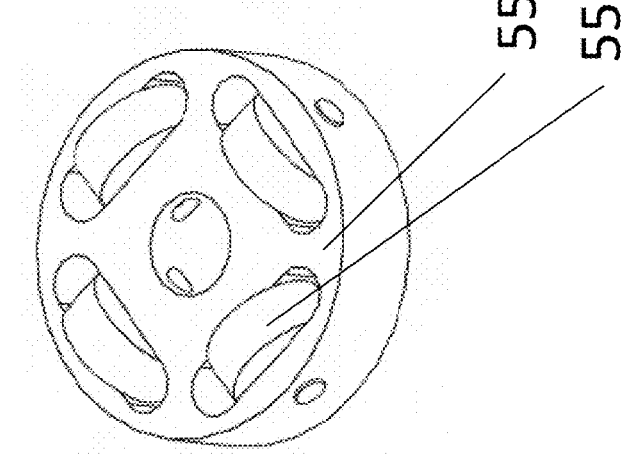
FIG. 55A

|   | Wired | Bluetooth | ZigBee | WiFi | Cellular |
|---|---|---|---|---|---|
| Pro | • Fastest | • Fast<br>• Use built-in hardware on mobile devices | • Lowest power<br>• Many devices on same PAN<br>• Many mesh/topology options | • Very Fast<br>• Many devices per router | • Longest range<br>• Handoff technology well established |
| Con | • Connections limited by # of serial ports on host.<br>• Host needs a USB or serial port<br>• Cable must be connected for operation | • Connections limited to 5-8 slaves per Bluetooth host | • Slowest data rate<br>• Requires USB dongle for PCs<br>• Switching between PANs may not be seamless | • High power requirements | • Handoff switching technology is complicated<br>• Highest power requirements |
| Notes | • Best for a high-bandwidth point-to-point connection<br>• Best for 1-10 connections<br>• Theoretically limitless connections but 10+ is a lot of wires...<br>• Could form a PAN entirely out of parallel wired connections | • Good wired serial replacement<br>• Could form a PAN by using several Bluetooth hosts in parallel, each with multiple slaves connected in parallel | • Best for IOM to IOM communication<br>• Allows large number of devices to communicate on a PAN with only 1 master-slave connection to a PC | • Large number of devices on PAN<br>• Power + processor requirements might be too high | |

FIG. 67

ORGAN ON CHIP INTEGRATION AND APPLICATIONS OF THE SAME

CROSS-REFERENCE TO RELATED PATENT APPLICATIONS

This application claims priority to and the benefit of, pursuant to 35 U.S.C. § 119(e), U.S. provisional patent application Ser. No. 61/729,149, filed on Nov. 21, 2012, entitled "MICROFLUIDIC FLUID DELIVERY SYSTEMS (VMFDS) AND APPLICATIONS OF SAME", by Frank E. Block III et al., U.S. provisional patent application Ser. No. 61/808,455, filed on Apr. 4, 2013, entitled "IMPROVED RPPM/RPV DESIGNS AND IMPLEMENTATIONS OF SAME", by John P. Wikswo et al., and U.S. provisional patent application Ser. No. 61/822,081, filed on May 10, 2013, entitled "ORGAN ON CHIP INTEGRATION AND APPLICATIONS OF SAME", by John P. Wikswo et al. Each of the above-identified applications is incorporated herein in its entirety by reference.

This application is a continuation-in-part application of PCT application Serial No. PCT/US2012/068771, filed on Dec. 10, 2012, entitled "INTEGRATED ORGAN-ON-CHIP SYSTEMS AND APPLICATIONS OF THE SAME", by John P. Wikswo et al., which itself claims priority to and the benefit of, pursuant to 35 U.S.C. § 119(e), U.S. provisional patent application Ser. No. 61/569,145, filed on Dec. 9, 2011, entitled "PERFUSION CONTROLLER, MICROCLINICAL ANALYZER AND APPLICATIONS OF THE SAME", by John P. Wikswo et al., U.S. provisional patent application Ser. No. 61/697,204, filed on Sep. 5, 2012, entitled "INTELLIGENT CHIP CARRIER AND CHIP CARRIER WITH MICROCHEMICAL ANALYZER AND APPLICATIONS OF THE SAME", by John P. Wikswo et al., and U.S. provisional patent application Ser. No. 61/717,441, filed on Oct. 23, 2012, entitled "INTEGRATED ORGAN MICROFLUIDICS (IOM) CHIP AND APPLICATIONS OF SAME", by John P. Wikswo et al. Each of the above-identified applications is incorporated herein in its entirety by reference.

This application is also a continuation-in-part application of U.S. patent application Ser. No. 13/877,925, filed on Jul. 16, 2013, entitled "PERISTALTIC MICROPUMP AND RELATED SYSTEMS AND METHODS", by Parker A. Gould et al., which is a national phase application under 35 U.S.C. § 371 of PCT application Serial No. PCT/US2011/055432, filed on Oct. 7, 2011, entitled "PERISTALTIC MICROPUMP AND RELATED SYSTEMS AND METHODS", by Parker A. Gould et al., which itself claims priority to and the benefit of, pursuant to 35 U.S.C. § 119(e), U.S. provisional patent application Ser. No. 61/390,982, filed on Oct. 7, 2010, entitled "PERISTALTIC MICROPUMP AND RELATED SYSTEMS AND METHODS", by Parker A. Gould et al. Each of the above-identified applications is incorporated herein in its entirety by reference.

Some references, which may include patents, patent applications, and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT AS TO RIGHTS UNDER FEDERALLY-SPONSORED RESEARCH

This invention was made with government support under grant numbers NIH/NCI R21 CA126728-01A1, NIH/NIDA RC2DA028981-02, and NIH 1UH2-TR000491-01, awarded by the National Institutes of Health, DTRA grants HDTRA1-09-1-00-13 and CBMXCEL-XL1-2-001, awarded by the Defense Threat Reduction Agency, and DARPA contract W911NF-12-2-0036, awarded by the Defense Advanced Research Projects Agency. The government has certain rights in the invention.

FIELD OF THE INVENTION

The present invention relates generally to a microfluidic system, and more particularly to integration platforms, interconnects, modules, and fluidic handling of organ constructs, engineered tissue, and human-on-a-chip platforms including organ-respective perfusion controllers, fluidic analyzers, MicroFormulators, and applications of the same.

BACKGROUND INFORMATION

Over the past 50 years engineers, scientists, and physicians working in biology, medicine, and physiology have constructed an entire, self-consistent intellectual framework using monolayer monocultures on plastic. Currently there are only a limited number of techniques for growth and maintenance of cell cultures. As shown in FIG. 1, these include a Petri dish 100 that enables the culture of cells 103 in cell-culture media 102; a culture flask 110 with removable cap 111; a well plate 120 with wells 121; and a well-plate 120 that supports a Transwell device 130 that has as its bottom a porous filter 132 that supports cells 103 and enables communication through the cell layer of culture media 102 on the outside of the wall of the insert 131 with culture media on the inside. Cells are grown to high density in a perfused hollow fiber bioreactor 140 that has cells 103 growing on either the inside, outside, or both sides of hollow fibers 146. The end caps 142 and 143 couple the inlet and outlet flows 148 of culture media 102. Additional ports, not shown, can provide access to the fluid and cells outside of the fibers. Adherent or suspended cells can be grown in high volume in a rotating bioreactor 150, in which the bottle 151 with cap 111 is supported on rollers 153 that are rotated by a mechanism 155 to ensure continuous mixing of the solution inside the bottle, thereby nourishing the cells that are either adherent to the inner surfaces of the bottle or are suspended in the media 102. Cells can be grown at high density in a suspended bead bioreactor 160 that utilizes a magnetic stirrer 161 and magnet 168 or a direct mechanical connection 162 attached to the top 165 to rotate a paddle 167. As a result of the rotation of the paddle, cells 103 attached to neutral-buoyancy beads 169 are kept in close contact with the volume of media 102. These examples are representative of the many types of systems that have been devised to culture cells in vitro. The ultimate accomplishment of this fifty-year effort has been the introduction of the multi-well, micro-titer plate that can allow individual experiments to be conducted in as many as 1536 wells, each of which contains about 8 µL of cell culture media, serviced by an automated robot (FIG. 2) that moves well plates between different preparation and measurement stations and incubators.

There are a number of major limitations of existing cell culture technology. The small-volume wells with a supposedly homogeneous cellular phenotype do not recapitulate the heterogeneous tissue microenvironment. Nutrient and metabolite transport is limited by diffusion. The local microenvironment, and hence the cellular phenotype and dynamic response, may differ between the corners and the center of each well. It is hard to create controlled concentration gradients. It is difficult to reverse the course of an experiment—it is easier to inject a drug, nutrient, or toxin than to wash it out. The plastic of Petri dishes, flasks, and well plates for growing adherent cells is quite foreign to a realistic biological environment: the Young's modulus for cell culture plastic is 10,000 to 100,000 times higher than that of living tissue. Only bone has a stiffness that approaches that of cell culture plastic. It is difficult to provide the shear forces that are required to maintain endothelial and epithelial polarization in Petri dishes or well plates. It is also difficult to provide appropriate mechanical forces to cells such as is experienced in the heart, skeletal and smooth muscle, lungs, and skin. The centralized robotic fluid handler and the isolated plate reader are not well suited for fast, real-time, closed-loop control of dynamic cellular processes. It is difficult to invoke complex exposure protocols or to create well-to-well connections that simulate organ-organ interactions. The most important convention in cell culture is the desire to change culture media only once every day or two. This infrequent media change results in the volume of culture media being approximately 1000 times that of the cells themselves. Hence paracrine and autocrine factors and metabolites secreted by cells are diluted a thousand-fold by the infrequent changing of the media above the cells.

FIG. 2 shows a robot well-plate handling system 200 including, for example, a robot well-plate manipulation system 201 with a rotating base 202 and an articulated arm 203 that has been optimized to allow a gripper jaw 204 to perform automated transfers of well plates 120 between various fixed stations, which include, but are not limited to, incubators 210, fluid handlers 220 with internal X-Y position control of pipettes 221 and 222, plate readers 230, bar-code readers 235, lid hotels 240, plate sealers 250, plate stackers 205, and other plate-oriented instruments 270 and 260, as shown in FIG. 2B. The entire system, if desired, can be enclosed in a sterile environment supported by windows 280 and HEPA filters 290, as shown in FIG. 2A. While it might be possible to create a jaw system 204 that can handle a pair of interconnected plates, as the number of interconnected plates grows it obviously becomes impractical to use this topology to manipulate the plates. Point-to-point transfer is not suitable for the manipulation of a plurality of interconnected modules.

Three commercial well-plate fluid-handling systems as indicated by 220 in FIG. 2 are in widespread use and are worthy of examining: the Agilent Bravo™ Liquid Handling System; the Agilent Encore Multispan™ Liquid Handling System, and the Hamilton MICROLAB® STAR Liquid Handling Workstation. The Bravo has a single 96-pipette movable head that can X-Y address (221, 222) a 3×3 array of well plates. It has an on-board gripper that can be used to move a well plate from one location to another. It provides no means for interconnecting multiple well plates or moving more than one well plate at a time. The newer Agilent Encore Multispan has an articulated robot arm and eight variable-span pipetters that provide independent X and Y axis motion. It can pipette to and from up to 24 well plates, and its gripper can reach up to 32 well plates stored on a common deck. It provides no means for interconnecting multiple well plates or moving more than one well plate at a time. The Hamilton MICROLAB® STAR system has both a 96 or 384 pipetting head and 8 or 16 multi-span individual pipettes and other features. It has both a plate gripper and a separate articulated arm gripper. In the context of this invention, it provides a variety of Eppendorf and well-plate carriers that can be manually delivered to an automatic feed system that uses a rack and pinion system to slide these carriers into predefined locations, with the gear-teeth of the rack being formed into the bottom of one side of the carrier. The system has 30 parallel tracks that can support tube or well-plate carriers. The carriers can be equipped with a variety of functions, including thermal regulation or onboard, addressable single-well imaging. Most important, the system does not provide the capability of the autonomous relocation of carriers from one predefined location to another, nor is there a provision to move these carriers from this instrument to an incubator or other instrument spatially separated from the fluid-handling unit. Both of these operations must be performed manually. These systems are viewed as exemplary of an entire class of fluid-handling robots utilized for high-throughput well-plate screening. None of these support fluidic communication between different well plates.

The recognition of the limitations of conventional cell culture techniques is leading to an increased interest in the creation of heterogeneous cell cultures growing in three-dimensional (3D) extracellular matrices with organotypic perfusion and stiffness in addition to proper mechanical, chemical, and electrical cues. Furthermore, the advance of biology, medicine, and physiology will be facilitated by the introduction of tools and techniques that enable closed-loop control of biology, including the dynamic control of extracellular matrix chemistry and mechanical properties. The challenges of closed-loop control of biological systems are summarized in the review article: P. R. LeDuc, W. C. Messner, and J. P. Wikswo, "How do control-based approaches enter into biology?" Annu. Rev. Biomed. Engr. 13:369-396, 2011. Tools and techniques enabling closed-loop control of biology would also support automated design of experiments, wherein cell type, matrix chemistry and architecture, and the addition or subtraction of metabolic and signaling molecules and other cues are adjusted automatically by machine learning algorithms that are attempting to identify and test hypotheses related to biological function. As an example, there is a need to refine the selection and timing of the application of cytokines and other signaling molecules whose sequence and concentration are optimized to cause an induced pluripotent stem cell (iPSC) to differentiate into a desired, specific cell type. FIG. 3 shows several well-plate topologies in common use, such as a single well plate 120 (FIG. 3A), a row of well plates 120 (FIG. 3B), a rectangular array of well plates 120 (FIG. 3C), or a stack of well plates 120 (FIG. 3D). None of these are interconnected, and in none of these devices or topologies do different, distinct populations of cells communicate with other distinct cell populations. Combinatorics alone will not be sufficient for identifying the complex chemical control trajectories required to obtain a particular cell phenotype. Furthermore, 3D bioreactors benefit from quantitative, real-time measurements of a breadth of analytes that span different molecular classes, such as proteins, oligonucleotides, lipids, carbohydrates, peptides and other small molecules. The difficulty is that most existing bioanalytical techniques are slow and require substantial sample volumes—both of which compromise the ability to control in real time a small 3D tissue bioreactor, and are often applied in a targeted manner that detects only preselected molecules of interest. Rapid, low-volume, untargeted assays are needed to track the complex biosignatures of cellular differentiation, development, and the response to growth factors, nutrients, toxins and other chemical, electrical, and mechanical stimuli.

Organs-on-chips (OoCs) and 3D tissue engineering present promising new technologies in the fields of automated biology, physiology, and the discovery, development, and toxicity/safety screening of new pharmaceuticals. OoCs are unique in the sense that an OoC can provide significant data on drug/organ interactions and multi-organ physiology without the use of animal studies. To date, there has been little research into integrating these organ systems with intra-device fluid handling. Two recent journal articles provide a critical review of coupled OoCs: "Engineering Challenges for Instrumenting and Controlling Integrated Organ-on-Chip Systems," Wikswo et al., IEEE Trans. Biomed. Eng., 60:682-690 (2013), and "Scaling and Systems Biology for Integrating Multiple Organs-on-a-Chip," Wikswo et al., Lab Chip, 13:3496-3511 (2013), which together provide one of the most thorough overviews of the major technical and biological challenges that need to be addressed in the development of coupled microphysiological systems. The challenges facing OoC design, development, and use are paralleled by comparable challenges in the engineering of tissue, for example tissue-engineered cardiac valves, blood vessels, peripheral nerve, or skin grown from the iPSCs of a patient whose tissues are in need of repair or grafting due to illness or injury. A multi-disciplinary approach is required to integrate these "organs" with the required maintenance devices for their growth and support, and ultimately may enable use of machine learning algorithms driving automated robotic scientists that can perform biological experiments without user intervention.

Therefore, a heretofore unaddressed need exists in the art to address the aforementioned deficiencies and inadequacies.

SUMMARY OF THE INVENTION

In one aspect, the invention relates to a platform for cultivation, maintenance, and/or analysis of one or more bio-objects, where each bio-object includes an organ, a tissue construct, or a group of cells. In one embodiment, the platform includes one or more integrated bio-object microfluidics modules.

Each integrated bio-object microfluidics module is configured to cultivate, maintain, analyze and/or mimic functionalities of a respective bio-object, and includes one or more on-chip pumps, a plurality of fluidic switches, and a microfluidic chip in fluid communication with the one or more on-chip pumps and the plurality of fluidic switches. The microfluidic chip has at least one chamber for accommodating the bio-object and a plurality of fluidic paths connecting the at least one chamber, the one or more on-chip pumps, and the plurality of fluidic switches.

Further, each integrated bio-object microfluidics module also includes a power and control unit programmed to selectively and individually control the one or more on-chip pumps and the plurality of fluidic switches for performing bio-object microfluidics functions. In one embodiment, the bio-object microfluidics functions include perfusion of the bio-object, analysis of metabolic activities of the bio-object, formulation of custom media to support the bio-object and guide stem cell differentiation, or the like.

In addition, each integrated bio-object microfluidics module further includes a reservoir having one or more ports for providing a plurality of solutions. In one embodiment, each reservoir port includes a double-ended vial.

Moreover, each integrated bio-object microfluidics module may have one imaging unit for operable evaluation of a respective bio-object. In one embodiment, at least one imaging unit includes a self-contained imaging unit, or a combinational condenser/microscope unit.

Furthermore, each integrated bio-object microfluidics module may also include at least one bubble trap coupled to at least one of the plurality of fluidic paths for removing bubbles therefrom.

In one embodiment, the power and control unit includes a microcontroller, a sensor array, and a power supply.

In one embodiment, the one or more on-chip pumps include a rotary planar peristaltic micropump (RPPM). Each of the plurality of fluidic switches includes a rotary planar valve (RPV). In one embodiment, the RPPM and each RPV are driven by a respective motor that is controlled by the microcontroller. In one embodiment, each RPV includes a normally closed (NC) valve.

In one embodiment, the one or more integrated bio-object microfluidics modules include a plurality of integrated bio-object microfluidics modules spatially arranged in an array.

In one embodiment, the platform also includes fluidic interconnects and nodes for connecting each of the plurality of integrated bio-object microfluidics modules to one another.

In one embodiment, the plurality of integrated bio-object microfluidics modules is mechanically and fluidically interconnected to each other in series, in parallel, or in a combination of both in the array. The array of the integrated bio-object microfluidics modules is a one-dimensional (1D) linear array, a two-dimensional (2D) array, or a three-dimensional (3D) array.

In one embodiment, the array of the integrated bio-object microfluidics modules is storable in an incubator tunnel or a vertical stacking incubator.

In another embodiment, the array of the integrated bio-object microfluidics modules is movable as a unit.

In yet another embodiment, the array of the integrated bio-object microfluidics modules is movable by utilizing a transporting means.

In one embodiment, the fluidic and mechanical connections between the integrated bio-object microfluidics modules are flexible. The array of the integrated bio-object microfluidics modules is aligned in a straight line or in a curved line.

In one embodiment, the platform further includes a propulsion unit for applying a bidirectional traction force collinear with the array of the integrated bio-object microfluidics modules; a support module connected between the propulsion unit and the array of the integrated bio-object microfluidics modules; and a specialized module connected to the array of the integrated bio-object microfluidics modules to define a train-based interconnect platform that is movably disposed on the transporting means, where the train-based interconnect platform is configurable and interchangeable.

In another embodiment, the platform further includes a station having a base, and one or more subsystems fixed on the base at predetermined positions. The station is placed in relation to the transporting means such that when the train-based interconnect platform is moved at the predetermined positions, the one or more subsystems perform desired operations on the linear array of the plurality of integrated bio-object microfluidics. In one embodiment, the desired operations on the array of the integrated bio-object microfluidics modules include performing at least one of analytical functions, mechanical functions, maintenance functions, fluid handling, microscopy, removal of one integrated bio-object microfluidics module, replacement of one integrated bio-object microfluidics module with another on the array of the integrated bio-object microfluidics modules, and the like.

In one embodiment, the transporting means on which the train-based interconnect platform moves includes a guideway including a pair of parallel tracks, a central monorail, a lateral rail, a guiding channel, or an overhead conveyor system.

In one embodiment, the guideway includes a pair of closed tracks placed inside an incubator or a container, for moving the array of the integrated bio-object microfluidics modules past the station.

In one embodiment, the guideway further includes one or more branched tracks placed in relation to the pair of closed tracks.

In one embodiment, the transporting means further includes switches placed between the pair of closed tracks and each branched track, for switching all or parts of the array of the integrated bio-object microfluidics modules to desired locations.

In one embodiment, the transporting means further includes a rotary turntable coupled between the pair of closed tracks and at least one of the one or more branched tracks for inserting propulsion units onto selected locations of the guideway, thereby allowing an automated assembly of module arrays of a desired configuration.

In another embodiment, the transporting means includes wheels, air bearings, roller bearings, low-friction pads, or desired mechanisms on each integrated bio-object microfluidics module to ensure the required linear displacement without undue stresses on the mechanical or fluidic connections.

In one embodiment, the plurality of integrated bio-object microfluidics modules includes at least one of an integrated brain module, an integrated lung module, an integrated heart module, an integrated liver module, an integrated stomach module, an integrated kidney module, an integrated gut module, an integrated testis module, an integrated skin module, and the like.

In one embodiment, the plurality of integrated bio-object microfluidics modules further includes at least one of an integrated perfusion controller (PC) module for perfusing the bio-object maintained on the microfluidics chip, an integrated microclinical analyzer (µCA) module for analyzing activities of the bio-object maintained on the microfluidics chip, and an integrated MicroFormulator (µF) module for providing desired substances to cultivate, maintain, and/or analyze the bio-object maintained on the microfluidics chip.

In one embodiment, the microcontroller of each integrated bio-object microfluidics module is provided with at least one of a wireless communication protocol and a wired communication protocol.

In one embodiment, the plurality of integrated bio-object microfluidics modules defines a wired or wireless communications network, such that each integrated bio-object microfluidics module is capable of electronic communication with one another module in the network and/or with a server that is in electronic communication with the network.

In another aspect, the invention relates to a method for cultivation, maintenance, and/or analysis of one or more bio-objects, where each bio-object includes an organ, a tissue construct, or a group of cells.

In one embodiment, the method includes providing a platform having one or more integrated bio-object microfluidics modules fluidically interconnected to each other. Each integrated bio-object microfluidics module includes one or more on-chip pumps; a plurality of fluidic switches; and a microfluidic chip in fluid communication with the one or more on-chip pumps and the plurality of fluidic switches, comprising at least one chamber for accommodating the bio-object and a plurality of fluidic paths connecting the chamber, the one or more on-chip pumps, and the plurality of fluidic switches.

The method further includes selectively and individually controlling the one or more on-chip pumps and the plurality of fluidic switches of each integrated bio-object microfluidics module to perform bio-object microfluidics functions for cultivation, maintenance, and/or analysis of the respective bio-object, wherein the bio-object microfluidics functions include perfusion of the respective bio-object, analysis of metabolic activities of the respective bio-object, formulation of custom media to support the respective bio-object or to guide stem cell differentiation or otherwise influence the biological behavior of a collection of cells.

In one embodiment, the method also includes selectively removing one integrated bio-object microfluidics module from the platform.

In another embodiment, the method also includes replacing the removed integrated bio-object microfluidics module with a desired integrated bio-object microfluidics module.

In yet another embodiment, the method also includes transporting the platform from one location to another location.

In yet another aspect, the invention relates to a system for cultivation, maintenance, and/or analysis of one or more bio-objects, where each bio-object includes an organ, a tissue construct, or a group of cells.

In one embodiment, the system includes at least one bio-object platform comprising one or more integrated bio-object microfluidics modules. Each integrated bio-object microfluidics module configured to cultivate, maintain, analyze and/or mimic functionalities of a bio-object includes one or more on-chip pumps; a plurality of fluidic switches; a microfluidic chip in fluid communication with the one or more on-chip pumps and the plurality of fluidic switches, comprising at least one chamber for accommodating the bio-object and a plurality of fluidic paths connecting the chamber, the one or more on-chip pumps and the plurality of fluidic switches; and a power and control unit programmed to selectively and individually control the one or more on-chip pumps and the plurality of fluidic switches for performing bio-object microfluidics functions.

Further, the system also includes a transporting means on which the at least one bio-object platform is movably disposed, for selectively moving at least one bio-object platform to desired locations; and at least one station having a base, and one or more subsystems fixed on the base at predetermined positions, wherein the at least one station is placed in relation to the transporting means such that when the at least one bio-object platform is moved at the predetermined positions, the one or more subsystems perform desired operations on the one or more integrated bio-object microfluidics, where the desired operations on the one or more integrated bio-object microfluidics include performing at least one of analytical functions, mechanical functions, maintenance functions, fluid handling, microscopy, removal of one integrated bio-object microfluidics module, replacement of one integrated bio-object microfluidics module with another on the array of the integrated bio-object microfluidics modules, and the like.

In one embodiment, the transporting means includes a guideway including a pair of parallel tracks, a central monorail, a lateral rail, a guiding channel, or an overhead conveyor system.

In one embodiment, the guideway includes a pair of closed tracks for moving the at least one bio-object platform past the station.

In one embodiment, the guideway further includes one or more branched tracks placed in relation to the pair of closed tracks.

In one embodiment, the transporting means further includes switches placed between the pair of closed tracks and each branched track, for switching all or parts of the at least one bio-object platform to desired locations.

In one embodiment, the transporting means further includes a rotary turntable coupled between the pair of closed tracks and at least one of the one or more branched tracks for inserting propulsion units onto selected locations of the guideway, thereby allowing an automated assembly of module arrays of a desired configuration.

In one embodiment, the system further includes at least one incubator placed in relation to the transporting means for accommodating the at least one bio-object platform, wherein the at least one incubator includes a temperature regulation means.

In one embodiment, the transporting means further includes at least one guideway carrier for carrying sections of the guideway on which the at least one bio-object platform is disposed, and means for vertically storing the sections of the guideway in the guideway carriers in the at least one incubator.

In one embodiment, the transporting means includes wheels, air bearings, roller bearings, low-friction pads, or desired mechanisms on each integrated bio-object microfluidics module to ensure the required linear displacement without undue stresses on the mechanical or fluidic connections.

In one embodiment, each integrated bio-object microfluidics module further includes a reservoir having one or more ports for providing a plurality of solutions, wherein each reservoir port includes a double-ended vial.

In one embodiment, each integrated bio-object microfluidics module further includes one imaging unit for evaluation of a respective bio-object.

In one embodiment, each integrated bio-object microfluidics module further includes at least one bubble trap coupled to at least one of the plurality of fluidic paths for removing bubbles therefrom.

In one embodiment, the power and control unit includes a microcontroller, a sensor array, and a power supply.

In one embodiment, the one or more on-chip pumps include an RPPM. Each of the plurality of fluidic switches includes an RPV. In one embodiment, the RPPM and each RPV are driven by a respective motor that is controlled by the microcontroller. In one embodiment, each RPV includes an NC valve.

In one embodiment, the one or more integrated bio-object microfluidics modules include a plurality of integrated bio-object microfluidics modules spatially arranged in an array.

In one embodiment, the at least one bio-object platform further includes fluidic interconnects and nodes for connecting each of the plurality of integrated bio-object microfluidics modules to one another.

In one embodiment, the plurality of integrated bio-object microfluidics modules is mechanically and fluidically interconnected to each other in series, in parallel, or in a combination of both in the array, wherein the array of the integrated bio-object microfluidics modules is a 1D linear array, a 2D array, or a 3D array.

In one embodiment, the at least one bio-object platform further includes a propulsion unit for applying a bidirectional traction force collinear with the array of the integrated bio-object microfluidics modules; a support module connected between the propulsion unit and the array of the integrated bio-object microfluidics modules; and a specialized module connected to the array of the integrated bio-object microfluidics modules to define a train-based interconnect platform that is movably disposed on the transporting means, wherein the train-based interconnect platform is configurable and interchangeable.

In one embodiment, the plurality of integrated bio-object microfluidics modules includes at least one of an integrated brain module, an integrated lung module, an integrated heart module, an integrated liver module, an integrated stomach module, an integrated kidney module, an integrated gut module, an integrated testis module, an integrated skin module, and the like.

In one embodiment, the plurality of integrated bio-object microfluidics modules further includes at least one of an integrated perfusion controller module for perfusing the bio-object maintained on the microfluidics chip, an integrated microclinical analyzer module for analyzing activities of the bio-object maintained on the microfluidics chip, and an integrated MicroFormulator module for providing desired substances to cultivate, maintain, and/or analyze the bio-object maintained on the microfluidics chip.

In one embodiment, the microcontroller of each integrated bio-object microfluidics module of each bio-object platform is provided with at least one of a wireless communication protocol and a wired communication protocol.

In one embodiment, the plurality of integrated bio-object microfluidics modules of each bio-object platform defines a network of wired or wireless communications, such that each integrated bio-object microfluidics module in the bio-object platform is capable of electronic communication with one another in the network and/or with a server that is in electronic communication with the network.

In a further aspect, the invention relates to an integrated MicroFormulator. In one embodiment, the integrated MicroFormulator includes a plurality of inlets for providing a plurality of solutions; a plurality of outlets; a plurality of fluidic switches in fluid communication with the plurality of inlets and the plurality of outlets; one or more on-chip pumps in fluid communication with the plurality of fluidic switches; a microfluidic chip having a mixer region and a plurality of fluid connections in fluid communication with the at least one pump, the plurality of valves, the plurality of inlets and the plurality of outlets; and a power and control unit programmed to selectively and individually control the one or more on-chip pumps and the plurality of fluidic switches for providing a desired substance that is a mixture of selected solutions from the plurality of solutions for cultivation, maintenance, and/or analysis of a bio-object. The integrated MicroFormulator operably has a Load Sample mode, a Sample to Mixer mode, a Mix mode, and a Sample Output mode.

In one embodiment, the power and control unit includes a microcontroller and a power supply. In one embodiment, the microcontroller is provided with at least one of a wireless communication protocol and a wired communication protocol.

In one embodiment, the one or more on-chip pumps include an RPPM. Each of the plurality of fluidic switches includes an RPV. In one embodiment, each RPV includes an NC valve. In one embodiment, the RPPM and each RPV are driven by a respective motor that is controlled by the microcontroller.

In one embodiment, the plurality of fluidic switches includes an input RPV fluidically connected to the plurality of inlets; a first RPV having five ports fluidically connected to the input RPV, the mixer region, the RPPM, a sample output port of the outlets, and a first waste port of the outlets, respectively; and a second RPV having three ports fluidically connected to the mixer region, the RPPM, and a second waste port of the outlets, respectively.

In one embodiment, the microfluidic chip further has a shuttle region suitable for holding fluids on-chip before mixing.

In one embodiment, the shuttle is integrated with the RPPM.

In one embodiment, the plurality of fluidic switches includes an input RPV fluidically connected to the shuttle region, and stock solution ports of the inlets; a first RPV having five ports fluidically connected to the mixer region, the RPPM, an input buffer port of the inlets, a sample output port of the outlets, and a first waste port of the outlets, respectively; and a second RPV having four ports fluidically connected to the mixer region, the RPPM, the shuttle region, and a second waste port of the outlets, respectively.

In another embodiment, the plurality of fluidic switches includes an input RPV fluidically connected to the shuttle region, and stock solution ports of the inlets; and an operation mode selector valve fluidically connected to the input RPV, the shuttle region, the mixer region, the RPPM, a sample output port of the outlets, and a waste port of the outlets, wherein the RPPM is fluidically connected to the mixer.

In yet a further aspect, the invention relates to an RPPM. In one embodiment, the RPPM has the actuator comprising a shaft engaged with a motor such that activation of the motor causes the shaft to rotate; and a bearing assembly engaged with the shaft, wherein the bearing assembly includes a bearing cage defining a plurality of spaced-apart openings thereon, and a plurality of rolling-members accommodated in the plurality of spaced-apart openings of the bearing cage, such that when the shaft rotates, the plurality of rolling-members of the bearing assembly rolls along a circular path.

The RPPM also has a fluidic path in fluidic communication with a first port and a second port, wherein the fluidic path is positioned under the actuator and is coincident with the circular path, such that when the shaft of the actuator rotates, the plurality of rolling-members of the bearing assembly rolls along the fluidic path to cause a fluid to transfer between the first port and the second port.

In one embodiment, each of the plurality of rolling-members includes a ball, a roller, or a wheel.

In one embodiment, the bearing cage has a first cylindrical portion on which the plurality of spaced-apart openings is defined, and a second cylindrical portion extending coaxially from the first cylindrical portion, wherein the first cylindrical portion has a diameter that is greater than that of the second cylindrical portion, where the second cylindrical portion defines a hole along its central axis into which the shaft is mounted.

In one embodiment, the bearing assembly further includes a thrust bearing positioned between the motor and the second cylindrical portion of the bearing cage; an alignment bearing positioned against the first cylindrical portion of the bearing cage; and a tensioning spring positioned between the thrust bearing and the alignment bearing.

In one embodiment, the RPPM further includes a substrate having a first surface containing a fluidic path formed by a process of hot-embossing, or injection-molding, or etching or mechanical machining and a second surface comprising an elastomeric membrane positioned between the bearing cage and the first surface of the substrate. Motor alignment/attachment pins are vertically positioned on the first surface of the substrate such that the actuator is located between the motor alignment/attachment pins. In one embodiment, the bearing assembly further includes a driving pin and an interface collar for providing the attachment of the driving pin to the shaft.

In one embodiment, the bearing assembly further includes a washer positioned between the shaft and the bearing cage, and a second elastomer sheet positioned between the washer and the bearing cage.

In one embodiment, the bearing assembly further includes an auto-centering needle bearing positioned at an edge of the bearing cage.

In another embodiment, the bearing assembly further includes a press-fit washer positioned on the bearing cage; a pressure transfer bearing positioned on the pressed fit washer; a tension holding plate positioned on the pressure transfer bearing and adjustably mounted to the motor alignment/attachment pins for transferring tensioning pressure via the pressure transfer bearing to fluidic paths thereunder; and centering pins positioned against the edge of the bearing cage.

In one aspect, the invention relates to an RPV. In one embodiment, the RPV includes the actuator comprising a shaft engaged with a motor such that activation of the motor causes the shaft to rotate; and a bearing assembly engaged with the shaft, wherein the bearing assembly includes a bearing cage defining a plurality of spaced-apart openings thereon, and a plurality of rolling-members accommodated in the plurality of spaced-apart openings of the bearing cage, wherein the number of the plurality of rolling-members is less than that of the plurality of spaced-apart openings of the bearing cage such that the bearing assembly has at least one no-rolling-member opening that accommodates a no-rolling-member.

The RPV also includes a plurality of selectively controllable fluidic paths coupled to each other, positioned under the actuator in relation to the plurality of equally spaced-apart openings of the bearing cage such that at least one selectively controllable fluidic path is positioned under the at least one no-rolling-member opening so that a fluid flow is allowed through the at least one selectively controllable fluidic path, while the other selectively controllable fluidic paths are respectively positioned under the openings having the rolling-members so that no fluid flows are allowed through the other selectively controllable fluidic paths.

In one embodiment, each of the plurality of rolling-members includes a ball, a roller, or a wheel.

In one embodiment, the plurality of spaced-apart openings of the bearing cage is spaced-equally defined on the bearing cage, wherein each two adjacent openings through the center of the bearing cage define an angle $\theta=2\pi/K$, K being the number of the plurality of equally spaced-apart openings.

In one embodiment, when the shaft of the actuator rotates a desired angle of (k×θ), k being 1, 2, . . . K, the at least one no-rolling-member opening is selectively placed over a desired one of the selectively controllable fluidic paths.

In one embodiment, the RPV further includes at least one always-open fluidic path coupled to the plurality of selectively controllable fluidic paths, positioned under the actuator in offset from the plurality of equally spaced-apart openings, such that the at least one offset fluidic path is in fluid communication with the at least one selectively controllable fluidic path under the at least one no-rolling-member opening, and the other selectively controllable fluidic paths under the openings having the rolling-members are closed.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 6A-6B show two different views of the linear array of IOM modules described in FIG. 5.

FIG. 25 shows an organ Perfusion Controller with a small microcontroller housing offset from the body of the device, according to one embodiment of the invention: (A) an outside view, (B) a perspective view. This device is well-plate-sized and compatible with existing commercial microscopes. Vials that would be in the row of six holes in the base are not shown.

FIGS. 53A-53E show a MicroFormulator according to yet another embodiment of the invention and an overview of its operation.

FIGS. 55A-55E show various roller-based RPPMs for high-flow perfusion according to different embodiments of the invention.

FIG. 58B shows the channels connecting the valve to external ports. FIG. 58C shows tubing, wrapped around a glass cylinder, containing solutions from the different ports loaded. FIG. 58D shows the valve, vials, the motor for the valve, and the tubing wrapped around the glass cylinder, and the syringe used to draw fluid from each port of the valve.

FIG. 67 shows a comparison table of the wireless technologies shown in FIG. 66.

DETAILED DESCRIPTION OF THE INVENTION

Figure 1:
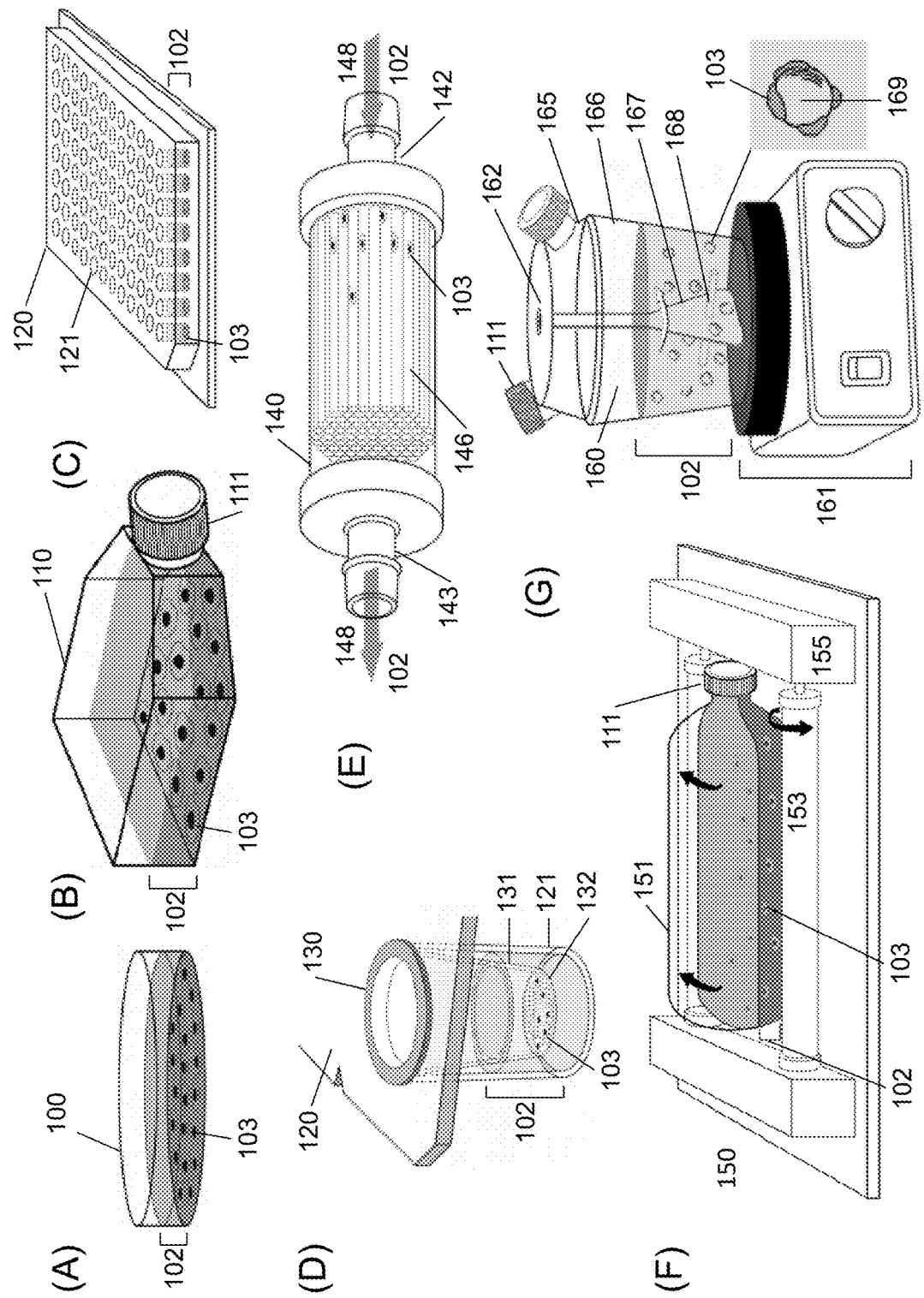
FIG. 1 shows current cell culture devices such as (A) Petri dishes, (B) cell culture flasks, (C) well plates, (D) Transwell inserts in a well-plate, (E) hollow fiber systems, (F) rolling bottle bioreactors, and (G) bead suspension bioreactors.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the FIGS. It will be understood that relative terms are intended to encompass different orientations of the device in addition to the orientation shown in the FIGS. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the terms "MicroClinical Analyzer", "MicroChemical Analyzer", and their abbreviation "µCA" are exchangeable. The term "Perfusion Controller" and its abbreviation "PC" are exchangeable. The term "MicroFormulator" and its abbreviation "µF" are exchangeable. The term "Rotary Planar Peristaltic Micropump" and its abbreviation "RPPM" are exchangeable. The term "Rotary Planar Valve" and its abbreviation "RPV" are exchangeable. The term "Integrated Organ Microfluidics" and its abbreviation "IOM" are exchangeable. The term "Organ-on-Chip" and its abbreviation "OoC" are exchangeable.

As used herein, the terms "fluidic path" and "fluidic channel" are exchangeable, and refer to a passage, a conduit, a groove, a furrow, or the like that allow a fluid flow through it.

The description is now made as to the embodiments of the present invention in conjunction with the accompanying drawings. In accordance with the purposes of this invention, as embodied and broadly described herein, this invention relates to integration platforms, interconnects, modules, and fluidic handling of organ constructs, engineered tissue, and human-on-a-chip platforms including organ-respective perfusion controllers, fluidic analyzers, MicroFormulators, and applications of the same.

This invention relates generally to scalable cell culture techniques that include not only 2D cell culture but also thick-tissue bioreactors. Automated bioreactors with perfusion and fluid handling are disclosed. Particularly, this invention aims to improve fluidic routing between multiple automated bioreactors. The system architectures of these bioreactors include, but are not limited to, linear fixed, rectangular fixed, circular rotational, train, or vertical stacked. These architectures allow fluidic connection between each automated organ chip to its respective upstream and/or downstream automated bioreactor. Disclosed herein, but not limited to, are the Organ Chip's Perfusion Controller (PC), MicroClinical Analyzer (μCA), and MicroFormulator (μF). Detailed fluidic channel analysis and designs of each of these devices are described as examples, but different controllers and measurement devices, such as miniature mass spectrometers, can also be used to practice the invention.

The PC, the μCA, and the μF all rely upon the Vanderbilt Institute for Integrative Biosystems Research and Education (VIIBRE)'s Rotary Planar Peristaltic Micropump (RPPM) and Rotary Planar Valve (RPV) technologies. The effort has advanced far beyond the original designs disclosed by Parker A. Gould et al. in PCT publication No. WO2012/048261, which is incorporated herein in its entirety by reference, and now is building upon a standardized, low-cost Integrated Organ Microfluidics (IOM) module design that has three subsystems: power, communication, sensing and control; motorized pumps and valves; and a microfluidic chip that provides the connectivity and chambers required to perform the IOM functions, such as controlled perfusion of an organ or a three-dimensional tissue construct, electrochemical measurement of organ or tissue metabolic activity, or formulation of custom media to support the organ and guide stem cell differentiation. The designs according to the invention allow ready customization of both hardware and software to a particular type and scale of organ. The key innovation of this invention is the use of wireless communication with an on-board microprocessor that controls miniature, low-cost pumps and valves. This enables independent asynchronous operation of a large number of organ modules, as might be required in the initial culturing and growth of individual organs, and, with simple linear connectivity, allows multiple organs to operate in a coordinated, interconnected manner made possible through an interconnect system that allows making and breaking of fluidic connections without the introduction of bubbles or loss of fluid. The use of a pair of input and output RPVs on the PC allows each organ/tissue construct to operate either independently with on-module recirculation, or in a connected manner wherein media that is conditioned by one organ/tissue construct is then allowed to perfuse one or more other organs/tissue constructs. While the dedicated microprocessor approach may initially appear complicated, the complexity is being hidden through careful design of both the hardware and the user interface, just as we are in general shielded from the internal complexity and normal function of both our cell phones and our intracellular organelles, such as mitochondria. Hence we describe in detail the design of numerous novel infrastructure hardware sub-components and systems required for successful implementation of multi-Organ-on-Chip systems and for the culture of engineered tissue.

These and other aspects of the present invention are further described in the following section. Without intent to limit the scope of the invention, further exemplary implementations of the same according to the embodiments of the present invention are given below.

Interconnect Platforms

In one aspect, the invention relates to a platform for cultivation, maintenance, and/or analysis of one or more bio-objects, where each bio-object includes an organ, a tissue construct, or a group of cells. The platform includes one or more integrated bio-object microfluidics modules. Each integrated bio-object microfluidics module is configured to cultivate, maintain, analyze and/or mimic functionalities of a respective bio-object, and includes one or more on-chip pumps; a plurality of fluidic switches; and a microfluidic chip in fluid communication with the one or more on-chip pumps, and the plurality of fluidic switches. The microfluidic chip has at least one chamber for accommodating the bio-object and a plurality of fluidic paths (or fluidic channels) connecting the at least one chamber, the one or more on-chip pumps and the plurality of fluidic switches. In addition, each integrated bio-object microfluidics module may include one imaging unit for operable evaluation of a respective bio-object, at least one bubble trap coupled to at least one of the plurality of fluidic paths for removing bubbles therefrom, and a reservoir having one or more ports for providing a plurality of solutions. In one embodiment, the one or more on-chip pumps include an RPPM. Each of the plurality of fluidic switches includes an RPV. The RPPM and each RPV are driven by a respective motor that is controlled by the microcontroller. In one embodiment, each RPV includes an NC valve.

The one or more integrated bio-object microfluidics modules having a plurality of integrated bio-object microfluidics modules are spatially arranged in an array and connected to each other in series, in parallel, or in a combination thereof through fluidic interconnects and nodes. The array of the integrated bio-object microfluidics modules can be a one-dimensional (1D) linear array, a two-dimensional (2D) array, or a three-dimensional (3D) array. Further, the array of the integrated bio-object microfluidics modules is storable in an incubator tunnel or a vertical stacking incubator. Also, the array of the integrated bio-object microfluidics modules is movable as a unit, for example, by utilizing a transporting means, such as a guideway.

In addition, the plurality of integrated bio-object microfluidics modules includes at least one of an integrated brain module, an integrated lung module, an integrated heart module, an integrated liver module, an integrated stomach module, an integrated kidney module, an integrated gut module, an integrated testis module, an integrated skin module, and the like.

Furthermore, the plurality of integrated bio-object microfluidics modules further includes at least one of an integrated perfusion controller (PC) module for perfusing the bio-object maintained on the microfluidics chip, an integrated microclinical analyzer (μCA) module for analyzing activities of the bio-object maintained on the microfluidics chip, and an integrated MicroFormulator (μF) module for providing desired substances to cultivate, maintain and/or analyze the bio-object maintained on the microfluidics chip.

Moreover, the power and control unit of each integrated bio-object microfluidics module has a microcontroller that is provided with at least one of a wireless communication protocol and a wired communication protocol. Accordingly, the plurality of integrated bio-object microfluidics modules defines a network of wired or wireless communications, such that each integrated bio-object microfluidics module is capable of electronic communication with one another in the network and/or with a server that is in electronic communication with the network.

In the following exemplary embodiments, the invention describes the characteristics of an Organ Interconnect Platform for investigating and analyzing biochemical and microphysiological interactions between various combinations of Integrated Organ Microfluidics (IOM) modules (also referred to as Perfusion Controllers (PC), MicroClinical Analyzers (µCA), and MicroFormulators (µF)) for the purpose of providing computer-controlled maintenance of an organ or tissue-engineered construct and on-line analysis of the functionality of multiple tissue constructs or multiple interacting organ modules, i.e., a system of organs. The overarching purpose of this Organ Interconnect Platform is to create a platform that can replicate key elements of human physiological function in situ and thus provide an experimental platform suitable for investigating the effects of drugs and other biological factors on multi-organ systems. It can also be used to control the seeding, growth, and maintenance of individual tissue-engineered constructs, including but not limited to cardiac valves, blood vessels, peripheral nerves, and skin. To accomplish these tasks, the Organ Interconnect Platform relies on the availability of specific Integrated Organ Microfluidics modules, each of which is designed to mimic, to some physiological extent, the functionality of a particular type of organ, for example, heart, liver, etc., and also provide the requisite analytical capabilities required for organ qualification and maintenance. Hence this Organ Interconnect Platform addresses many of the engineering challenges outlined in Wikswo et al., "Engineering Challenges for Instrumenting and Controlling Integrated Organ-on-Chip Systems," IEEE Trans. Biomed. Eng., 60:682-690 (2013), and "Scaling and Systems Biology for Integrating Multiple Organs-on-a-Chip," Lab Chip, 13:3496-3511 (2013), including the need to restrict the volume of tubing that connects the different modules, and it enables the integration of a collection of such Integrated Organ Microfluidics, control, and analytical modules in such a fashion to maintain organ health and allow for physiologically relevant experimentation on in situ, interconnected multi-organ systems, or the culture of multiple tissue-engineered constructs.

The multi-Organ Interconnect Platform of the invention contains internal fluidic connections between each respective organ maintained on its respective Integrated Organ Microfluidics modules. For example, the liver Organ Chip resides within the liver Integrated Organ Microfluidics module, which is mechanically, fluidically, and electronically connected via the Organ Interconnect Platform to other organs, tissues, or analytical modules. The Organ Interconnect Platform provides additional connections to the liver's respective MicroClinical Analyzer, MicroFormulators, and the other organs located on the Organ Interconnect Platform. The Organ Interconnect Platform may also contain imaging units for evaluation of the respective organs while in the incubator or at other times in the operation of the system.

Figure 4A:
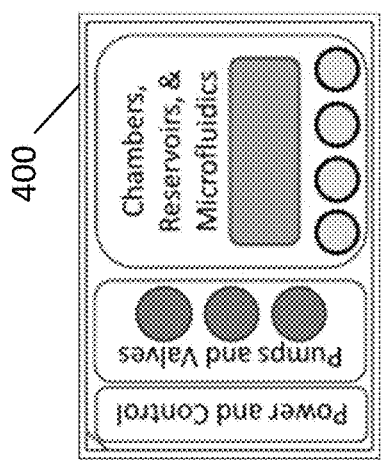
FIGS. 4A-4F show different topologies/configurations of integrated organ microfluidics (IOM) modules that are either independent of each other or are interconnected according to embodiments of the invention.
Figure 4B:
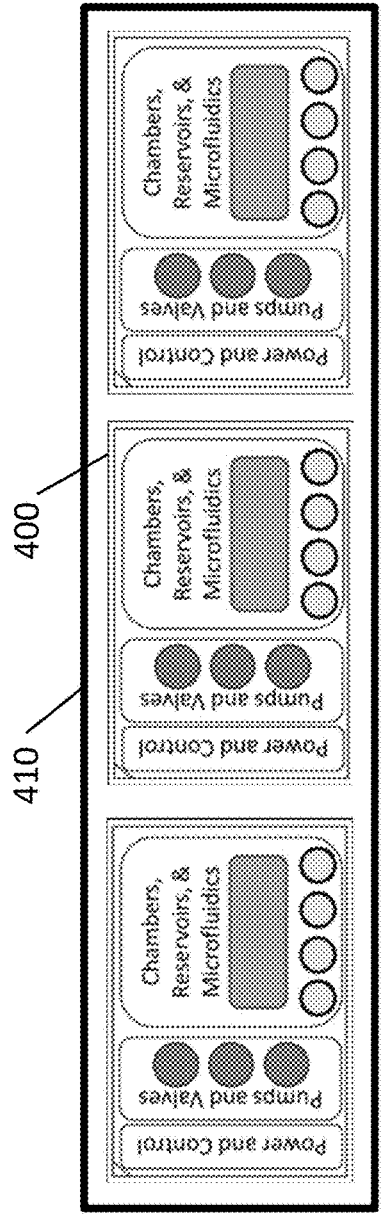
Figure 4C:
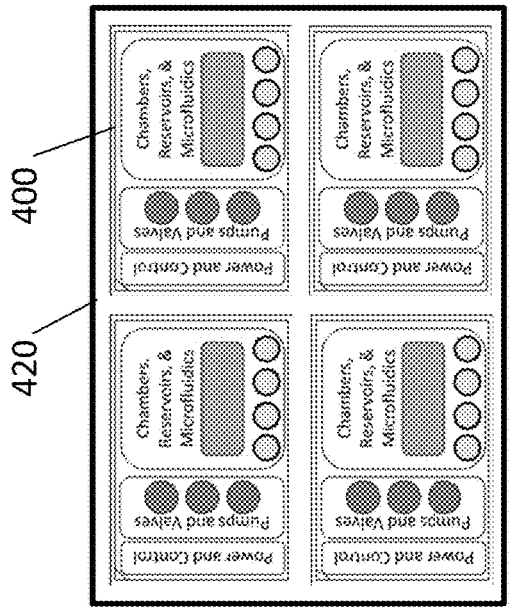
Figures 4D, 4E:
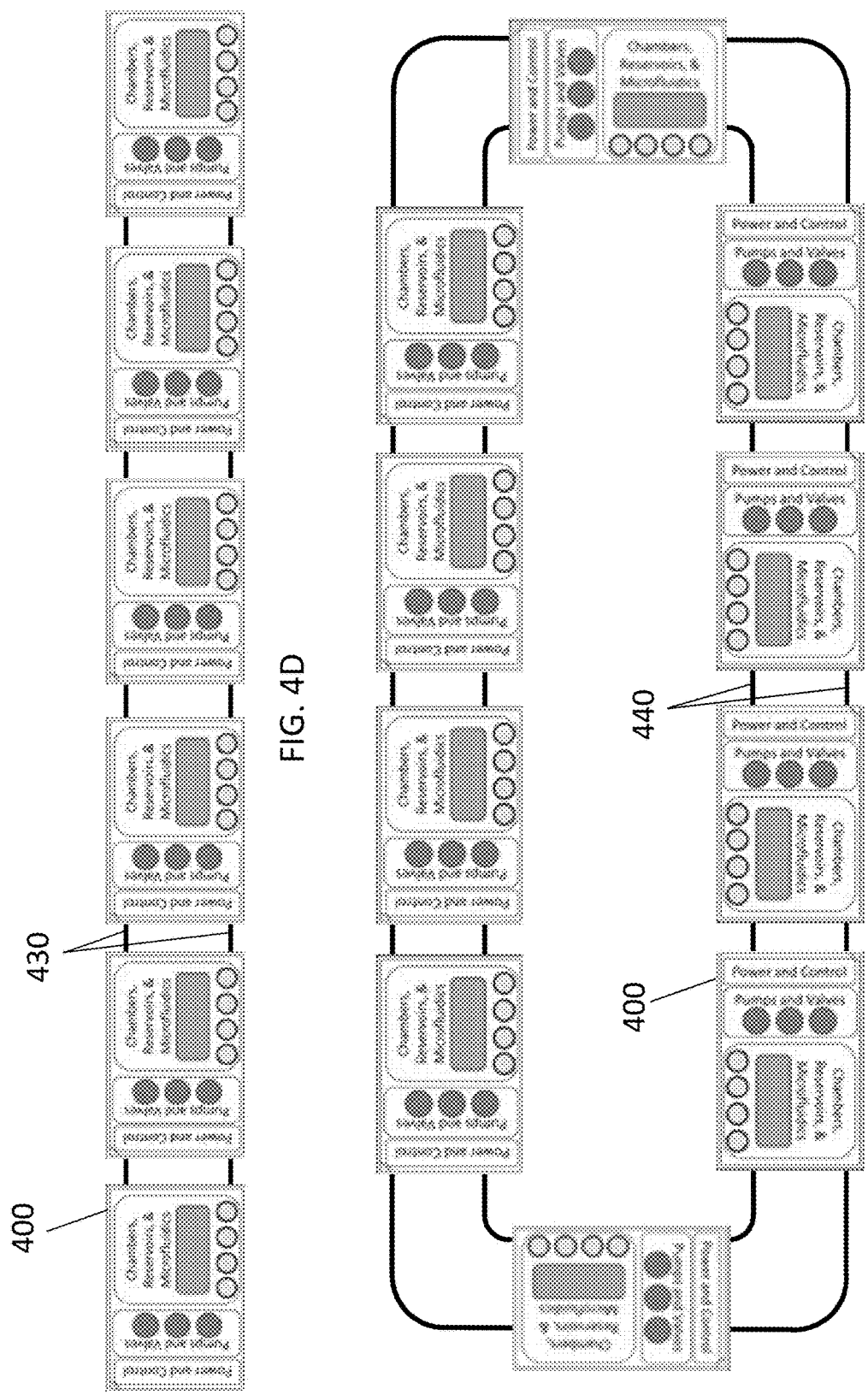
Figure 4F:
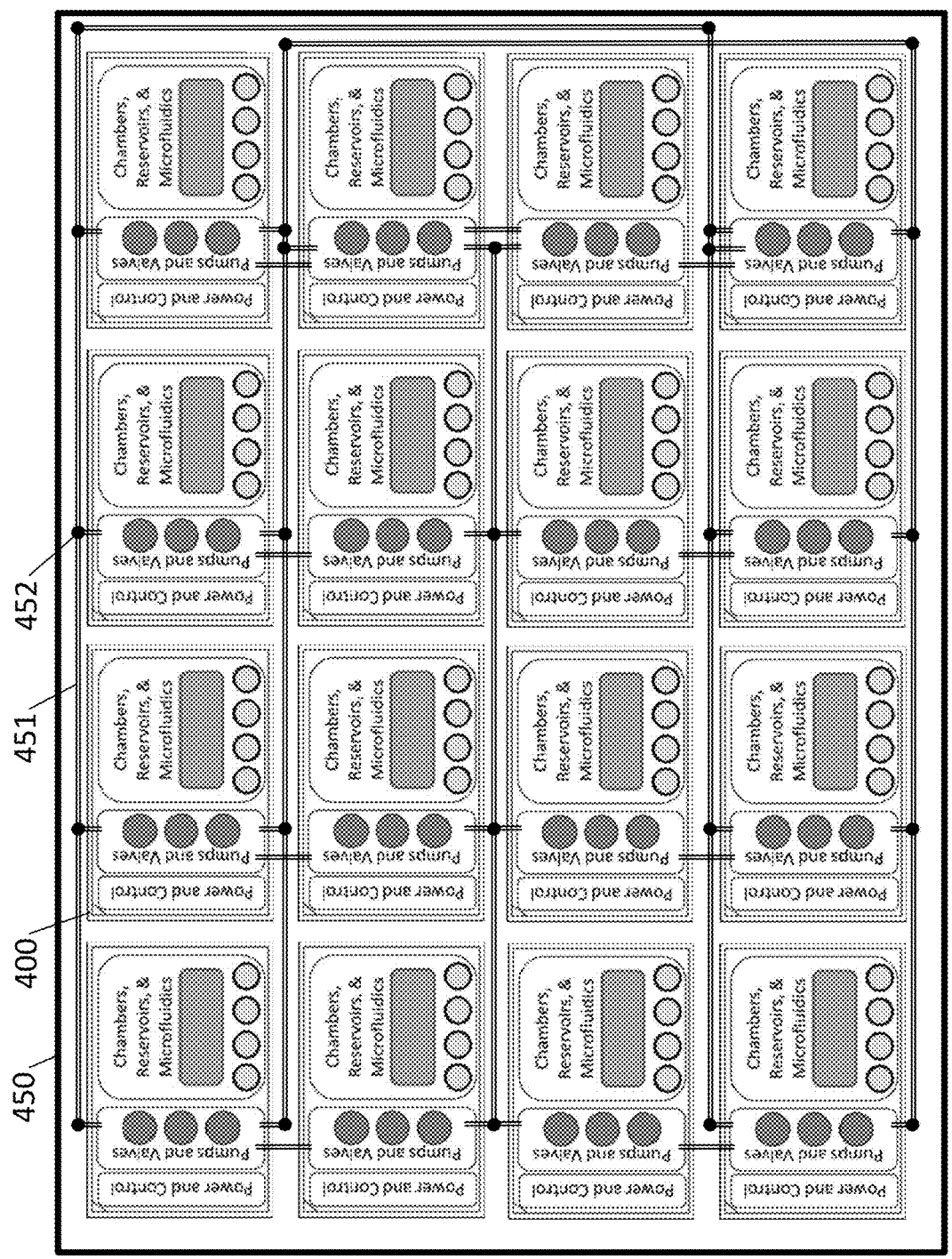

According to the invention, there are a multitude of different Organ Interconnect Platform topologies and according to this invention individual OoC modules could be exchanged or moved from a location in one topology into a different location in another topology. Various configurations representing static topologies are shown in FIG. 4. Briefly, one can utilize an OoC module in isolation as the generic module 400, as shown in FIG. 4A, or assemble two or more modules 400 in a linear array 410, as shown in FIG. 4B, or rectangular array 420, as shown in FIG. 4C, where each module operates independently without connections to other modules, for example in the seeding and growth of individual organs or tissue constructs. Alternatively, fluidic interconnects 430 between the modules 400 can create an interconnected linear array of modules containing organs or tissue constructs, as shown in FIG. 4D. Other topologies can also be utilized to practice the invention. For example, in the configuration shown in FIG. 4E, these interconnects 440 between the modules 400 form a closed loop. FIG. 4F shows a multi-nodal topology on a platform 450 in which a plurality of modules 400 are interconnected in a complex topology through the use of on-platform interconnects 451 and nodes 452. In this embodiment, the generic modules may support organ or tissue perfusion as PCs, or serve as µCAs or µFs. Other topologies are possible, including vertical stacks of the modules.

Figure 5:
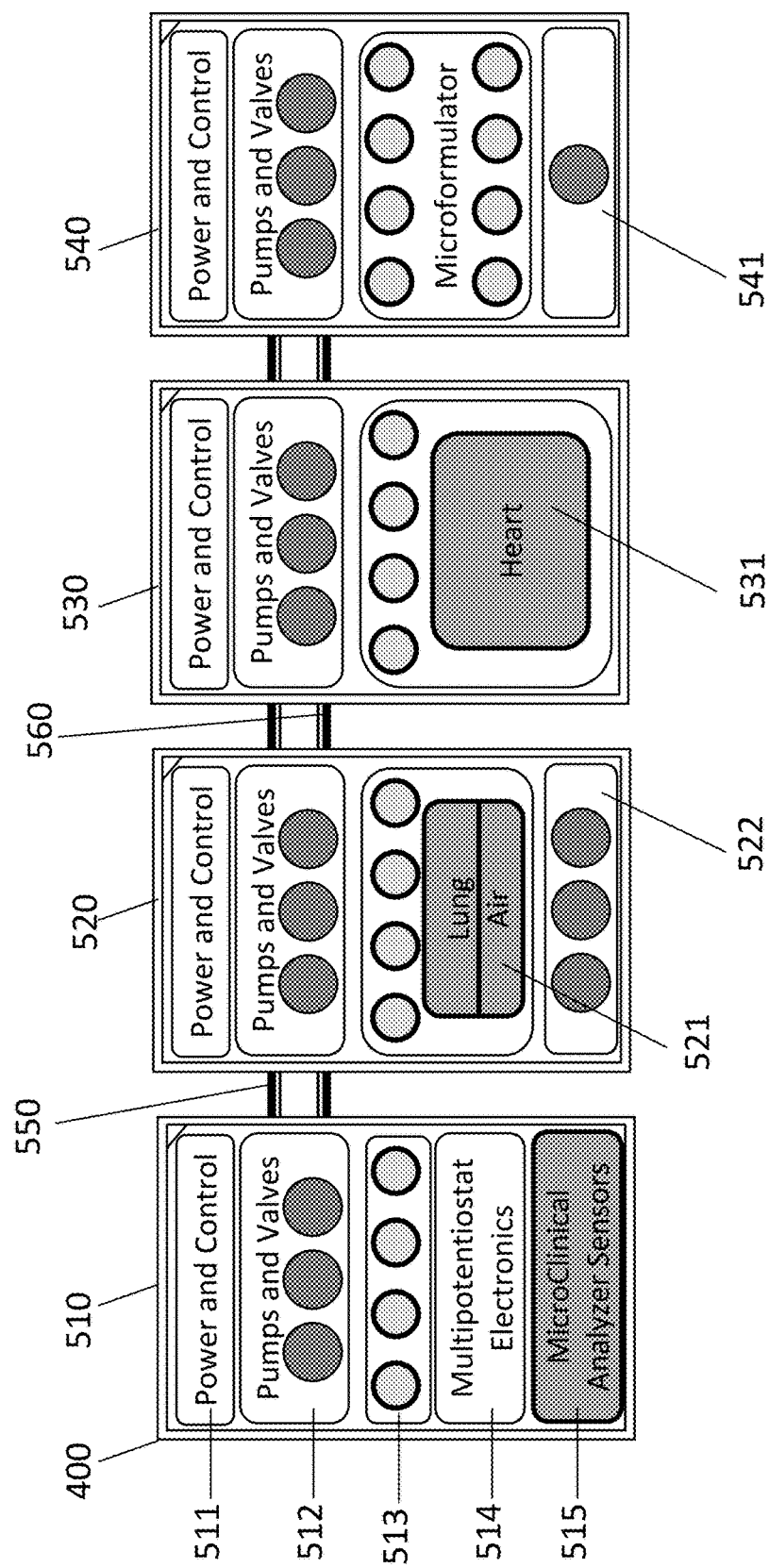
FIG. 5 shows schematically a linear array of IOM modules in which the four IOM modules are integrated with interconnects according to one embodiment of the invention.
Figure 6C:
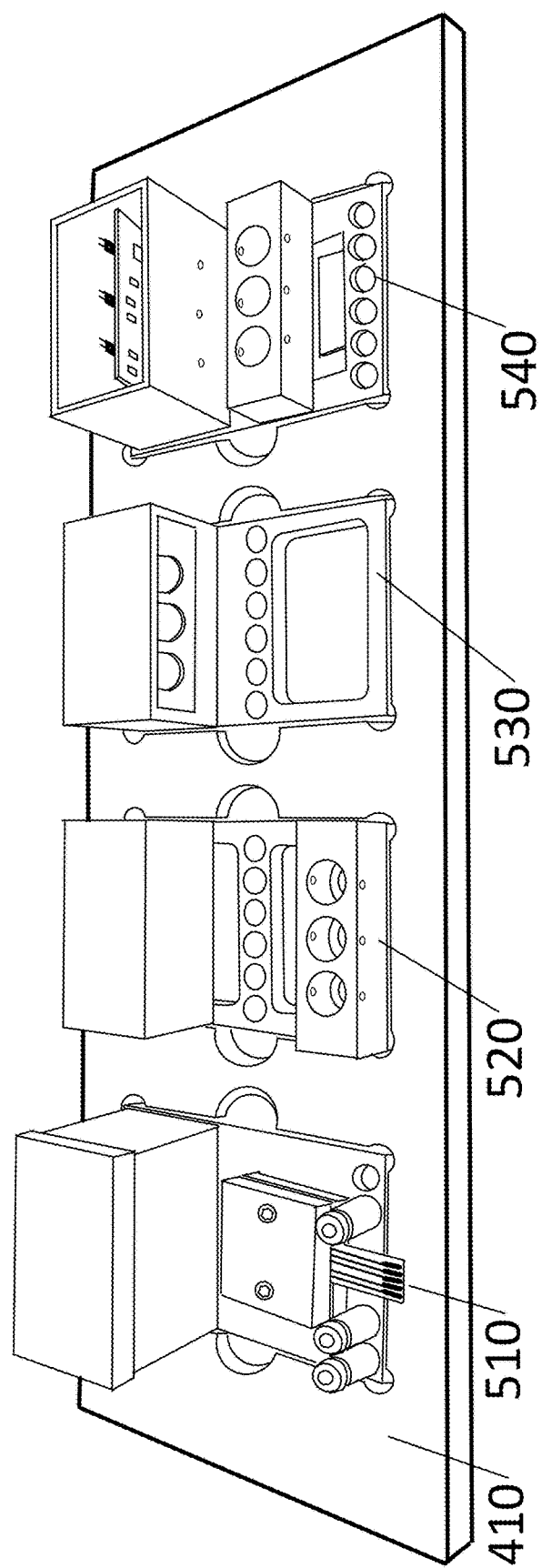
FIG. 6C shows a prototype of the linear array of IOM modules.

FIG. 5 presents an exemplary embodiment in which four generic modules 400 are interconnected to provide an integrated MicroClinical Analyzer module 510, a lung module 520, a heart module 530, and a MicroFormulator module 540 to support arterial 550 and venous 560 circulations. In this example, each module has a power and control subsection/unit 511, a set of pumps and valves 512, and reservoir bottles 513, all of which are interconnected by a microfluidic device (not shown). The MicroClinical Analyzer 510 achieves its desired function by the inclusion in the generic module of multipotentiostat electronics 514, and MicroClinical Analyzer sensors 515 using electrochemical or other types of sensor. The lung module 520 contains a lung chip 521, as well as additional pumps and valves 522 that allow for the perfusion and control of the pulmonary epithelial cells growing on the air side of the alveolar membrane, and also control the respiration of the lung if desired. The heart module 530 contains the heart chip 531, which may contain either a working heart with one or more chambers with or without valves, or a nonworking cardiac construct utilized to ascertain the effects of drug on cardiac or valve tissue with perfusion provided by an external pump. The MicroFormulator module 540 contains an additional valve 541 and a plurality of vials 513 from which the solutions to be mixed are drawn. FIGS. 6A and 6B show two different views of the linear array of IOM modules, while FIG. 6C shows a line drawing of a prototype that indicates how this linear module array might be arranged with the platform 450 containing a MicroClinical Analyzer (µCA) 510, a two-sided lung Perfusion Controller (PC) 520, a heart Perfusion Controller 530, and an RPPM-RPV MicroFormulator (µF) 540. This linear array can also be readily accessed by an external robot or other fluid-handling device that delivers or removes fluid from the modules or provides other services to the module array. Similarly, the module array can be moved past fixed devices such as fluid handlers, microscopes, or imaging units. The module array can be readily utilized in an incubator since with this design it is straightforward to utilize components that can operate without difficulty at 37° C. If required, the electronics and motor modules can be encapsulated for internal environmental control.

Figure 7:
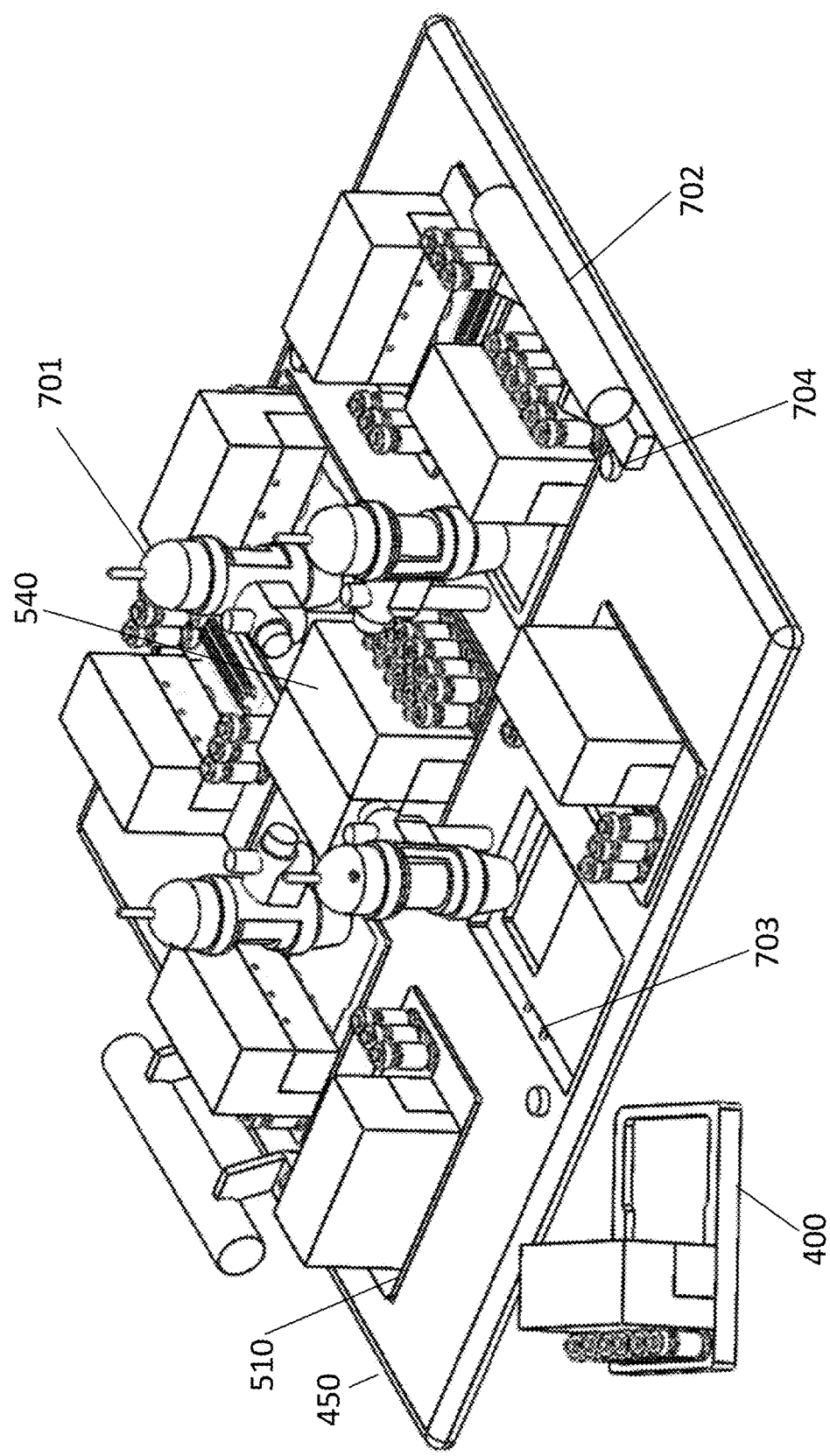
FIG. 7 shows an Organ Interconnect Platform according to one embodiment of the invention. The Organ Interconnect Platform is configured so that it fits into any commercially available 18" incubator.

Alternatively, a rectangular arrangement of the platform 450 allows improved connectivity between a plurality of IOM modules, as shown in FIG. 7. The Organ Interconnect Platform contains the internal fluidic interconnections to route fluid between each respective organ. For instance, this embodiment provides a self-sealing atrial interconnect bus, a venous bus, and a storage system for fluid on the centralized MicroFormulator. RPVs on each module determine whether the respective module is connected to a particular interconnect port. This embodiment also shows on-board imaging units for each organ, such as four USB microscopes suitable for in-incubator upright imaging. The eject buttons adjacent to each IOM retract the internal fluidic connection between the Interconnect System and the Organ Module. An individual Integrated Organ Microfluidics module interfaces to the platform through fluidic interconnection ports. The fluidic connection ports can be self-sealing, septum-based interconnects to facilitate simple sterile interfaces to fluidic routing channels contained within the Organ Interconnect Platform without the loss of fluid or the addition of air. Appropriate fluidic switches can accomplish the same functions, particularly when the switch includes vent, drain, or flush positions to either empty or fill the volume of the interconnect without perturbing the fluids in the body of the module. When the Integrated Organ Microfluidics module is removed from the Organ Interconnect Platform, the septum seal or other interconnect sealing mechanism prevents fluid leakage. Hence, the central innovation of this design is not just simple tubing or channel connections between the modules, but a controlled interconnect system wherein the connections between modules and how these connections are routed within each module are dynamic and can be controlled by either the user or the automated control system.

As shown in FIG. 7, each module resides in a rectangular arrangement of the platform 450 which provides fluidic connection, power, and the ability to image. In one embodiment, attached imaging units 701 allow for evaluation of the biological samples. Handles 702 allow easy transport between the incubator and bench-top. Fluid interconnects between these modules are shared, and the fluidic routing is handled both internally and by the valves of each module. Devices interface to the rectangular platform 450 through valved, fluidic interconnects 703 that can be mechanically removed from the modules via an eject button 704.

Figure 8:
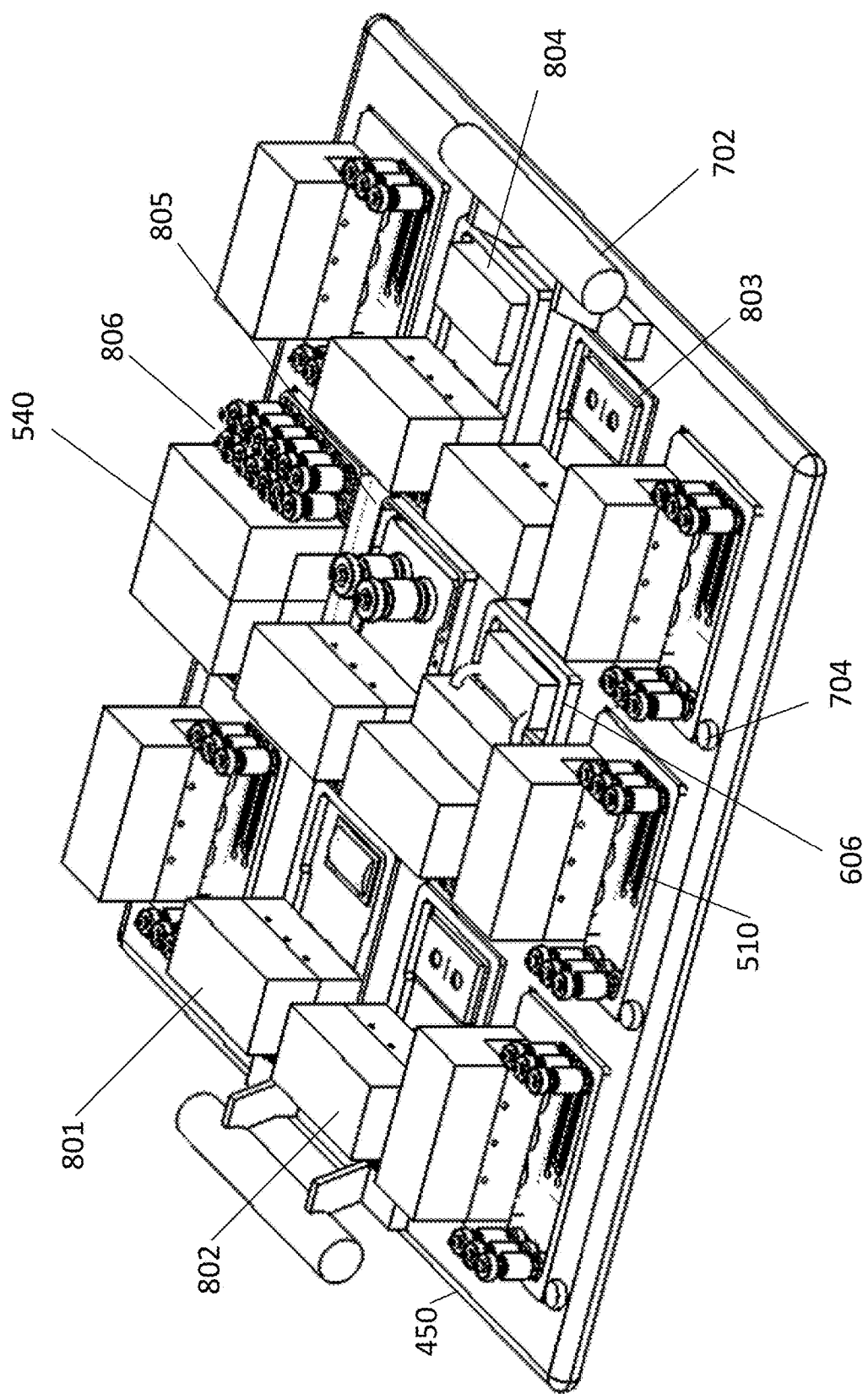
FIG. 8 shows an alternative configuration of the Organ Interconnect Platform with separate right and left heart modules according to another embodiment of the invention. A single heart with multiple chambers can also be utilized. Also present on this device is a cardiac assist/cardiopulmonary assist device for aid in fluidic routing between the heart and lung chips. This would ensure the proper perfusion and oxygenation of the organs/tissues should the resistance of these modules be too high for the cardiac module to provide an adequate perfusion rate or adequate oxygenation for the lung module.

FIG. 8 shows an alternative embodiment of the invention, with additional organs including a liver 801, left heart 802, right heart 803, and kidney 804. Each organ has its own respective MicroClinical Analyzer 510. In one embodiment, a cardiopulmonary assist device 805 provides fluidic storage for the atrial and venous lines, as well as supporting perfusion pressures to the modules and gas exchange should the heart and lung not have the capacity to support the entire system alone. A centralized MicroFormulator 540 provides on-board reagent mixing and additional sample storage 806 for each organ.

Figure 9:
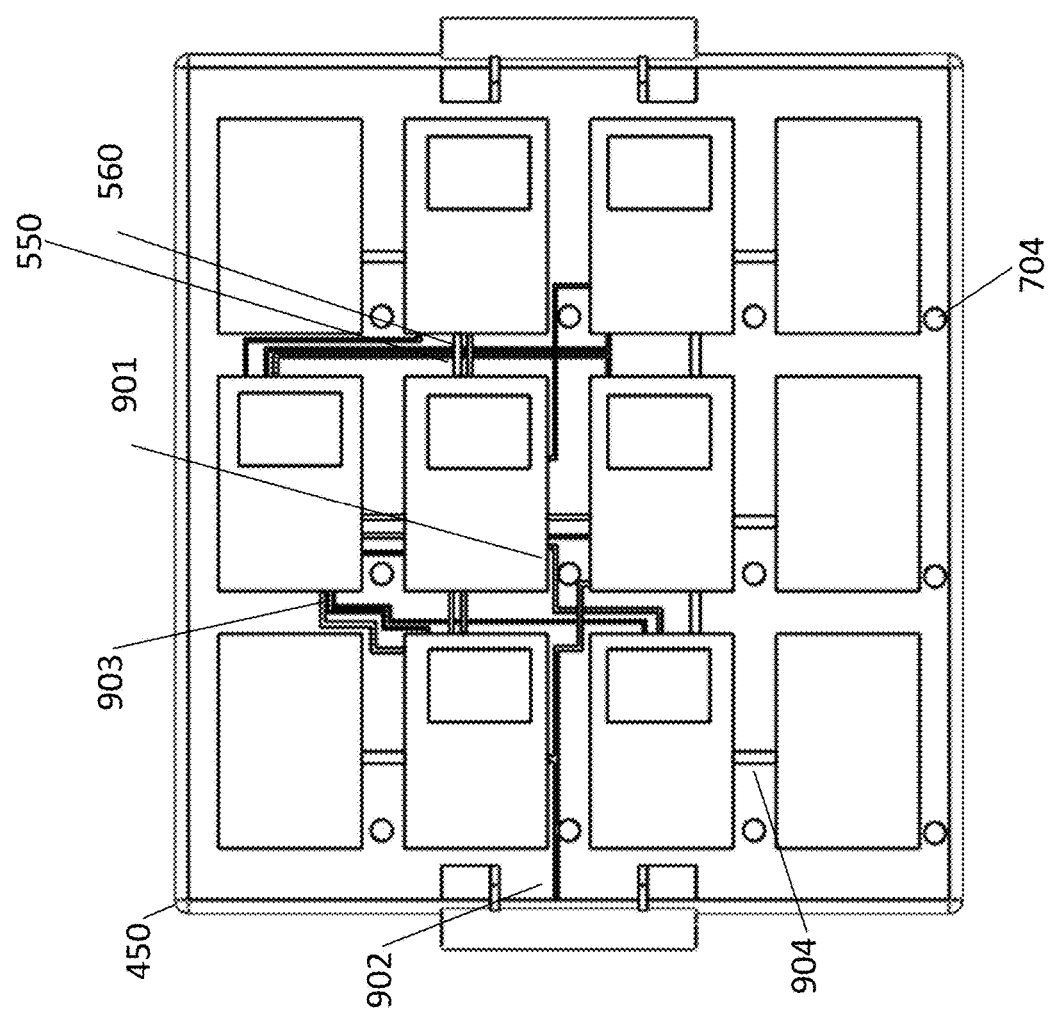
FIG. 9 shows schematically the fluidic interconnect routing within an Organ Interconnect Platform according to one embodiment of the invention.
Figure 10:
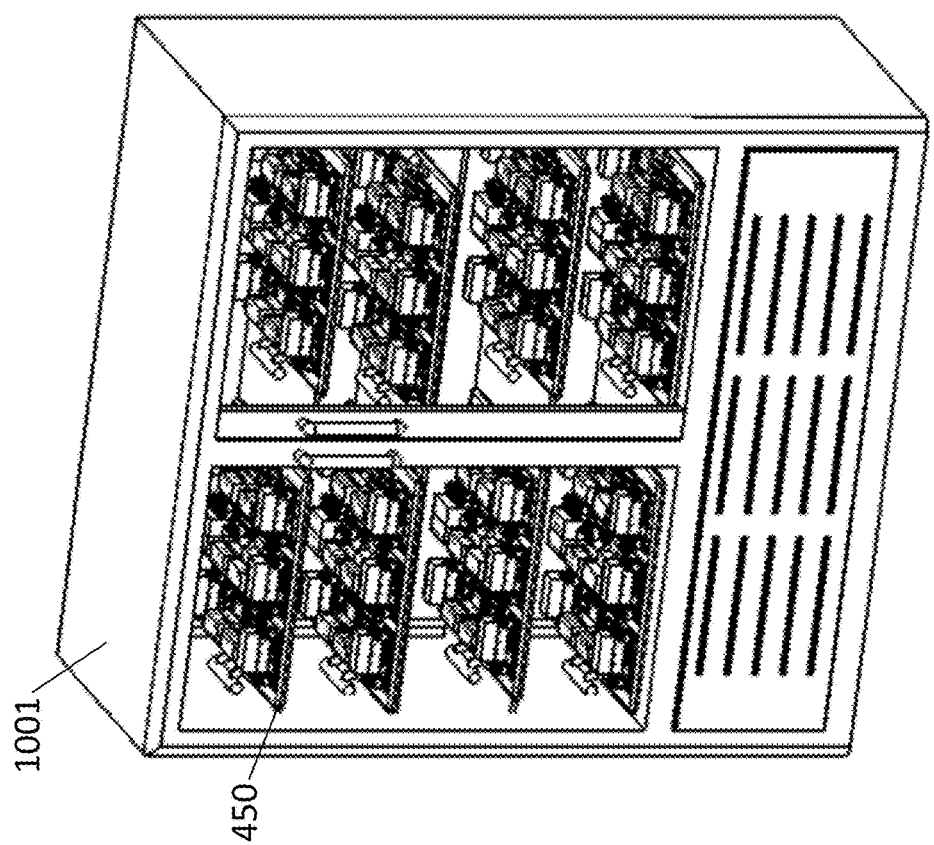
FIG. 10 shows schematically multiple Organ Interconnect Platforms stored in an incubator according to one embodiment of the invention. Note that when the Organ Interconnect Platforms are located in an incubator environment, electrical connectors or wireless inductive power provides charging current for the on-board batteries, and an antenna located inside the incubator allows wireless communication to and from each instrumented Organ Module.

As shown in FIG. 9, fluidic handling within the platform 450 is performed by valved or switched bus interconnects such that when an organ module is added or subtracted, there is minimal loss of fluid or introduction of bubbles. Platforms can contain standardized atrial 550, venous 560, and a centralized MicroFormulator fluidic bus 901. Oxygen 902 supply lines, transport for bile 903, and interfaces for MicroClinical analyzers 904 to the organ modules can be provided internally. The MicroFormulator can control drug and reagent delivery to each IOM, while allowing mixing of any organ's supernatant and redistribution to other organs. In one embodiment, these linear platform arrangements 450 are designed such that they can fit in a standard commercial incubator for cell culture. One advantage of the rectangular fixed architecture is the ability to store multiple platforms 450, each containing multiple organs and their required support modules in an incubator 1001 shown schematically in FIG. 10, which can have integrated intra-incubator power supply for charging multiple platforms, each of which can have integrated wireless connectivity for communication. The incubator can also use wireless inductively coupled or resonant magnetic power or other means to provide power to individual modules or platforms that contain multiple modules without the need for physical electrical connections between the module or platform and the incubator. Physical electrical connections could alternatively be installed on each incubator shelf such that insertion of the platform 450 automatically provides electrical power to the platform.

Figure 11:
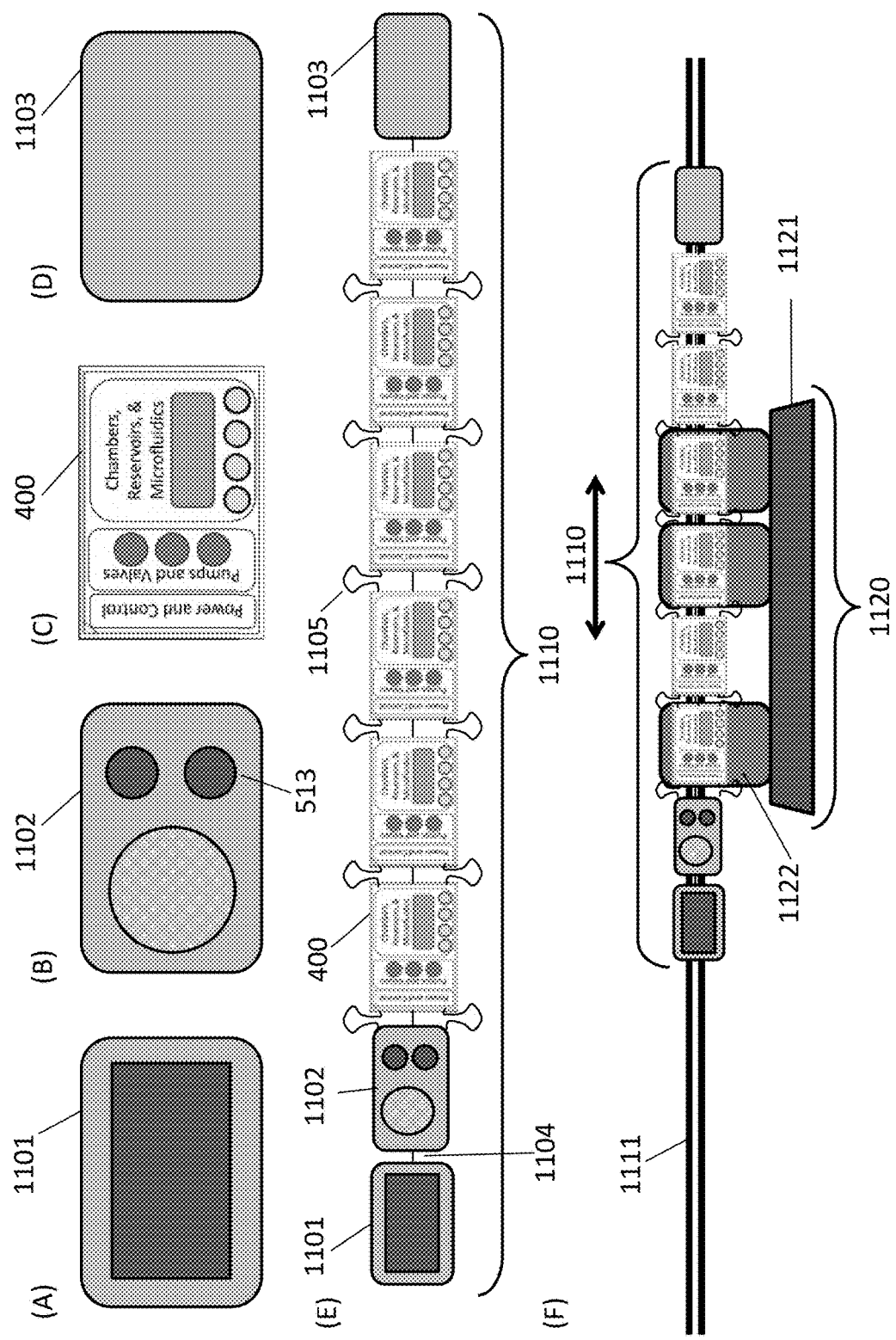
FIG. 11 shows dynamic IOM topologies/configurations according to embodiments of the invention, where a propulsion unit moves a linear array of organ/tissue modules containing a perfusion supply and/or cardiopulmonary assist system that can also serve as a storage system for fresh and used culture media, multiple IOM modules, and other analytical instruments, including, but not limited to, miniature mass spectrometers. The propulsion unit allows the linear array to position itself in such a way that the IOM modules can be examined under a microscope or undergo fluid exchange.
Figure 12:
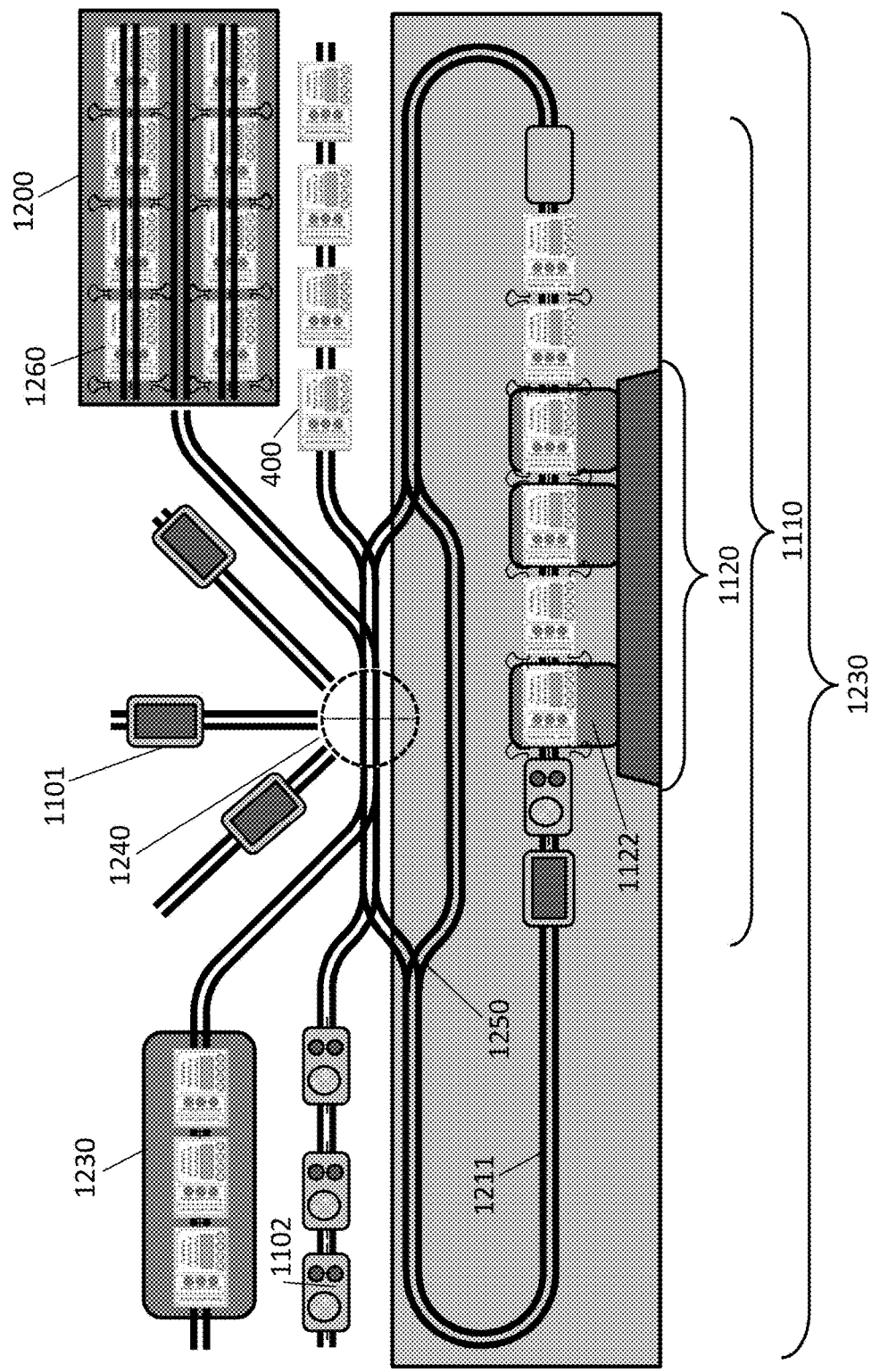
FIG. 12 shows an alternate configuration of a module array according to the invention, with a switchyard for moving IOMs to locations for undergoing further analysis or manipulation, switching locations of IOMs within the same array, and moving IOMs from one array to another, and additional IOM storage and analysis bays.

According to the invention, the fixed linear array of modules 410 is well suited for translation of the entire array as a unit. One embodiment of this is shown in FIG. 11. A linear array of modules includes several module types 1110 and is configured for running on a guideway 1111. A propulsion unit 1101 can apply a bidirectional traction force collinear with the linear array. A support module 1102 in one embodiment can contain a cardiopulmonary unit to ensure adequate perfusion and oxygenation of all organ/tissue modules, as well as large fluid reservoirs 513 for fresh and spent perfusion media. A series of interconnected modules 400 can perform the various functions illustrated in FIGS. 5 and 6. Additional analytic and control functions can be performed by specialized modules 1103 that might provide sample analysis by means of a miniature mass spectrometer. Because the modules are connected by a mechanical interconnect 1104, the linear array 1110 can be moved as a unit past a station 1120 that has multiple subsystems 1122 that are fixed in position by a base 1121 to perform a variety of analytical, mechanical, or other maintenance functions on the array, including, but not limited to, fluid handling, microscopy, and the removal of one module and its replacement with another. As such, when the train-based interconnect platform is moved at the predetermined positions, subsystems perform the above desired operations on the linear array of the integrated organ microfluidics. The motion of the array can utilize guideways, wheels, air bearings, roller bearings, low-friction pads, or other mechanisms on each module to ensure the required linear displacement without undue stresses on the mechanical 1104 or fluidic 1105 connections. As shown in FIGS. 11 and 12, a guideway 1111 is utilized for the movement. The guideway 1111 upon which the linear array moves can be arranged in the form of a pair of parallel tracks, a central monorail, a lateral rail, a guiding channel, or an overhead conveyor system.

If the fluidic and mechanical connections between the modules 1105 and 1104 are made flexible, it is not necessary for the linear array to be held in a straight line, but the linear array can be curved as required to manipulate or move the array. There are multiple means by which the controlled movement of coupled modules along a chosen trajectory can be accomplished. FIG. 12 develops a transporting means for the controlled movement of coupled modules that builds upon the classic train where cars are pulled or pushed along a track. As shown in FIG. 12, a pair of closed tracks 1211 is utilized for moving the array past the station 1120 or other locations. Further, one or more branched tracks are placed in relation to the pair of closed tracks 1211; switches 1250 are placed between the pair of closed tracks and each branched track for switching all or parts of the array to desired locations; and a rotary turntable 1240 is coupled between the pair of closed tracks and at least one of the one or more branched tracks for inserting propulsion units onto selected locations of the guideway, thereby allowing an automated assembly of module arrays of a desired configuration. In the example shown in FIG. 12, the linear array 1110 described in FIG. 11 can be propelled around a closed track 1211 inside an incubator or other container 1230 that allows the array to be moved past the analytical and manipulation stations 1120. Switches 1250 allow all or parts of the array to be moved to other locations, including but not limited to sections of track that contain modules of different types, e.g., 1102 and 400. Coupled modules 1260 can be moved either individually or as a coupled unit into an incubator 1200. A rotary turntable 1240 is used to insert propulsion units 1101 onto the main tracks, thereby allowing the automated assembly of module arrays of a desired configuration. For example, a propulsion unit 1101 can assemble an array of three organ/tissue modules 400 and transfer them to a station 1230 in which the modules are seeded with cells and maintained until the cells are ready to be transferred to the incubator 1200 for cell growth prior to assembly into the functional array 1110 that will then undergo detailed analysis.

Train-based interconnect platforms, with moving IOM modules and fixed microscope, analysis, and manipulation stations, have significant advantages over fixed platforms in that the interconnected organs are readily configurable and interchangeable; for instance, one Organ Array can serve as an incubation train for the initial growth phases of these organs. Once the organs reach a desired level of maturity they can be connected to a larger array of mature organs. Each array 1110 has on-board organ maintenance modules, which would provide perfusion, oxygenation, debubbling, imaging, reagent synthesis, and storage of reagents for later analysis, as shown in FIG. 12. Additionally, one embodiment has stations 1120 to replenish fresh culture media, remove waste, and perform regular cellular analysis procedures. In one embodiment, the Organ Array has a cardiopulmonary assist module 1102 that can provide perfusion and gas exchange to each of the Organ Modules.

Using the configuration shown in FIG. 12, the array can drive through any number of analytical or imaging modules, which can perform a variety of functions. An imaging station would require a condenser module inserted above the Organ Chip to provide illumination to the microscope located between different locations on the guideway.

There are additional implications of this novel technology for the manipulation of biological instruments and bioreactors. FIGS. 11 and 12 effectively describe a system for the automated assembly and transport of biological and bioanalytical modules. As the cost and size of analytical instruments reduce to those of a well plate, it will be possible through this invention to configure bioreactors and modular instruments for automated biology in a manner specific to a particular experiment or objective. The components of such a system include, but are not limited to, propulsion units, analytical modules, biomodules, interconnects, power delivery (possibly through energization of the rails of a metallic guideway), control signals, switches, incubators, vertical storage lifts, angular and rotary guideway switches, optical stations, fluid delivery systems, position sensors, connection means, guideways, and guideway end stops, all of which can provide a new methodology for conducting complex and dynamic biological experiments beyond what is afforded by the simple robot shown in FIG. 2.

It is important to realize that the system described in FIGS. 11 and 12 in fact can be viewed as a practical implementation of a Turing machine. In the classic Turing machine, a tape is passed through a reading unit and a writing unit, wherein the instructions on the tape can be used to modify data stored elsewhere on the tape and even modify other instructions. The Turing machine is viewed as the universal model of a digital computer. In this case, the topology allows us to manipulate media concentration, module interconnections, and other system parameters based upon the data obtained from the linear array itself. Hence the combination of the array 1110 and the stations 1120 and the ancillary hardware in FIG. 12 constitutes a bioreactor Turing machine for the automated production, generation, modification, maintenance, and measurement of multiple bioreactors.

Figure 13:
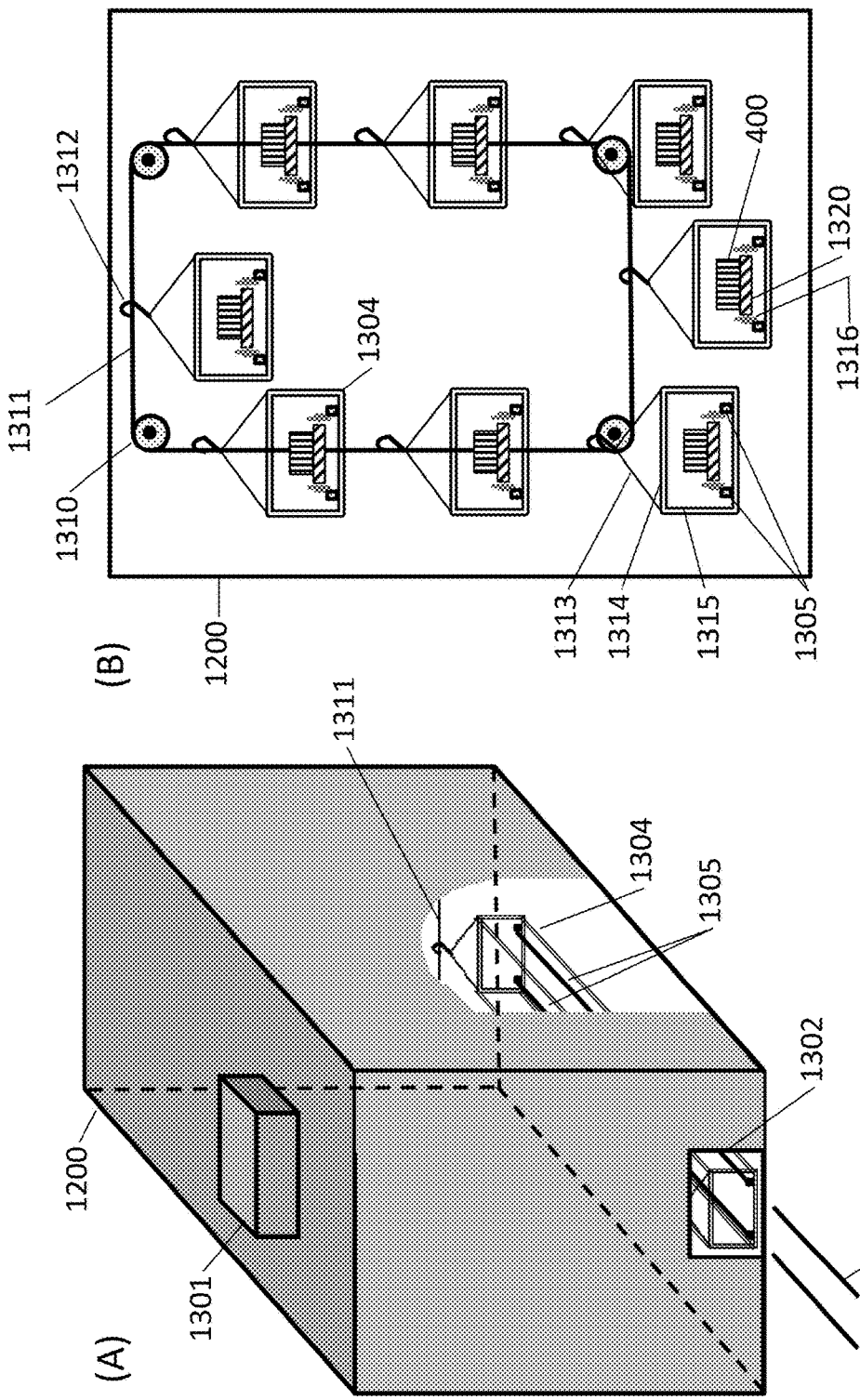
FIG. 13 shows an IOM array vertical storage incubator according to one embodiment of the invention, where an IOM array is placed into the incubator and moved to a storage location when not in use: (A) a perspective view, and (B) a section view.

According to the invention, the coupled Organ Arrays can be stored in an "incubator tunnel" or vertical stacking incubator, as shown in FIG. 13. In this embodiment, the incubator 1200 of FIG. 12 comprises a system wherein pulleys 1310, cables 1311, and attachment points 1312 enable the vertical storage of sections of guideway 1305 in guideway carriers 1304. The guideway carrier includes support devices 1313, 1314, and 1315 for the guideway 1305. Wheels 1316 on module carriers 1320 support IOM modules 400. An opening in the incubator 1302 allows the array of modules to be driven into the module carrier, whose track 1305 is separated from the main track 1303 connecting the incubator to the larger system. The incubator has a temperature regulation means 1301.

Further, in one aspect of the invention, a method for cultivation, maintenance, and/or analysis of one or more bio-objects includes providing a platform having one or more integrated bio-object microfluidics modules fluidically interconnected to each other. Each integrated bio-object microfluidics module includes one or more on-chip pumps; a plurality of fluidic switches; and a microfluidic chip in fluid communication with the one or more on-chip pumps and the plurality of fluidic switches, comprising at least one chamber for accommodating the bio-object and a plurality of fluidic paths connecting the chamber, the one or more on-chip pumps, and the plurality of fluidic switches.

The method further includes selectively and individually controlling the one or more on-chip pumps and the plurality of fluidic switches of each integrated bio-object microfluidics module to perform bio-object microfluidics functions for cultivation, maintenance, and/or analysis of the respective bio-object, wherein the bio-object microfluidics functions include perfusion of the respective bio-object, analysis of metabolic activities of the respective bio-object, formulation of custom media to support the respective bio-object and guide stem cell differentiation, or the like.

In one embodiment, the method also includes selectively removing one integrated bio-object microfluidics module from the platform.

In another embodiment, the method also includes replacing the removed integrated bio-object microfluidics module with a desired integrated bio-object microfluidics module.

In yet another embodiment, the method also includes transporting the platform from one location to another location. The use of a guideway and interconnected modules that can move along the guideway enables the assembly, manipulation, storage, and analysis of multiple interconnected biological modules in a manner that is not possible with existing fluid-handling workstations such as those shown in FIG. 2.

In another aspect, the invention discloses a system for cultivation, maintenance, and/or analysis of one or more bio-objects. The system includes at least one bio-object platform comprising one or more integrated bio-object microfluidics modules. As disclosed above, each integrated bio-object microfluidics module configured to cultivate, maintain, analyze and/or mimic functionalities of a bio-object includes one or more on-chip pumps; a plurality of fluidic switches; a microfluidic chip in fluid communication with the one or more on-chip pumps and the plurality of fluidic switches, comprising at least one chamber for accommodating the bio-object and a plurality of fluidic paths connecting the chamber, the one or more on-chip pumps and the plurality of fluidic switches; and a power and control unit programmed to selectively and individually control the one or more on-chip pumps and the plurality of fluidic switches for performing bio-object microfluidics functions. In addition, each integrated bio-object microfluidics module may include one imaging unit for operable evaluation of a respective bio-object, at least one bubble trap coupled to at least one of the plurality of fluidic paths for removing bubbles therefrom, and a reservoir having one or more ports for providing a plurality of solutions. In one embodiment, the one or more on-chip pumps include an RPPM. Each of the plurality of fluidic switches includes an RPV. The RPPM and each RPV are driven by a respective motor that is controlled by the microcontroller. In one embodiment, each RPV includes an NC valve.

The integrated bio-object microfluidics modules are spatially arranged in an array and connected to each other in series, in parallel, or in a combination thereof through fluidic interconnects and nodes. The array of the integrated bio-object microfluidics modules can be a 1D linear array, a 2D array, or a 3D array. Further, the array is storable in an incubator tunnel or a vertical stacking incubator. Also, the array is movable as a unit. The array can be closed upon itself in the form of a circular ring or a flexible ring of variable shape. As required the rings could be opened or closed to insert or remove modules or to transport the modules in the ring to another location. All of this can be accomplished without having to support the weight of the modules, as would be the case with a conventional articulated-arm robot manipulator. Instead, the guideway provides the support of the weight of the individual modules and arrays of modules. The guideway switches and other mechanisms that can be used to configure or reconfigure the pathway provided by the guideway can do so in a manner that does not require large mechanical forces or supporting the weight of a large number of modules. Furthermore, the guideways can be configured in such a way that they are not restricted to lie on a single plane and can in fact with appropriate control of the slope of the guideway be used to have modules on one guideway passing either above or below modules on another guideway. Guideway systems can be stacked vertically for more efficient utilization of laboratory space.

The system also includes a transporting means on which the at least one bio-object platform is movably disposed, for selectively moving at least one bio-object platform to desired locations; and at least one station having a base, and one or more subsystems fixed on the base at predetermined positions, wherein the at least one station is placed in relation to the transporting means such that when the at least one bio-object platform is moved at the predetermined positions, the one or more subsystems perform desired operations on the one or more integrated bio-object microfluidics. The desired operations on the one or more integrated bio-object microfluidics include, but are not limited to, performing at least one of analytical functions, mechanical functions, maintenance functions, fluid handling, microscopy, removal of one integrated bio-object microfluidics module, replacement of one integrated bio-object microfluidics module with another on the array of the integrated bio-object microfluidics modules, and the like.

The system further includes at least one incubator placed in relation to the transporting means for accommodating the at least one bio-object platform. The at least one incubator includes a temperature regulation means.

The integrated bio-object microfluidics modules of each bio-object platform define a network of wired or wireless communications, such that each integrated bio-object microfluidics module in the bio-object platform is capable of electronic communication with one another in the network and/or with a server that is in electronic communication with the network.

The integrated bio-object microfluidics modules include one or more of an integrated brain module, an integrated lung module, an integrated heart module, an integrated liver module, an integrated stomach module, an integrated kidney module, an integrated gut module, an integrated testis module, an integrated skin module, and the like.

The integrated bio-object microfluidics modules further include one or more of an integrated perfusion controller module for perfusing the bio-object maintained on the microfluidics chip, an integrated microclinical analyzer module for analyzing activities of the bio-object maintained on the microfluidics chip, and an integrated MicroFormulator module for providing desired substances to cultivate, maintain, and/or analyze the bio-object maintained on the microfluidics chip.

Figure 14:
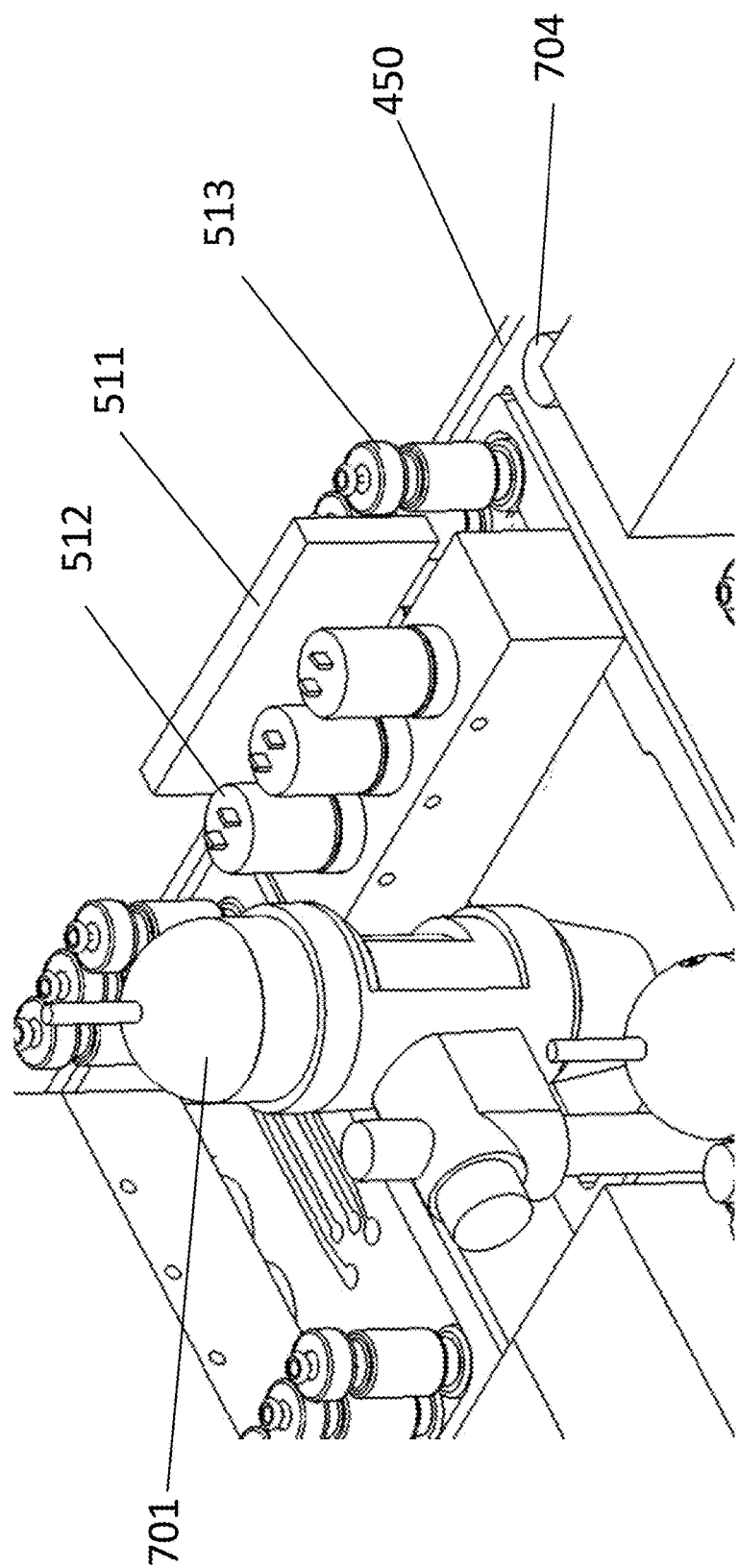
FIG. 14 shows a generic Integrated Organ Microfluidics module according to one embodiment of the invention, with the ability to maintain an Organ Chip both within the Organ Interconnect Platform and during stand-alone operation. The stand-alone operation is useful for cases when it is appropriate to initially seed an individual Organ Module or visualize the organ construct on an external microscope or other analytical instrument. Electrical connections between the motors and the microcontroller are not shown.
Figure 15:
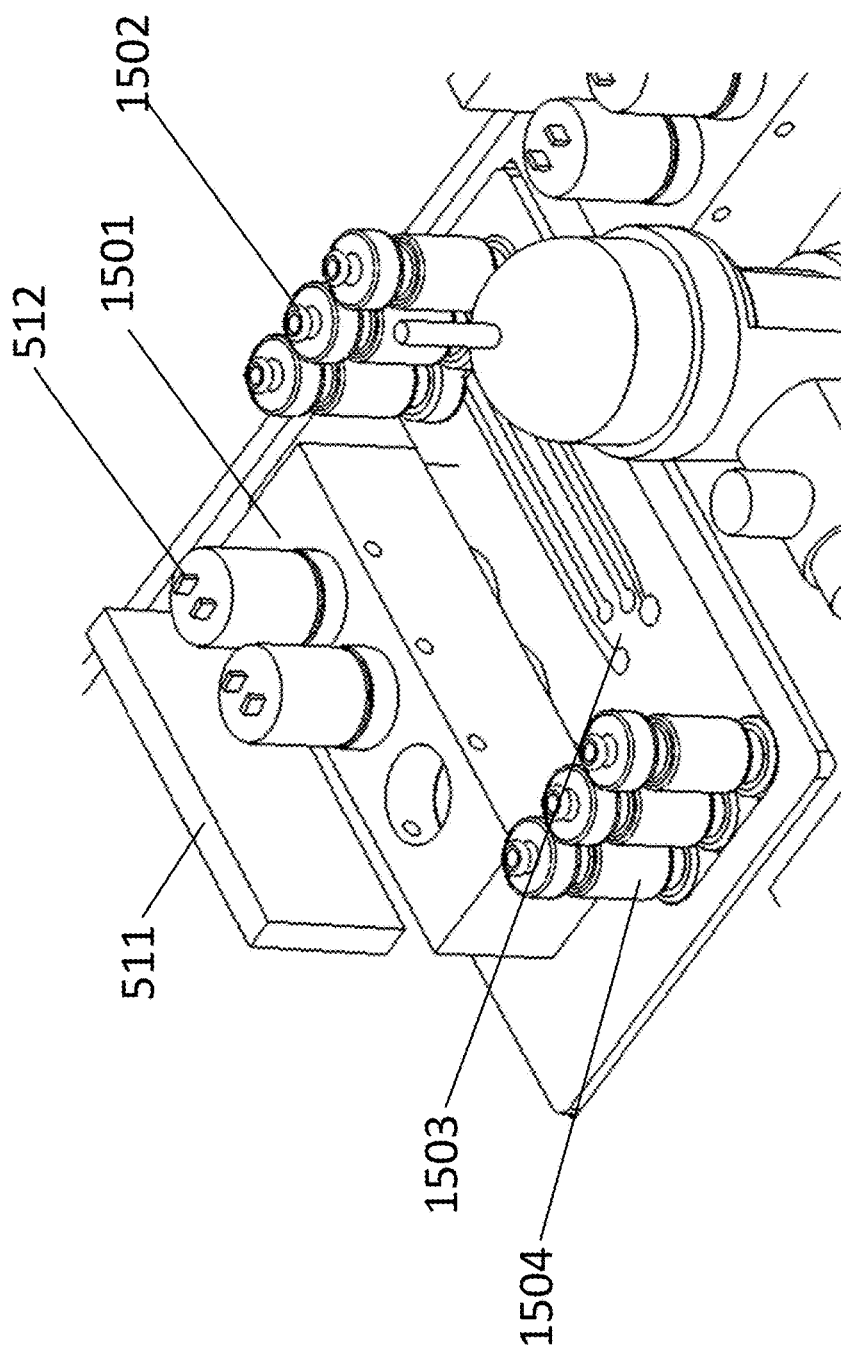
FIG. 15 shows the MicroClinical Analyzer according to one embodiment of the invention. A MicroClinical Analyzer module can provide electrochemical or other means to measure key metabolic parameters on an organ-by-organ basis.
Figure 16:
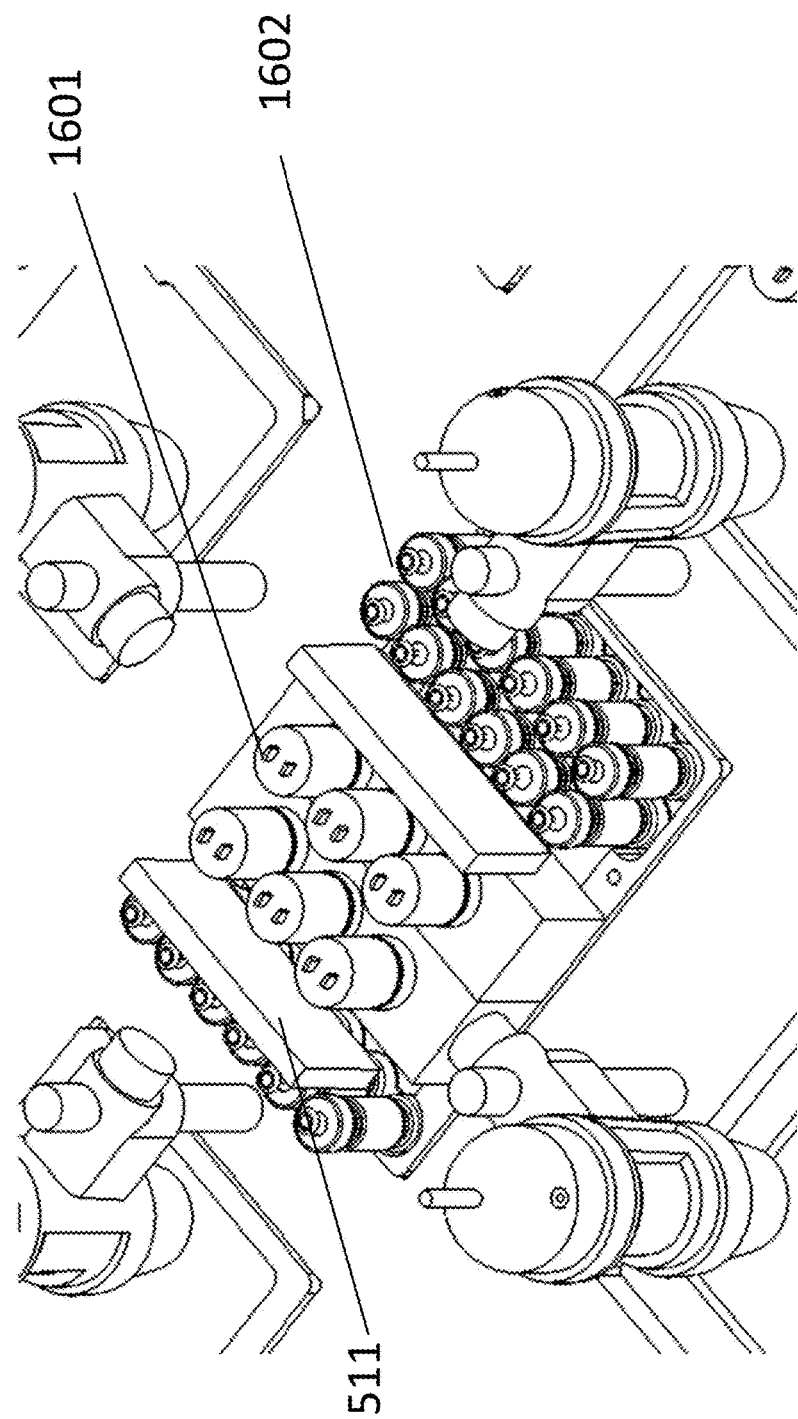
FIG. 16 shows a centralized MicroFormulator for aid in maintaining homeostasis and viable cell cultures on the Organ Interconnect Platform according to one embodiment of the invention. A key feature of the Organ Interconnect Platform is the inclusion of a MicroFormulator module that can be programmed to provide precise mixtures of the biochemical components necessary to keep individual organ cultures in a physiological state similar to that of organs in a living animal or human. The MicroFormulator can be used to provide hormonal or other biologically relevant chemicals to the various organs in situations when some of the organs are "missing" or not represented on the Organ Interconnect Platform, e.g., an Organ Interconnect Platform populated with only heart and liver Organ Modules.
Figure 17:
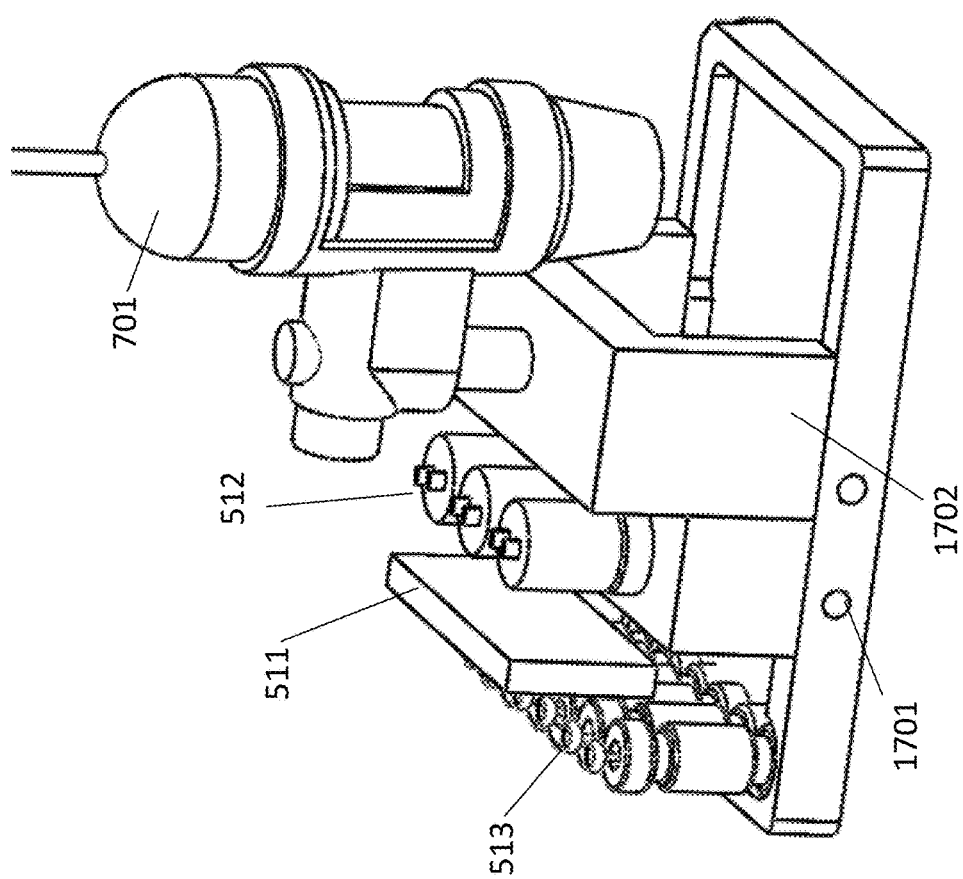
FIG. 17 shows an individual Integrated Organ Microfluidics module with the on-module imaging module and fluidic interconnection ports according to one embodiment of the invention. The fluidic interconnection ports can be septum-based to facilitate simple sterile interfaces to fluidic routing channels contained within the Organ Interconnect Platform. When the Integrated Organ Microfluidics module is removed from the Organ Interconnect Platform, the septum, valve, switch, or other sealing mechanism prevents fluid leakage or the entry of air into the system.
Figure 18:
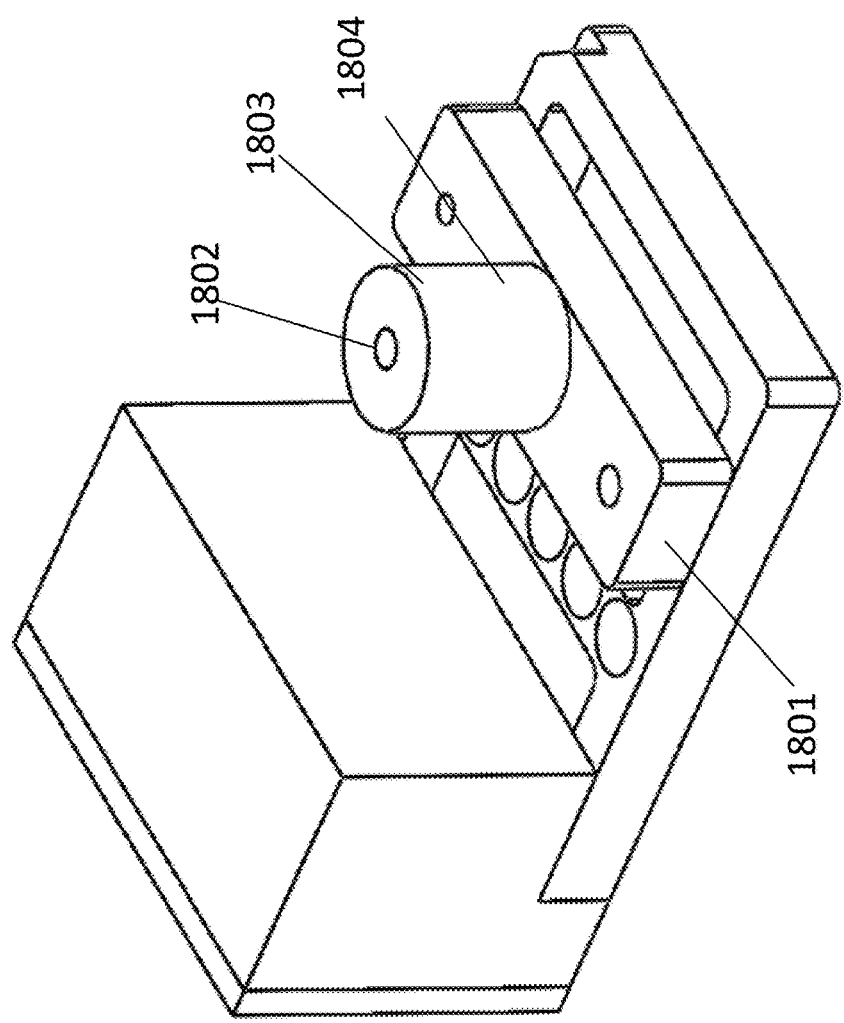
FIG. 18 shows an Organ Module according to one embodiment of the invention, where the IOM has an on-board microscope condenser for providing illumination through the Organ Chip for analysis by a microscope objective and imaging device placed beneath the Organ Module, possibly within the guideway.

Three IOM modules are also described herein as examples of modular systems that enable studies of organs-on-chips (OoC) and engineered tissue: the Perfusion Controller (PC), the MicroClinical Analyzer (μCA) that can analyze the metabolic or other activity of the organ on a chip, and the MicroFormulator (μF), which can produce upon command small volumes of custom-mixed solutions of nutrients, drugs, toxins and other substances needed to maintain or test the organ, as shown in FIGS. 14-16. Each of these modules can be used to support and analyze an individual organ construct. Typically, a single organ on a chip will be maintained in a self-contained Integrated Organ Microfluidics (IOM) module, described previously, that implements the functions of the PC, and possibly the μCA and even the μF. An embodiment of each of these modules is required to maintain and perfuse any human- or organ-on-a-chip system. One feature of this configuration is the ability to analyze the Organ Chips with a microscope, either with a self-contained imaging unit, or a combinational condenser/microscope unit, as shown in FIGS. 17-18. As shown in FIG. 17, an imaging module is positioned above the Organ Chip. As shown in FIG. 18, the imaging module is placed beneath the chip (not shown), with a condenser unit that contains a light source, a phase contrast filter, and a focusing lens above. Kinematic alignment pins allow the rapid and accurate positioning of the condenser unit onto the module when imaging is required.

Overview of Modules

In the most basic realization, perfusion controllers are required to provide fluid flow to an Organ Chip. PCs can allow continuous, intermittent, variable, or constant flow to an Organ Chip for perfusion, delivery of nutrients, and removal of waste products. They can provide cells with the shear forces required to maintain, for example, the physiologically realistic polarization of endothelial cells growing on the inner surfaces of a microchannel that represents the vascular compartment of tissue, or the polarization of epithelial cells growing in channels representative of the kidney tubule system. Such flow is difficult to achieve reliably and constantly with gravity flow as is typically utilized in microfluidic devices, but instead is achieved today primarily with peristaltic pumps or periodic compression pumps with check valves that are large, expensive, and require large fluid volumes. The Perfusion Controller addresses many of these limitations by providing a small, low-cost, and compact means to maintain cells in a tissue-like environment in vitro.

Depending on the type of Organ Chip, a variety of supporting structures is required. In the embodiment shown in FIG. 14, each organ module contains 3 motors and the required microfluidics 512, has a microcontroller and wireless connectivity 511, internal interconnects with septa for off-cartridge fluid transfer, autonomous control of fluid within organs, charging interconnects or wireless power transfer incorporated on the platform 450 that supports one or more modules, on-board fluid storage 513, and a battery to power the module when it is detached from the platform for out-of-incubator operation. The electrical wiring connecting the motors to their microcontroller is not shown, FIG. 15 shows a MicroClinical Analyzer that has the function of determining the instantaneous metabolic state of cells by monitoring the consumption of glucose and oxygen, the consumption or release of lactate, and the acidification of the media. The system could also detect other chemical species in the media, for example but not limited to neurotransmitters. This real-time analysis capability is not present in the devices shown in FIG. 1, and is necessary to monitor and adjust the microenvironment of cells growing in the bio-objects or organs in other modules. The capability to do this is important given the fact that the cells are being grown to tissue-like densities and the normal microvascular control of physiological activity is not provided by the devices in FIG. 1. Much of the motivation for the development of organs on chips is to identify the actions of drugs and toxins on cell viability and ascertain the mechanism of action of said drugs and agents. The feasibility of using such sensors for this purpose has been demonstrated by S. E. Eklund, R. G. Thompson, R. M. Snider, C. K. Carney, D. W. Wright, J. Wikswo, and D. E. Cliffel, Metabolic discrimination of select list agents by monitoring cellular responses in a multianalyte microphysiometer. Sensors 9 (3):2117-2133, 2009, and is described in "Device and Methods for Monitoring the Status of at Least One Cell," J. P. Wikswo, F. J. Baudenbacher, and O. McGuinness, U.S. Pat. No. 7,435,578 B2 (Oct. 14, 2008) and U.S. Pat. No. 7,981,649 B2 (Jul. 19, 2011); "Apparatus and Methods for Monitoring the Status of a Metabolically Active Cell," F. Baudenbacher, J. P. Wikswo, R. R. Balcarcel, D. Cliffel, S. Eklund, J. M. Gilligan, O. McGuinness, T. Monroe, A. Prokop, M. A. Stremler, A. A. Werdich, U.S. Pat. No. 7,704,745 B2 (Apr. 27, 2010); and "Device and Methods for Detecting the Response of a Plurality of Cells to at Least One Analyte of Interest," D. Cliffel, R. R. Balcarcel, J. M. Gilligan, S. Eklund, J. P. Wikswo, F. J. Baudenbacher, U.S. Pat. No. 7,713,733 B2 (May 11, 2010).

In this exemplary embodiment of a MicroClinical Analyzer, a microcontroller with a battery backup 511 is integrated into the device. The motors and microfluidics 512 contain a single pump and valve 1501 for selecting the appropriate calibration solution 1502 to deliver to the sensing electrodes 515. Waste storage is provided on ports 1504 of the device. Sensing electrodes can be configured to measure the electrical conductivity of the medium and thereby infer the amount of water lost through evaporation through the walls of the channels and chambers of the device. One of the vials 1502 can contain cell-culture grade water to replace any water lost from the system, delivered under the control of the pump and valve 1501 or another means.

FIG. 16 shows a MicroFormulator. In conventional well-plate culture as shown in FIG. 1 and in particular with the automated capabilities shown in FIG. 2, fluid is added or removed from wells by manual or automated pipetting. It is difficult to pipette volumes smaller than one microliter, and hence it is not readily possible to make rapid and accurate changes in the concentration of multiple components of the media that contains the cells, particularly when there is a large range in the concentrations of the various components being adjusted. This problem is exacerbated with the growth of engineered tissue constructs and/or organs-on-chips, in that the perfusion volumes must be kept small to minimize the dilution of the paracrine, autocrine, and other signaling factors and metabolites that are secreted by cells and to allow the measurement of those media components consumed by the cells. Furthermore, real-time challenge-response experiments require the transient delivery of a drug, toxin, growth factor or other chemical species, and this is difficult to achieve simultaneously for multiple bio-objects using the pipetting and well-plate manipulation architecture of FIG. 2.

We have devised a MicroFormulator module that is small enough and manufacturable at a low enough cost to be fully compatible with the modular approach described in FIGS. 4 through 13. In the exemplary embodiment shown in FIG. 16, the MicroFormulator contains an on-board microcontroller with battery backup 511, an array of integrated pumps and valves 1601, and vials for storage 1602 of reagents as well as analytes from each organ. The electrical connections between the microcontroller and the motors are not shown for clarity.

Figure 2:
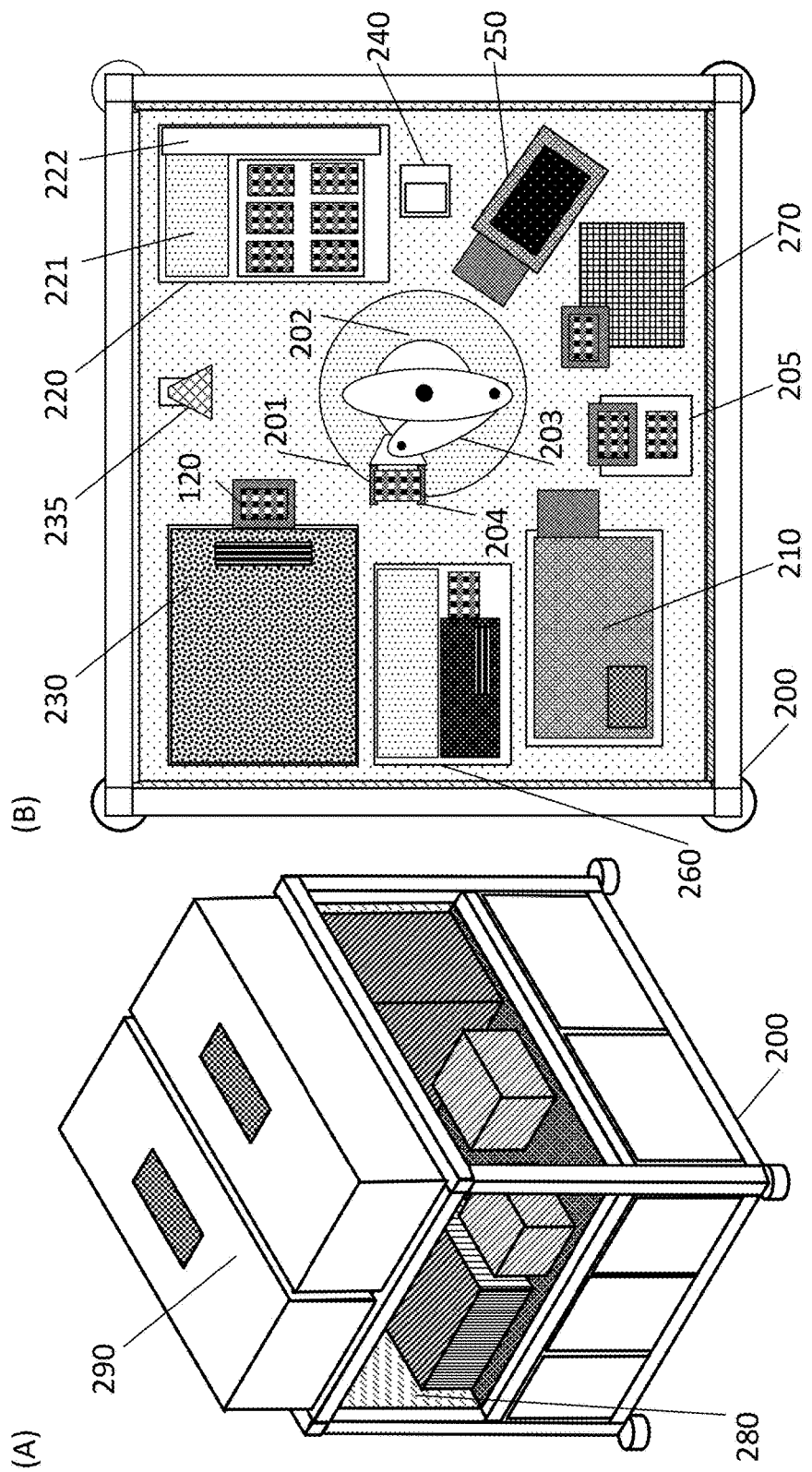
FIG. 2 shows a schematic representation of an automated robot well-plate handling system capable of automatic transfer, manipulation, and measurements of well plates between different stations: (A) a perspective view, and (B) a sectional view. Fluid delivery is accomplished by using automated micropipettes to transfer fluids between multiple well plates in a fluid-handling unit designed specifically for that purpose.
Figure 3:
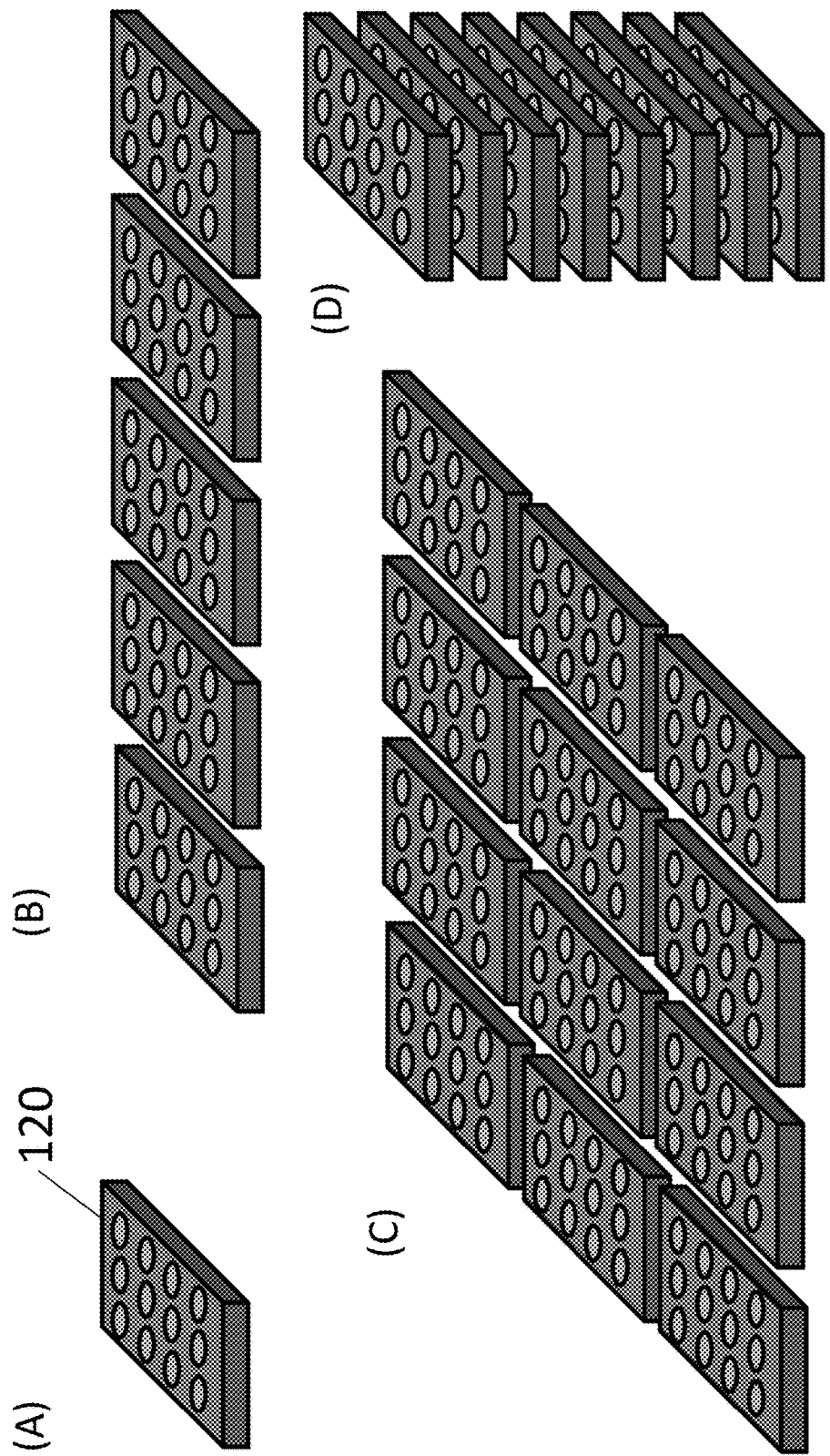
FIG. 3 shows various configurations (A)-(D) of well plates, either stand-alone (A), a linear array (B), a rectangular array (C), or a vertical stack (D), or combinations thereof. Note that none of the well plates is interconnected.

In the architecture of FIG. 2, the imaging of cells grown in well plates is performed using a separate plate reader 230. While the Hamilton MICROLAB® STAR Liquid Handling Workstation can incorporate an X-Y translatable well imager in its carriers, it does not provide for the dedicated imaging of an individual organ-on-chip or other bio-object being grown in a well-plate-sized module. In certain embodiments, each perfusion controller as exemplified in FIG. 17 can contain an integrated imaging unit 701 mounted directly to the module 1702. The module can also contain internal valved or switched interconnects or septa 1701 for interfacing with an organ interconnect platform. In other embodiments, using the configuration shown in FIG. 12, an organ module array can be configured to drive through any number of analytical or imaging modules, which can perform a variety of functions. As shown in FIG. 18, transmission or phase-contrast illumination would require a condenser module inserted above the Organ Chip 1801 to provide illumination to the microscope located between different locations on the guideway. An illumination source 1802 would shine light through a condenser 1803 and through a focusing lens 1804 onto the biological sample. It would also be possible to attach the imaging unit above the module and have the condenser if required beneath it. These units could either be permanently attached to each module, attached when required, or moved into the correct position by an imaging system 1122 as indicated in FIG. 12.

Figure 19:
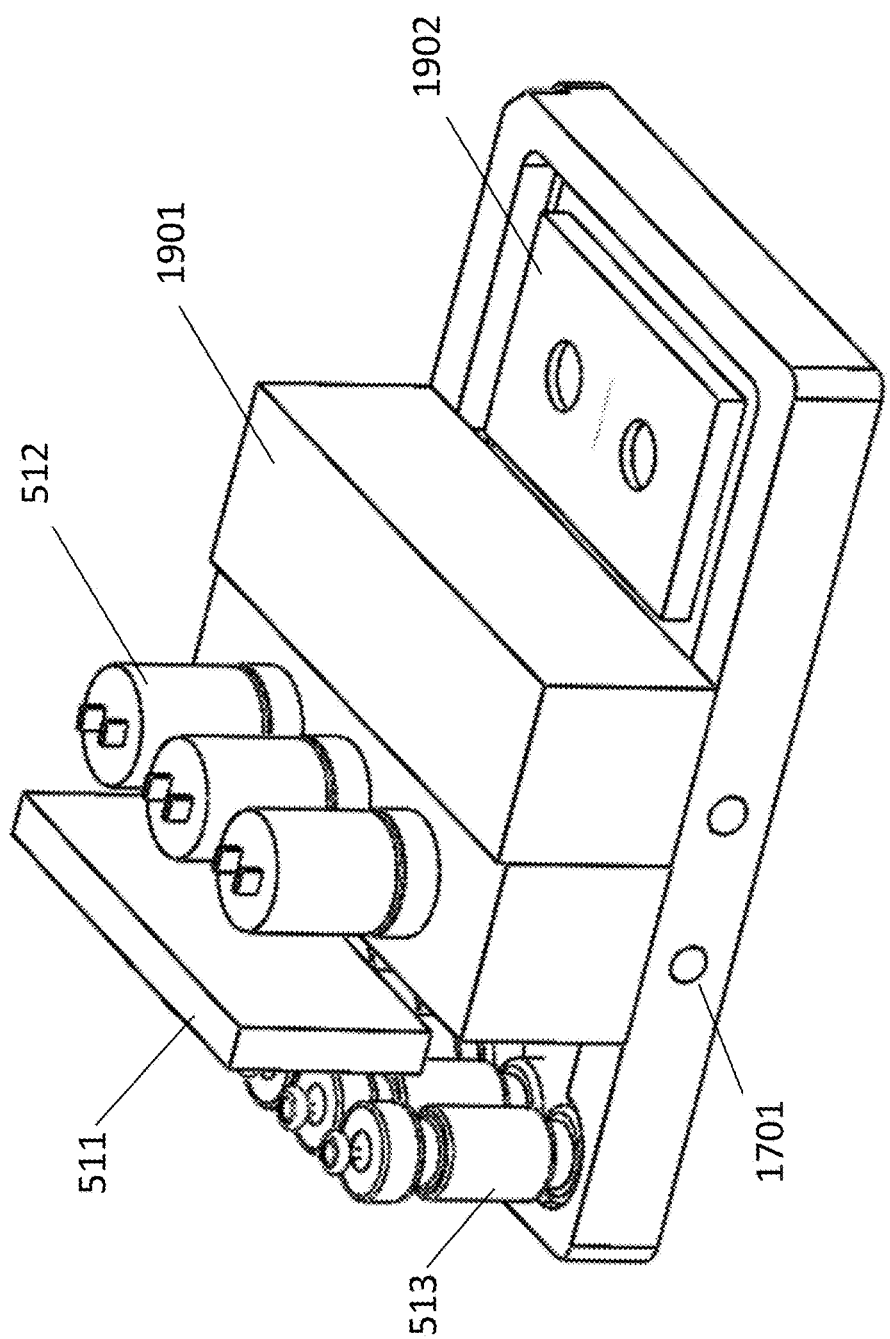
FIG. 19 illustrates a heart Organ Module with an electrophysiology module for delivering and/or examining electrical signals on the heart Organ Chip according to one embodiment of the invention. The electrophysiology module can be controlled and monitored by the on-module microcontroller, which also controls the various pumps and valves that provide fluid control. As with the other images, the electrical connections are not shown.

In certain embodiments, a heart Organ Chip as shown in FIG. 19 requires at a minimum pumps and valves 512 to perfuse the cardiac cells, provide fresh media with nutrients, and remove waste products. In certain embodiments, the PC for the heart IOM module can contain an electrophysiology module 1901, which provides a rudimentary electrocardiogram or other electrophysiological measurements of the electrical activity of the heart Organ Chip shown in FIG. 19. In this embodiment, a hemispherical extracellular matrix (ECM) scaffold supports contracting cardiomyocytes to provide the functions of the left and right heart, in which mechanical contraction of cells replicates cardiac function 1902.

Figure 20:
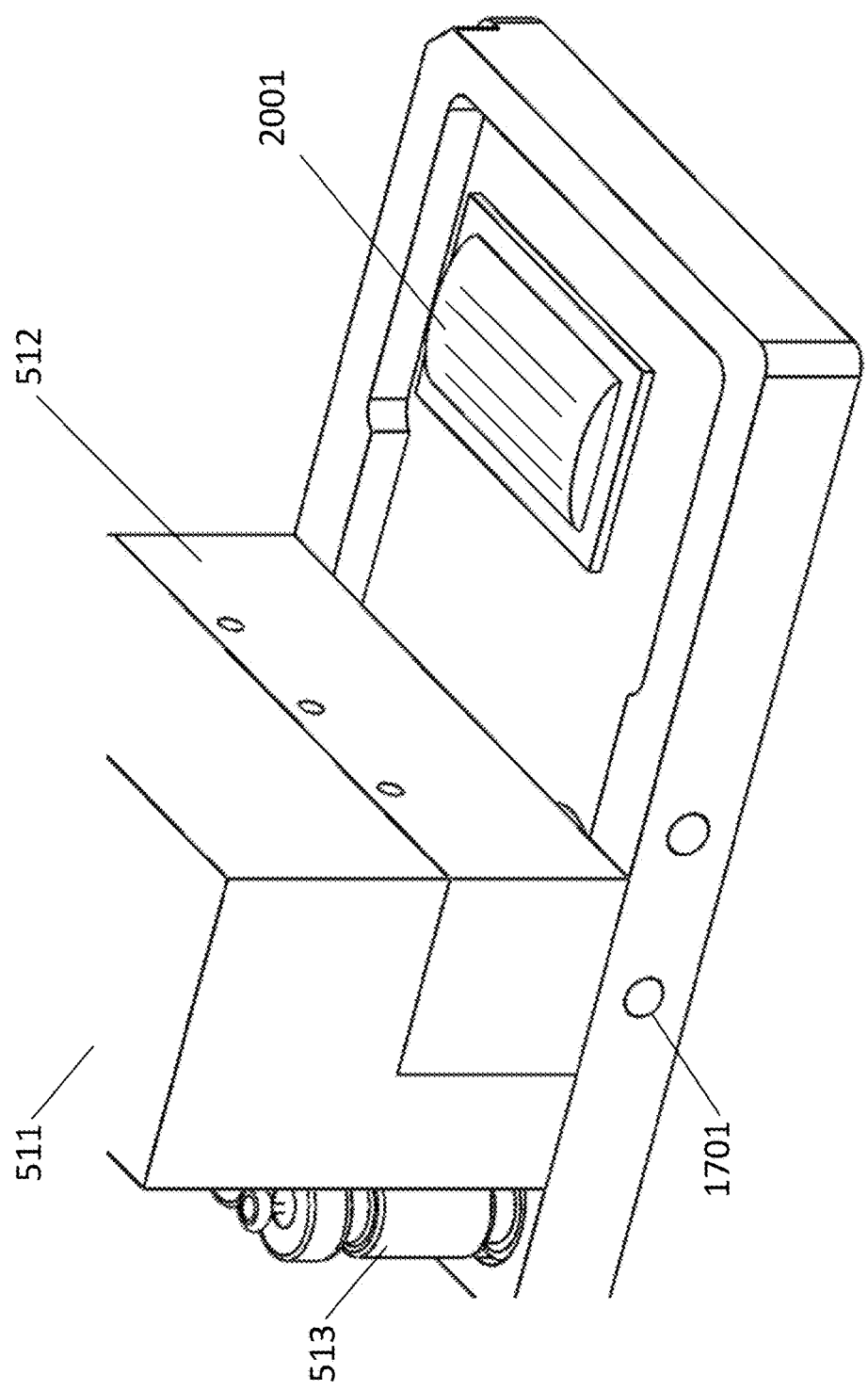
FIG. 20 shows a liver Organ Module according to one embodiment of the invention, which incorporates a hollow fiber chamber to support the perfusion of hepatocytes supported by the hollow fibers.
Figure 21:
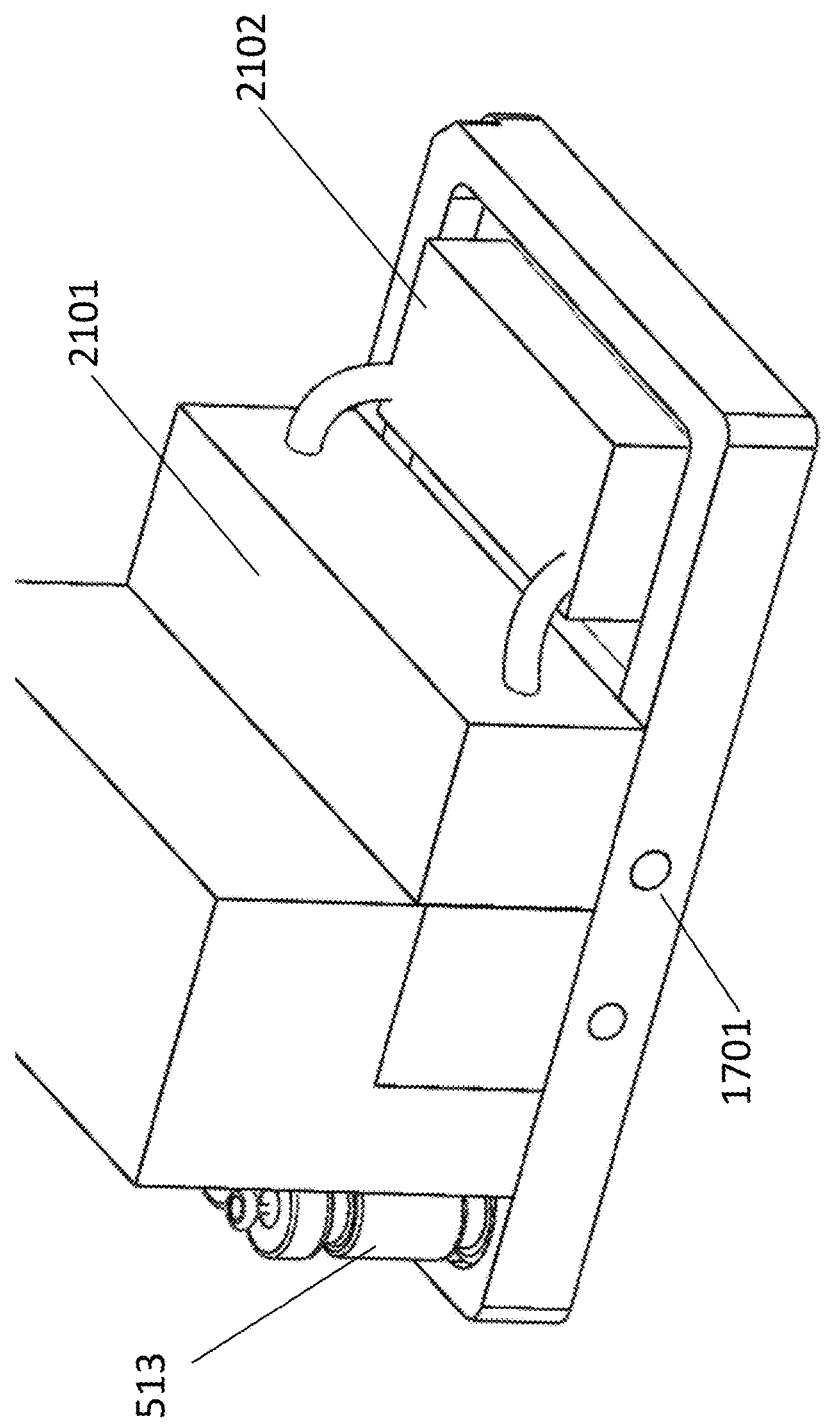
FIG. 21 shows a lung Organ Module with an on-module ventilator for providing air exchange with the lung Organ Chip according to one embodiment of the invention. The on-board microcontroller can provide signals to drive the ventilator functionality to deliver oxygen to the bio-object upon inspiration and remove carbon dioxide upon expiration.
Figure 22:
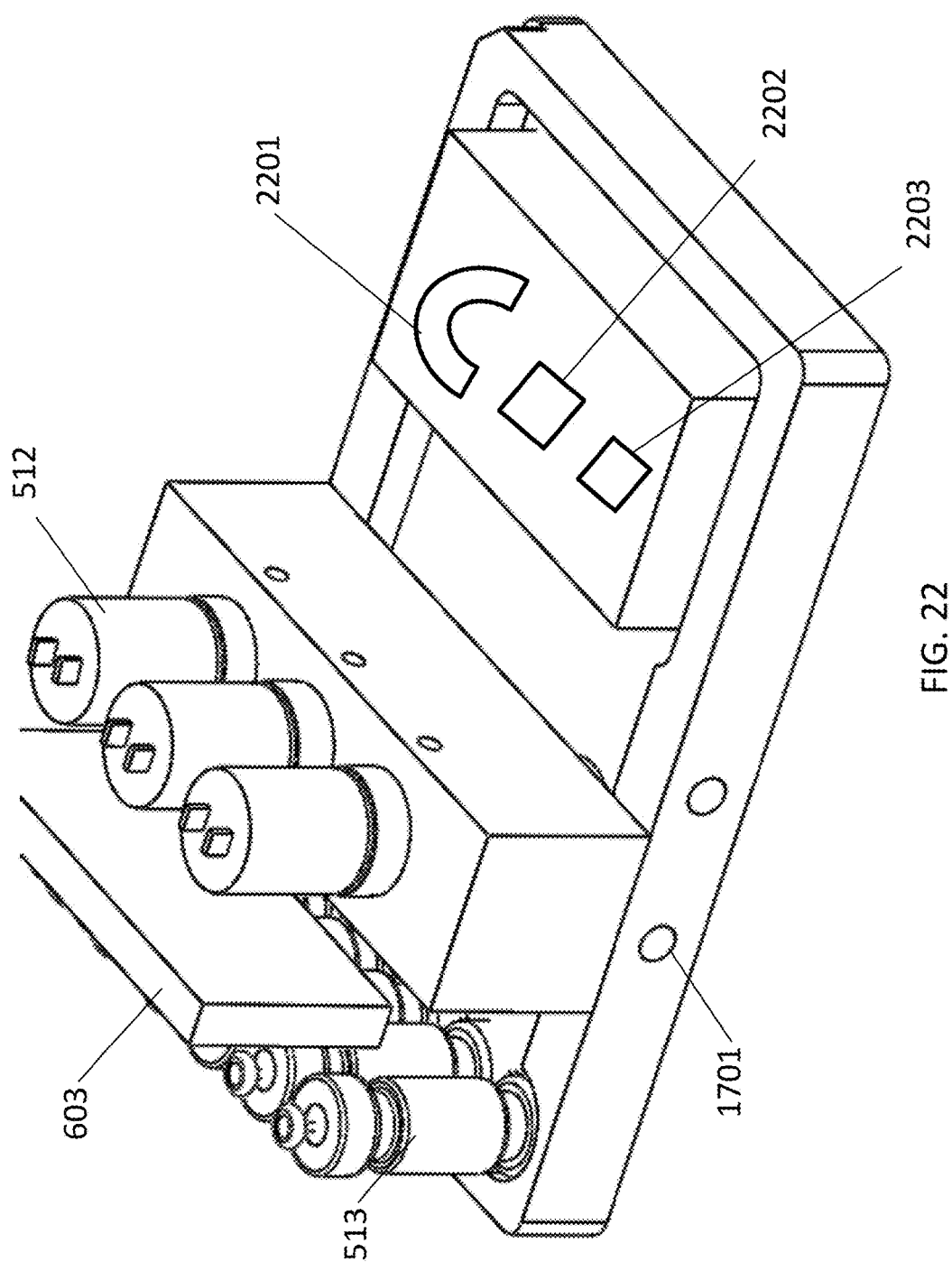
FIG. 22 shows a kidney Organ Module according to one embodiment of the invention.

FIG. 20 shows a configuration of a perfusion controller for perfusing a liver Organ Chip, wherein hepatocytes and other cells as required are perfused by an array of hollow fibers 2001. FIG. 21 illustrates a possible embodiment of a lung Organ Module with a ventilator 2101 to provide respiratory pressures to the lung for delivery of oxygen and removal of carbon dioxide, either continuously or in a tidal manner. The ventilator provides cycle breathing by means of gas chambers beneath the lung membrane 2102 that ensure the mechanical stretching of the lung membrane and also the transport of gas into and out of the lung chambers. Upper and lower chambers provide biphasic gas exchange without large fluctuations in the vascular volume associated with the lung module. A possible kidney configuration is shown in FIG. 22, wherein the kidney chip has sub-modules for the loop of Henle 2201, glomerular filtration 2202, and the proximal tubules 2203.

Other organs not contained herein may require different configurations of Organ Modules. One skilled in the art can adapt any Organ Module to perform required physiological functions for its Organ Chip. These include the seeding, growth, and maintenance of other tissue constructs, such as engineered tissue for repair or replacement of defective or missing tissue. A key feature of the modular design described herein is that a common design for the overall well-plate-sized module configuration and the use of standardized rotary pumps and valves, sensors, and their microcontrollers allow a module to be adapted with minimal effort to accommodate the needs of a particular Organ Chip without compromising the functionality of the entire system.

Figure 23:
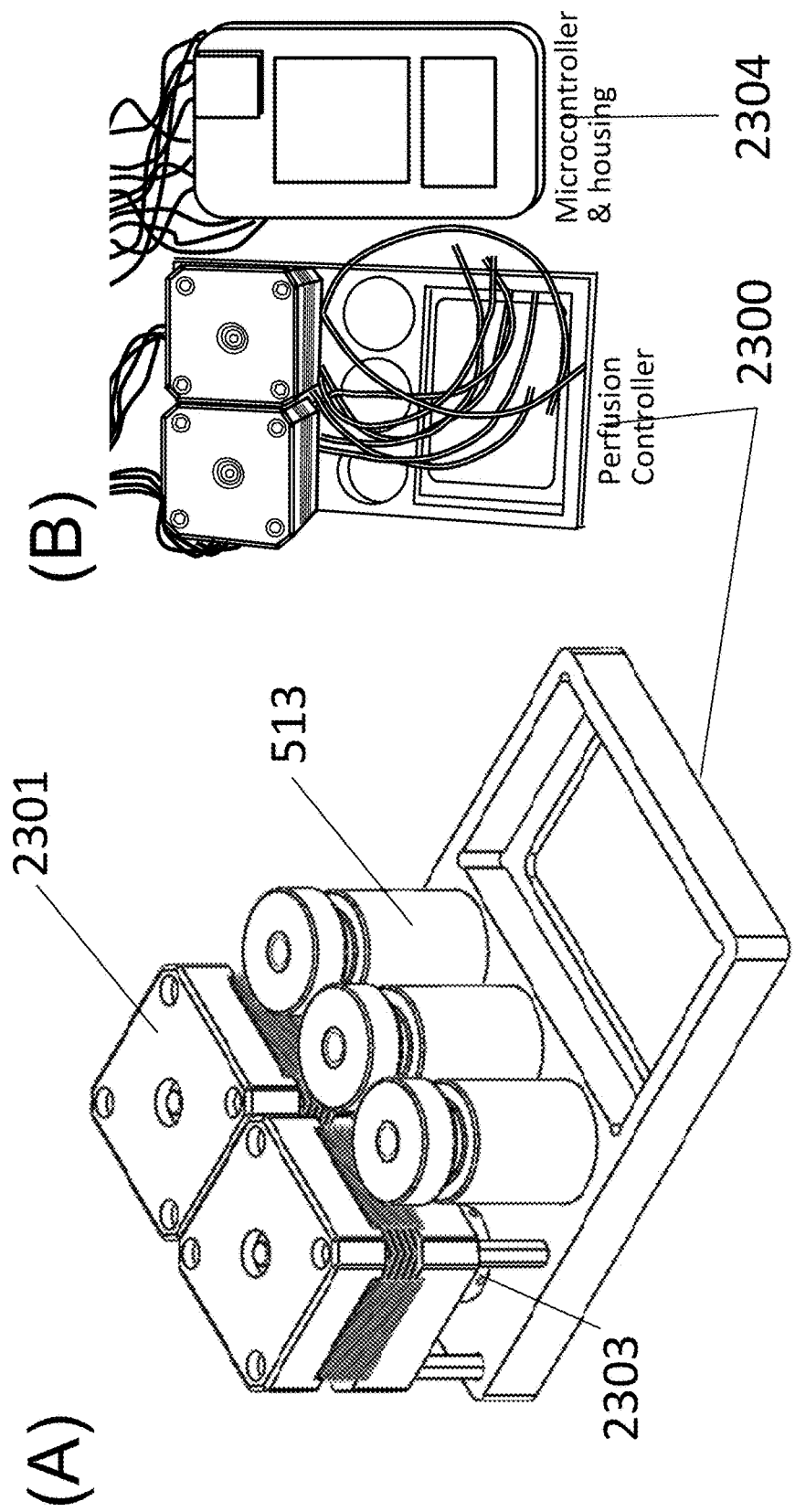
FIG. 23 shows roller-based pumps integrated into a well-plate format with on-board storage of media and the ability to perfuse any organ or tissue-engineering device located on a 50 mm×75 mm glass slide, according to one embodiment of the invention: (A) a perspective view, and (B) a prototype. The pumps are instructed by a microcontroller.
Figure 24:
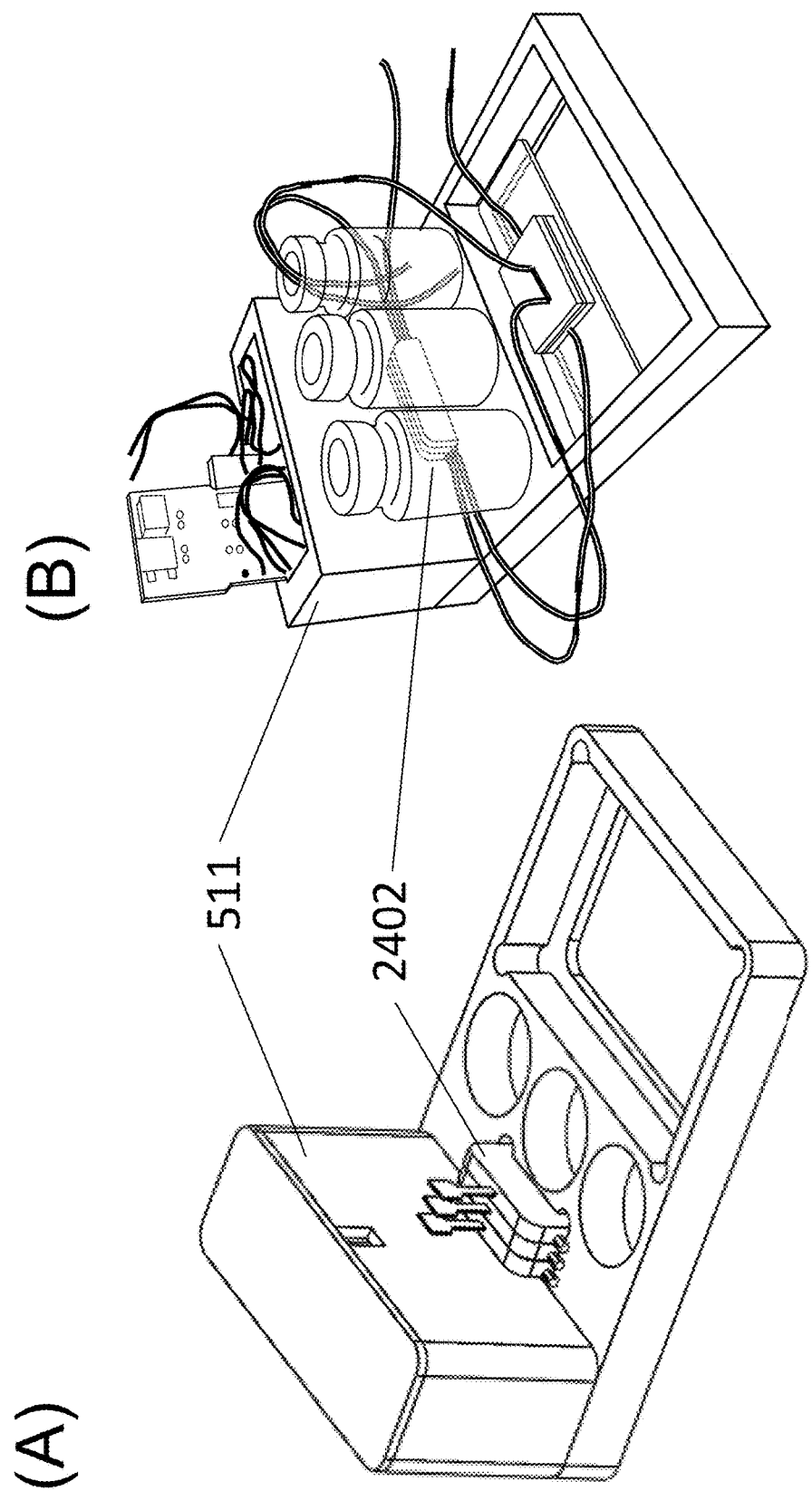
FIG. 24 shows an organ Perfusion Controller based on piezoelectric pumps, according to one embodiment of the invention: (A) a perspective view, and (B) a prototype. This device is controlled by a computer over ZigBee wireless and can provide flows up to 5 mL/min.

Described herein are various implementations of RPPMs to create high-flow perfusion controllers 2300 as required for certain Organ Chips, with such a device shown in FIG. 23. In its most simplified embodiment, a PC includes rotary pumps 2301 attached to a well-plate-sized platform capable of perfusing any Organ Chip or tissue construct, as shown in FIGS. 23-24. These pumps contain a driving mechanism 2303 for providing fluid flow to the Organ Chip and can contain on-board fluid storage 513. In the embodiment shown in FIG. 23B, the microcontroller 2304 is not mounted on the module 2300. In another embodiment shown in FIG. 24, flow can be provided from piezoelectric pumps 2402.

In certain embodiments, to reduce the height of the Perfusion Controller, the microcontroller can be relocated away from the well plate in such a manner that the overall size of the well plate is still in standard format as shown in FIG. 25, but the microcontroller is beneath the horizontal plane of the Organ Chip 2501. Fluid storage 2502 can be provided on this module. The use of smaller microcontrollers and motors will allow these devices to become more compact, either requiring a smaller fraction of module space, or allowing more functions to be incorporated into a module.

Figure 26B:
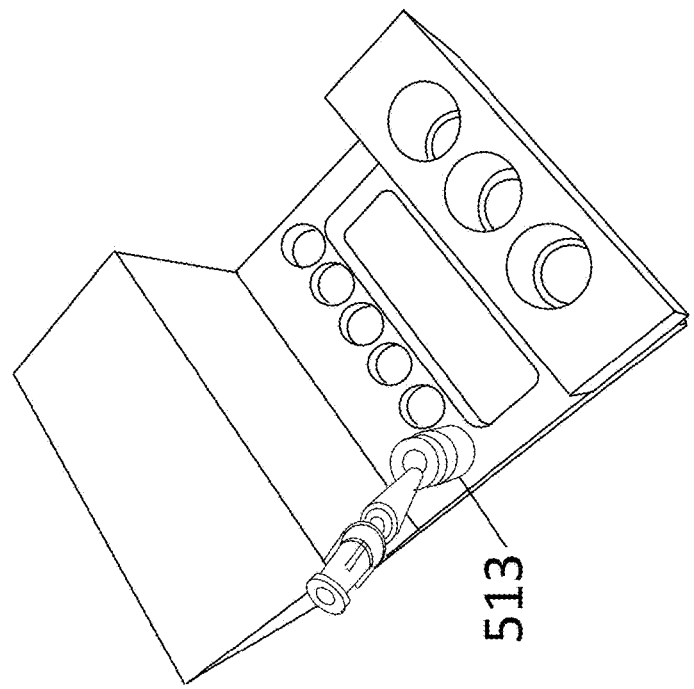
FIGS. 26A-26E show respectively different views of a double-sided Perfusion Controller capable of perfusing an Organ Chip with two cell culture chambers, according to one embodiment of the invention. This configuration allows each cell culture chamber to be perfused with its own culture medium and flow rate.
Figure 26A:
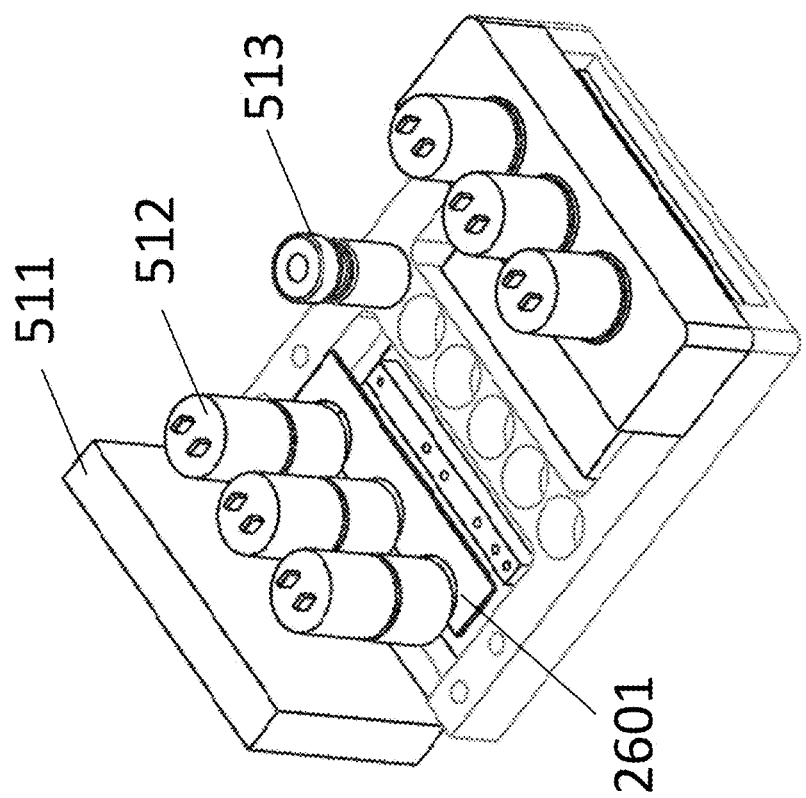
Figure 26C:
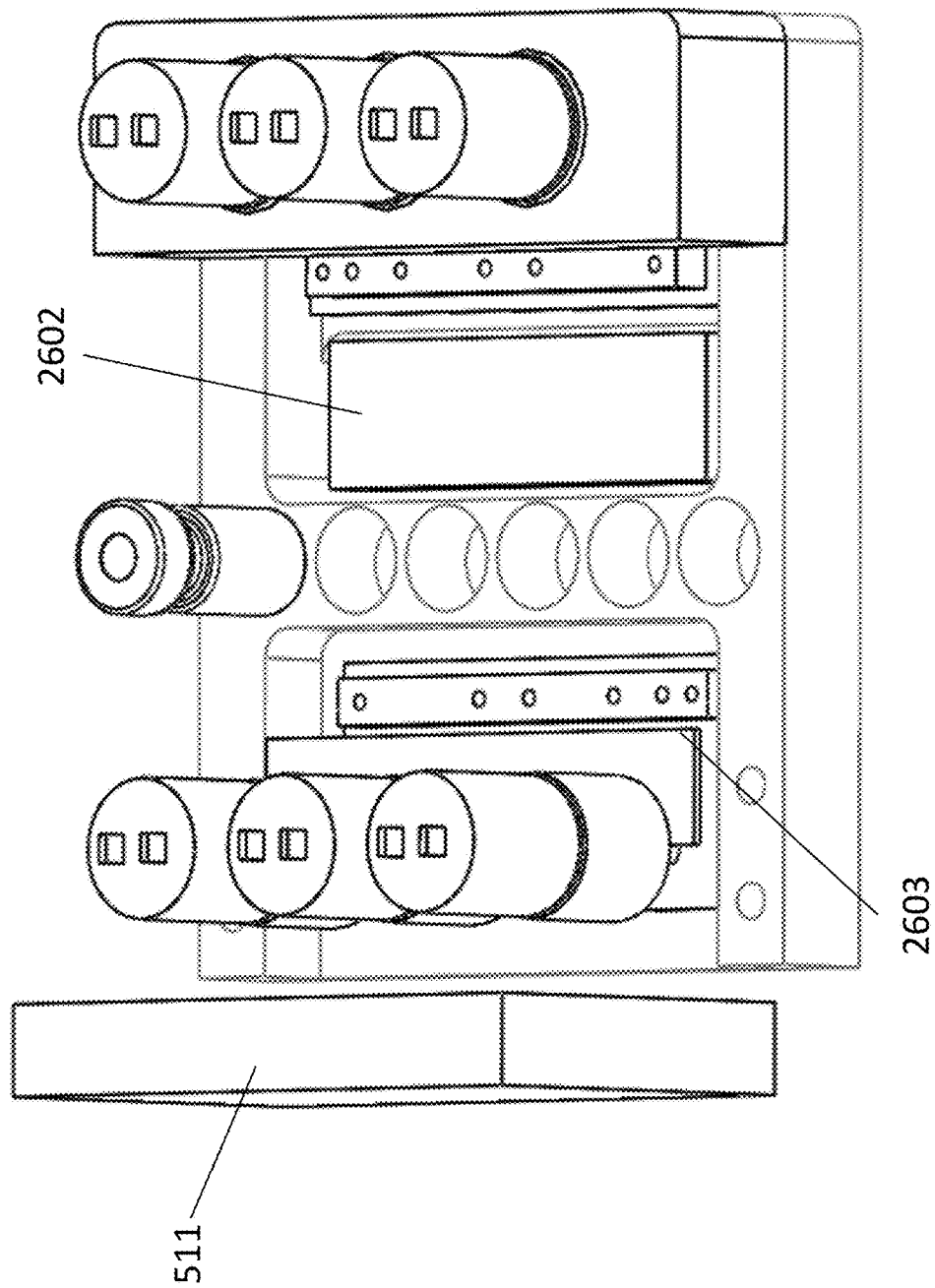
Figure 26D:
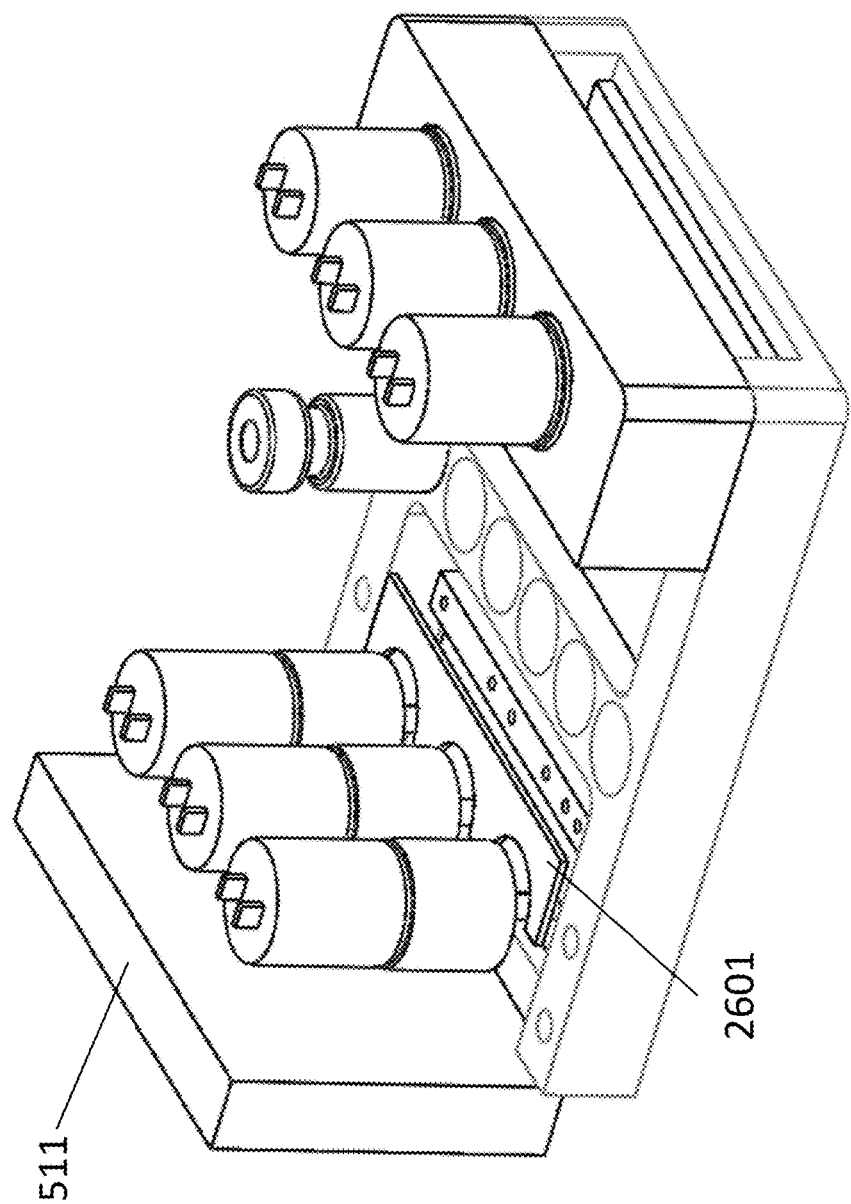
Figure 26E:
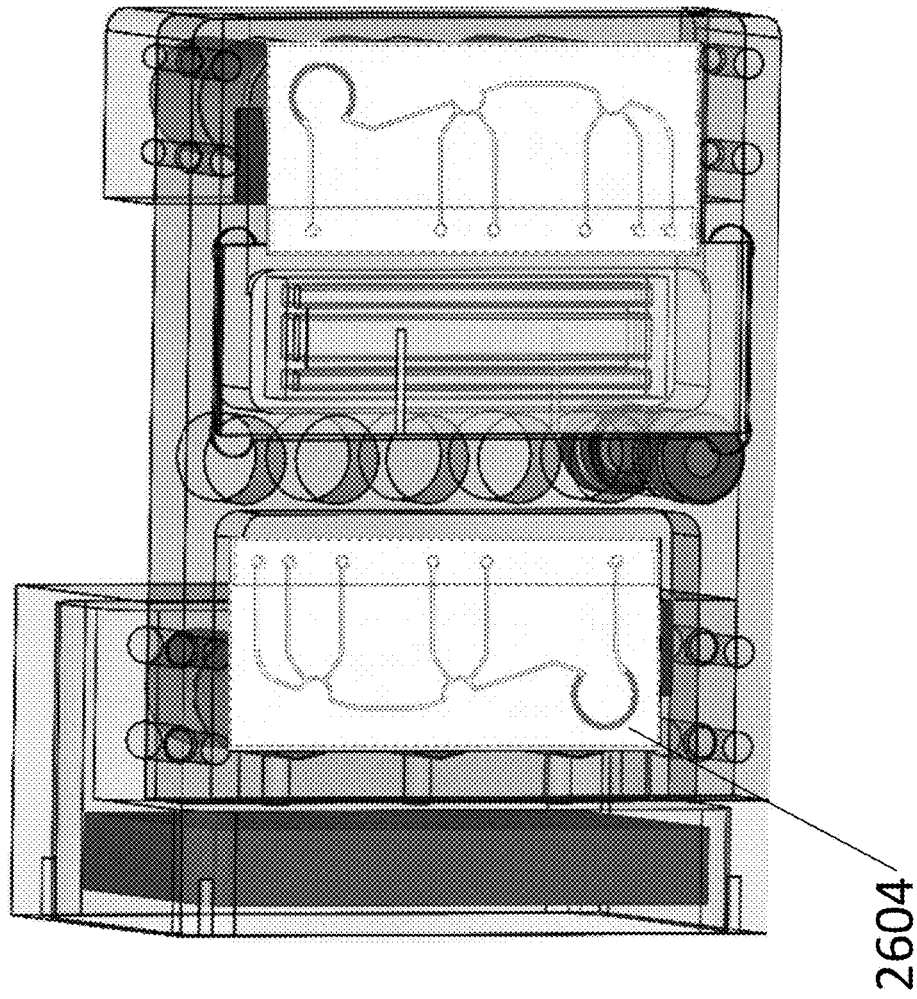

For organs with complex architectures including multiple cell chambers, multiple sets of pumps and valves may be required for perfusing each cell chamber. An example of this configuration is shown in FIG. 26, which is appropriate, for example, for a lung module that has an alveolar space containing pulmonary epithelial cells separated by an alveolar membrane from a vascular space with microvascular endothelial cells. A separate encoder board 2601 can provide information regarding the position of the valves and speed of the pump. This module can perfuse any Organ Chip located on a glass slide 2602. Perfusion as well as selectable fluid delivery can be delivered by the pumps and valves 2603. In one embodiment, integrated pumps and valves 2604 can provide fluid delivery. FIG. 26E shows a view of the underside of the device.

Figure 27:
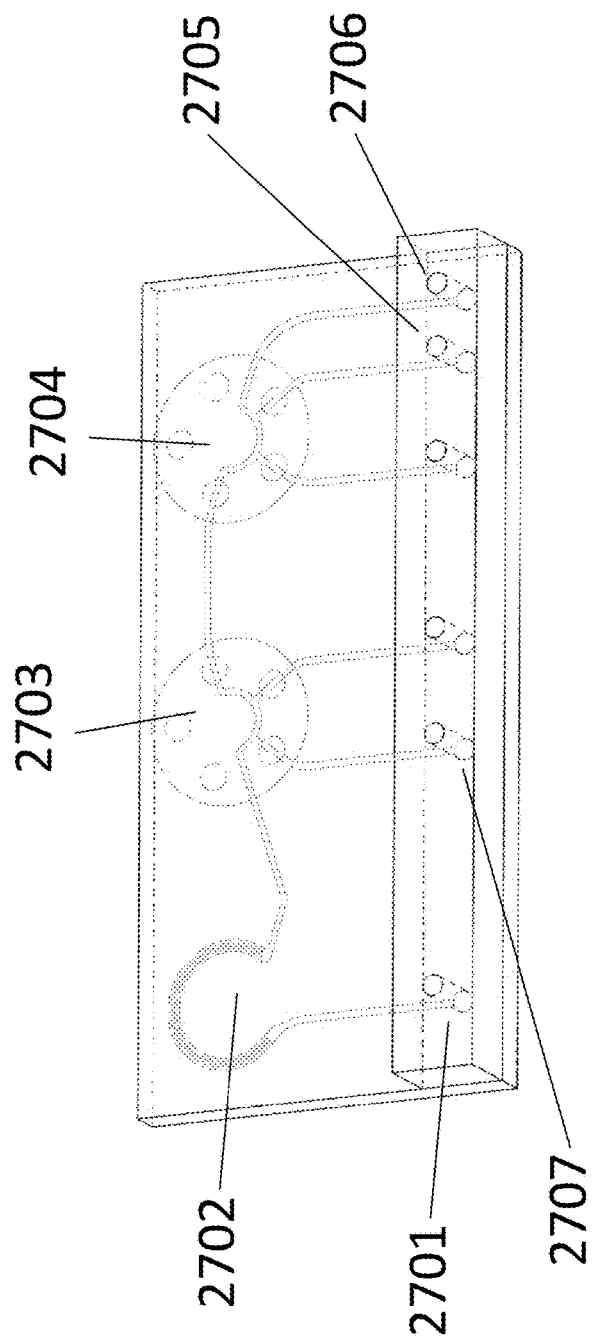
FIG. 27 shows a microfluidics layout for integrated pumps and valves according to one embodiment of the invention, for selectively perfusing a cell culture chamber with multiple types of culture media and output ports for on-device storage of waste for further analysis.

A key advantage of the modular approach described herein is that the fluidic layout can be readily adapted to a particular need without requiring modification of the module configuration. FIG. 27 shows one embodiment of a fluidic layout with two integrated valves 2703 and 2704 and an integrated pump 2702. In one embodiment, the pump 2702 can perfuse upstream fluids 2707 to the cell culture 2701. Waste from the cell culture is forced into the outlet side 2706 of the module and into the waste or sample collection ports 2705. In other embodiments, the pump can be run in the opposite direction to allow the pump to be downstream from the input solutions. Changing the order of the pumps and valves in FIG. 27 would simply require changing the disposable microfluidic device and reprogramming the controller for the three motors.

Figure 28:
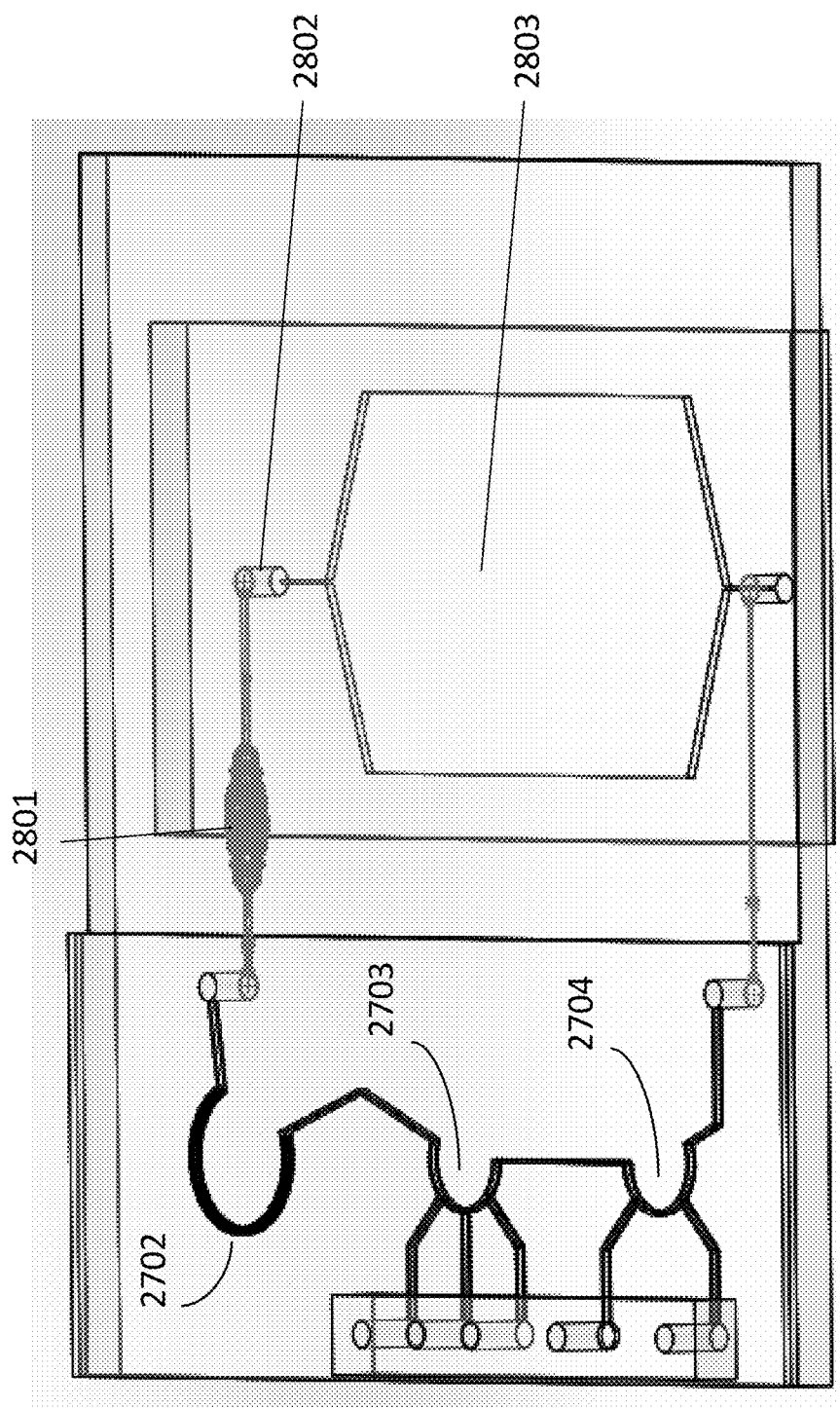
FIG. 28 shows a generic Integrated Organ Microfluidics chip with the ability to maintain an Organ Chip both within the Organ Interconnect Platform and during stand-alone operation, according to one embodiment of the invention. The stand-alone operation is useful for cases when it is appropriate to initially seed an individual Organ Module or visualize the organ construct on an external microscope or other analytical instrument. This particular embodiment has a single integrated chip containing all fluidic routing necessary for supporting embedded cells within the body of the device. This device also incorporates an integrated bubble trap for debubbling the media before delivery to the cells.
Figure 29:
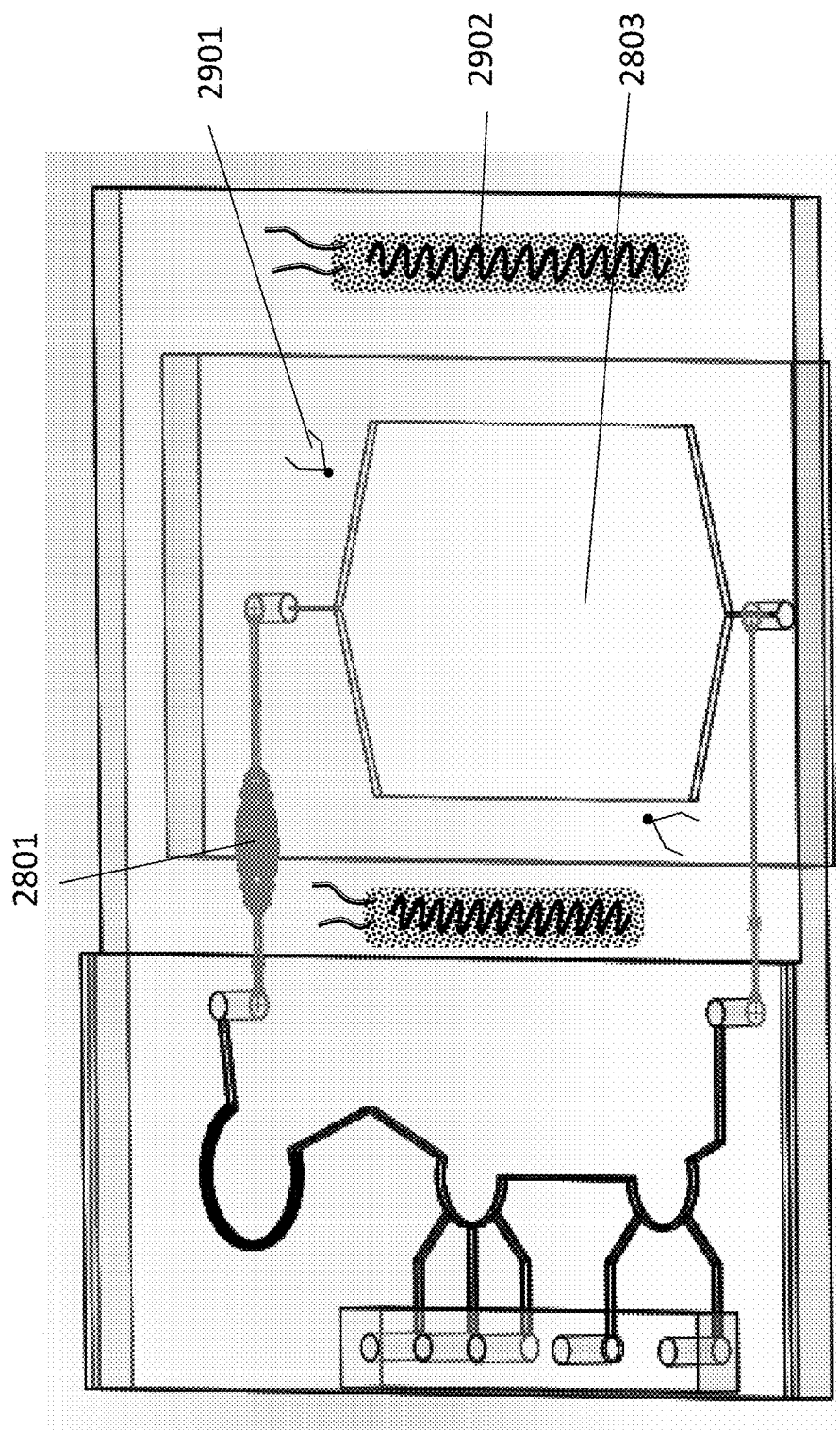
FIG. 29 shows an IOM with integrated heating elements for on-chip incubation of cell cultures according to one embodiment of the invention. In addition to an integrated bubble trap that prevents bubbles from entering the cell chamber, the unit can be equipped with integral temperature sensors, such as thermistors or semiconductor devices, and heating elements that can utilize the on-board microcontroller to maintain temperature of the critical fluid path portions of the microfluidics when the whole device is temporarily moved out of a laboratory incubator and placed on a microscope. The heating element can be a simple resistive element or a transparent layer of conductive indium tin oxide (ITO) applied to the bottom of the glass slides and powered by the on-board IOM module battery.
Figure 30:
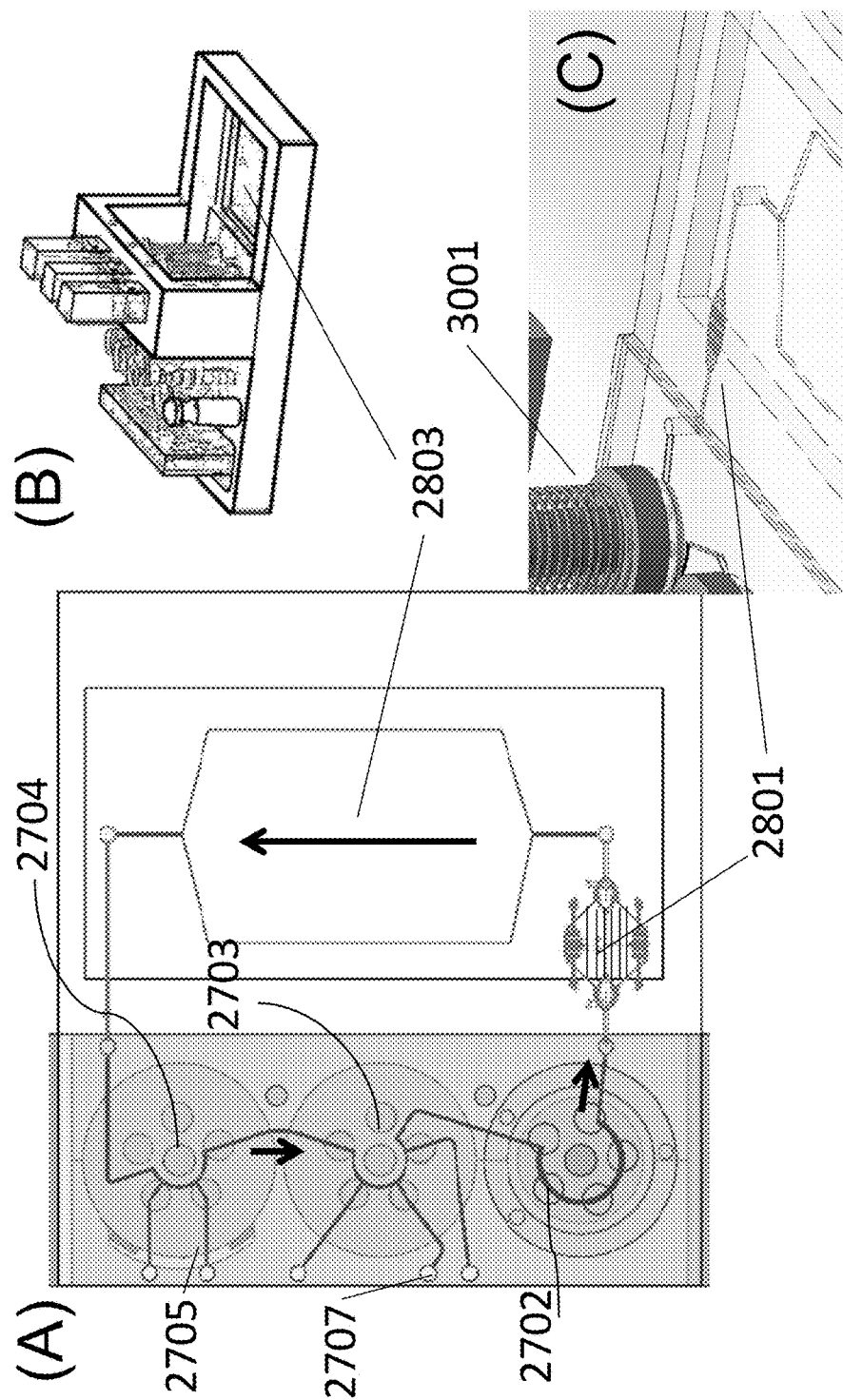
FIG. 30 shows a schematic layout for the bottom-most layers of an IOM chip designed to minimize the volume of interconnect fluidic pathways between the RPPM/RPV assembly responsible for providing perfusion fluid (left) and the cell organ construct chamber (right), according to one embodiment of the invention: (A) a section view, (B) a perspective view, and (C) a partial perspective view. Minimizing interconnect volume is a very important consideration for maintaining physiological relevance of organ-on-chip devices, and this is a key feature of the IOM chip design. This layout also illustrates two key microfluidic bubble control design features of the IOM chip.

While FIG. 27 shows the pumps and valves on a discrete chip, as shown in FIG. 28 cell culture chambers 2803 can be further integrated to form a totally integrated microfluidic device, or Integrated Organ Microfluidics (IOM) Chip. Such a structure requires integrated bubble traps 2801 to prevent air from harming the encapsulated biological sample. In the exemplary embodiment shown in FIG. 28, the three-segment device has 6 layers of PDMS, with a 25 mm×50 mm number one glass slide on the bottom and 5 ports for tubing interface to stock solutions/waste/analysis. Interfaces 2802 between these layers are provided internally. In certain embodiments as shown in FIG. 29, integrated thermistors 2901 and heaters 2902 can provide on-chip regulation of temperature. The IOM design is highly advantageous because it allows the recirculation, input, and output of the biological sample with the addition of only minimal fluid volume to the perfusion system as compared to what can be achieved with the conventional approaches shown in FIGS. 1 and 2. FIG. 30 provides alternative views of the IOM chip. The pump heads 3001 can be interfaced to the device with compression springs.

Bubbles and Gas Exchange

Figure 31:
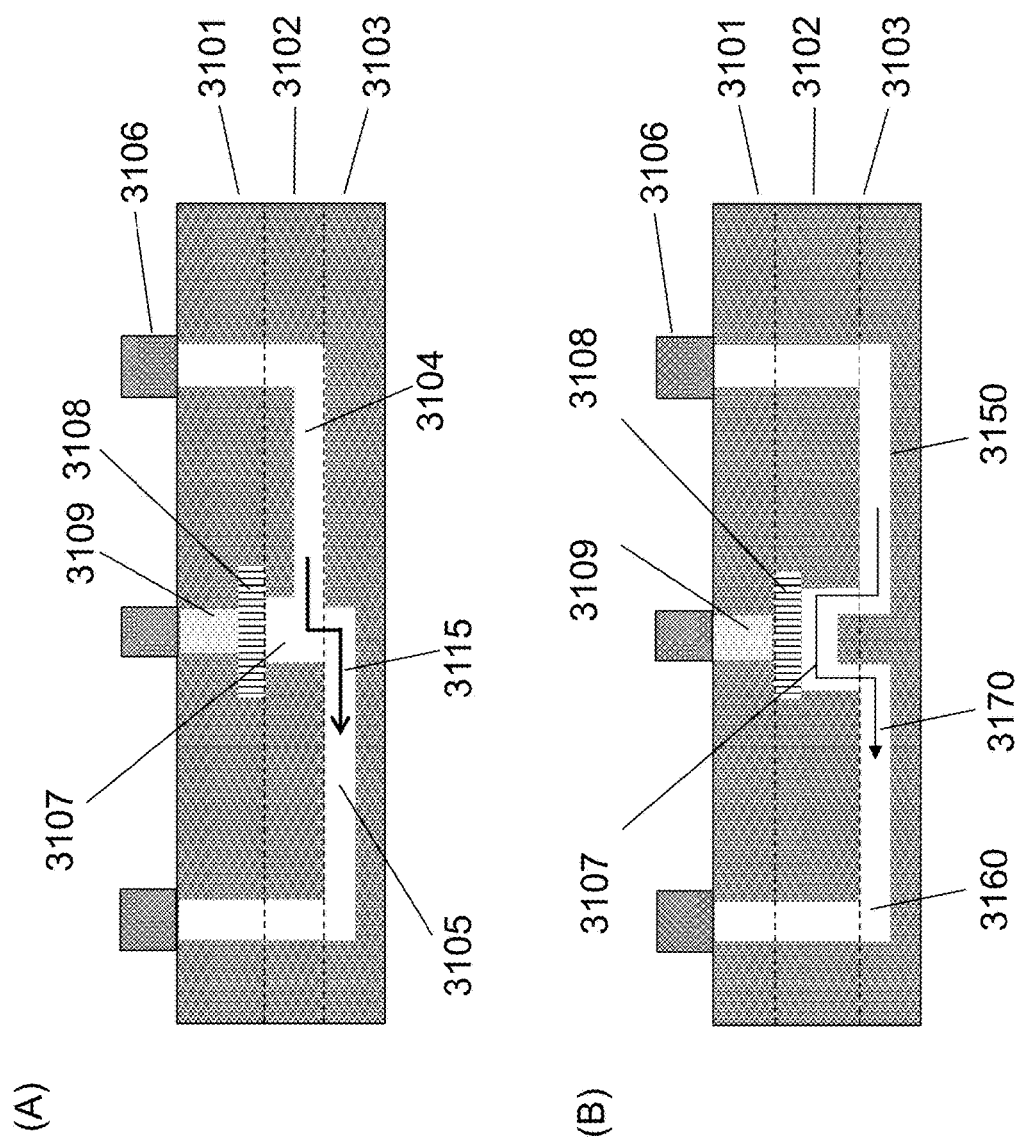
FIG. 31 shows a bubble trap according to one embodiment of the invention: (A) a bubble accumulation area added above the vertical transition of the fluidic path, and (B) an alternative rerouting of the fluid flow suitable for capturing large bubbles that occlude the cross-sectional area of the microfluidic channel.

The inventors have paid particular attention to solving problems that involve the deleterious action of small air bubbles in long-term microfluidic cell and tissue culture experiments. Even very small air bubbles in microfluidic structures can disrupt or reroute fluid flow in such a way as to cause the death of biological cells and tissue constructs. FIG. 30 illustrates an exemplary integration of a bubble trap into the flow path of a multi-reservoir dual Rotary Planar Valve (RPV)/single Rotary Planar Peristaltic Micropump (RPPM) system being used to supply nutrients/drugs to a microfluidic chamber containing an organ tissue construct. This section provides further details regarding the invented Integrated Organ Module Cassette system as the basic design of the stand-alone debubbler shown in FIG. 31, disclosed by Wikswo et al. in PCT application Serial No. PCT/US2012/068771, which is incorporated herein in its entirety by reference. This includes a small bubble accumulation zone. In addition to trapping bubbles, which potentially can form in the recirculating loop of such devices, it is important to minimize the formation of new air bubbles. One important trigger for the formation of new air bubbles is the transient changing of fluid temperature, which can occur, for example, when the module is removed from an enclosed incubator environment and temporarily mounted on a bench-top laboratory microscope in order to observe and document cell health and organ construct structure. An important feature of the invented IOM module system is the inclusion of an on-board battery and microprocessor system. This feature, in combination with local on-module temperature sensors and battery-powered heaters, will allow the cell bioreactor chamber to maintain constant temperature when the module is temporarily removed from a constant-temperature laboratory incubator. This maintenance of constant-temperature fluidics will both minimize deleterious bubble formation and provide a more physiologically relevant uniform temperature for cells growing within the device.

The exemplary embodiment of the bubble trap shown in FIG. 31A is a three-layer device with a top layer 3101, a middle layer 3102, and a bottom layer 3103. The device has a bubble accumulation area 3107 above the vertical transition between incoming 3104 and outgoing 3105 channels to trap bubbles against the hydrophobic gas exchange membrane or filter 3108 until the gas can cross the membrane and be removed by the bubble-withdraw vacuum channel 3109. Connections to the device are made by means of interface ports 3106 on the input 3104, output 3105, and vacuum 3109 channels. The flow between the input and the output is shown by the flow-path arrow 3115. FIG. 31B shows another embodiment of the bubble trap in which both the input 3150 and output 3160 channels are located in the third layer 3103 to provide a flow path 3170 past the bubble accumulation area 3107. The use of multiple layers in these examples is to show one means of incorporating the three-dimensional configuration required to provide both a bubble accumulation area and a means to support the membrane that is used to separate the bubbles from the fluid stream through either passive diffusion, for example through a PDMS membrane or gas transport across a hydrophobic filter, both represented by 3108. It is also possible to incorporate optical or electrical sensors in the bubble accumulation volume to determine when the accumulated bubble has grown to a predetermined fraction of the volume of the bubble accumulator, at which point the microcontroller 511 in FIG. 26D can be programmed to vent the accumulated gas automatically. This represents another major advantage of using microcontroller-enabled bio-object culture modules: it is straightforward to incorporate new features to the modules as the need arises.

On-Board Microprocessor Functionality

Figure 32:
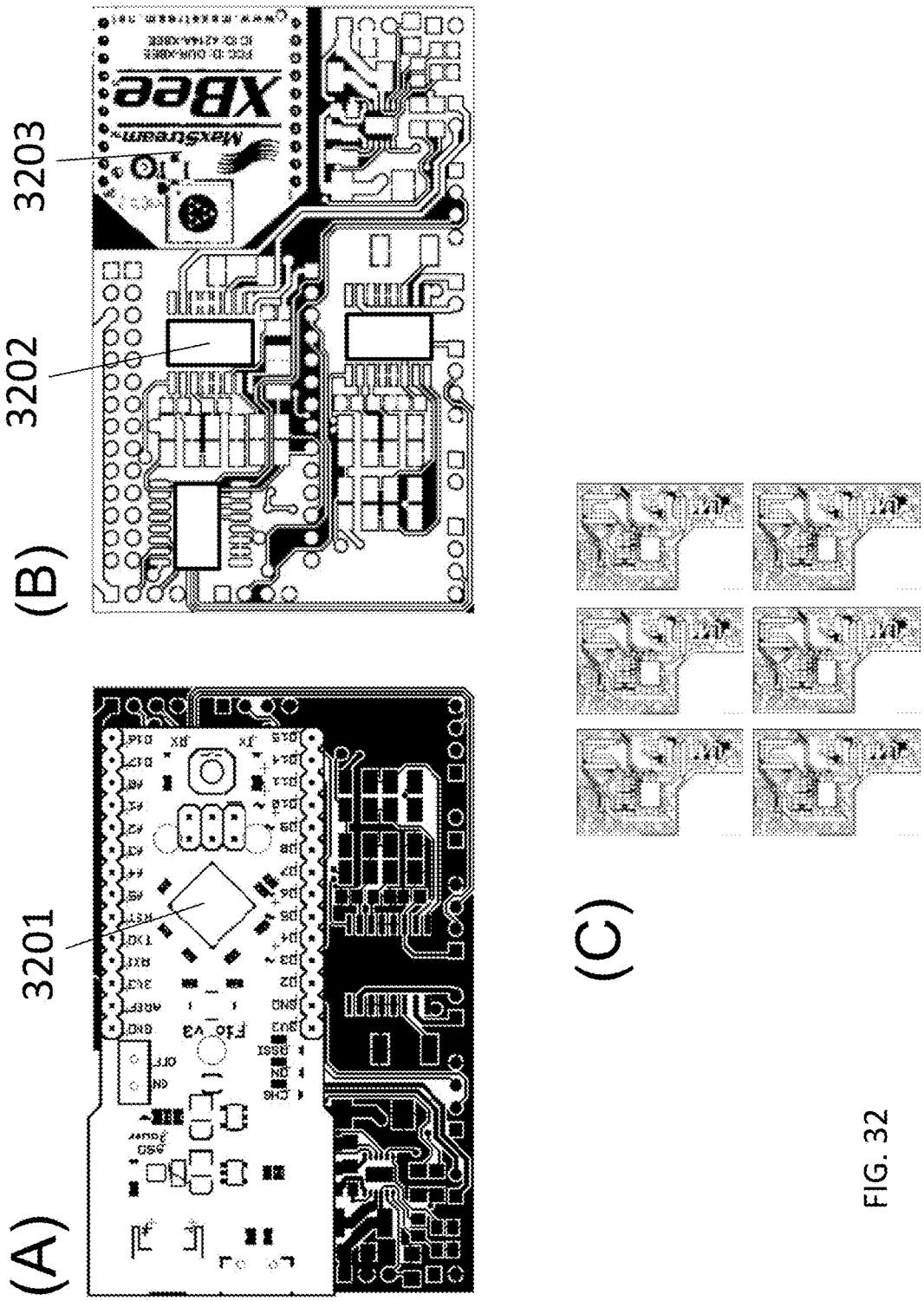
FIG. 32 shows line drawings (A)-(C) of a wireless microcontroller used to coordinate control of the RPPMs/RPVs.

The invented Integrated Organ Microfluidics (IOM) module design contains an on-board, general-purpose microprocessor 3201, battery, motor controller circuitry 3202, wireless communication device 3203, and wireless delivery of electrical power, as shown in FIG. 32. This combination of elements can provide the system with the following key functional characteristics.

1) Programmable control of fluid delivery rates for organ maintenance and for organ development conditioning sequences, such as shear stress or drug or growth factor dosage modulation.
2) Programmable control of drug delivery or growth factor schedules for cell maintenance or programmed cellular differentiation, for example, from induced pluripotent stem cells into progenitor cells or specific terminally differentiated cells.
3) Thermostatic control of cell growth chamber for periods when the module is in a room-temperature microscope. The advantage of this is that constant temperature reduces the adverse effects of temperature shock on cells and tissue constructs cultured within the module and lessens the probability of bubble formation.
4) Remote control of experimental protocol, including initiation, conditioning, organ maintenance, and organ drug challenge via wireless connectivity.
5) Downloading of experimental results via wireless control from a centralized controlling computer.
6) Detailed experiment condition logs of flow patterns, sequences, timing details, temperature histories, loading times, drug delivery schedules, etc. can all be archived and later downloaded from each IOM module. This offers the merits of high-quality experiment control and documentation with possibility of autonomous control.
7) The on-board monitoring of various parameters in the module, for example the aforementioned bubble accumulation, and performing the requisite actions in response to a measured value.
8) The on-board IOM module battery can be recharged via standard hard-wired connection technology when docked to a receptacle in an incubator or when connected to a power source, or it can be recharged wirelessly using commercially available inductive wireless charging pads or magnetic resonance longer-distance power transfer. Certain wireless microcontrollers are shown in FIG. 32.

FIG. 32 illustrates one embodiment of a microcontroller 3201, DC motor controller 3202, and wireless interface 3203 for total control of an Integrated Organ Microfluidics module. FIG. 32C shows multiple electronic control boards. As designs are refined, the size and cost of these components will undoubtedly decrease, enabling more features to be incorporated into modules while requiring a smaller fraction of the space on the module, just as the size and capabilities of cell phones have evolved.

Figure 33:
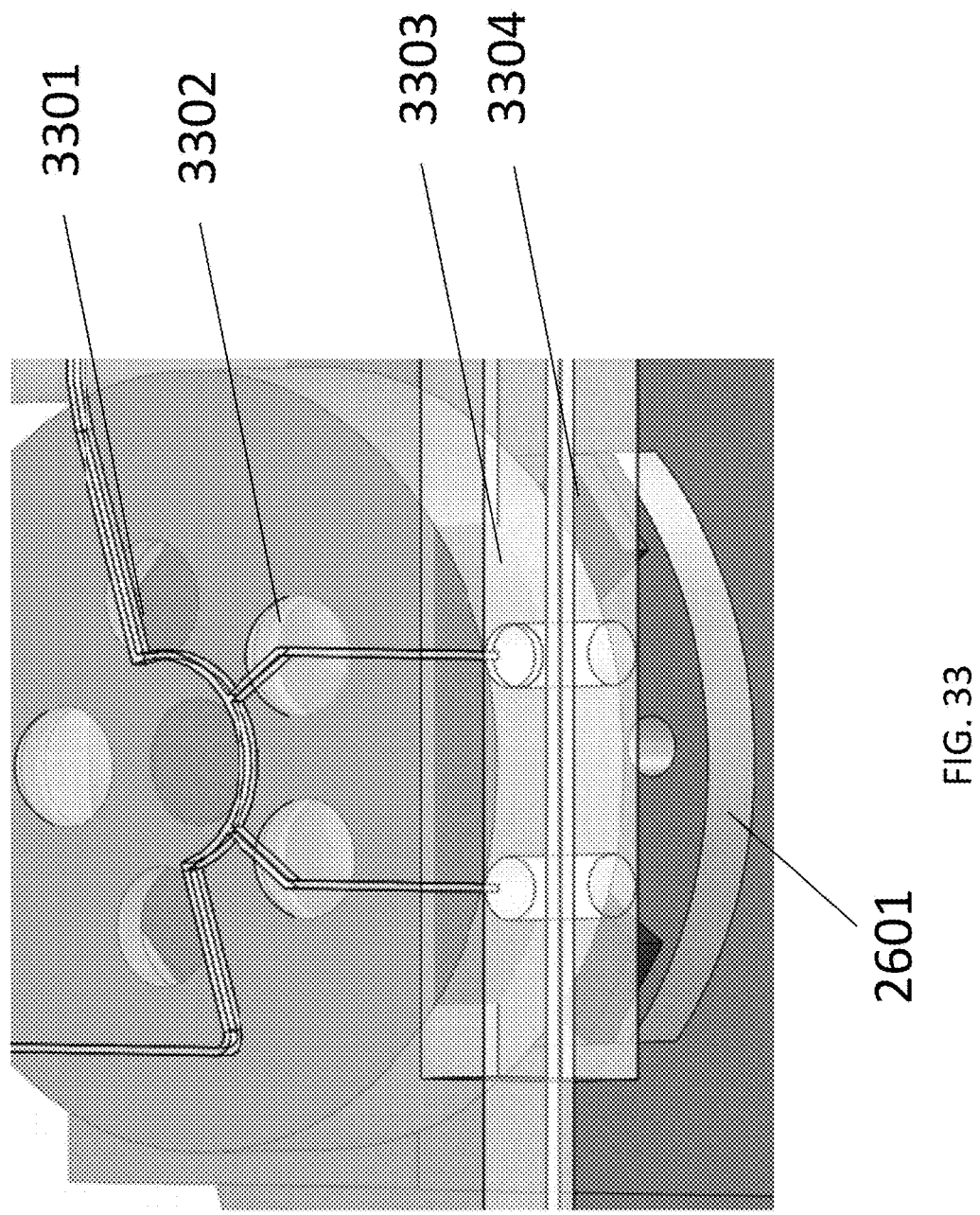
FIG. 33 shows an encoder for resolving one of 5 positions with a set of magnets and Hall effect sensors according to one embodiment of the invention. One can also use this design with a single magnet to index a start position in a stepper motor.

FIG. 33 shows a scheme for using tiny magnets 3303 and Hall effect sensors 3304 on an encoder board 2601 to act as encoders to encode the position of the valve rotor. In this embodiment, the open channel 3301 and the closed channel 3302 are located at about 72 degrees relative to each other. Other encoding schemes would also be possible. In one implementation, three magnets indicating the location of the ball bearings can be used to index a valve. Alternatively, as the magnet passes each Hall effect sensor, the revolutions per minute (rpm) of the motor can be calculated and adjusted accordingly.

Microclinical Analyzer

Figure 37:
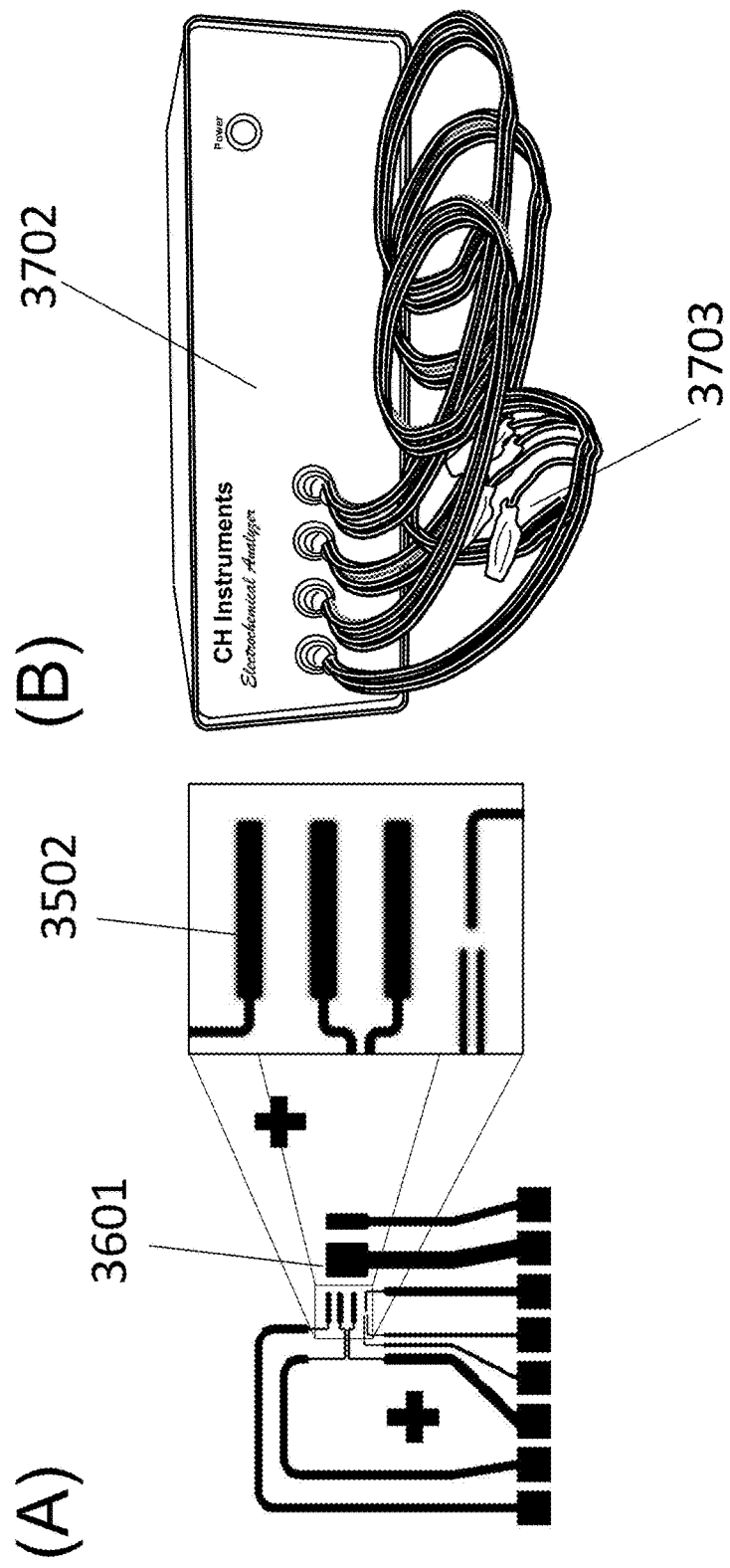
FIG. 37 shows (A) electrochemical sensors in a MicroClinical Analyzer according to one embodiment of the invention, and (B) an appropriate electronic device for sensing and control.

One aspect of the invention, among other things, is focused on improvements to the Integrated Organ Microfluidics (IOM) devices with regard to the integration of supporting fluid networks and interconnects. These developments aim to address the engineering challenges involved when maintaining biological samples, including engineered tissue and organs-on-chips, in microfluidic devices. Major improvements to the designs according to the invention are:

1) Technical details of fluid reservoir structures for providing convenient sterile supply to the invented self-contained Integrated Organ Microfluidics (IOM) Module.
2) Technical details of an integrated "MicroFormulator" valve and pump system capable of on-demand production of mixtures of fluid reagents, drugs, biological suspensions, and nutrients at user-specified ratios for immediate delivery to the on-board biological tissue or organ construct.
3) Technical details associated with the management of air bubbles and gas exchange within the microfluidic organ perfusion loop.
4) Technical review of the various functionalities provided by the on-board microcontroller, battery, and wireless interface that contribute to the overall suitability of the invention to long-term organotypic culture and assay technology and that are not provided by conventional tissue culture and well-plate technologies. Each of these capabilities contributes to and benefits from the real-time sensing and control afforded within the IOM module. Such real-time sensing and control of a large number of independent or interconnected modules is not possible with the standard approaches shown in FIGS. 1 and 2. In the exemplary embodiment of the MicroClinical Analyzer shown in FIG. 15, an integral microcontroller drives one pump and two valves, and vials provide solutions for continuous perfusion and calibration of the sensors and also for collection of waste perfusion solution and perfusion solution for off-line analysis. The MicroClinical Analyzer sensing electronics 3702 shown in FIG. 37 may eventually be miniaturized to fit on an organ cartridge along with the Perfusion Control system.

Figure 34:
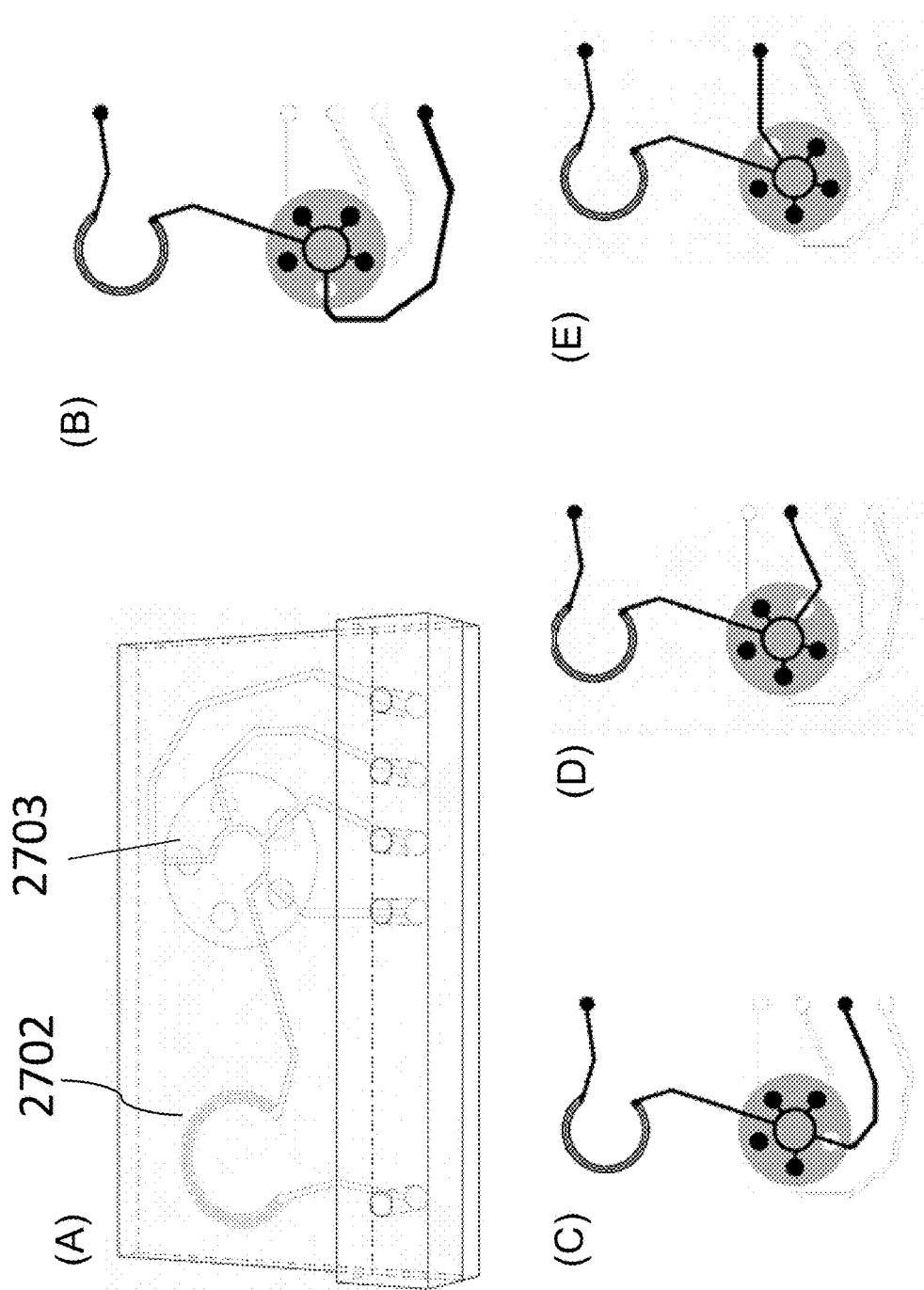
FIG. 34 shows fluidics required for a MicroClinical Analyzer that self-calibrates using three on-board predetermined calibration solutions and that has an additional port for input from the Perfusion Controller or Organ Chip, according to one embodiment of the invention: (A) a perspective view, and (B), (C), (D), and (E) different views showing the operation of the integrated pump and valve with ball cage.

One of the limitations of existing approaches for measuring metabolic activity using electrochemical sensors is that the sensors tend to drift with time and can be fouled by proteins in the perfusion media or released by the cells being cultured. As shown in FIG. 34, in one embodiment of the MicroClinical Analyzer addresses both of these problems by using a four-port input valve 2703 and an integrated RPPM 2702 to provide calibration and supernatant flow across the sensing electrodes for the sensor calibration and measurements required. Each calibration solution can be sequentially delivered, as shown in the series of panels in FIGS. 34B-34E. When the measurement is complete, the sensing electrodes can be washed with one of the calibration media or another solution to extend longevity of the electrodes over extended periods of time, for example at least one month.

Figure 35:
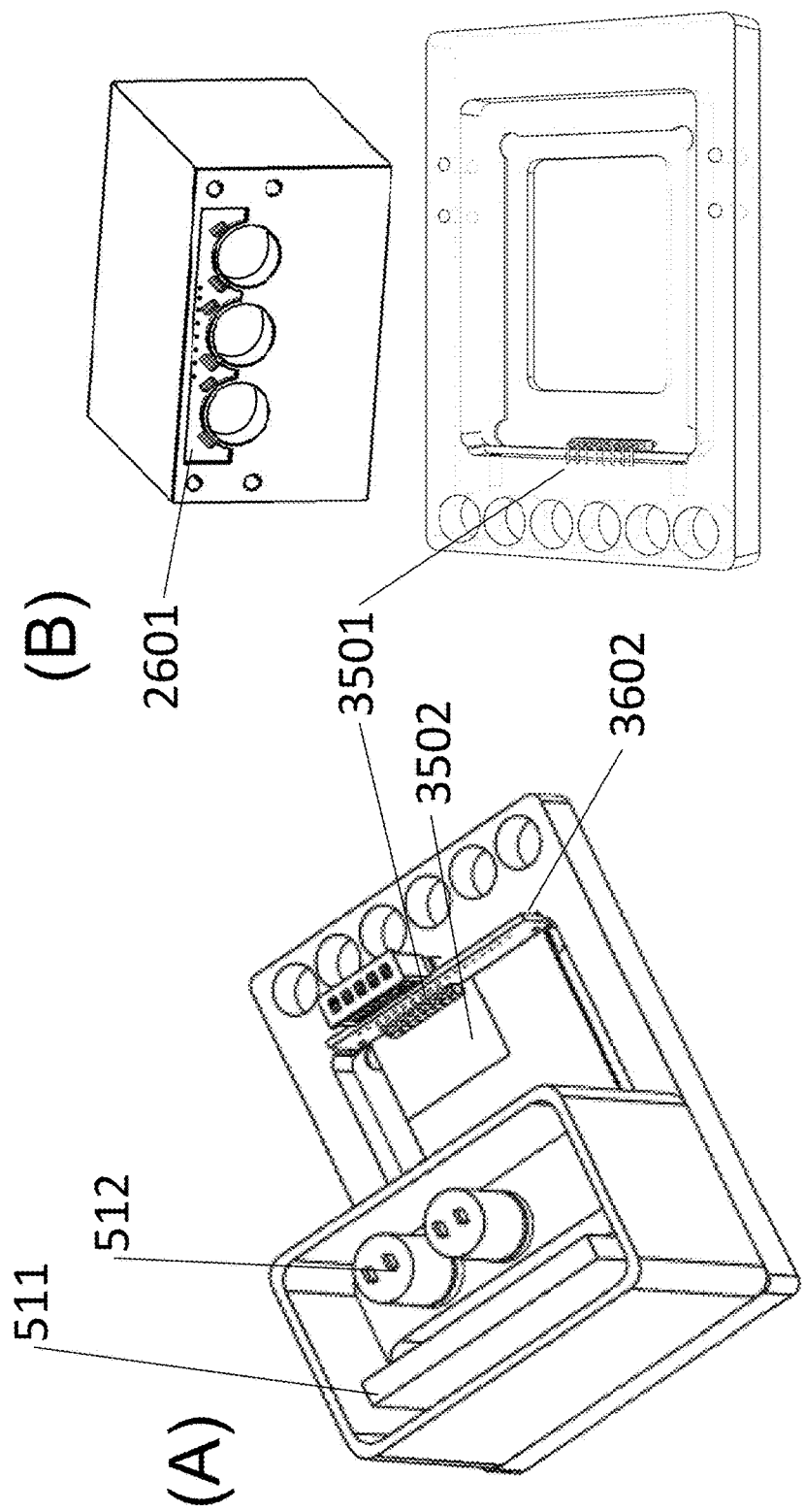
FIG. 35 shows a MicroClinical Analyzer according to one embodiment of the invention: (A) a perspective view, and (B) different parts.
Figure 36:
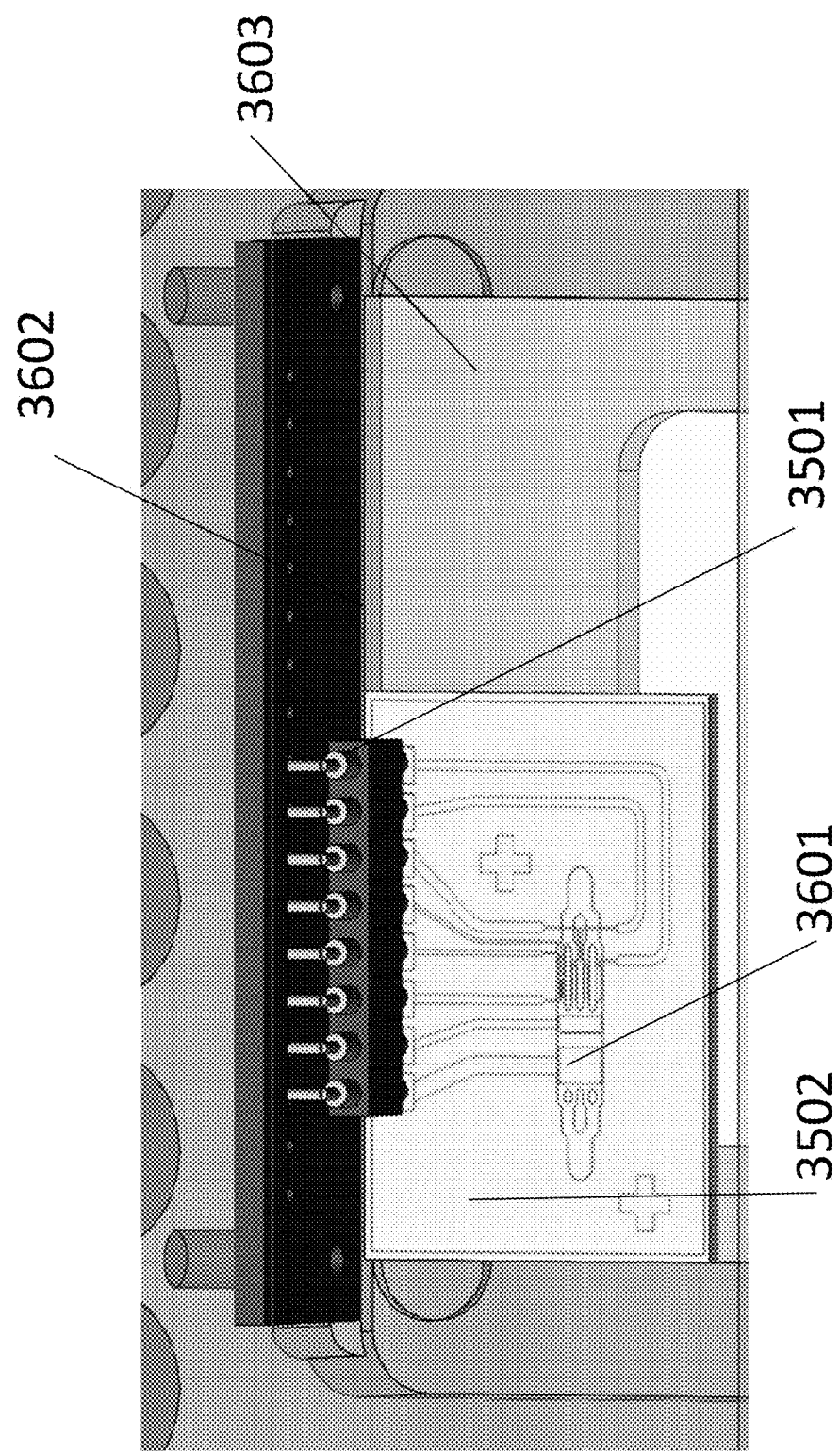
FIG. 36 shows an interface board required to interface between the electrochemical sensor embedded within a MicroClinical Analyzer and an external analyzer, according to one embodiment of the invention.

In another implementation of the MicroClinical Analyzer shown in FIG. 35, electronic connections are made between a glass slide and the measuring instrument through a separate electronic board 3602 with pogo-pin connectors 3501. FIG. 36 shows patterned platinum films 3601 on glass 3502 with associated microfluidic channels as required for the electrochemical measurement of metabolites. FIG. 37A shows the microfluidic electrochemical analyzer sensor array which requires the amplification electronics 3702 and interface cables 3703 shown in FIG. 37B for proper operation of the sensors.

In another embodiment of the MicroClinical Analyzer, the driving pump and valve fluidics are integrated with the sensing fluidics, providing a total integrated chip for performing calibration and analysis.

Reservoir Fluid Supply Structures

Figure 38:
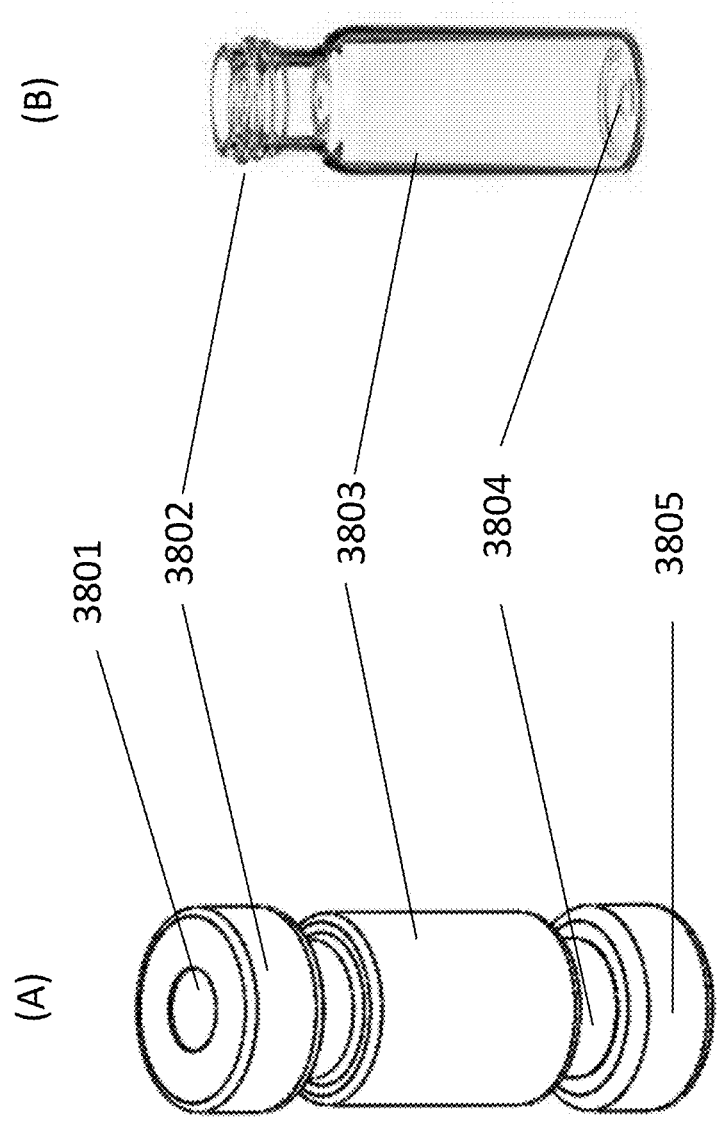
FIG. 38 shows a double-ended vial (A) and a screw-top vial (B), which can be used to store media for cells on-board the SBS form factor module. These devices also allow for sterile filtering of make-up air entering the vial as fluid is withdrawn from the bottom, quick fluid level checking/refilling by user, sample delivery from the bottom, and refill/vent on the top end through the plenum, all while minimizing the injection of bubbles.
Figure 39:
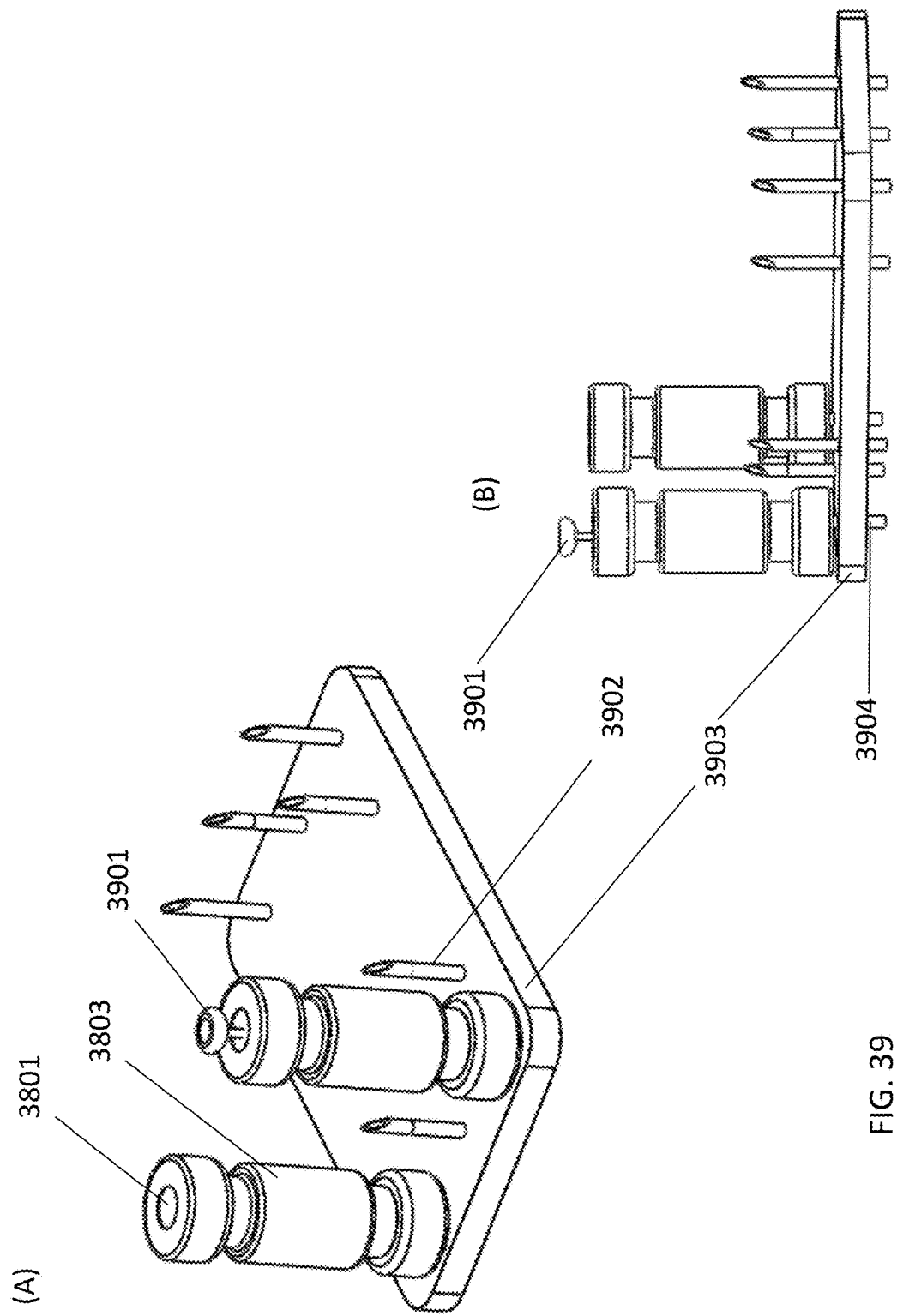
FIG. 39 shows a double-headed needle apparatus required for interfacing the double-ended vial with the microfluidic chip, according to one embodiment of the invention: (A) a perspective view, and (B) a section view. The needles provide fluid pass-through between vial and microfluidics. The fixed needle configuration is matched to pre-punched holes in the microfluidic chip.

One challenge in developing a self-contained integrated microfluidic supply system for organotypic culture is supplying living cells with the required nutrients, drugs, and other biological factors in a sterile and conveniently reloadable fashion. Also, since the invented IOM system is designed for long-term incubation experiments, sterile on-board storage of waste fluids is also a necessity. The current alternative is the use of the robot system in FIG. 2 wherein the well plate has to be removed from the incubator, its cover removed and stored, fluid added by the pipetting system, the cover replaced, and the well-plate returned to the incubator. In the IOM approach, adequate fluid can be provided on the module to support long-term cell or tissue culture, and waste vials can be provided to store spent media. The inventors have designed and demonstrated a technique involving double-ended septum sterile containers that can meet the challenge of long-term fluid handling by providing fluid access to reservoir 3803 content through hollow needles 3902 that pierce the septum. FIGS. 38 and 39 illustrate the functional features of this design. Note that a disposable or sterile filter vent 3901 that pierces the top septum is used to prevent airborne contamination of the reservoir while providing both 1) make-up air to compensate for fluid withdrawn from reservoir and 2) equilibration with atmospheric pressure changes which, if not compensated for, can cause unintended fluid flows in the microfluidic supply network. An alternative design (not shown) involves the use of a specialty two-prong, two-level septum piercing needle set that can, at the expense of more complicated layout, provide both fluid access 3904 and make-up air for each individual fluid reservoir through the lower septum alone. Additionally, a screw top that contains a pierceable septum may be advantageous for ease of both sterilization of all vial components and refilling of stock solutions. In certain embodiments, a fluid-handling robot or other automated device can manage the fluid levels on these devices, adding or removing fluid as necessary.

In the embodiment shown in FIG. 38, sample delivery is from the bottom 3804 and refill/vent on the top side 3802 through the plenum 3801. The double-ended vial is for ease of insertion, separate venting, and rapid refilling. The vial can have either a crimp top (shown) or a screw top for exchanging and refilling vials. The screw top allows easy removal of any intubated tubing or gas-exchange outlets. The transparent nature of the vials allows the user or an automated fluid-level detector system to easily determine the fluid level in each vial. In the case of automated fluid-level detection, the module microcontroller can communicate wirelessly to the operator the need to adjust the volume in one or more vials.

Microformulator

A MicroFormulator is a microfluidic device that can prepare upon demand a small volume of fluid that contains a specified mixture of various chemical species. Typically, perfusion media is prepared in large volumes. Automated design of experiments, automated model inference, and combinatorics exploration of stem cell differentiation trajectories all require the preparation of small volumes of perfusion media whose formulation is determined by the results from the preceding experiment. This is difficult to accomplish using the pipetting approach shown in FIG. 2. One microfluidic example of a device that is capable of producing small volumes of custom media is provided by Hansen et al. (Alan H. Diercks, Adrian Ozinsky, Carl L. Hansen, James M. Spotts, David J. Rodriguez, and Alan Aderem, A microfluidic device for multiplexed protein detection in nano-liter volumes, Anal. Biochem. 386 (1):30-35, 2009; Carl L. Hansen, Scott Classen, James M. Berger, and Stephen R. Quake, A Microfluidic Device for Kinetic Optimization of Protein Crystallization and In Situ Structure Determination. J. Am. Chem. Soc. 128 (10):3142-3143, 2006; Carl L. Hansen. Microfluidic technologies for structural biology, Caltech. 2004. Ph. D. Dissertation).

In one aspect, the invention discloses an integrated Micro-Formulator, as shown in FIGS. 41-54E. The integrated MicroFormulator includes a plurality of inlets for providing a plurality of solutions; a plurality of outlets; a plurality of fluidic switches in fluid communication with the plurality of inlets and the plurality of outlets; one or more on-chip pumps in fluid communication with the plurality of fluidic switches; a microfluidic chip having a mixer region and a plurality of fluid connections in fluid communication with the at least one pump, the plurality of valves, the plurality of inlets and the plurality of outlets; and a power and control unit programmed to selectively and individually control the one or more on-chip pumps and the plurality of fluidic switches for providing a desired substance that is a mixture of selected solutions from the plurality of solutions for cultivation, maintenance, and/or analysis of a bio-object. In addition, the microfluidic chip may further have a shuttle region.

The power and control unit includes a microcontroller and a power supply. In one embodiment, the microcontroller is provided with at least one of a wireless communication protocol and a wired communication protocol.

The one or more on-chip pumps include an RPPM. Each of the plurality of fluidic switches includes an RPV. In some embodiments, each RPV includes an NC valve. The RPPM and each RPV are driven by a respective motor that is controlled by the microcontroller.

In one embodiment, as shown in FIGS. 41-50, the plurality of fluidic switches includes an input RPV 4130 fluidically connected to the shuttle region 4160, and stock solution ports 4172 of the inlets; a first RPV 4110 having five ports fluidically connected to the mixer region 4150, the RPPM 4140, an input buffer port 4174 of the inlets, a sample output port 4182 of the outlets, and a first waste port 4186 of the outlets, respectively; and a second RPV 4120 having four ports fluidically connected to the mixer region 4150, the RPPM 4140, the shuttle region 4160 and a second waste port 4184 of the outlets, respectively.

Figure 52:
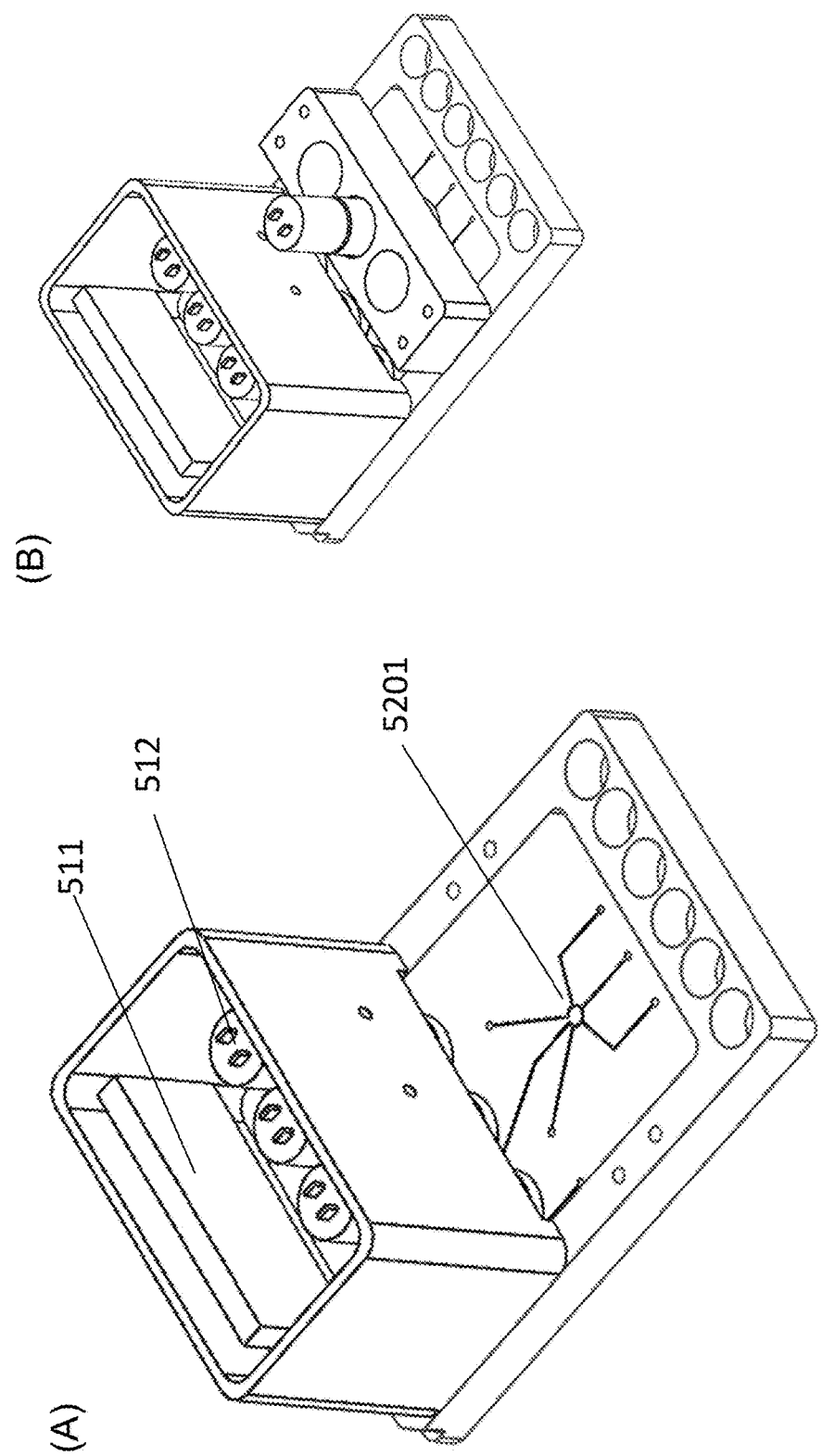
FIG. 52 shows a MicroFormulator based on two selector valves, an input valve, and an RPPM according to another embodiment of the invention. (A) shows the device with 5-port RPV fluidics exposed and (B) shows the assembled device with the input valve covered by its drive motor and housing.
Figure 53A:
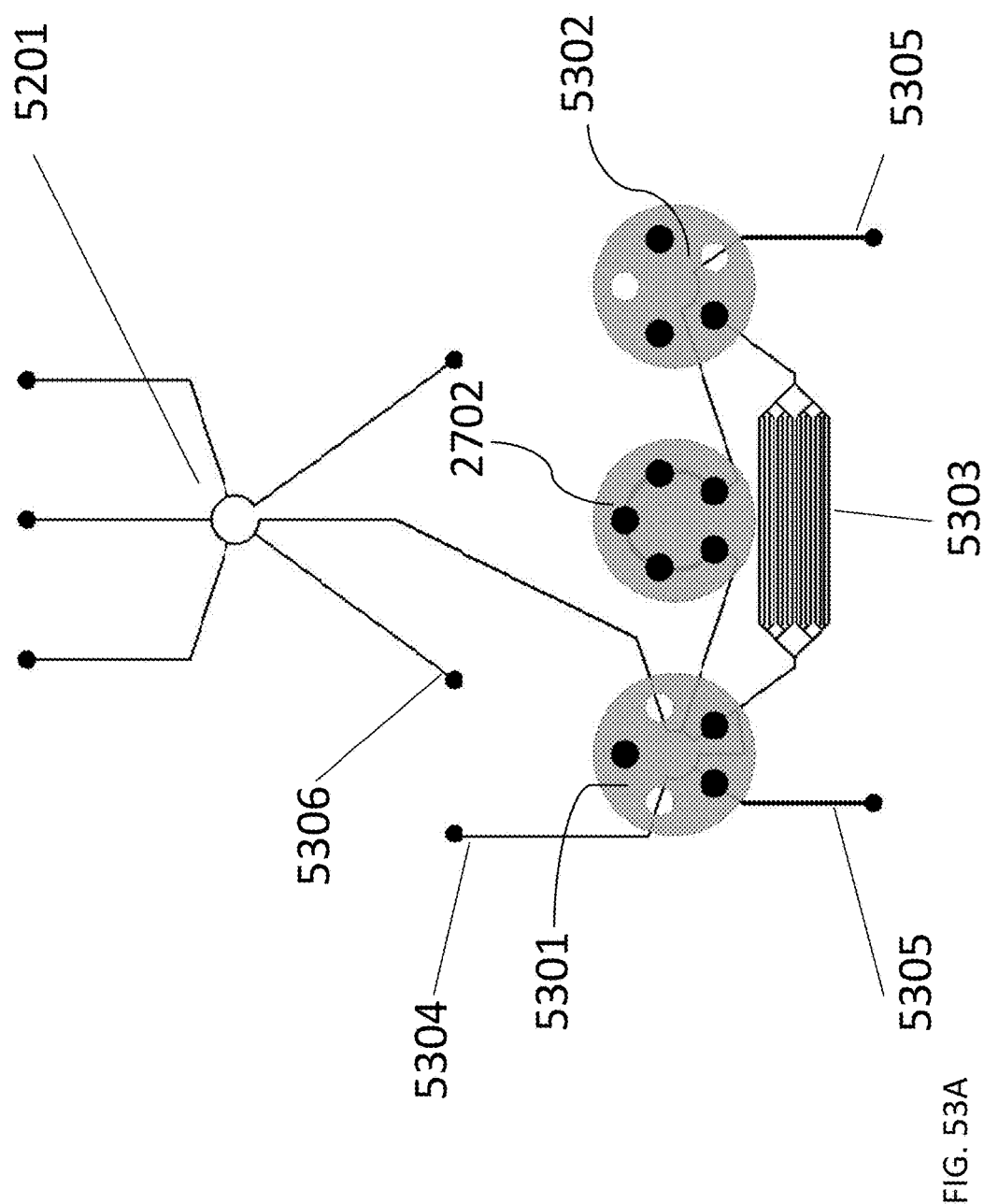
Figure 53B:
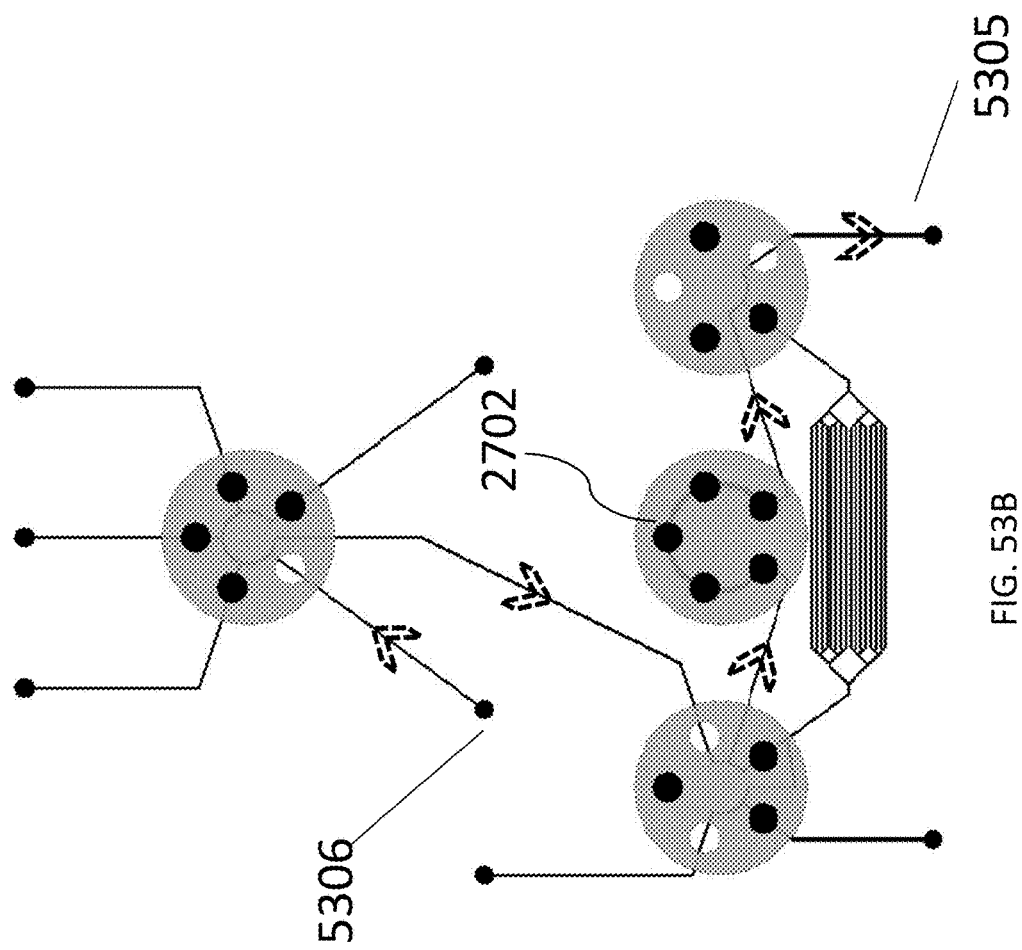
Figure 53C:
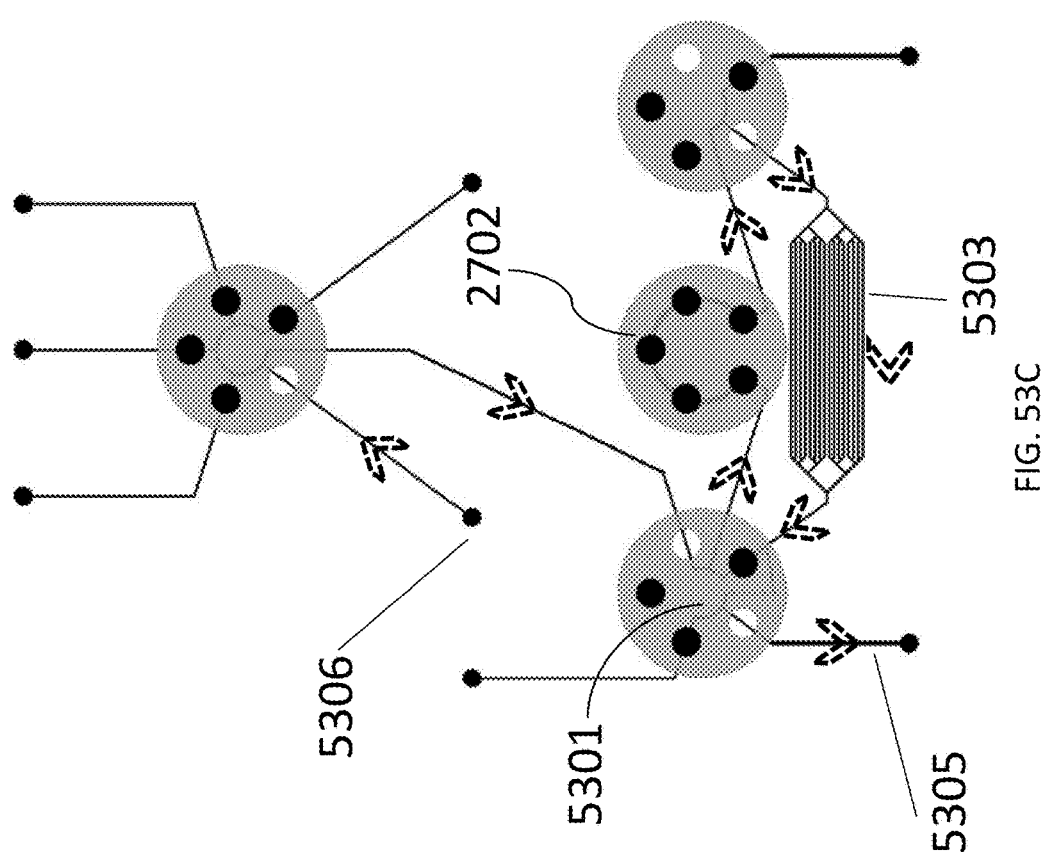
Figure 54A:
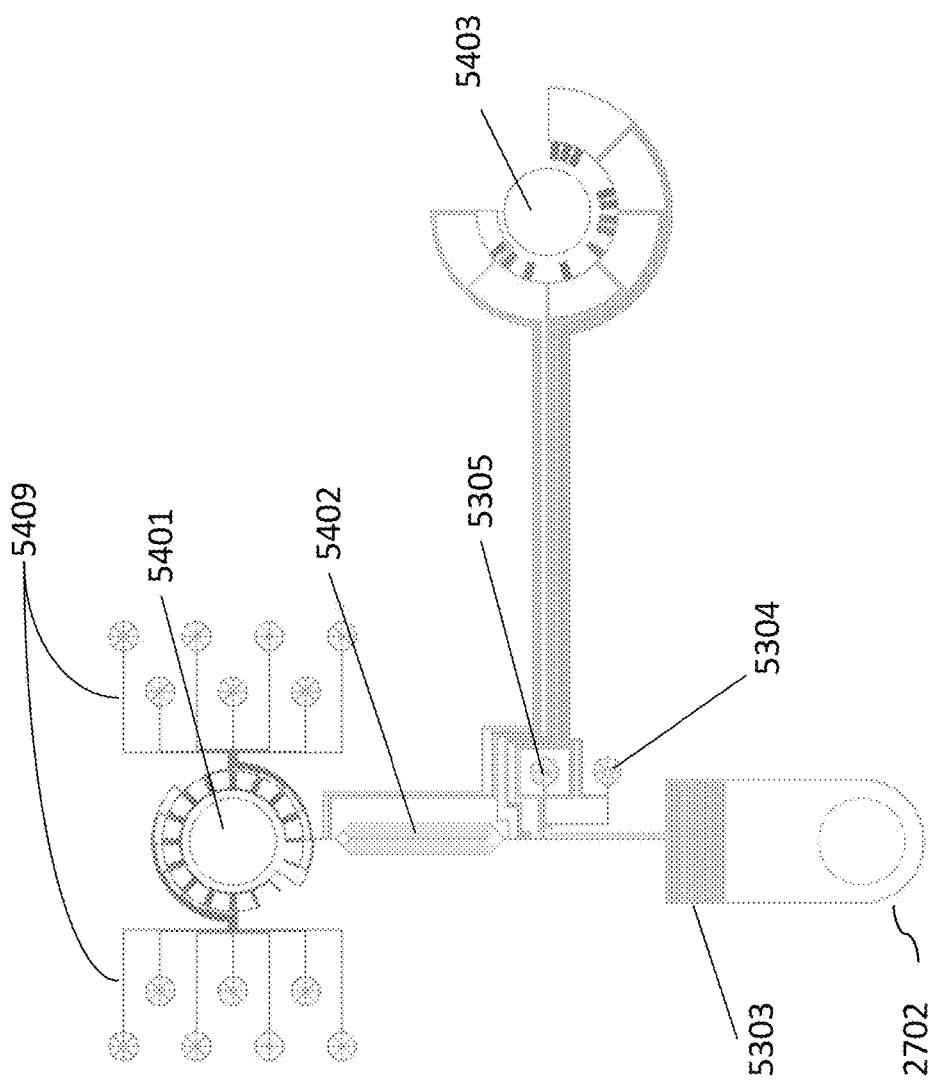
FIGS. 54A-54E show a mask layout of a MicroFormulator according to one embodiment of the invention, which uses a slightly different mode selector valve implementation from the simplified three-valve implementation illustrated in FIGS. 53A-53E. This design uses a more complicated four-position mode selector valve and has the advantage of requiring fewer motors. However, the fluid path lengths are longer and more complicated than the MicroFormulator design presented in FIGS. 52 and 53. Other microfluidic layouts can accomplish the same functions.
Figure 54B:
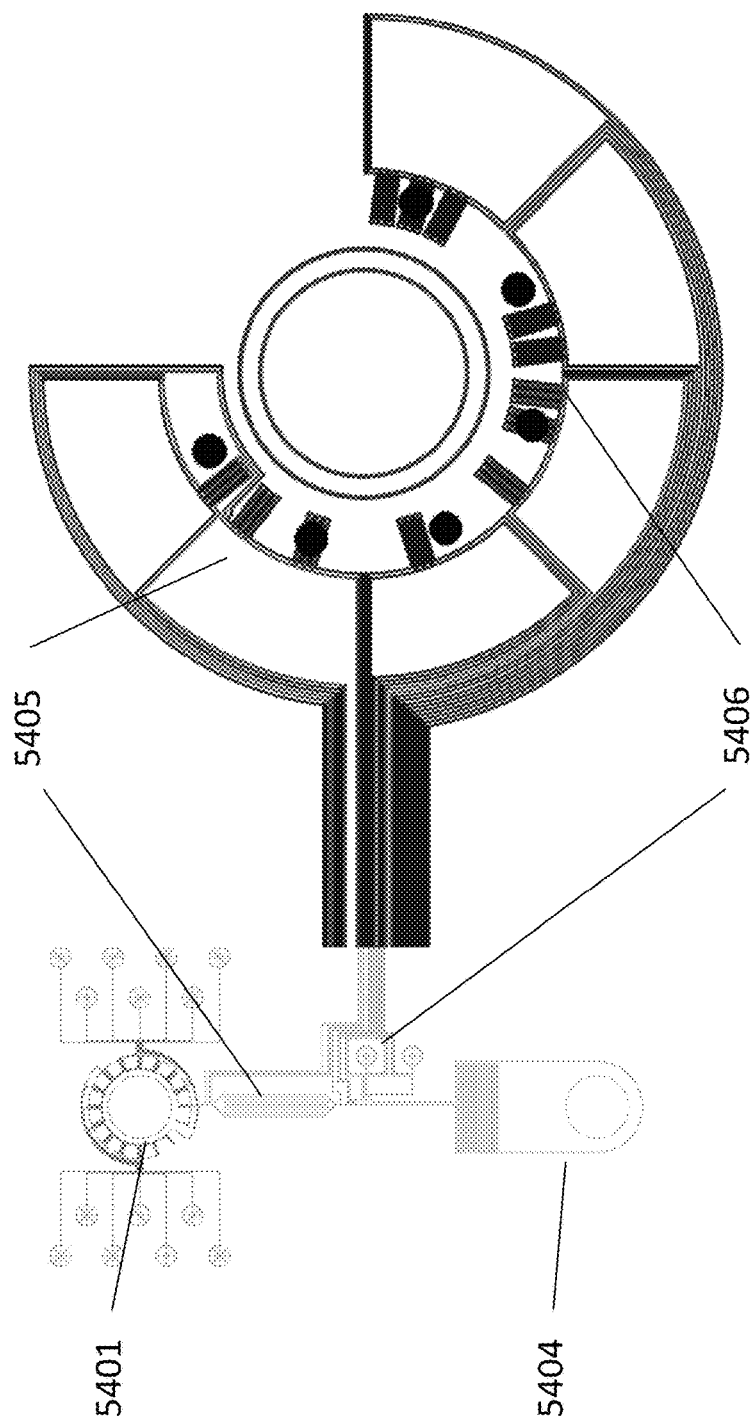
Figure 54C:
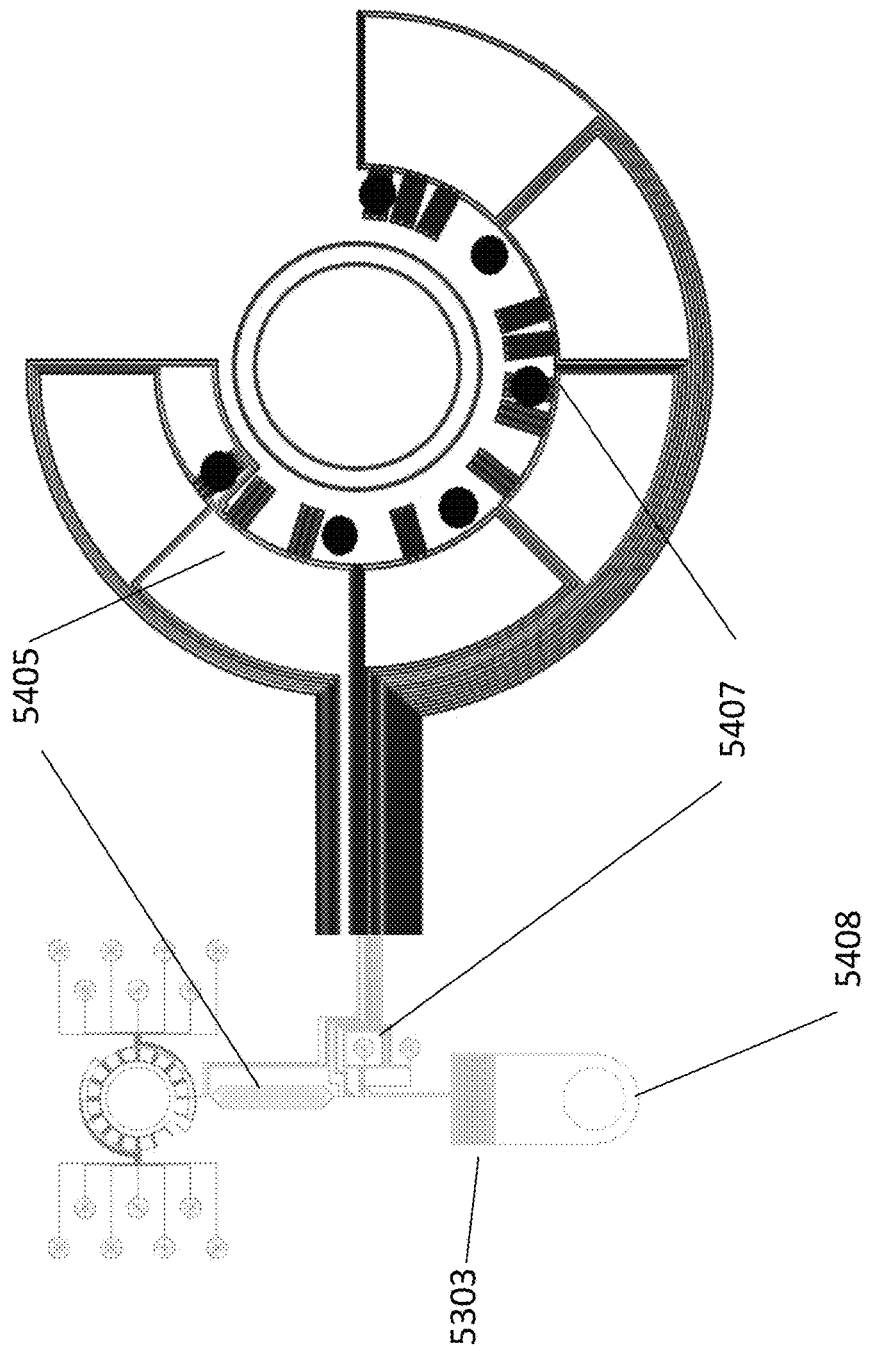
Figure 54D:
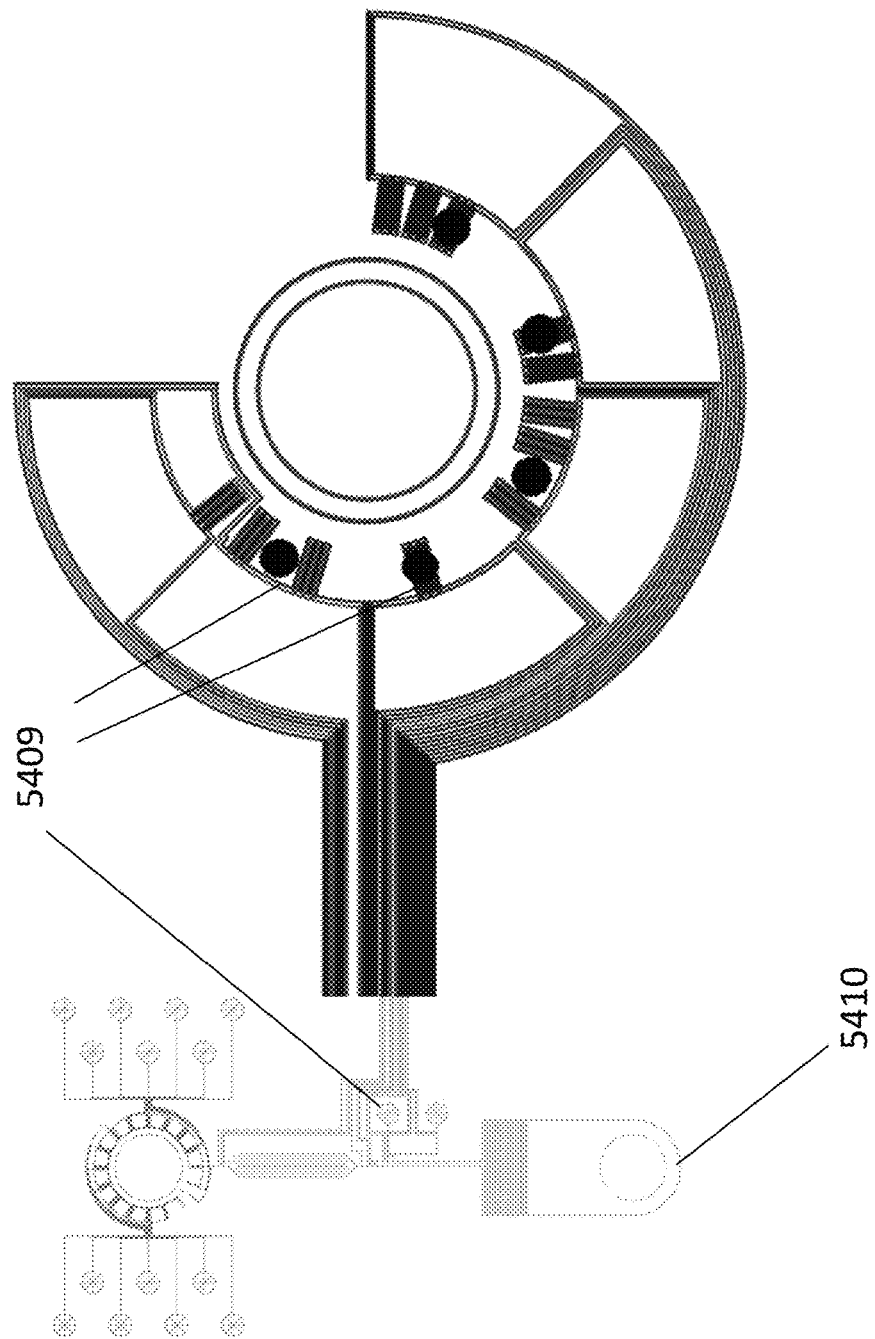
Figure 54E:
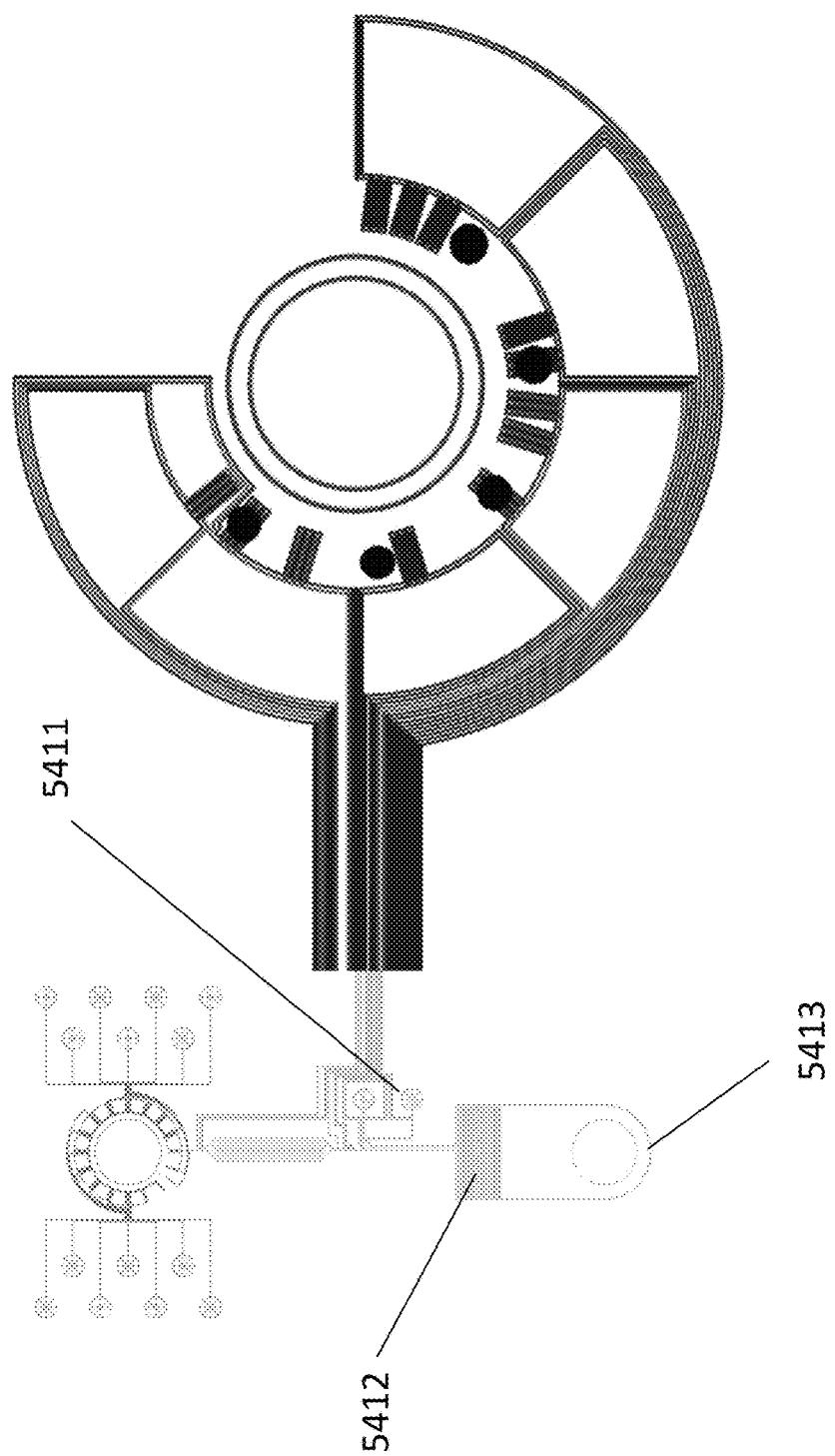

In another embodiment, as shown in FIGS. 52-53, the plurality of fluidic switches includes an input RPV 5201 fluidically connected to the plurality of inlets; a first RPV 5201 having five ports fluidically connected to the input RPV 5201, the mixer region 5303 and the RPPM 2702, a sample output port of the outlets, and a first waste port of the outlets, respectively; and a second RPV 5302 having three ports fluidically connected to the mixer region, the RPPM 2702, and a second waste port of the outlets, respectively.

In yet another embodiment, as shown in FIGS. 54A-54E, the plurality of fluidic switches includes an input RPV 5401 fluidically connected to the shuttle region 5405, and stock solution ports of the inlets; and an operation mode selector valve 5403 fluidically connected to the input RPV 5401, the shuttle region 5402, the mixer region 5303, the RPPM 2702, a sample output port of the outlets, and a waste port of the outlets, wherein the RPPM 2702 is fluidically connected to the mixer 5303.

Figure 40:
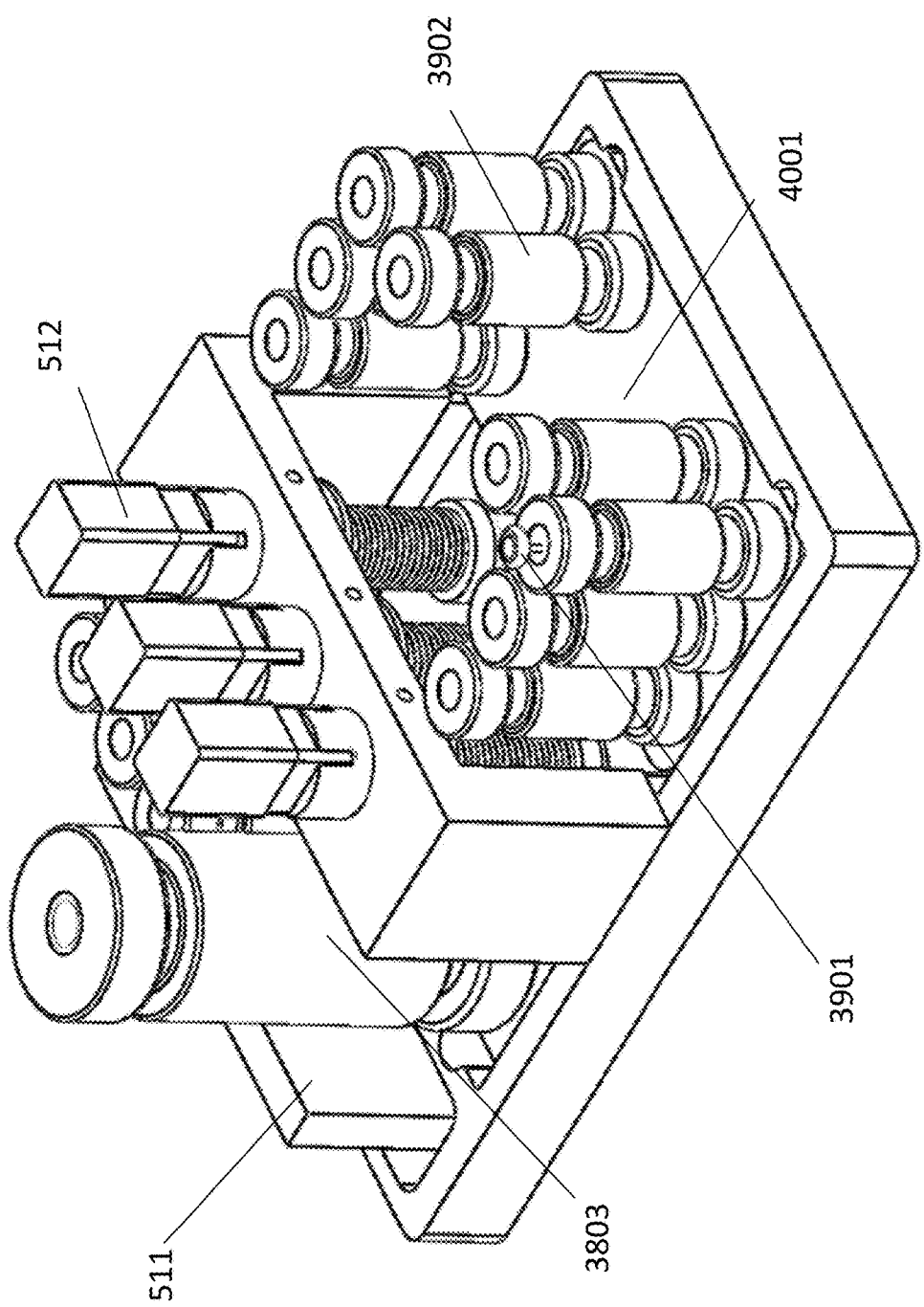
FIG. 40 shows a MicroFormulator implemented using the IOM technology according to one embodiment of the invention, where RPPMs and RPVs connect directly to the microfluidic insert. Also shown are the on-device vials for directly providing stock solutions for aliquoting into mixtures aboard the MicroFormulator. In this embodiment, the device can withdraw solutions from 14 different vials for delivery to the organ/cell region on the integrated chip. Double-ended vials allow fluid withdrawal from the bottom, while a user can visually check the fluid levels and add additional fluid from the top. The make-up air required after fluid removal can be provided by sterile needle filters through the top. These 14 input solutions can be mixed in selected quantities and the resulting concoction output and stored on-device.

According to the embodiments of the invention, the MicroFormulator capable of mixing extremely small volumes of variable specific ratio fluid components for the purpose of providing nutrients, controlled ratio drugs, and other biological factors to the on-board, long-term, cultured organ-on-a-chip construct can be integrated into a single microfluidic chip 4001. The basic functionality of the MicroFormulator subsystem, as shown in FIG. 40, is controlled by an on-board microprocessor 511, which sends specific time-sequenced signals to control the orientation of multi-port valves and a metering mode RPPM 512, which can deliver extremely precise, small-volume increments of fluid on demand more readily than can be accomplished using the system of FIG. 2, particularly when it is recognized that in practical applications of the approach a very large number of modules may need to be maintained independently for long periods of time.

According to embodiments of the invention, the MicroFormulator is configured to perform the following functions: load a solution into a shuttle or other device, deliver that solution into a mixer, deliver additional solutions to the mixer as required, mix the solutions, and output the mixture. One embodiment of the MicroFormulator and its operation procedures are shown in FIGS. 41-50, while FIGS. 51-54 show additional embodiments of the MicroFormulator with mask layouts and their required valve positions for proper operation.

Referring to FIGS. 41-50, the operational functions of the MicroFormulator are illustrated according to one embodiment of the invention.

Figure 41:
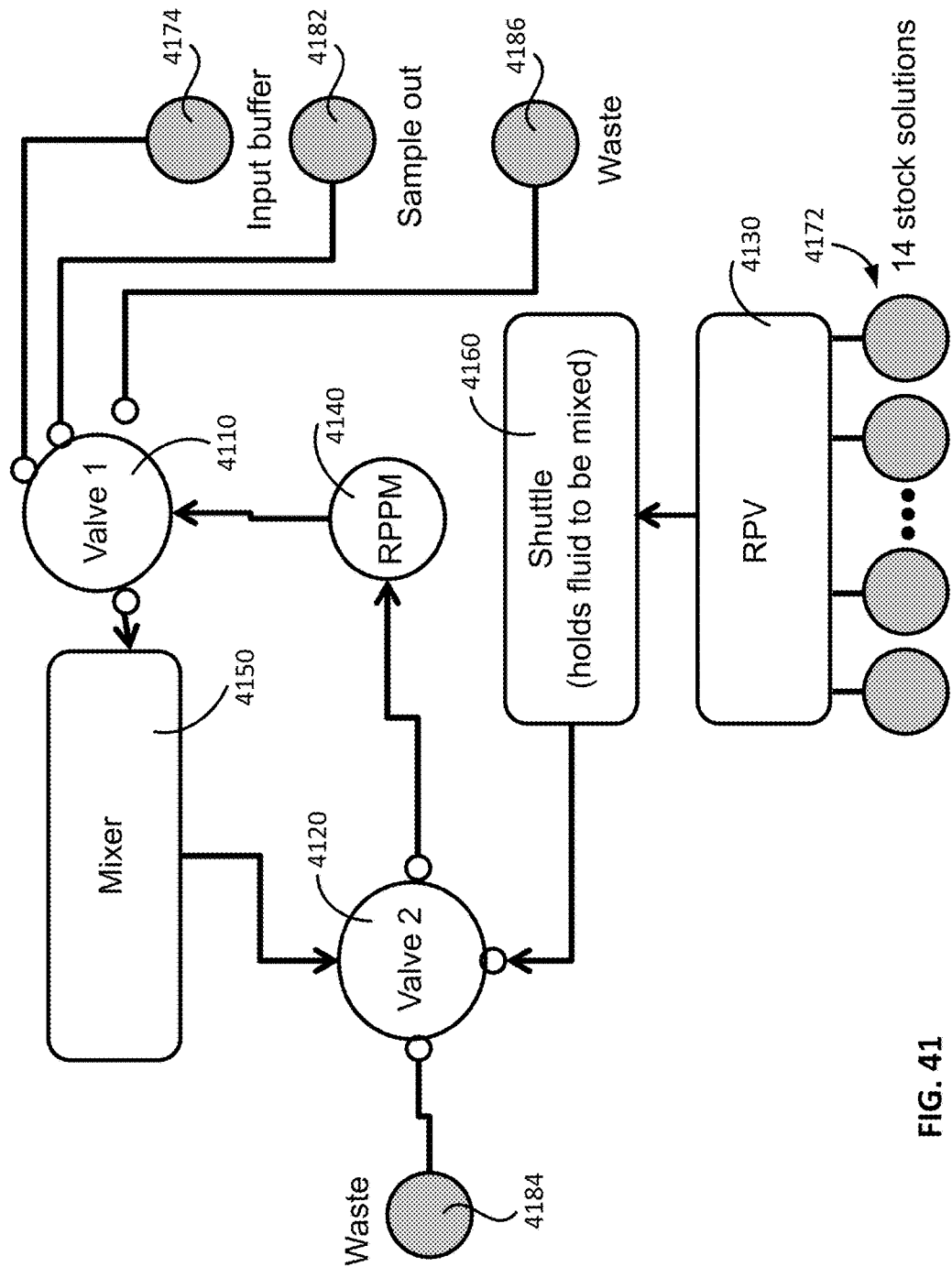
FIG. 41 shows schematic fluidics of a MicroFormulator according to one embodiment of the invention. There are three special-purpose computer-controlled multiport RPVs in the MicroFormulator and one computer-controlled metering RPPM. The basic process of providing a particular rationed mixture of a number of, e.g., fourteen (14) individual stock solutions involves cycling the MicroFormulator through four different valve configuration modes in a sequence of events in which the computer controls the precise pumping rate of the metering RPPM. The process of one low-volume sample of a specific mix involves the four following steps: 1) Load Shuttle: The computer sequentially selects which of the 14 stock solutions are to be used and sequentially loads an appropriate amount of each into the "Shuttle" microfluidic region by utilizing the metering capabilities of the RPPM. 2) Shuttle To Mixer: Valve 1 and Valve 2 are adjusted to allow the RPPM to move a precise volume of fluid from the shuttle to the mixer region where the serial oriented plugs of reagents will be mixed; 3) Mix: Valve 1, Valve 2, and the metering RPPM are operated in conjunction to create a uniformly mixed plug of the required stock solutions; 4) Empty Mixer/Sample Output: Valve 1, Valve 2, and the RPPM are operated in conjunction in order to move the appropriately selected portion of fluid located within the mixer to the Sample Output port.
Figure 43:
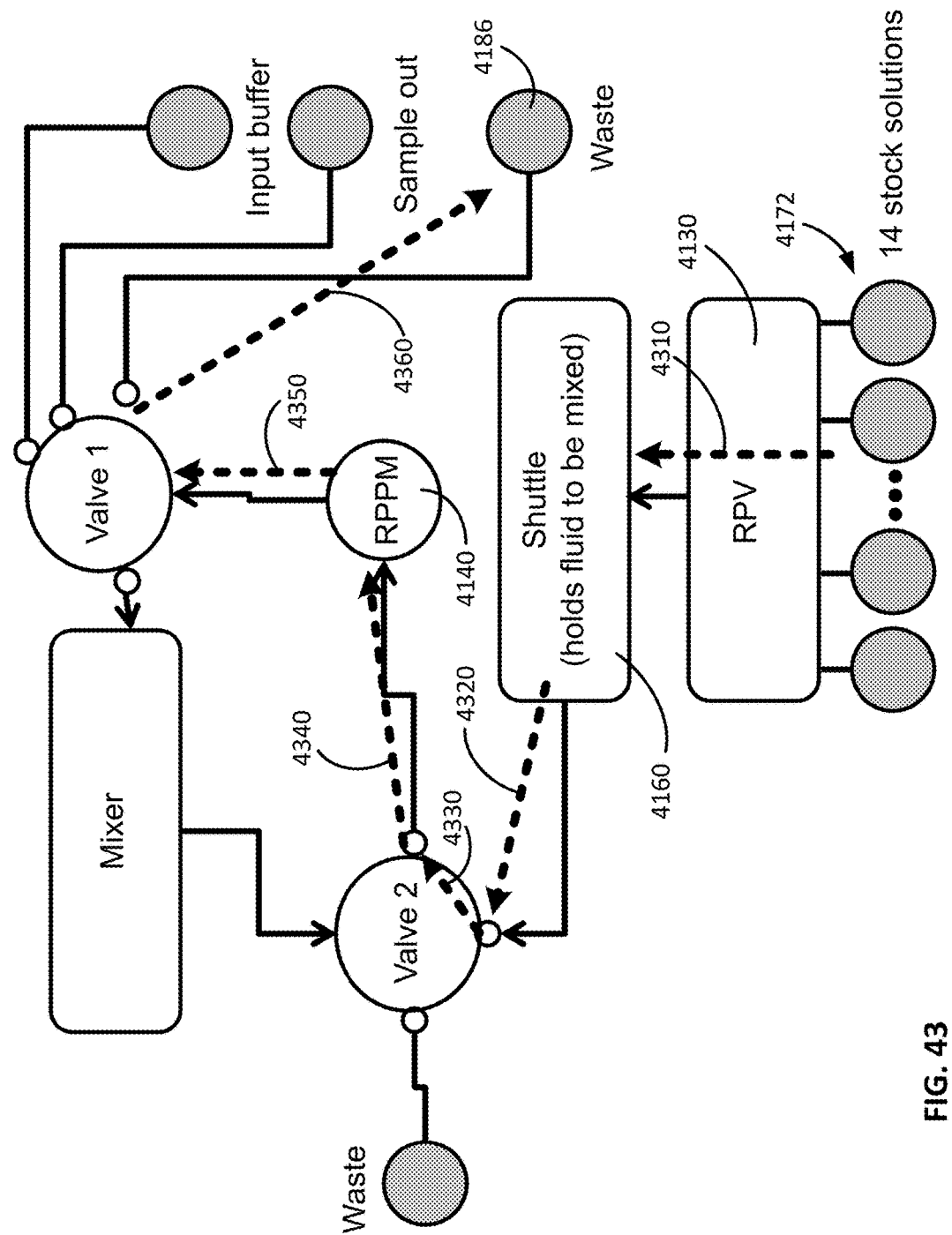
FIG. 43 shows schematically fluid flow directions through the MicroFormulator of FIG. 41 during the "Load Shuttle" phase of operation. Note that if all 14 stock solutions are used in a particular formulation, then the bottom-most RPV, a single pole 14 position fluidic switch, would cycle through all 14 positions, and at each position the metering RPPM would withdraw an appropriate amount of fluid from the stock solution reservoir and deposit it in the shuttle microfluidic region.
Figure 45:
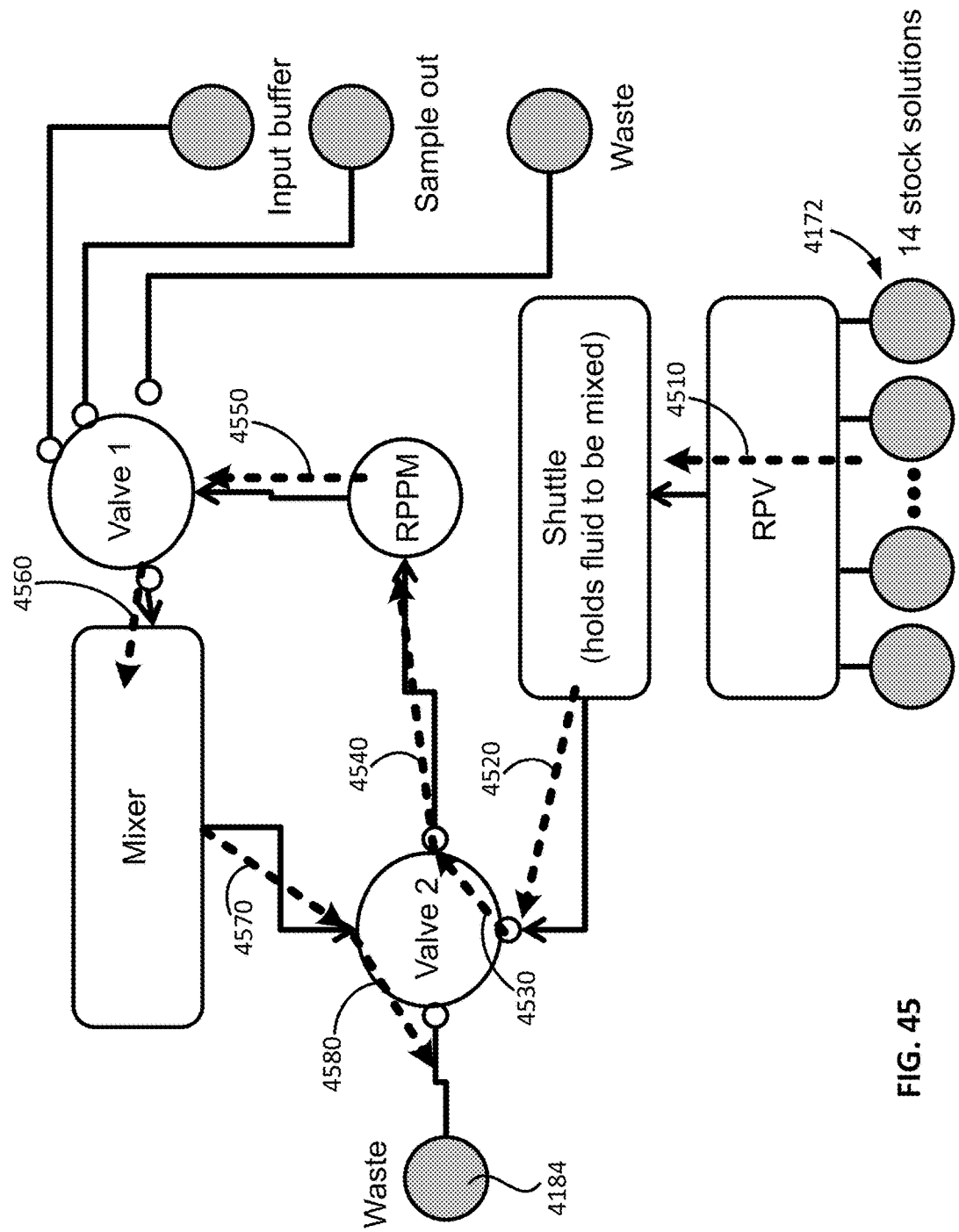
FIG. 45 shows schematically fluid flow directions through the MicroFormulator of FIG. 41 during the "Shuttle to Mixer" mode of operation. Note that the computer-controlled metering RPPM is responsible for moving a precisely defined volume of liquid from the shuttle microfluidic region into a precise location within the mixer portion of the device. Also note that this same fluid pathway mode of operation can be used when it is necessary to flush the entire contents of the shuttle and mixer into Waste for purposes of preconditioning the shuttle and mixer prior to a new microformulation assembly sequence.
Figure 47:
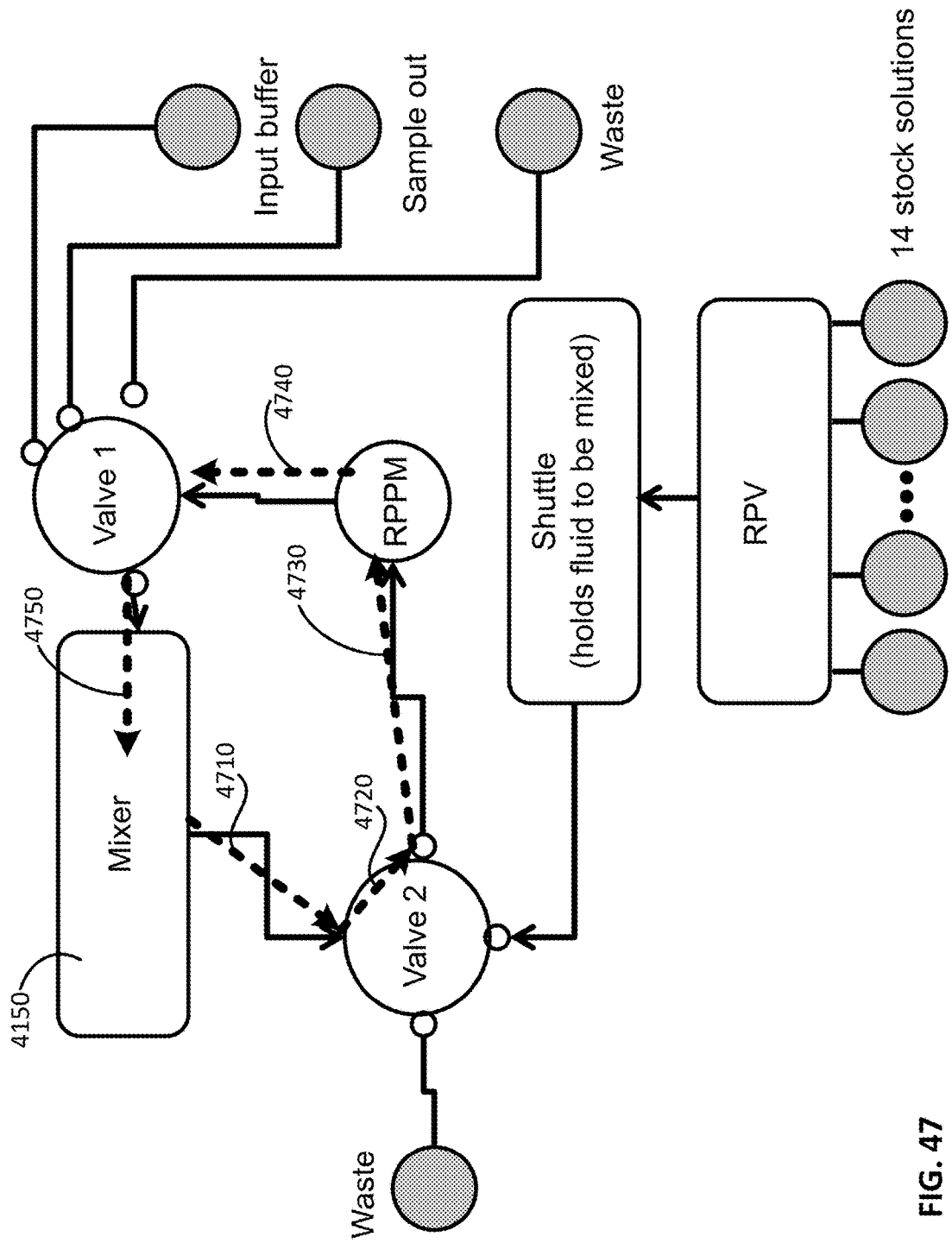
FIG. 47 shows schematically fluid flow directions through the MicroFormulator of FIG. 41 during the "Mix" mode of operation. Depending on the exact formulation desired and the amount of mixing required, the fluid in the mixer can be recirculated numerous times in order to promote complete mixing of the serial plugs of stock solution which were delivered from the shuttle. In one variation of this mixing method that may be appropriate for certain formulations, the RPPM can be caused to sequentially change pump direction to provide mixing within the Mixer microfluidic section.
Figure 49:
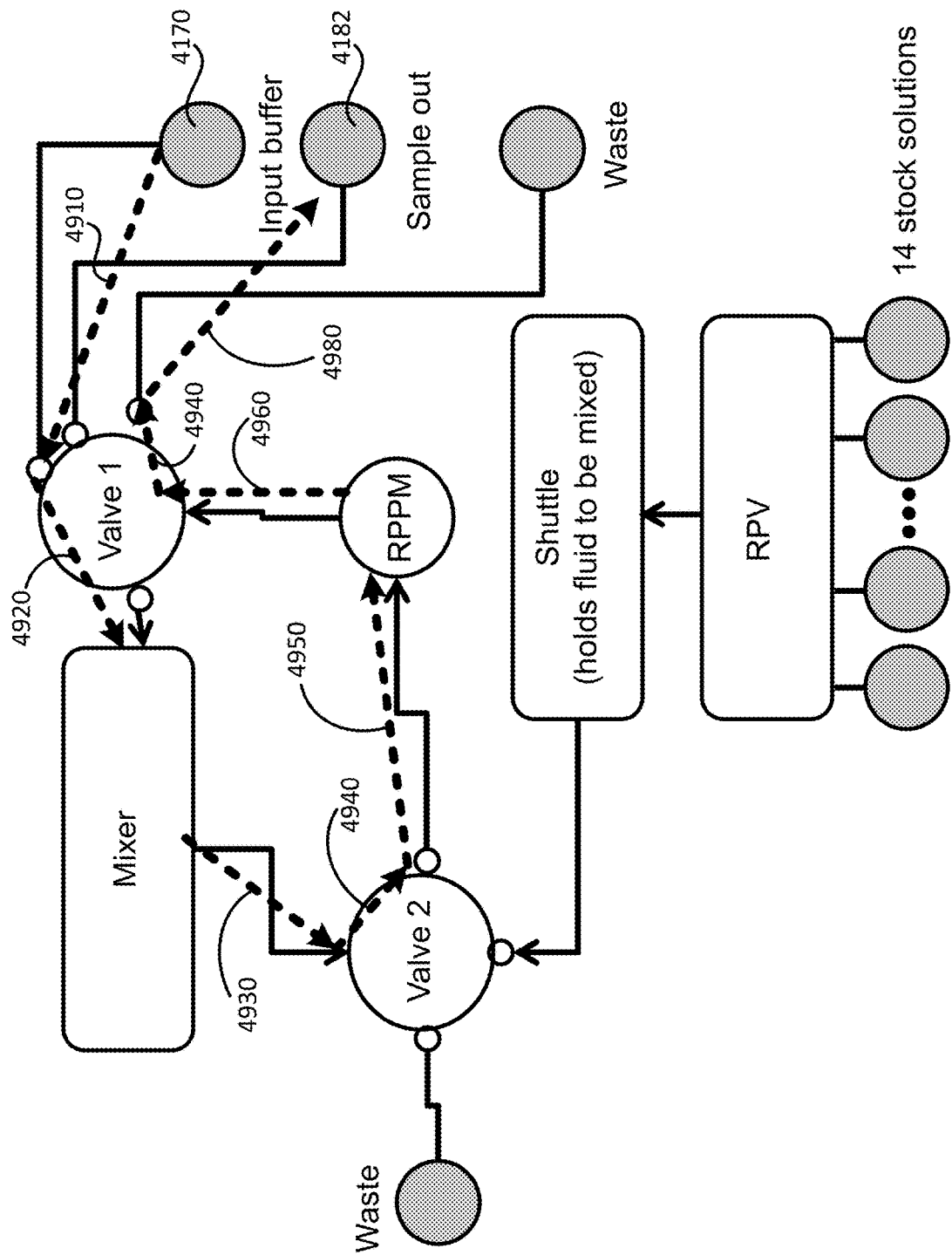
FIG. 49 shows schematically fluid flow directions through the MicroFormulator of FIG. 41 during the "Output Sample" mode of operation. In this mode the input buffer is used to displace fluid in the mixer portion and deliver the mixed formulation to the output port. Note that the computer-controlled metering RPPM is responsible for determining the precise volume of fluid to deliver to the sample output port.

FIG. 41 shows schematic fluidics of the MicroFormulator. There are three special-purpose computer-controlled multi-port RPVs 4110, 4120, and 4130 in the MicroFormulator and one computer-controlled metering RPPM 4140. The basic process of providing a particular rationed mixture of a number of, e.g., fourteen (14) individual stock solutions involves cycling the MicroFormulator through four different valve configuration modes in a sequence of events in which the computer controls the precise pumping rate of the metering RPPM 4140. The process of one low-volume sample of a specific mix involves the four following steps: 1) Load Shuttle: The computer sequentially selects which of the 14 stock solutions from the inlet port 4172 are to be used and sequentially loads an appropriate amount of each into the "Shuttle" microfluidic region 4160 by controlling the speed of the RPPM 4140, as shown in FIG. 43. 2) Shuttle To Mixer: Valve 1 (4110) and Valve 2 (4120) are adjusted to allow the RPPM 4140 to move a precise volume of fluid from the shuttle to the mixer region 4150 where the serial oriented plugs of reagents will be mixed, as shown in FIG. 45; 3) Mix: Valve 1 (4110), Valve 2 (4120), and the metering RPPM 4140 are operated in conjunction to create a uniformly mixed plug of the required stock solutions, as shown in FIG. 47; 4) Empty Mixer/Sample Output: Valve 1 (4110), Valve 2 (4120), and the RPPM 4140 are operated in conjunction in order to move the appropriately selected portion of fluid located within the mixer to the Sample Output port 4182, as shown in FIG. 49.

Figure 42:
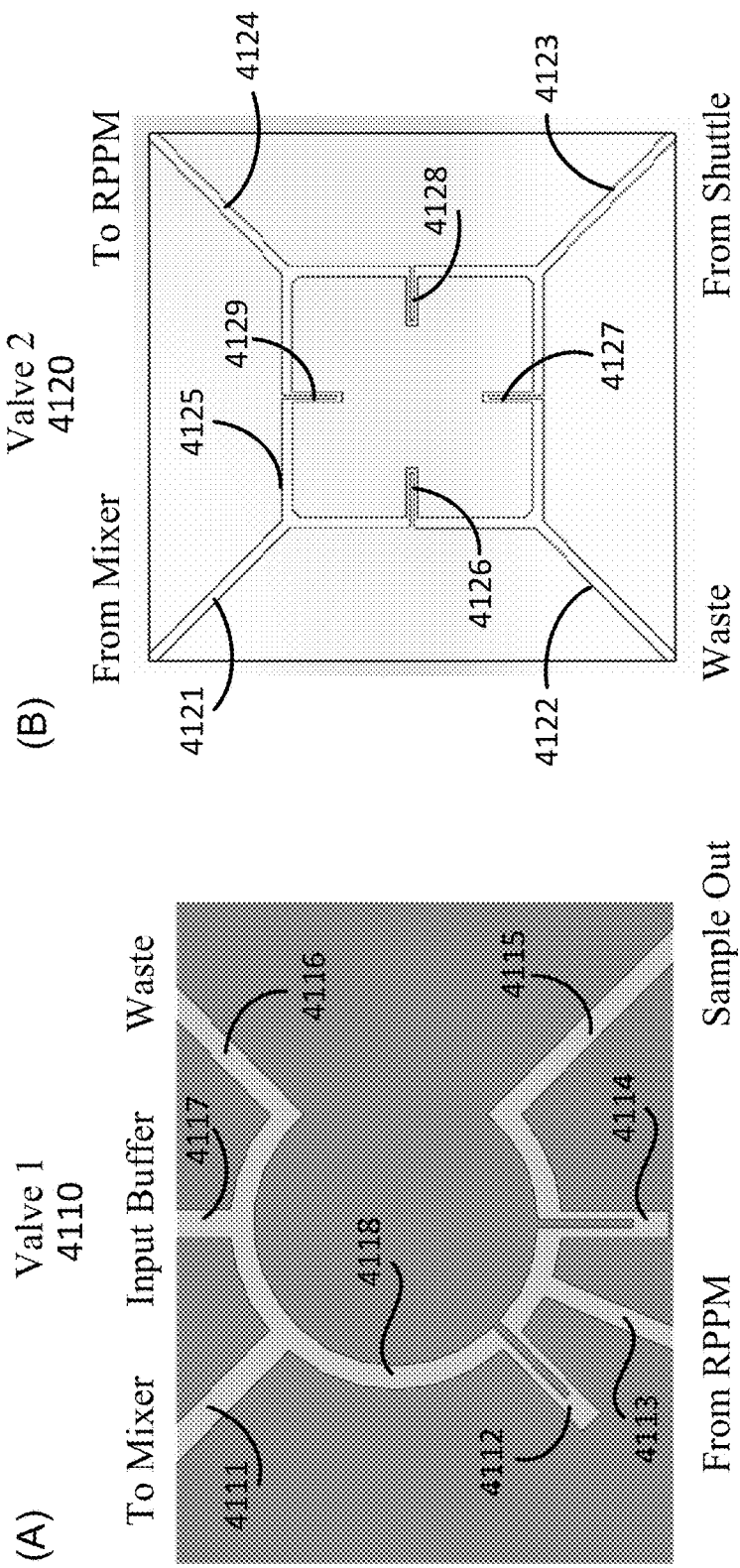
FIG. 42 shows a layout of particular Rotary Planar Valve fluid channel implementations for Valve 1 (A) and Valve 2 (B) of the MicroFormulator shown in FIG. 41. Depending on the orientation of ball bearings which compress the fluidic channels, various combinations of ports can be connected to one another.

FIG. 42 shows a layout of particular Rotary Planar Valve fluid channel implementations for Valve 1 (4110) and Valve 2 (4120) of the MicroFormulator shown in FIG. 41. Depending on the orientation of ball bearings which compress the fluidic channels, various combinations of ports can be connected to one another. As shown in FIG. 42A, Valve 1 (4110) has six selectively controllable channels 4111, 4112, 4114-4117 and an always-open fluidic channel 4113 connected to each other through a central arc fluidic path 4118. Valve 1 (4110) also has two node portions 4112 and 4114 connected to the central fluidic path 4118 such that when a force is applied onto the node portion 4112, no fluid flow from the always-open channel 4113 to any of the selectively controllable channels 4111, 4116 and 4117 is allowed, and when a force is applied onto the node portion 4114, no fluid flow from the always-open channel 4113 to the selectively controllable channel 4115 is allowed. As shown in FIG. 42B, Valve 2 (4120) has four selectively controllable channels 4121-4124 connected to corners of a square fluidic path 4125. Each portion of the square fluidic path 4125 has a node (4126, 4127, 4128, or 4129) formed such that when a force is applied onto the node, no fluid flow through the respective portion of the square fluidic path 4125 is allowed.

FIG. 43 shows schematically fluid flow directions 4310, 4320, 4330, 4340, 4350, and 4360 through the MicroFormulator of FIG. 41 during the "Load Shuttle" phase of operation. Note that if all 14 stock solutions are used in a particular formulation, then the bottom-most RPV 4130, a single-pole, 14-position fluidic switch connected to 14 solution reservoirs 4172, would cycle through all 14 positions, and at each position the metering RPPM 4140 would withdraw an appropriate amount of fluid from the stock solution reservoir and deposit it in the shuttle microfluidic region 4160.

Figure 44:
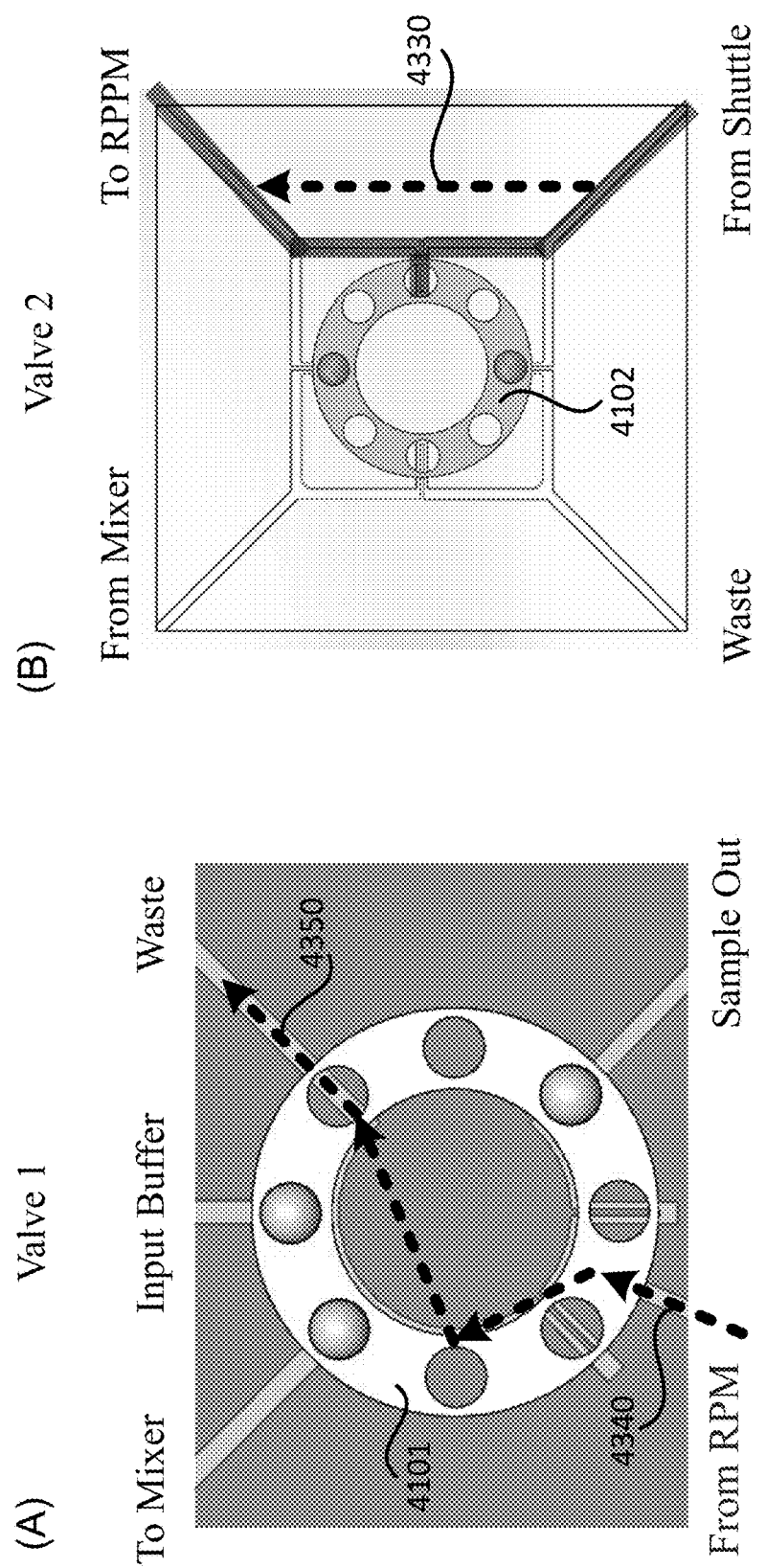
FIG. 44 shows the fluid flow paths through Valve 1 (A) and Valve 2 (B) when the MicroFormulator of FIG. 41 is in the "Load Shuttle" mode of operation.

FIG. 44 shows the fluid flow paths through Valve 1 (4110) and Valve 2 (4120) when the MicroFormulator of FIG. 41 is in the "Load Shuttle" mode of operation. For Valve 1 (4110), the actuator 4101 is configured and positioned such that the selectively controllable fluidic channels 4111, 4117, 4115, 4112 and 4114 are closed, and the selectively controllable channel 4116 is opened. Therefore, the fluid input from the always-open channel 4113 flows through the central arc channel 4118 to the selectively controllable channel 4116 and flows out from the selectively controllable channel 4116. For Valve 2 (4220), the actuator 4102 is configured and positioned such that a fluid flows from the bottom-right channel 4123 to the top-right channel 4124 through the node 4128 of the square fluidic path 4125.

FIG. 45 shows schematically fluid flow directions 4520, 4530, 4540, 4550, 4560, 4570, 4580 through the MicroFormulator of FIG. 41 during the "Shuttle to Mixer" mode of operation. Note that the computer-controlled metering RPPM 4140 is responsible for moving a precisely defined volume of liquid from the shuttle microfluidic region 4160 into a precise location within the mixer portion 4150 of the device. Also note that this same fluid pathway mode of operation can be used when it is necessary to flush the entire contents of the shuttle and mixer into Waste for purposes of preconditioning the shuttle and mixer prior to a new microformulation assembly sequence.

Figure 46:
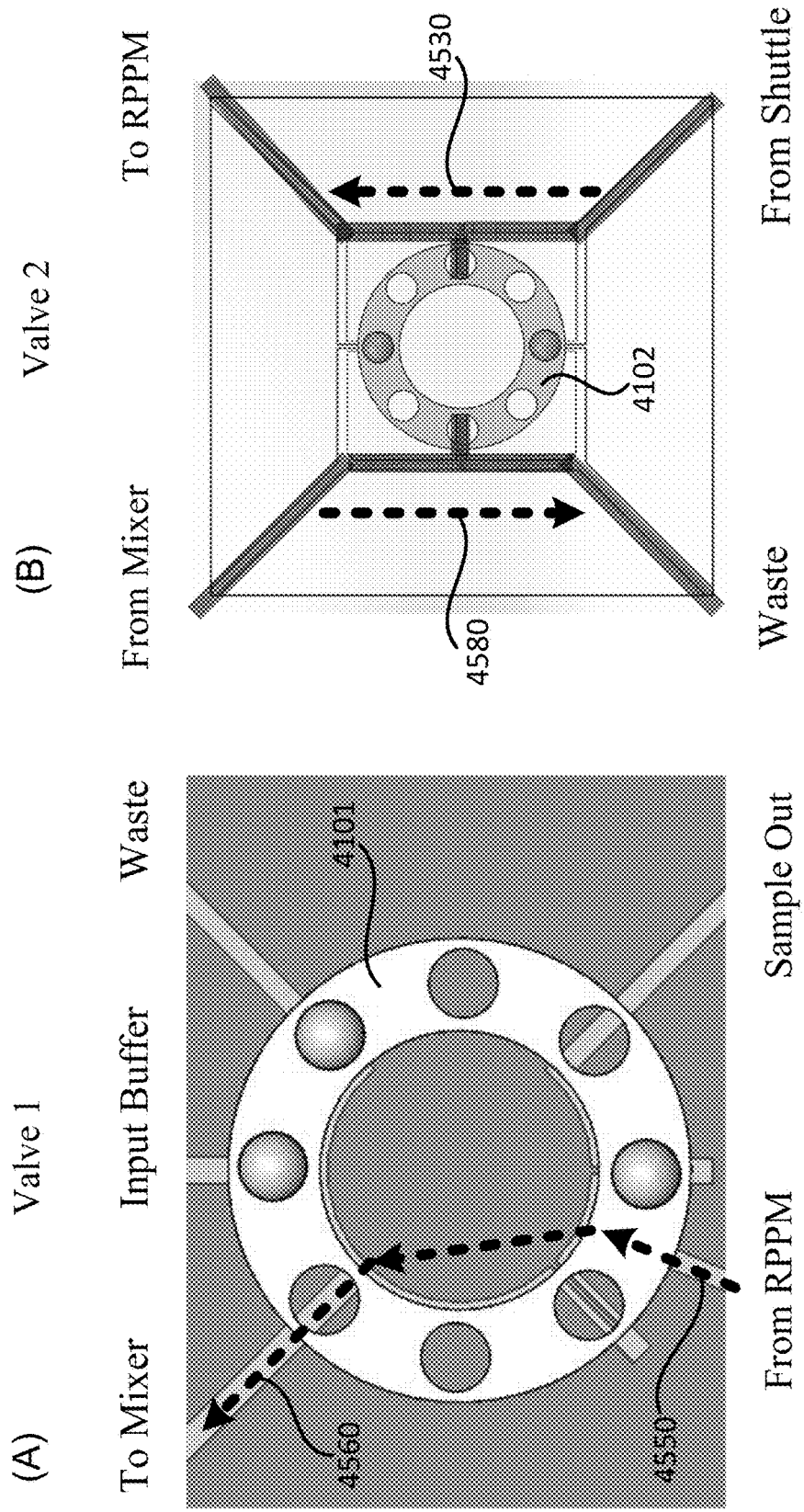
FIG. 46 shows the fluid flow paths through Valve 1 (A) and Valve 2 (B) when the MicroFormulator of FIG. 41 is in the "Shuttle to Mixer" mode of operation.

FIG. 46 shows the fluid flow paths through Valve 1 (4110) and Valve 2 (4120) when the MicroFormulator of FIG. 41 is in the "Shuttle to Mixer" mode of operation. For Valve 1 (4110), the actuator 4101 is positioned such that only fluid flow from the always-open channel 4113 to the selectively controllable channel 4111 is allowed. For Valve 2 (4220), the actuator 4102 is positioned such that fluids can flow from the bottom-right channel 4123 to the top-right channel 4124 through the node 4128 of the square fluidic path 4125, and from the top-left channel 4121 to the bottom-left channel 4122 through the node 4126 of the square fluidic path 4125.

FIG. 47 shows schematically fluid flow directions 4710, 4720, 4730, 4740 and 4750 through the MicroFormulator of FIG. 41 during the "Mix" mode of operation. Depending on the exact formulation desired and the amount of mixing required, the fluid in the mixer 4150 can be recirculated numerous times in order to promote complete mixing of the serial plugs of stock solution which were delivered from the shuttle. In one variation of this mixing method that may be appropriate for certain formulations, the RPPM 4140 can be caused to sequentially change pump direction to provide mixing within the Mixer microfluidic section.

Figure 48:
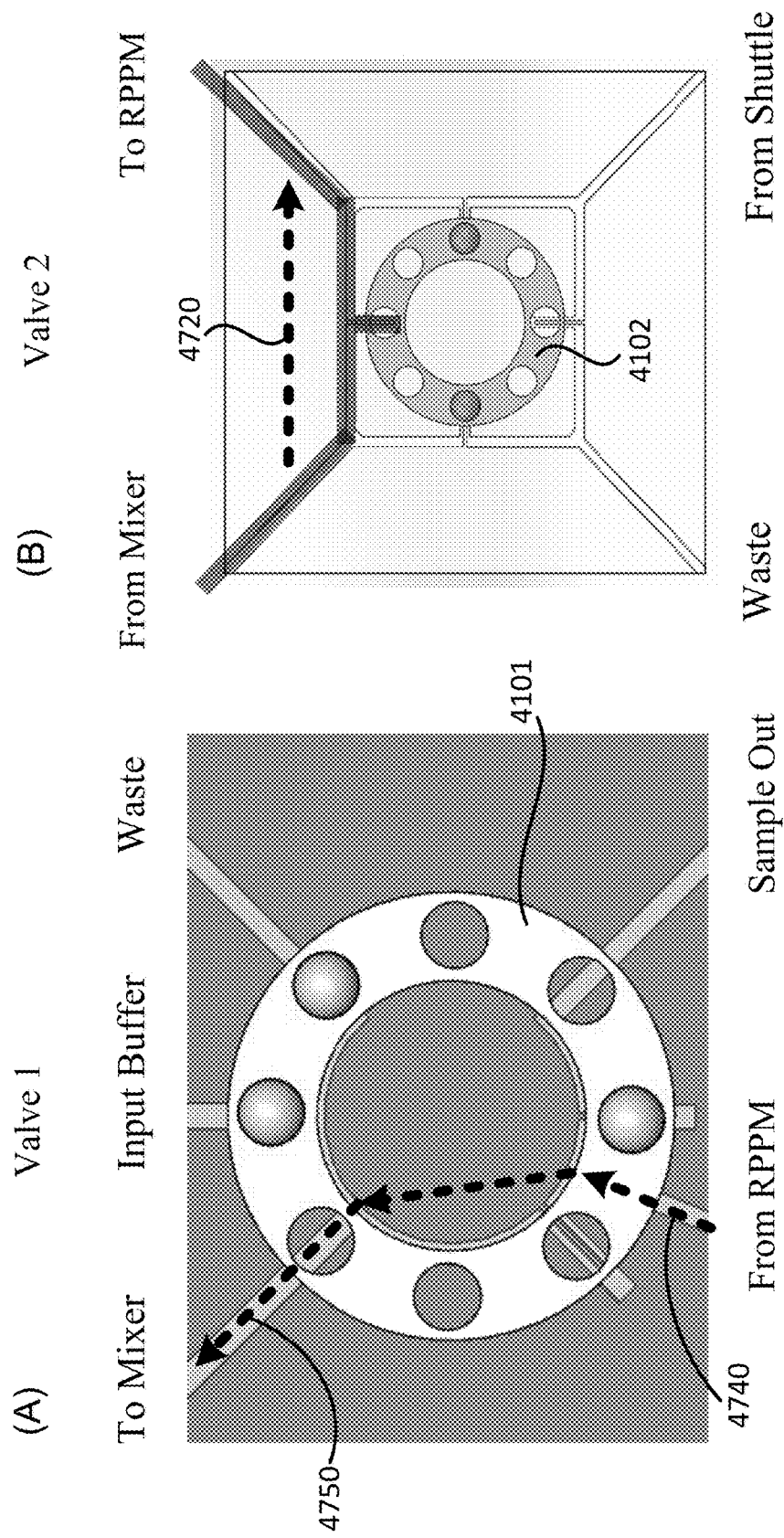
FIG. 48 shows the fluid flow paths through Valve 1 (A) and Valve 2 (B) when the MicroFormulator of FIG. 41 is in the "Mix" mode of operation.

FIG. 48 shows the fluid flow paths through Valve 1 (4110) and Valve 2 (4120) when the MicroFormulator of FIG. 41 is in the "Mix" mode of operation. For Valve 1 (4110), the actuator 4101 is positioned such that only fluid flow from the always-open channel 4113 to the selectively controllable channel 4111 is allowed. For Valve 2 (4220), the actuator 4102 is positioned such that a fluid flows from the top-left channel 4121 to the top-right channel 4124 through the node 4129 of the square fluidic path 4125.

FIG. 49 shows schematically fluid flow directions 4910, 4920, 4930, 4940, 4950, 4960, 4970, and 4980 through the MicroFormulator of FIG. 41 during the "Output Sample" mode of operation. In this mode the input buffer 4170 is used to displace fluid in the mixer portion 4150 and deliver the mixed formulation to the output port 4182. Note that the computer-controlled metering RPPM 4140 is responsible for determining the precise volume of fluid to deliver to the sample output port 4182.

Figure 50:
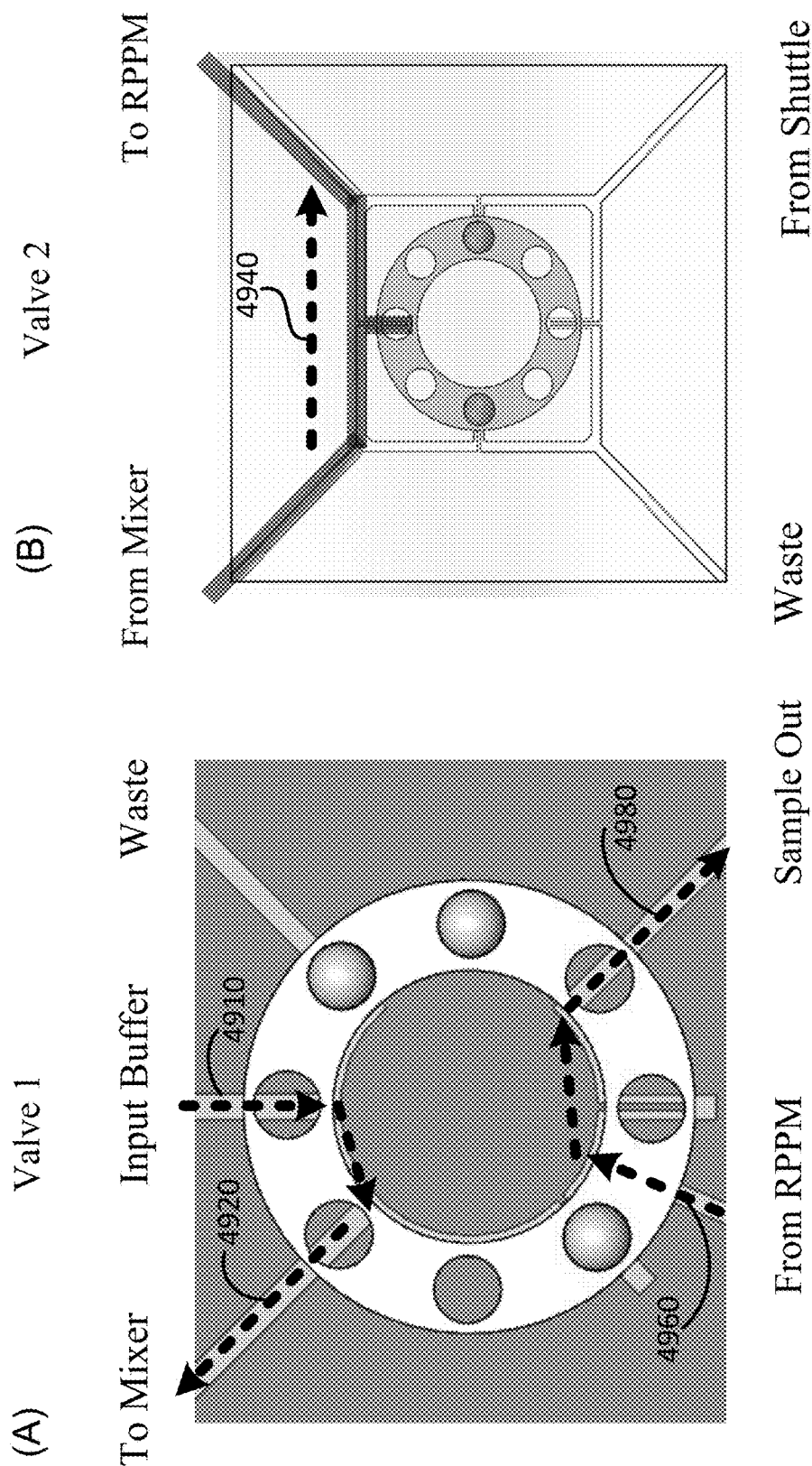
FIG. 50 shows the fluid flow paths through Valve 1 (A) and Valve 2 (B) when the MicroFormulator is in the "Output Sample" mode of operation.

FIG. 50 shows the fluid flow paths through Valve 1 (4110) and Valve 2 (4120) when the MicroFormulator is in the "Output Sample" mode of operation. For Valve 1 (4110), the actuator 4101 is positioned such that two fluid paths are opened: one is from the selectively controllable channel 4117 through the arc fluidic path 4118 to the selectively controllable channel 4111, and the other is from the always-open channel 4113 to the selectively controllable channel 4115. For Valve 2 (4220), the actuator 4102 is positioned such that a fluid flows from the top-left channel 4121 to the top-right channel 4124 through the node 4129 of the square fluidic path 4125.

Figure 51:
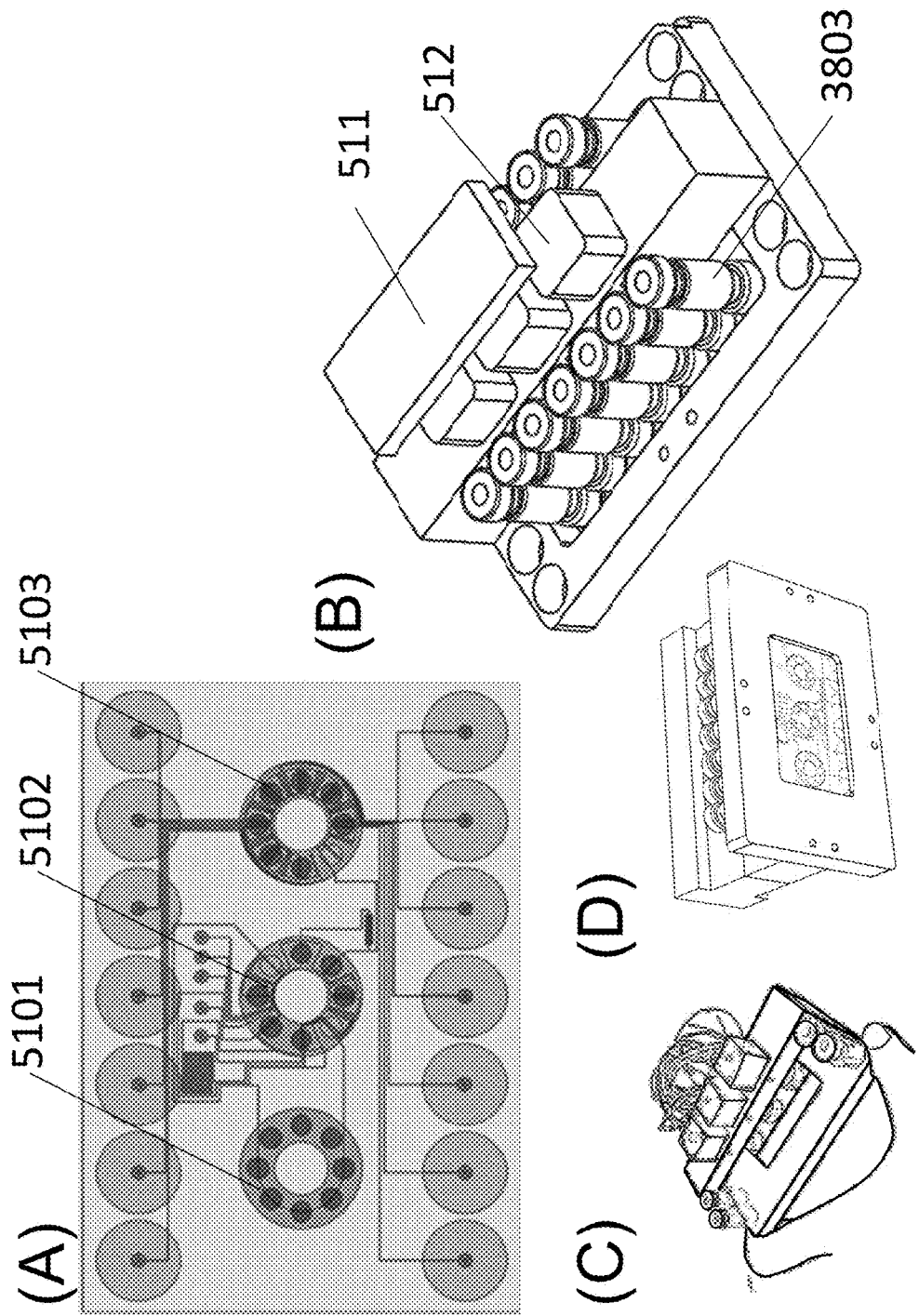
FIG. 51 shows a MicroFormulator with three in-line RPVs/RPPMs according to one embodiment of the invention.

FIG. 51 shows a MicroFormulator with three in-line RPVs/RPPMs 5101-5103 according to another embodiment of the invention.

FIG. 52 shows a MicroFormulator based on two selector valves, an input valve 5201, and an RPPM according to yet another embodiment of the invention.

FIGS. 53A-53E show the fluidics of the MicroFormulator depicted in FIG. 52 having an input RPV 5201, a first valve 5301, a second valve 5302, and an RPPM 2702 according to an alternative embodiment of the invention and overview of its operations. The inlets include Sample-In ports 5306, and the outlets have a Sample-Out port 5304, and Waste ports 5305. In the exemplary embodiment, the MicroFormulator has no shuttle region, and the input solutions are collected in the RPPM 2702. The operations are similar to that of the MicroFormulator shown in FIG. 41. FIGS. 53B-53E show respectively the four operation modes: the Load Sample mode, the Sample to Mixer mode, the Mix mode, and the Sample Output mode, where dashed arrows represent the fluidic directions in each operation mode.

Referring to FIGS. 54A-54E, a mask layout of a MicroFormulator is shown according to one embodiment of the invention, which uses a slightly different mode selector valve implementation from the simplified three-valve implementation. In this embodiment, fluid inputs are selected from inputs 5409 of a fourteen-port RPV 5401 and are drawn with an RPPM 2702 into a loading shuttle 5402 that holds inputs while RPPM 2702 flushes RPV 5401 with solvent to the waste port 5305. Inputs in loading shuttle 5402 are then drawn into the mixing chamber 5303 and recirculated with RPPM 2702 until sufficiently mixed, at which point they are pumped out with RPPM 2702 through the output port 5304. In this exemplary embodiment, mode switching of the device is achieved with an RPV 5403 that sequentially opens and closes channel paths with a thrust bearing located in the compression zone. The RPV 5403 controls washout, loading, mixing, and delivery of custom solutions, and is a four-position mode selector valve. This MicroFormulator has the advantage of requiring fewer motors. However, the fluid path lengths are longer and more complicated than the MicroFormulator design disclosed in FIGS. 52 and 53. Other microfluidic layouts can accomplish the same functions. FIGS. 54B-54E show respectively the four operation modes: the Load Sample mode, the Sample to Mixer mode, the Mix mode, and the Sample Output mode.

The embodiment of the MicroFormulator shown in FIG. 16 contains a total of 18 vials for fluid storage (waste, further analysis, arterial supply, venous supply, stock solutions, etc.), 6 motors to provide arterial pressure, and venous return, in addition to full MicroFormulator support. It has the ability to mix drugs, precondition organs, and provide signaling molecules, metabolites, and hormones that would otherwise be provided by missing organs. The interconnect system would allow the MicroFormulator to address organs individually, serially, or in parallel. It is important to realize that control of the Missing Organ MicroFormulator may be based upon the function or performance of other modules, and may do so in a model-dependent manner. For example, if the interconnected Microphysiological System (MPS) does not have a pancreas with insulin-releasing beta cells, the MicroFormulator can be programmed to release insulin in a glucose-dependent manner, with the insulin release being governed by a glucose sensor in a MicroClinical Analyzer.

Improvements to RPPM and RPV Technologies

In one aspect, the invention, among other things, is focused on improvements to the rotary planar peristaltic micropump (RPPM) and rotary planar valve (RPV) disclosed by Parker A. Gould et al. in PCT publication No. WO2012/048261, and Wikswo et al. in PCT application Serial No. PCT/US2012/068771, which are incorporated herein in their entireties by reference, with regard to improved performance and manufacturability of the interface between the motor providing torque and the flexible polymer or similar membrane allowing the pumping or occlusion of fluidic channels. The major aspects of this invention are 1) the removal of the PDMS washer between the drive shaft and ball cage containing bearings; 2) the working demonstration of an RPV; 3) RPPM/RPV designs utilizing a hot-embossed plastic substrate; 4) an implementation of a MicroFormulator; and 5) an implementation of wireless control of multiple DC and/or stepper motors.

According to embodiments of the invention, the RPPM has the actuator and a fluidic path in fluidic communication with a first port and a second port. The actuator includes a shaft engaged with a motor such that activation of the motor causes the shaft to rotate; and a bearing assembly engaged with the shaft. The bearing assembly includes a bearing cage defining a plurality of spaced-apart openings thereon, and a plurality of rolling-members accommodated in the plurality of spaced-apart openings of the bearing cage, such that when the shaft rotates, the plurality of rolling-members of the bearing assembly rolls along a circular path. The fluidic path is positioned under the actuator and is coincident with the circular path, such that when the shaft of the actuator rotates, the plurality of rolling-members of the bearing assembly rolls along the fluidic path to cause a fluid to transfer between the first port and the second port.

In one embodiment, each of the plurality of rolling-members includes a ball, a roller, or a wheel.

Figure 55D:
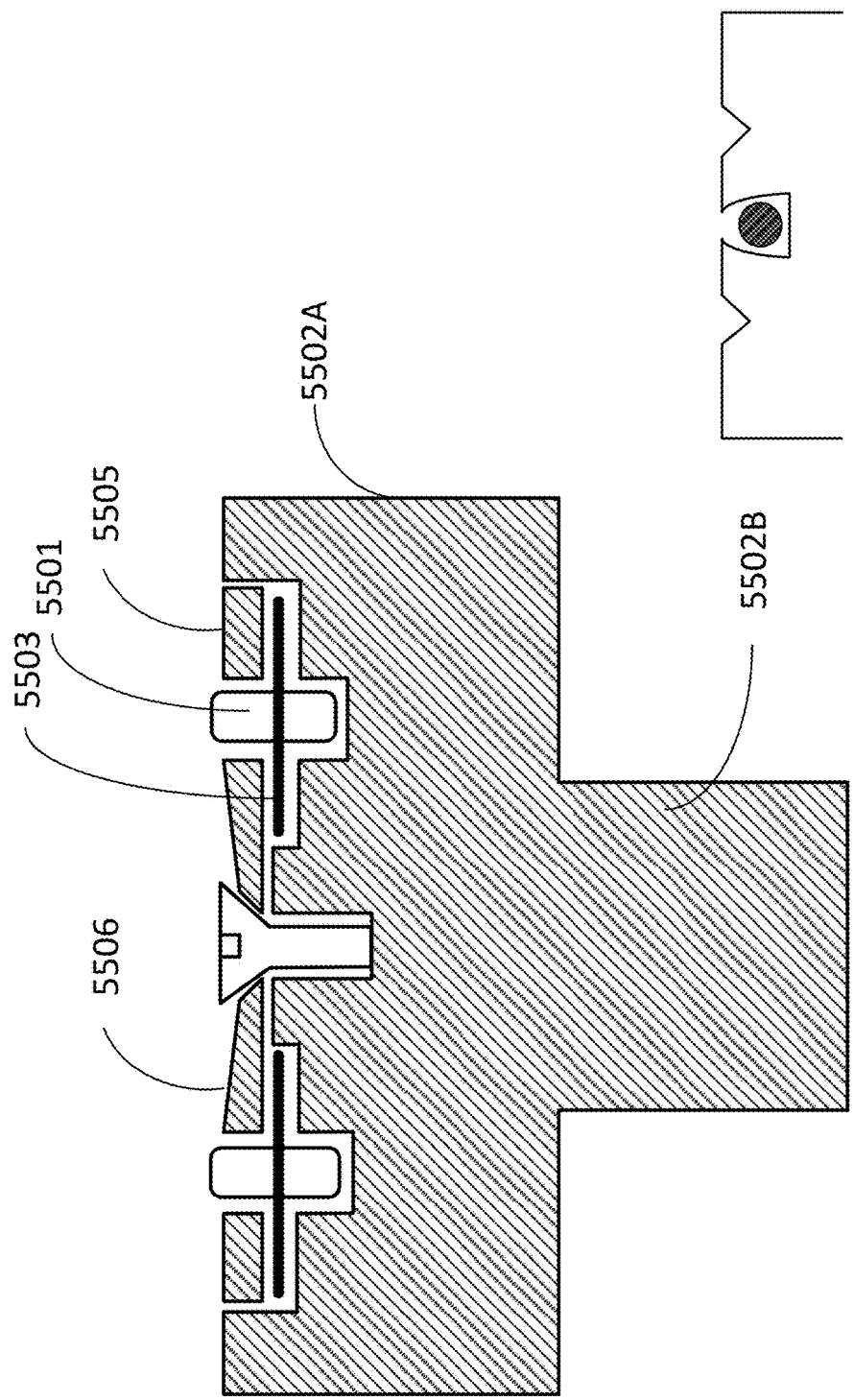
Figure 55E:
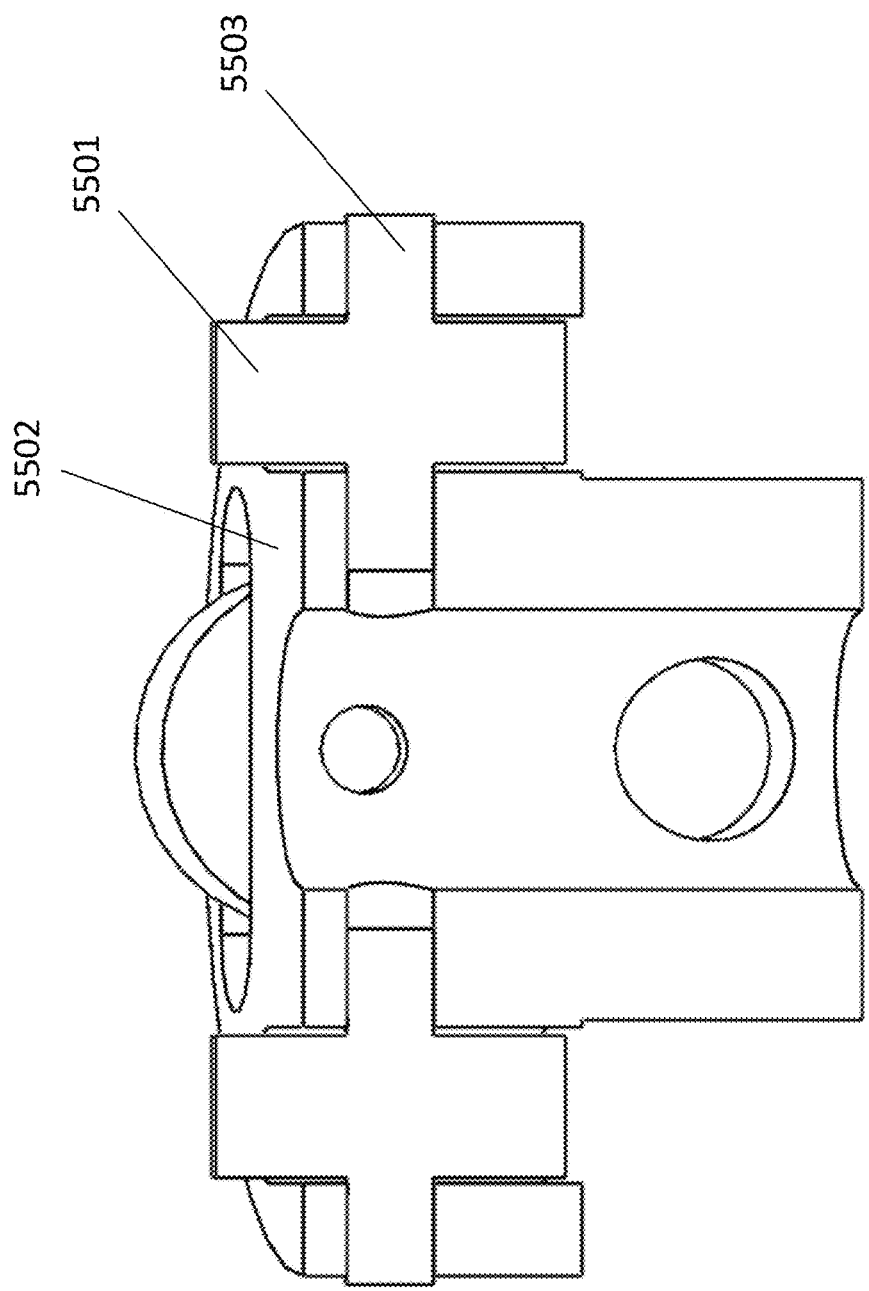
Figure 56:
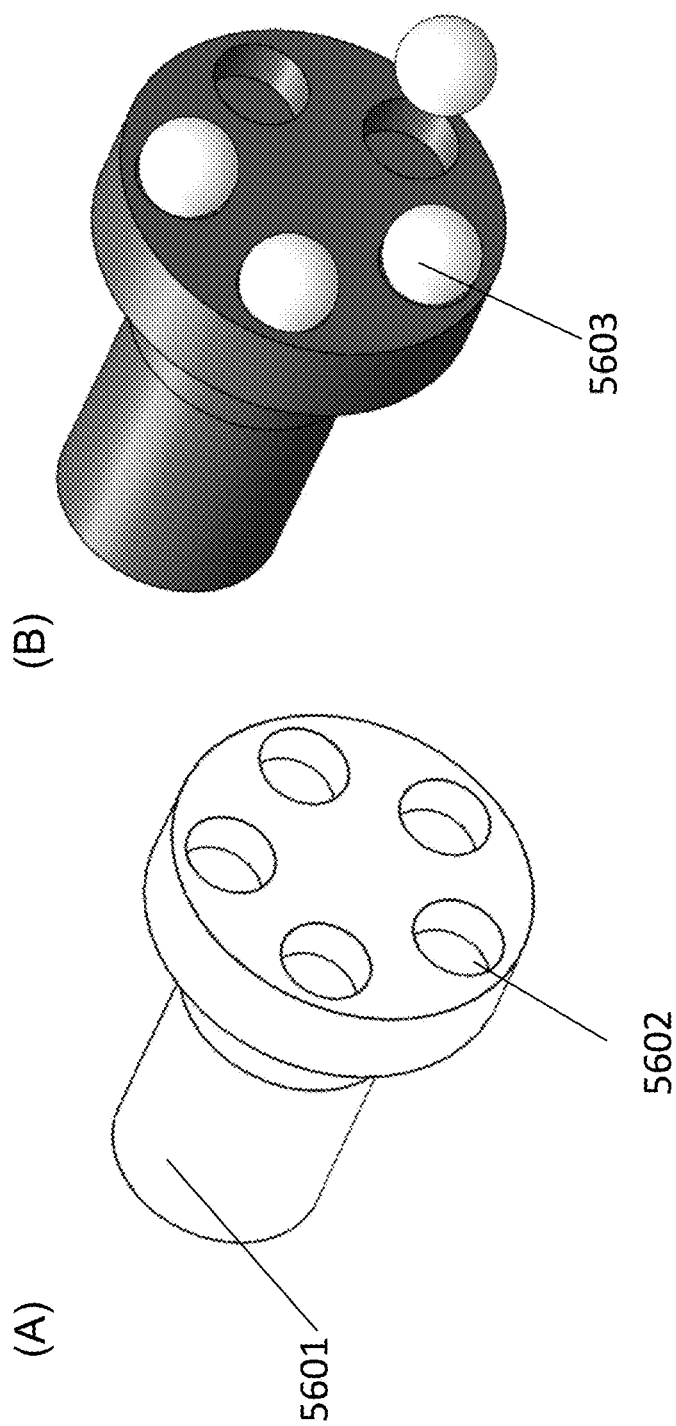
FIG. 56 shows a glass ball bearing in a brass ball-drive head for either a pump or valve according to one embodiment of the invention: (A) a bearing cage or socket, (B) bearing cage or socket with ball bearings. Previously, PDMS or other polymeric washers in addition to a ball cage were required to drive the bearings along the pump channels. In this new implementation, neither the washer nor the ball cage is required, as they have both been incorporated into the rotating pump head.
Figure 59:
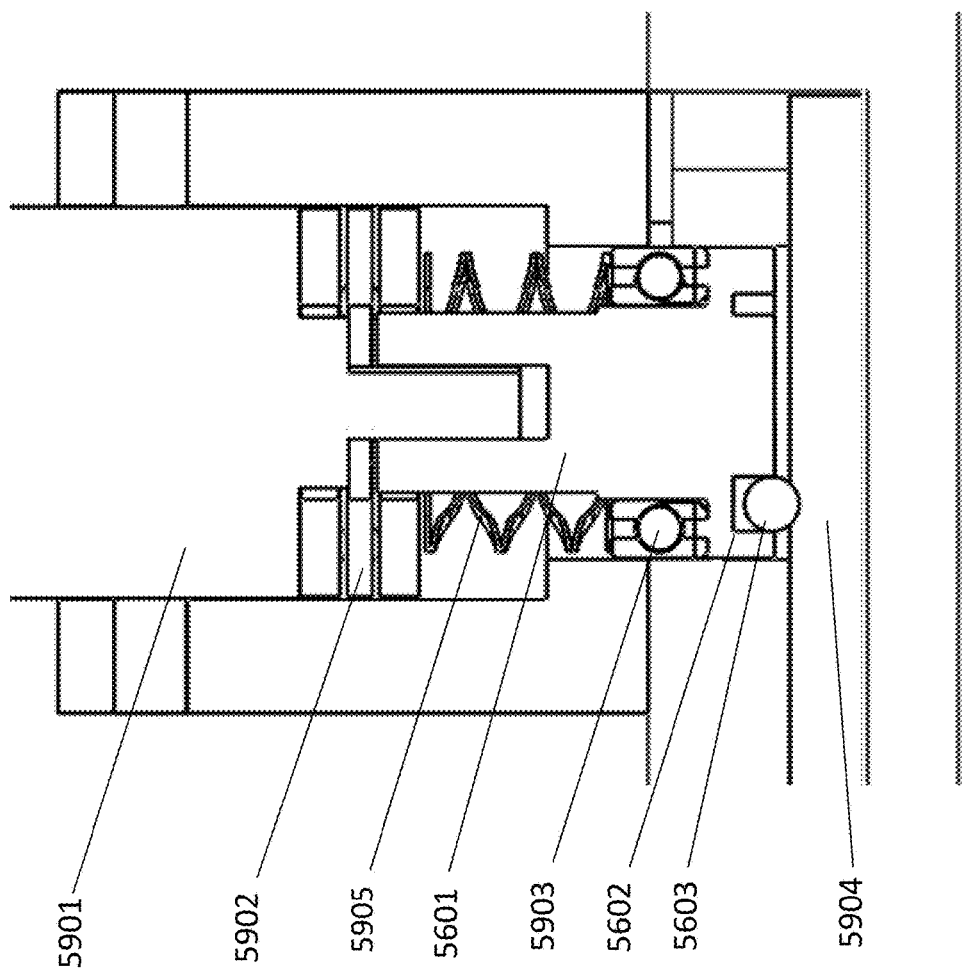
FIG. 59 shows a cut-away of a socket-connector or bearing assembly that drives the balls by means of a DC motor according to one embodiment of the invention. The motor is connected to the ball bearings by a single brass combination ball cage/drive head. Additional thrust bearings, tensioning springs, and alignment bearings are utilized to ensure little to no wobble of the pump head above the PDMS substrate.

In certain embodiments, as shown in FIGS. 55D, 55E, 56 and 59, the bearing cage has a first cylindrical portion 5502A on which the plurality of spaced-apart openings is defined, and a second cylindrical portion 5502B extending coaxially from the first cylindrical portion 5502A, where the first cylindrical portion 5502A has a diameter that is greater than that of the second cylindrical portion 5502B. The bearing cage may have an outer shaft retaining ring 5505, an inner shaft retaining disk 5506, and pins 5503 positioned in relation to the plurality of spaced-apart openings for securing the rollers 5501. FIG. 56 shows how the cylindrical portion 5602 captures balls 5603. As shown in FIGS. 55E and 59, the second cylindrical portion defines a hole along its central axis into which the shaft is mounted.

Referring to FIG. 55, rollers used for RPPMs are shown according to one embodiment of the invention. The rollers are advantageous because the fluid-driving elements are captured within the device, compliance matching between the fluidic drive head and ball bearings or rollers is not required, and creep-related slow drift in the angular alignment of the motor shaft and the balls is eliminated. The use of a DC stepping motor or a miniature servo mechanism that utilizes a geared motor and a potentiometer or other angular encoder would provide control of the exact angular location, given an initial alignment.

As shown in FIGS. 56-59, the ball-in-socket design provides a low kinetic coefficient of friction (glass ball bearings on brass pump head coefficient of sliding friction $\mu_k$ about 0.2 versus glass ball bearings on rubber $\mu_k$ about 0.7-2). This differential in friction assures that the ball bearings will roll rather than skid, i.e., the upper surface of the glass balls will slide on the brass while the static friction will cause the lower surface of the balls to roll on the PDMS. Other materials can be used instead of brass. Additionally, alternative RPV microfluidic layouts are described and demonstrated.

Figure 57:
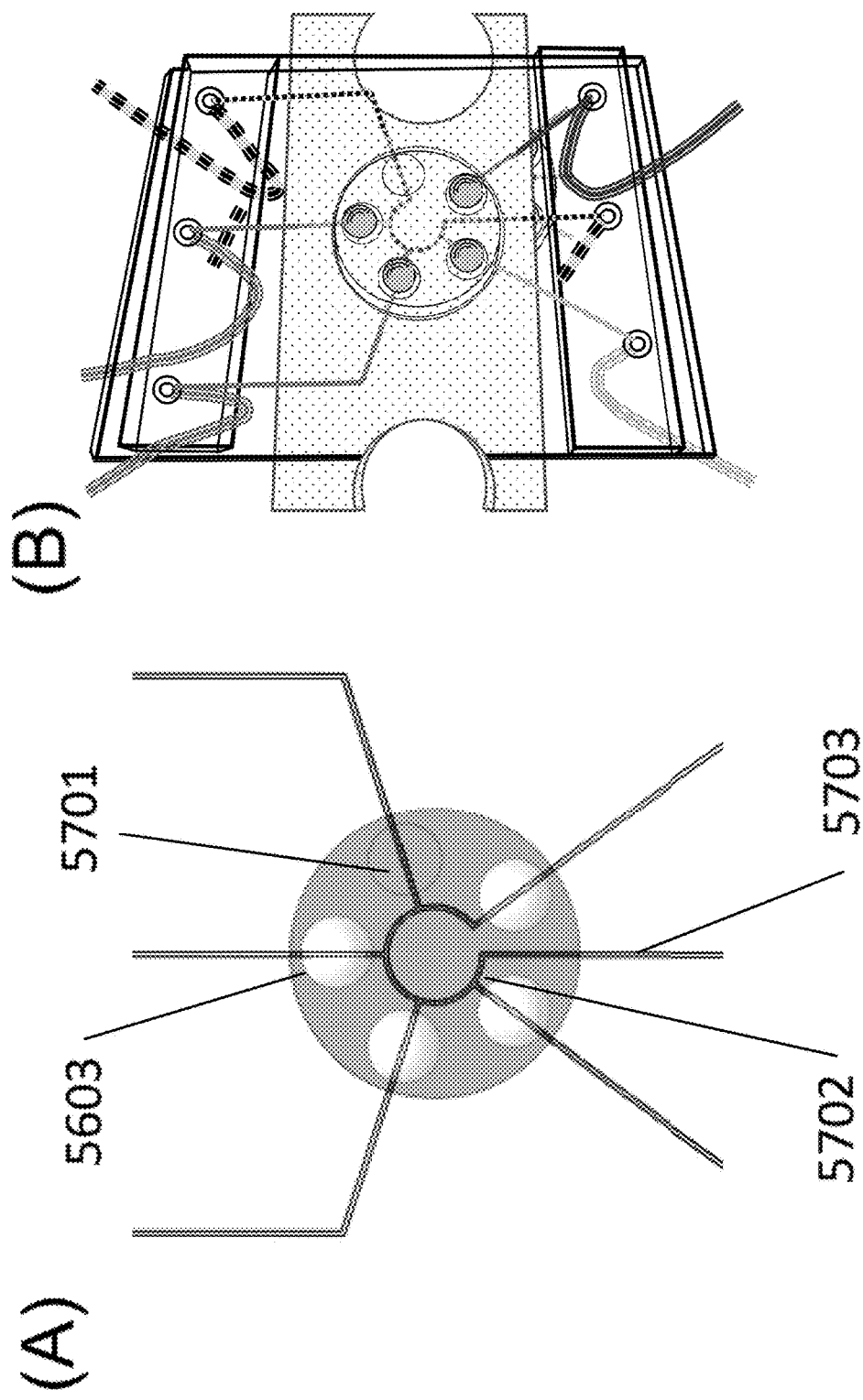
FIG. 57 shows (A) a 5-port RPV microfluidic structure according to one embodiment of the invention, and (B) a prototype of the design, with a red channel clearly visible where no ball bearing compresses the channel.
Figure 58:
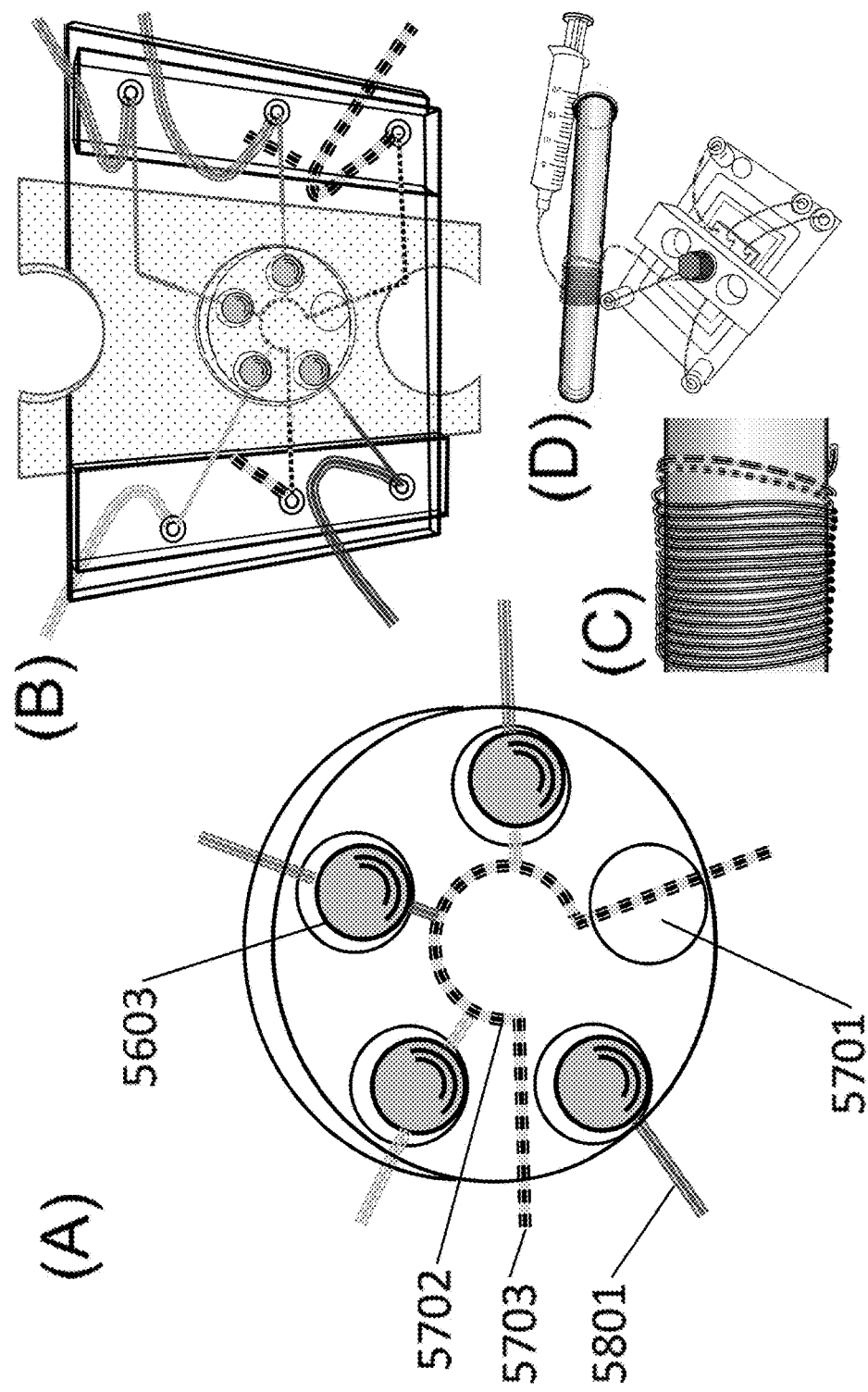
FIG. 58 shows a prototype of a missing ball RPV with the colors purple, green, and blue set to off by compressing their channels with the ball bearings, while red fluid flows freely when a vacuum is applied to the outlet port, according to one embodiment of the invention. By using this device, valve-selected input fluids can be routed to the output channel. In the configuration shown in FIG. 58A, the dotted fluid channel has been selected and routed to the output channel, while all other fluid channels have been closed by the action of the ball bearings. Suction or pressure drive is discontinued when the ball cage is rotated to minimize inadvertent mixing of the stock solutions, in that the channels act as normally open valves. This is readily accomplished by synchronized microcomputer control of the pumps and valves.

FIGS. 57 and 58 show a valve that operates by means of a missing ball 5701 that allows fluid to flow in only one of five radial channels at a time. By rotating the valve head that carries the balls 5603, the location of the missing ball can be arranged to be on top of one of the five channels connected together as the network 5702. The radial channel 5703 ensures that fluid will flow along the inner circuit of the network and to the selected open port 5701, or vice versa. This missing ball valve has all ports open when the balls are intermediate to the position shown in FIG. 57, but this normally open valve can be operated successfully in series with an RPPM that can be turned off while the balls are in the intermediate position so that fluid does not flow along undesired channels. During normal, study-state operation, the four balls would be in the five positions shown in FIG. 57A. FIG. 58 demonstrates the operation of the missing ball RPV. It is obvious that a much larger number of radial channels, separate subsets of networks based upon the design of 5702, and a combination of a large number of filled and vacant ball positions can be used to configure multi-port, multi-throw fluidic valves or switches that can produce a wide variety of controlled fluidic interconnections. This approach offers significant advantages over existing rotary fluidic valves, such as those typically produced for high pressure liquid chromatography (HPLC) that are designed to operate at pressures in excess of 1000 pounds per square inch. The elastomeric RPV and any of its implementations can be produced at lower cost and smaller physical volume, in part because the organ-on-chip and bio-unit modules operate at low fluidic pressures.

In certain embodiments, as shown in FIG. 59, the bearing assembly further includes a thrust bearing 5902 positioned between the motor 5901 and the second cylindrical portion of the bearing cage 5601; an alignment bearing 5903 positioned against the first cylindrical portion of the bearing cage 5601; and a tensioning spring 5905 positioned between the thrust bearing 5902 and the alignment bearing 5903.

Figure 60:
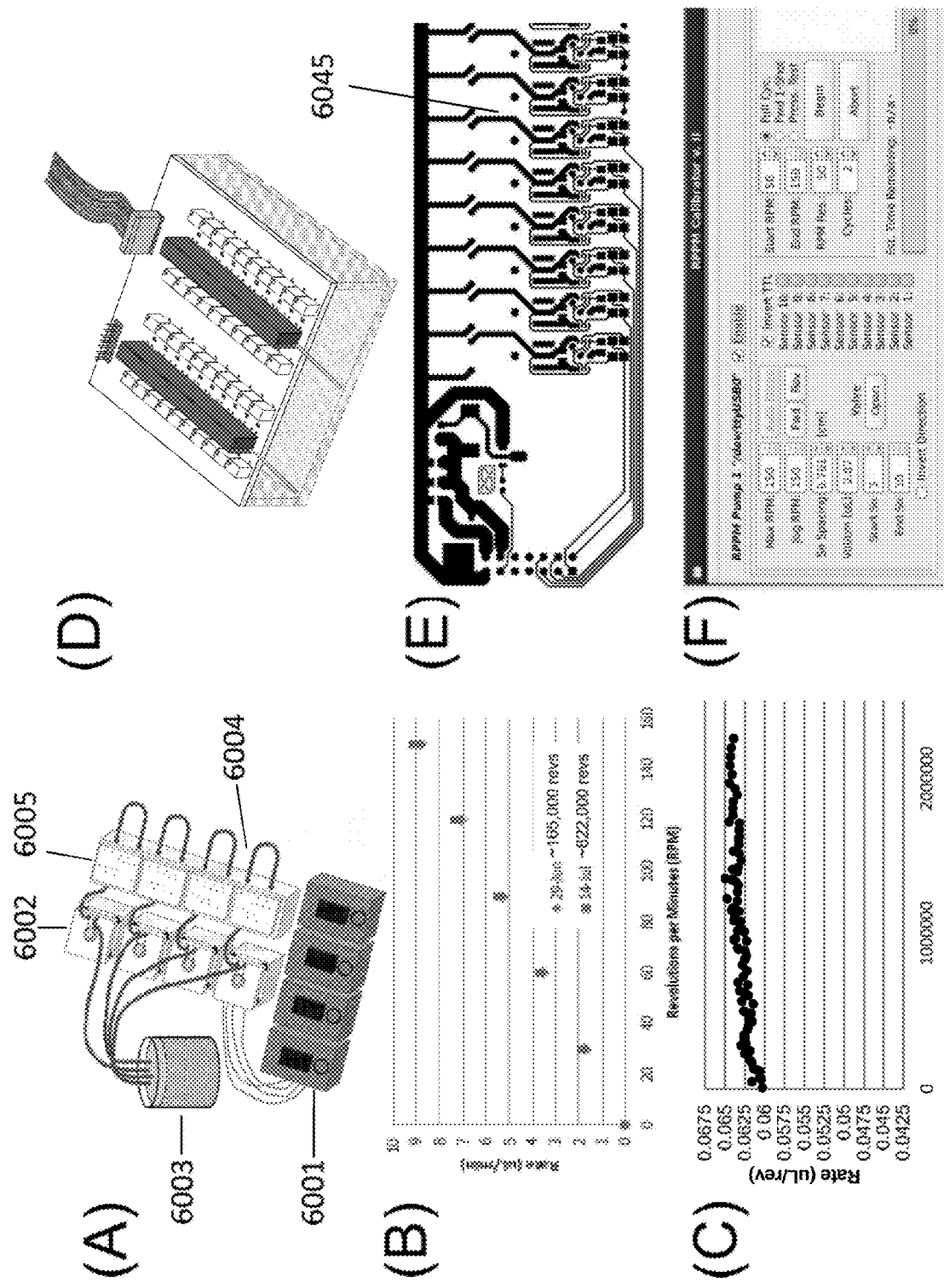
FIG. 60 shows automated RPPM testers that can characterize pump rate vs rpm and backpressure, according to one embodiment of the invention, and provides example test results.

FIG. 60 shows two examples of an automated pump calibration and testing unit. The units provide calibration curves of RPPM rotation versus delivered volume for up to four pumps simultaneously, as well as providing an automated platform for evaluating the reliability and longevity of each RPPM. The first version of the calibration and testing unit shown in FIG. 60A utilizes four microcontrollers 6001 to control the speed and direction of rotation of four RPPMs 6002. The inlet of each pump is connected to a common fluidic reservoir 6003 and the outlet of each is connected to a piece of tubing 6004 that passes through a photodetector unit 6005 with two LED-photodiode pairs. To calibrate a pump, each pump is run in reverse to empty the tubing of any fluid. The pump direction is reversed to forward pumping so that fluid is passed through the self-priming pump into the tube. The times at which the fluid meniscus crossed the first and second LED photodiode pairs are recorded as a function of pump speed measured in revolutions per minute (rpm). These data can be converted into the forward pumping rate. As soon as the fluid meniscus crosses the second detector, the pump can be reversed and the reverse pumping rate determined by measuring the time between the meniscus crossing the second and then the first detector. The known internal diameter and length of tubing located between the first and second photodetector are used to convert timing parameters into pumped volume parameters. The process is repeated at different pump speeds to obtain data such as that presented in FIG. 60B for tests performed at two different times. As shown in FIG. 60C, such tests show that the average forward pumping rate in µL/revolution varies by less than 8% in over 2 million revolutions of the pump. Flexure of the portion of the tubing suspended outside the optical unit contributed the majority of the scatter shown in the data.

The second version of the calibration and testing unit, shown in FIGS. 60D and E can measure the ability of the RPPM to pump against a self-generated pressure head. This two-channel device operates by characterizing the pump rate per revolution vs back pressure performance of RPPM devices, wherein a computer-controlled RPPM pumps fluid into a tube with a sealed end, thereby compressing the gas trapped in the tube by the fluid being pumped. As the gas is compressed, its pressure rises and the pumping rate may slow in a pressure-dependent manner. The unit shown has 10, in-line meniscus detectors 6045 along each fluid line, which is fully enclosed to maximize mechanical stability. It can test two pumps independently, and utilizes a computer-controlled solenoid valve to switch between measurement of flow vs rpm (open end) and measurement of flow vs pressure (sealed end), and produce reports with the computer interface in FIG. 60F.

In certain embodiments, as shown in FIGS. 61-65, the RPPM further includes a substrate 6101 having a first surface and a second surface; an elastomer member 6104 positioned between the bearing cage 6106 and the first surface of the substrate 6101; and motor alignment/attachment pins 6109 vertically positioned on the first surface of the substrate 6101 such that the actuator is located between the motor alignment/attachment pins 6109. The fluidic paths/channels 6102 are formed on the first surface of the substrate 6101 by a hot-embossing, an injection-molding, or an etching process, or in an elastomer member 6104.

Figure 62:
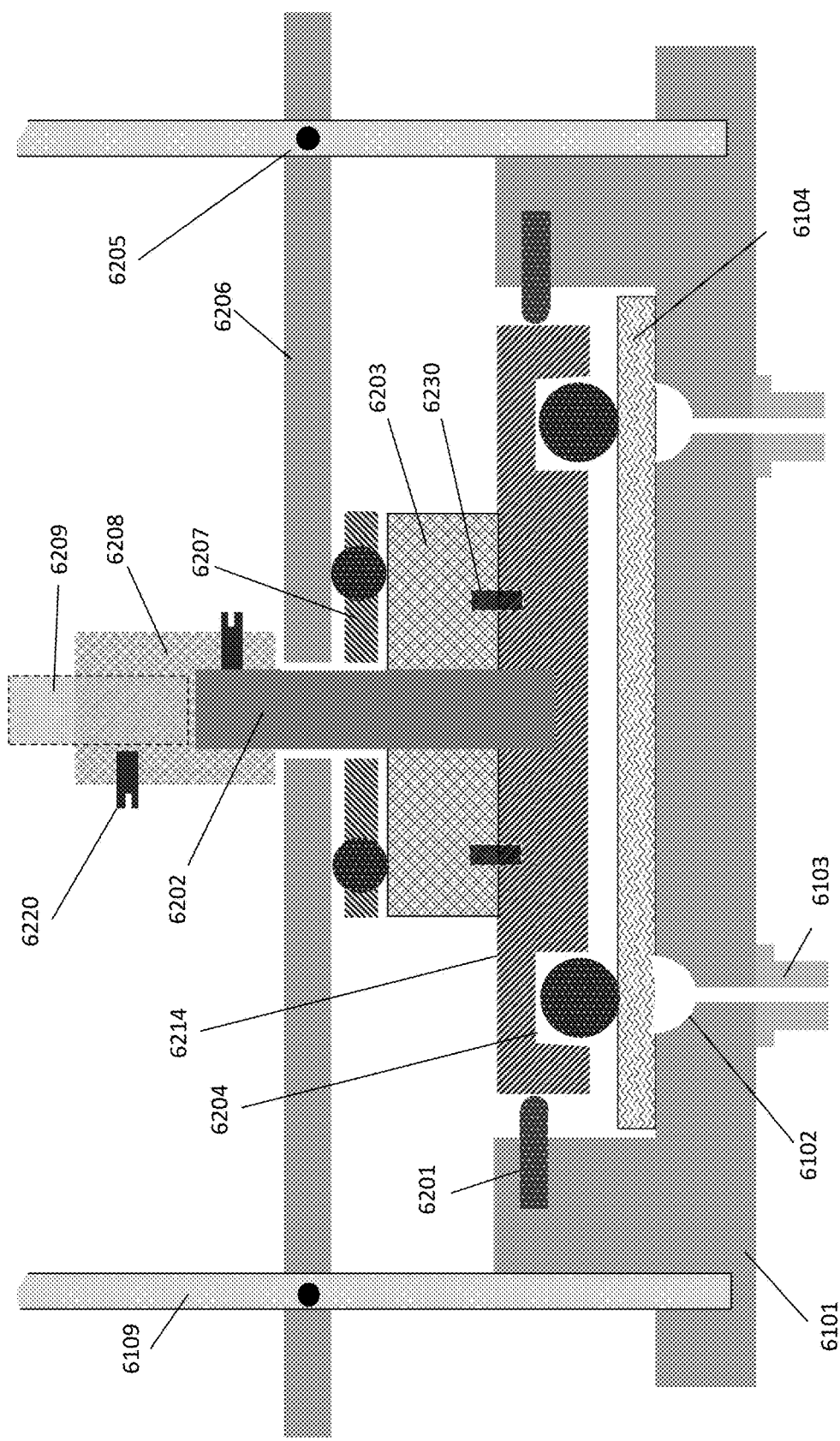
FIG. 62 shows schematically an RPPM according to one embodiment of the invention, which utilizes channels that are created in hard plastic such as polystyrene, via a hot embossing or injection molding process, but with the balls being captured by sockets in the drive flange, and a separate mechanism utilized to provide the compressive loading for the pump balls that compress an elastomeric membrane into the channel.
Figure 65:
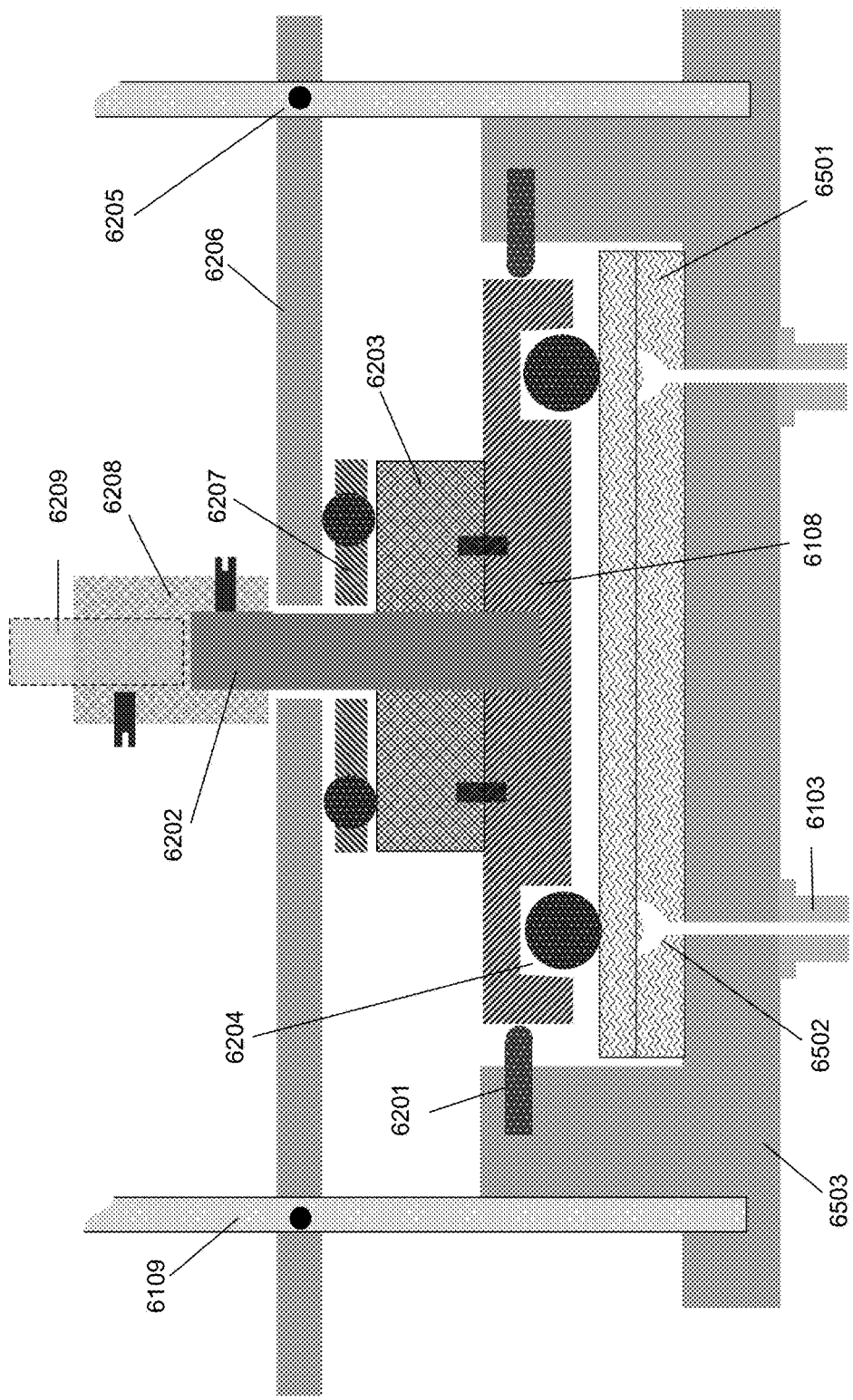
FIG. 65 shows schematically an RPPM according to one embodiment of the invention, which utilizes channels which are created in an elastomer such as PDMS to create a modular pump or valve head assembly. In this embodiment, the drive motor can be disconnected from the pump assembly without altering the compression of the balls into the elastomeric membrane.

In certain embodiments, as shown in FIGS. 62 and 65, the bearing assembly further includes a driving pin 6202; and an interface collar 6208 for providing the attachment of the driving pin 6202 to the shaft 6209, such that the motor can be disconnected from the pump head without affecting the compressive force applied to the balls by the thrust bearing 6207.

Figure 61:
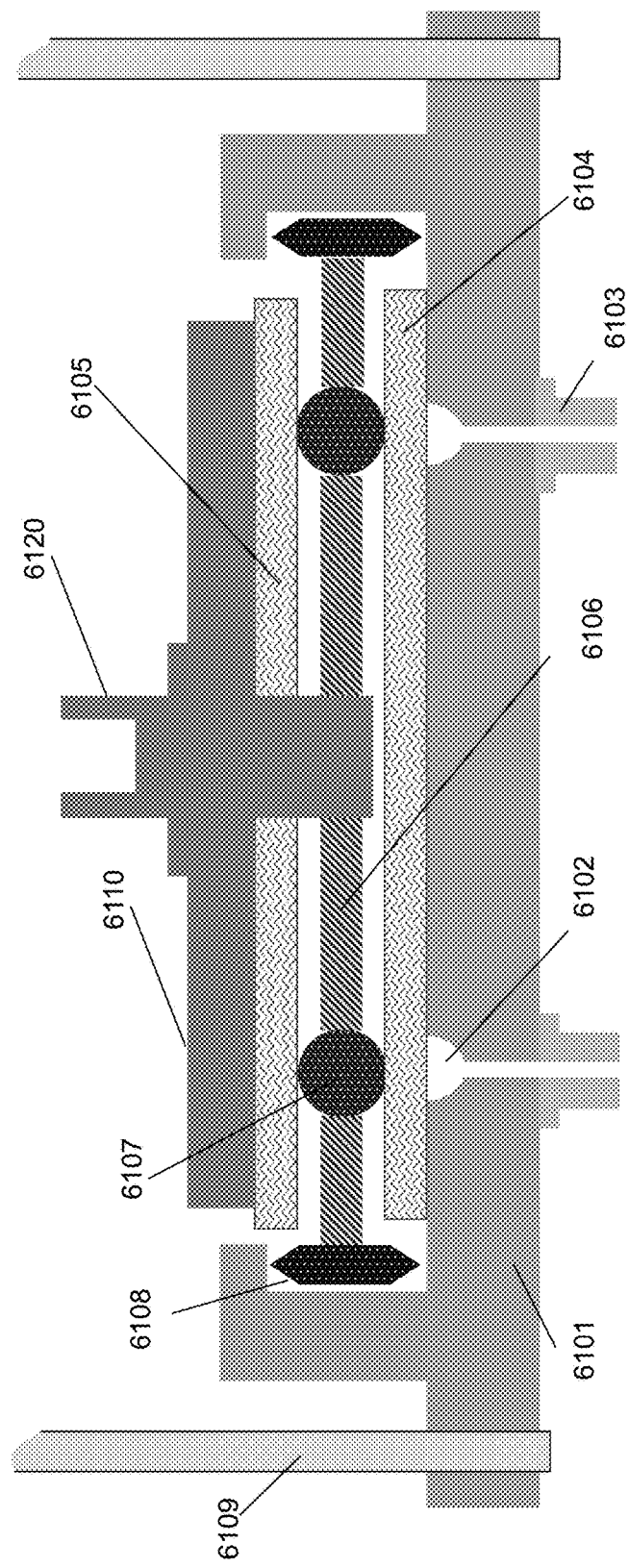
FIG. 61 shows schematically an RPPM according to one embodiment of the invention, which utilizes channels that are created in hard plastic such as polystyrene, via a hot embossing or injection molding process, and an elastomeric membrane that is pressed into those channels for pumping.

In one embodiment, as shown in FIG. 61, the bearing assembly further includes a washer 6110 positioned between the shaft 6120 and the bearing cage 6106; and a second elastomer sheet 6105 positioned between the washer 6110 and the bearing cage 6106.

In certain embodiments, as shown in FIGS. 62-65, the bearing assembly further includes an auto-centering needle bearing 6201 positioned at an edge of the bearing cage 6214.

In certain embodiments, as shown in FIGS. 62-65, the bearing assembly further includes a pressed fit washer 6203 positioned on the bearing cage 6214; a pressure transfer bearing 6207 positioned on the pressed fit washer 6203; and a tension holding plate 6206 positioned on the pressure transfer bearing 6207 and adjustably mounted to the motor alignment/attachment pins 6109 for transferring tensioning pressure via the pressure transfer bearing 6207 to fluidic paths 6102 thereunder.

The modular pump head designs shown in FIGS. 61-65 illustrate techniques which can be used to create pre-tensioned and pre-aligned RPPM pump heads (actuators) that can be attached to a drive motor via a simple coupling. The advantage of this technology is that it allows end users to attach new drive heads to existing motor drives without requiring any end-user adjustments of alignment or ball bearing tensioning. Such modular heads can be aligned and calibrated at initial factory assembly and then be attached at some later time to pump drive motor assemblies.

The embodiments presented and the calibration procedures are useful for optimizing RPPM manufacture and supporting a high level of quality control. For identical motor rpms on PDMS or deformable elastomer based RPPM pumps, the variation in pumping volumetric flow rate can arise from inconsistency in compression load (zone) and inconsistency and reproducibility of channel dimensions. The pump itself acts as the equivalent of a high-impedance current source. The volume delivered to the output is first order independent of the internal (circular path) fluid resistance of the pump channels. It is true, however, that the pressure delivered by the pump to downstream microfluidics will vary according to the fluid resistance of the downstream fluidics. The resistance of the pump channels will not cause different downstream pressures but will affect the torque required to drive the pump at a constant velocity. It is the volume per unit time delivered by a given pump multiplied by the downstream resistance that defines the output pressure. This may have implications in situations where pumps are connected in parallel or series, particularly through the use of valves. These concerns are addressed in embodiments presented in FIGS. 61-65.

Figure 63:
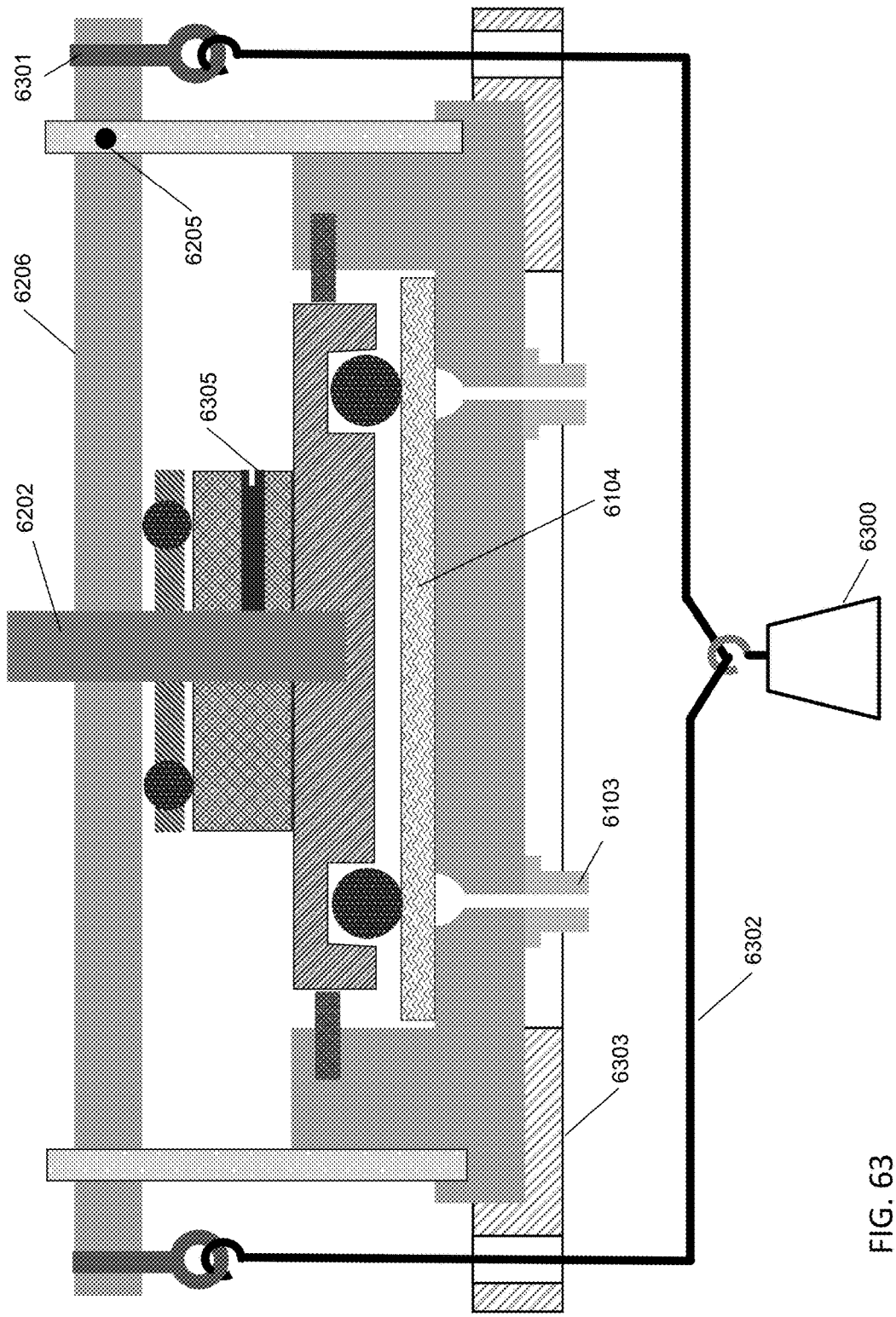
FIG. 63 shows schematically an RPPM according to one embodiment of the invention, which utilizes a simple calibrated weight to provide calibrated static tensioning to the deformable elastomeric membrane.

It is paramount that the compression zone for all given compression loading as shown in FIG. 63 be known or controlled. Ideally, one should know for each pump the relation between flow rate (Q), motor rpm, and the extent of the compression zone and how it affects the cross-sectional area of the channel. Variations in functional cross-sectional area can also come from either PDMS resiliency fatigue and inability to restore properly after days to weeks of operation, or from variations in photolithography used for PDMS molding, all of which are quality control issues. By understanding these parameters, a pump builder will be able to control for differences in microfluidic master height and properties of the elastomeric materials used, which in turn can be minimized by an appropriate manufacturing technique and quality control. It is also important to keep in mind that for rectangular channels in a particular range of flow rates the resistance to flow is proportional to $(\text{height} \times \text{width}^3)^{-1}$; height and width are interchangeable here and depend on the aspect ratio. This means that reducing channel dimensions by ½ can increase resistance 16 times.

FIG. 61 shows a method of utilizing channels that are created in hard plastic such as polystyrene, via a hot embossing or injection molding process. In this design the PDMS elastomer sheets provide the friction that causes the ball bearings to roll, while the Teflon drive cage constrains the ball bearings in an angular array disposition at some radius from the center of the drive shaft. The diagram shows the state of system prior to application of a vertical load that causes the ball bearings to deform the PDMS to the semi-circular shape of the embossed channels. In this embodiment, the body of the device 6101 is a hot embossed or injection molded hard plastics piece (polystyrene, polycarbonate, . . . ) with microfluidic channels 6102, Nanoport interfaces 6103, and a flat elastomer membrane sheet 6104 for channel sealing, e.g., PDMS. There is a corresponding flat elastomer sheet 6105 for ball bearing cushioning. The rotating Teflon ball bearing cage 6106 captures ball bearings 6107 that perform the pumping when the device is loaded so that the load from the drive flange 6110 and elastomer sheet 6105 press the ball bearings 6107 into the channels 6102 such that rotation of the drive shaft through its coupling 6120 forces fluid along the channel 6102 and in and out through the respective ports 6103. An optional autocentering bearing 6108 maintains the alignment of the ball cage 6106, and motor alignment/attachment pins 6109 connect the pump mechanism to the motor (not shown).

Using embossed/injection molded hard plastics, clear polymeric or silica-based substrates, or etched glass offers a number of advantages: it is easy to mass produce; it provides identical and constant cross-sectional area (consistent pumping with time and no batch-to-batch variation); it can be easily interfaced with Upchurch standard Nanoports; it provides very straightforward alignment that is amenable to "autocentering"; it can be further designed to allow for "snap-in" assembly; and PDMS has been shown to bond to glass, fused silica, and polystyrene.

FIG. 62 shows a method of utilizing channels that are created in hard plastic such as polystyrene, via a hot embossing or injection molding process, but with the balls being captured by sockets in the drive flange and a separate mechanism being utilized to provide the compressive loading for the pump balls. In this design circular wells 6204 machined into a Teflon or other low-friction drive disk 6214 are used to hold the ball bearings in place. The coefficient of friction of the ball bearing against the Teflon is much lower than the coefficient of friction of the ball bearing material against the deformable PDMS flat sheet 6104, thus ensuring that the ball will roll in the membrane 6104, rather than skid, but will slide within the low-friction socket 6204. The diagram shows the state of system prior to application of a vertical load that causes the ball bearings to deform the PDMS to the semi-circular shape of the embossed channels. Additional features shown in this diagram include a pressure transfer bearing 6207 that can be used to adjust the static tension against the tension holding plate 6206 such that the circular well ball bearings occlude the semi-circular channels, which are embossed in the hard polystyrene or other plastic base 6101. The plate 6206 is fixed to the motor mount 6109 by means of screws or pins 6205. The key feature of this design is that once the tension adjustment set screw 6205 has been properly adjusted, then the pump head becomes an interchangeable, and perhaps disposable, module which can be attached to any motor head shaft 6209 without requiring the end user to perform critical alignment and pump head tensioning procedures. The rotary motion of the drive shaft 6209 is transmitted by means of set screws, keys, or other means in the interface collar 6208 to drive the captured intermediate shaft 6202 that is centered in the plate 6206 by means of a separate ball bearing 6207 or other means. If necessary, the drive flange 6203 can be connected to the drive disk 6214 by pins 6230 or other means. Centering pins 6201 or other means can be used to keep the drive disk 6214 centered over the channel 6102.

FIG. 63 shows a schematic depiction of a method of using a simple calibrated weight 6300 to provide calibrated static tensioning to the deformable PDMS structure 6104. In this operation the tension adjustment set screw or screws 6305 and shaft screw 6202 are loosened, the weight applied, and then the set screws are tightened. This process requires a support 6303 beneath the pump body, tensioning attachment loops 6301, and a wire, rod, or other means 6302 to connect the weight 6300 to the loops 6301. Other implementations of this procedure, including the use of levers and springs, could ensure the proper application of compressive force to the balls.

Figure 64:
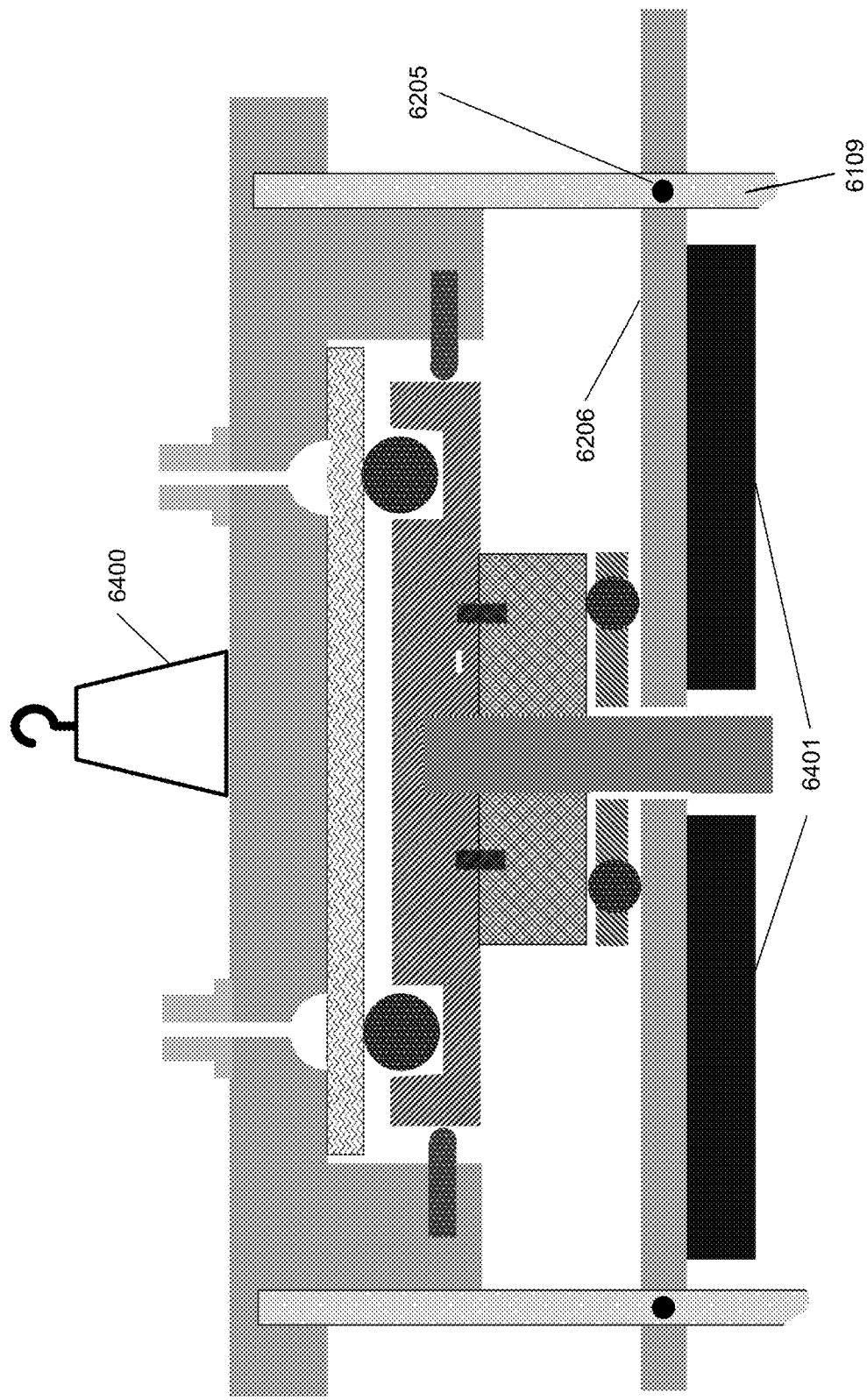
FIG. 64 shows schematically an RPPM according to one embodiment of the invention, which utilizes calibrated weights to apply calibrated tensioning forces to the deformable elastomeric membrane.

FIG. 64 shows schematically another method of using calibrated weights to apply calibrated tensioning forces to the deformable PDMS membrane. First the screws 6205 fixing the tension holding plate 6206 to the motor mount 6109 are loosened, then the device is placed on a fixed, slotted table-top jig assembly 6401 that is inserted between the tension holding plate and the motor (not shown). The weight of the device plus the weight of an externally added weight 6400 can be used to provide known tension to the deformable PDMS elastomer, after which the screws 6205 are tightened. The screws to the motor shaft (not shown) would then be tightened.

FIG. 65 shows a method of utilizing channels which are created in an elastomer such as PDMS to create a modular pump or valve head assembly. In this design circular wells machined into a Teflon drive plate are used to hold ball bearings in place. The coefficient of friction of the ball bearing against Teflon is much lower than the coefficient of friction of the ball bearing material against the deformable PDMS flat sheet, thus ensuring that the ball will roll along the deformable elastic sheet, rather than skid. The diagram shows the state of system prior to application of a vertical load that causes the ball bearings to deform the PDMS to fully close the PDMS channels. Additional features shown in this diagram include a pressure transfer bearing 6207 which can be used to adjust the static tension which allows the circular well ball bearings to occlude the PDMS channels. The key feature of this design is that once the tension adjustment set screw has been properly adjusted, then the pump head becomes an interchangeable, and perhaps disposable, module which can be attached to any motor head shaft without requiring the end user to perform critical alignment and pump head tensioning procedures. In this embodiment, 6501 is the PDMS or other elastomer pump, 6502 the partially closed pump channels, and 6503 a hard plastic bottom piece.

In another aspect, the invention also discloses an RPV. The RPV includes the actuator. The actuator is structurally and functionally similar to the actuator utilized in the RPPM above, except that the number of the plurality of rolling-members is less than that of the plurality of spaced-apart openings of the bearing cage such that the bearing assembly has at least one no-rolling-member opening that accommodates a no-rolling-member. The missing rolling-member opening is utilized to selectively control the routes of the fluid flow. The aforementioned compression-setting procedures apply to the RPV as well as the RPPM The RPV also includes a plurality of selectively controllable fluidic paths/channels coupled to each other (e.g., 4111, 4112, 4114-4117, and 4121-4124 in FIG. 42), positioned under the actuator in relation to the plurality of equally spaced-apart openings of the bearing cage such that at least one selectively controllable fluidic path is positioned under the at least one no-rolling-element opening so that a fluid flow is allowed through the at least one selectively controllable fluidic path, while the other selectively controllable fluidic paths are respectively positioned under the openings having the rolling-members so that no fluid flows are allowed through the other selectively controllable fluidic paths.

In certain embodiments, as shown in FIGS. 44, 51 and 53, the plurality of spaced-apart openings of the bearing cage is spaced-equally defined on the bearing cage, where each two adjacent openings through the center of the bearing cage define an angle $\theta=2\pi/K$, K being the number of the plurality of equally spaced-apart openings. When the shaft of the actuator rotates a desired angle of $(k\times\theta)$, k being 1, 2, ... K, the at least one no-rolling-member opening is selectively placed over a desired one of the selectively controllable fluidic paths.

In one embodiment, the RPV further includes at least one always-open fluidic path (e.g., 4113 in FIG. 42) coupled to the plurality of selectively controllable fluidic paths, positioned under the actuator in offset from the plurality of equally spaced-apart openings, such that the at least one offset fluidic path is in fluid communication with the at least one selectively controllable fluidic path under the at least one no-rolling-member opening, and the other selectively controllable fluidic paths under the openings having the rolling-members are closed.

Communication and Networking of IOMs

Communication, both physiologic and electronic, between organ/tissue modules is imperative in any coupled Microphysiological System (MPS).

According to the invention, the IOM modules of each platform define a wired or wireless network of communications, such that each IOM module in the platform is capable of electronic communication with one another in the network and/or with a master and/or server that is in electronic communication with the network. Further, each IOM module in one platform is also capable of electronic communication with one or more IOM modules in another platform. Also, operations of each IOM module are controlled by the master and/or server. The server can be a computer such as a master control computer that may relay instructions to subservient masters.

Figure 66:
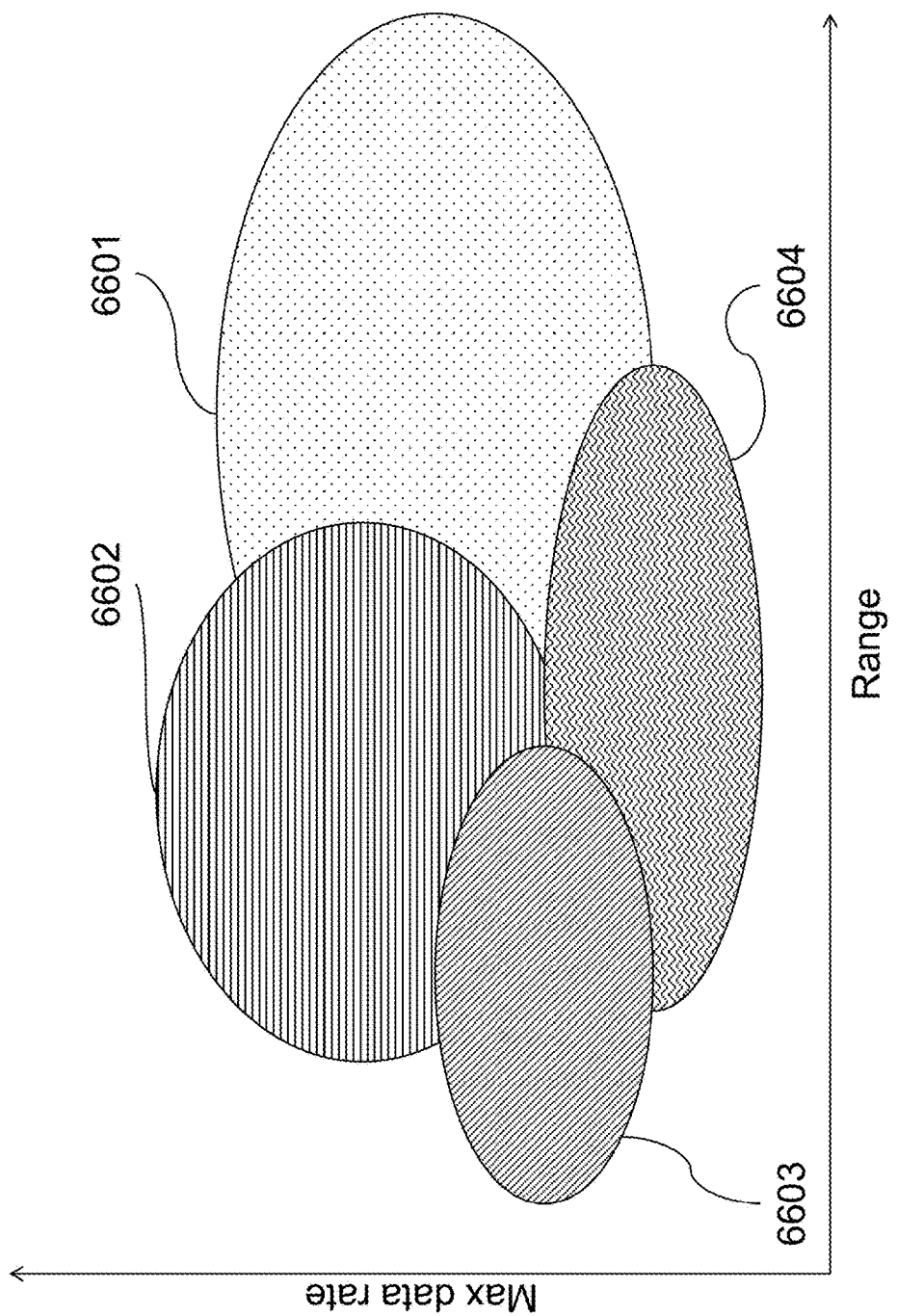
FIG. 66 shows schematically the maximum data rate and range for four prevalent wireless technologies.

Specifically, the ability to coordinate fluid handling, perform experiments in synchrony, and detach from the organ system and continue autonomous operation is required. To achieve this, there are a variety of network topologies that can be realized. Currently, there are four wireless technology options that are readily utilized: Cellular 6601, Wi-Fi 6602, Bluetooth 6603, and ZigBee 6604. Each technology has different data rates and ranges. These are elaborated in FIGS. 66 and 67. Any network to monitor and control the MPS during its operation will require a user-interface located on either a Master Control Computer or Tablet with control software. Connections to this device and any other networking device can be either wired or wireless depending on desired topology. In certain embodiments, all communication passes through the Master Control Computer. Alternatively, communication can pass through a coordinator or router with controlling authority. For instance, an IOM in an incubator can communicate with a router located immediately outside the incubator. Finally, each system can communicate directly with every other system. Buffering commands may be required, depending on the number of commands received, and how the network handles information flow.

Figure 68:
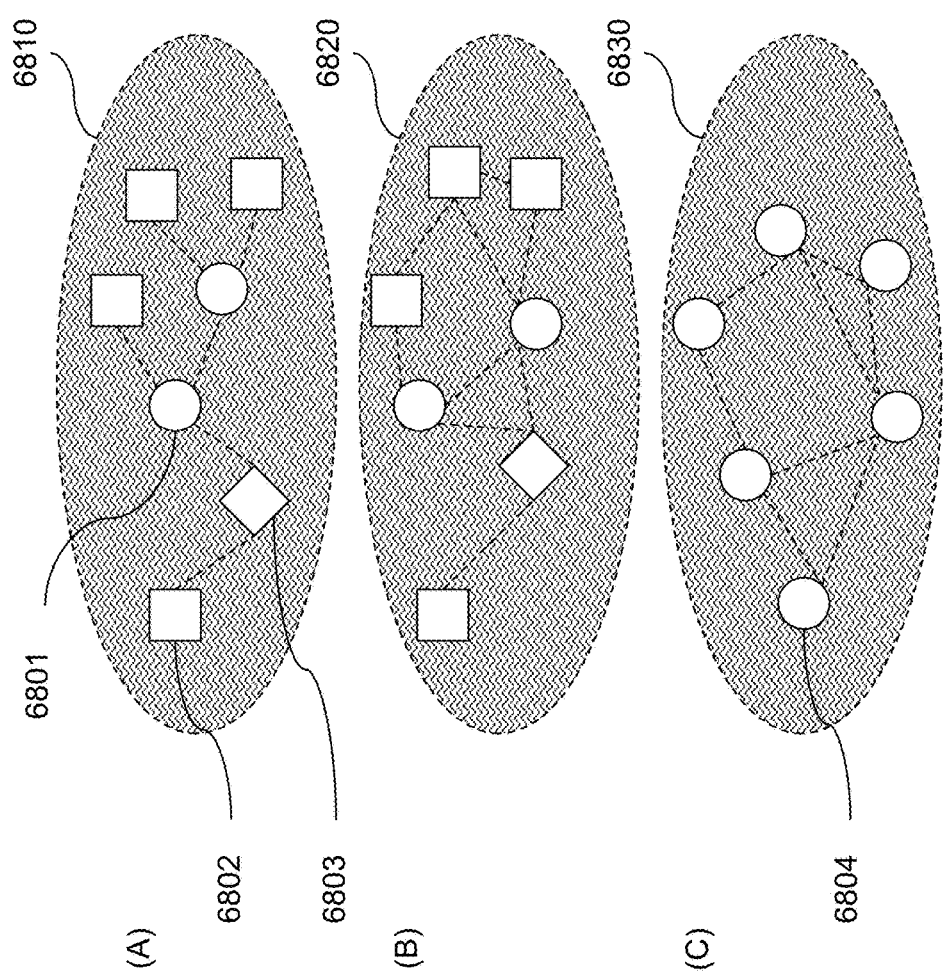
FIG. 68 shows typical configurations of a ZigBee network: (A) a tree mesh, (B) a stochastic mesh, and (C) a DigiMesh.

Given these criteria, the most desirable technology with the lowest power requirements, yet highest versatility, is ZigBee. ZigBee is a unique protocol in that networks can be formed in a variety of structures. The most common of these structures are outlined in FIG. 68. Briefly, ZigBee modems can be configured as a parent-child mesh consisting of a Coordinator Node 6801, zero or more Router nodes 6802, and zero or more End nodes 6803. Types of parent-child meshes include the Tree mesh 6810 and the Stochastic mesh 6820. Each of these network architectures requires a central coordinator node 6801 through which all communication must pass. DigiMesh 6830 is an alternate mesh network protocol in which each node acts as its own coordinator to pass messages, and all nodes 6804 are topologically identical. DigiMesh also allows the network to self-heal, meaning that if any node is brought to the extremes of the covered area, the node will search to find the most efficient route to its communication partner.

Figure 69:
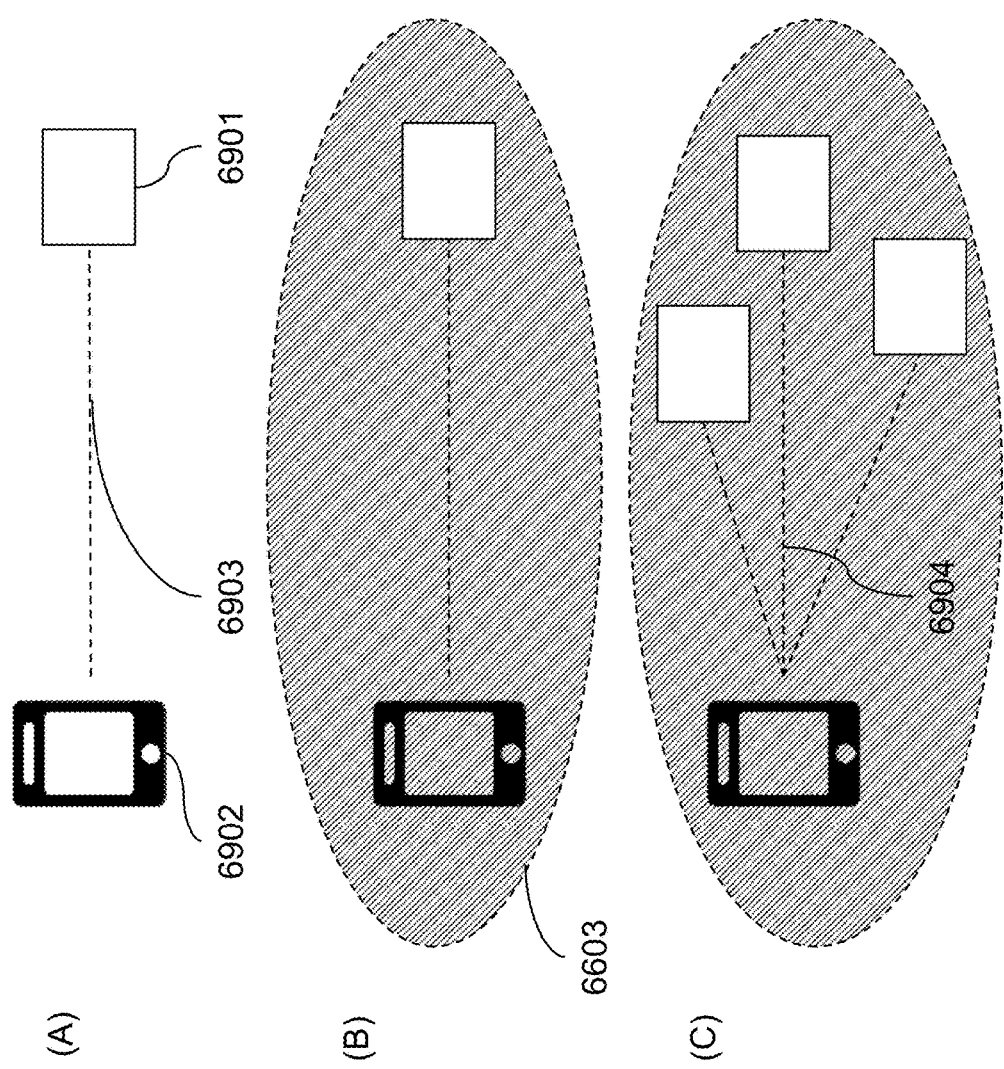
FIG. 69 shows three network configurations (A)-(C) of an isolated system with each IOM communicating directly to a Master according to embodiments of the invention.

For communication within a network of MPS or tissue construct modules that may be placed in one of two or more incubators, there exist a few feasible topologies for reliable communication between the module and the master controller. The first is an isolated system, as detailed in FIG. 69, in which each IOM acts as a slave 6901 in direct communication with its Master 6902. This topology is best realized with wired or wireless networks such as Bluetooth 6603, in which data are transmitted over a wired or wireless serial port 6903. In this embodiment, multiple slave devices may connect to multiple master ports on the PC in 6904. The slave devices can receive their power from the mains, wireless power, or batteries.

Figure 70:
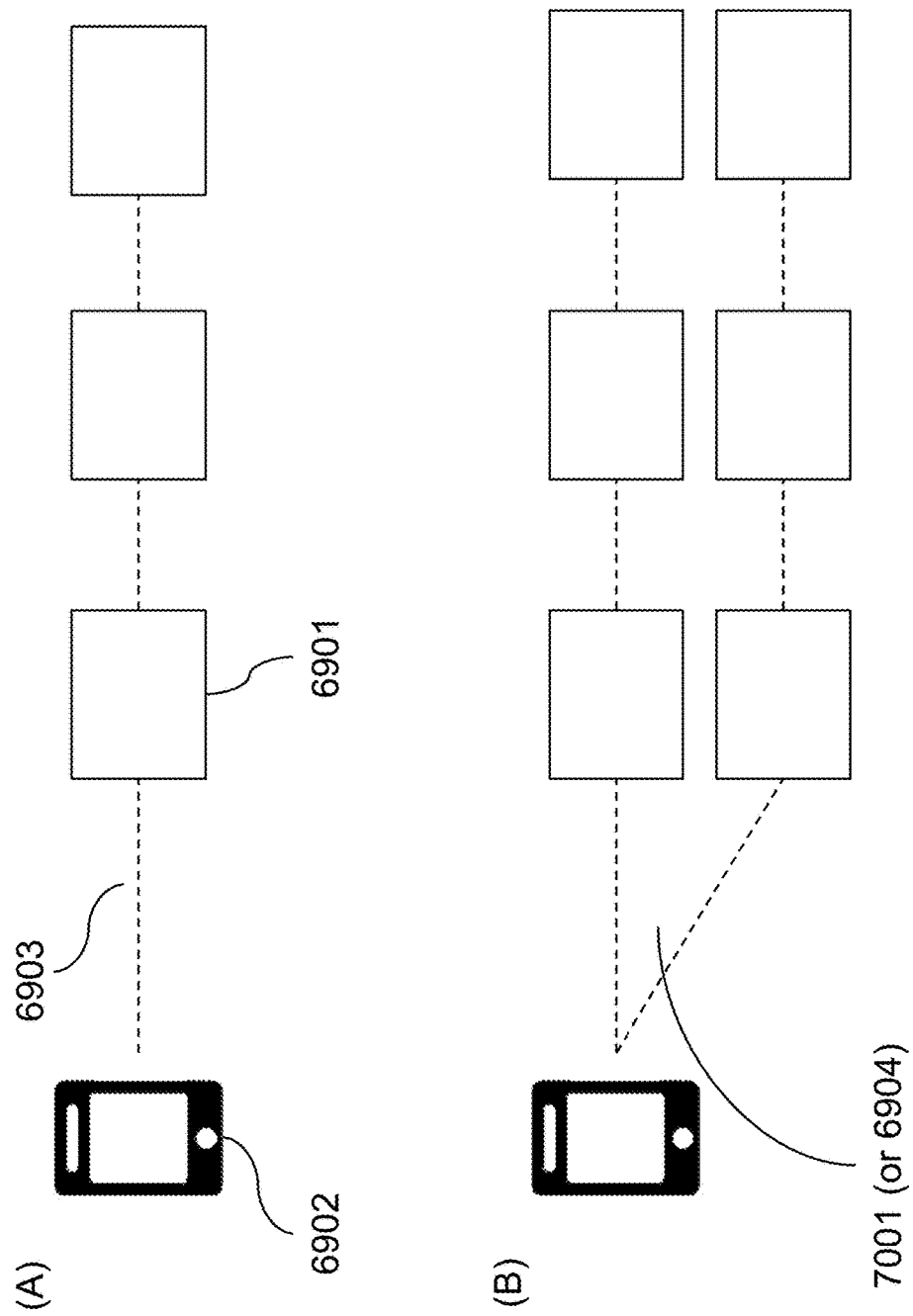
FIG. 70 shows daisy-chain network configurations (A) and (B) where each IOM communicates to the IOM next to it until it reaches the Master according to embodiments of the invention.

Alternatively, FIG. 70 shows a daisy-chain approach in which each IOM acts as a slave 6901 and communicates to its adjacent IOM over a wired or wireless serial connection 6903 until a route to the master 6902 is discoverable. In the example shown, slaves "relay" data serially until the command reaches its target. Each slave has two serial ports, in the style used by some commercial instrument controllers, for example, Harvard syringe pumps. This architecture can be realized with any networking technology, and as shown in FIG. 70B, a master can host multiple daisy-chains in parallel 7001.

Figure 71:
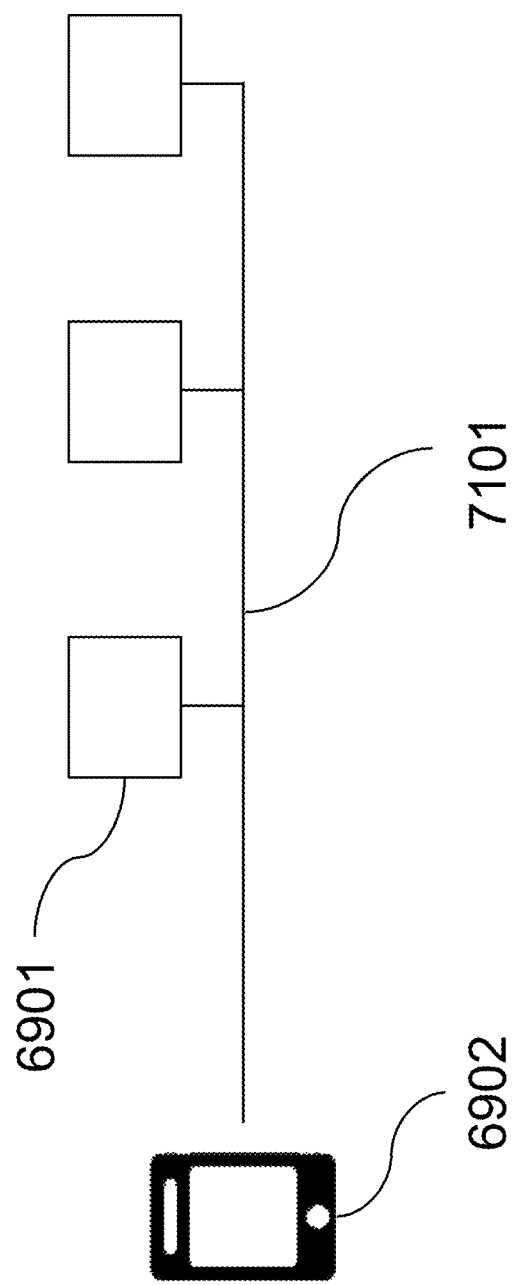
FIG. 71 shows a parallel network configuration in which each IOM communicates with the Master along a shared data line according to embodiments of the invention.

FIG. 71 shows a parallel topology in which each IOM is connected to the Master using the same backbone interface 7101, but each IOM must be individually addressed and monitor the communication line at all times. This will allow more modules than the daisy-chain approach, but there is limited bandwidth on the shared communication bus. In the embodiment shown, slaves are connected in parallel to a common "Rail" and listen to all commands, but only respond to those commands addressed to them.

Figure 72:
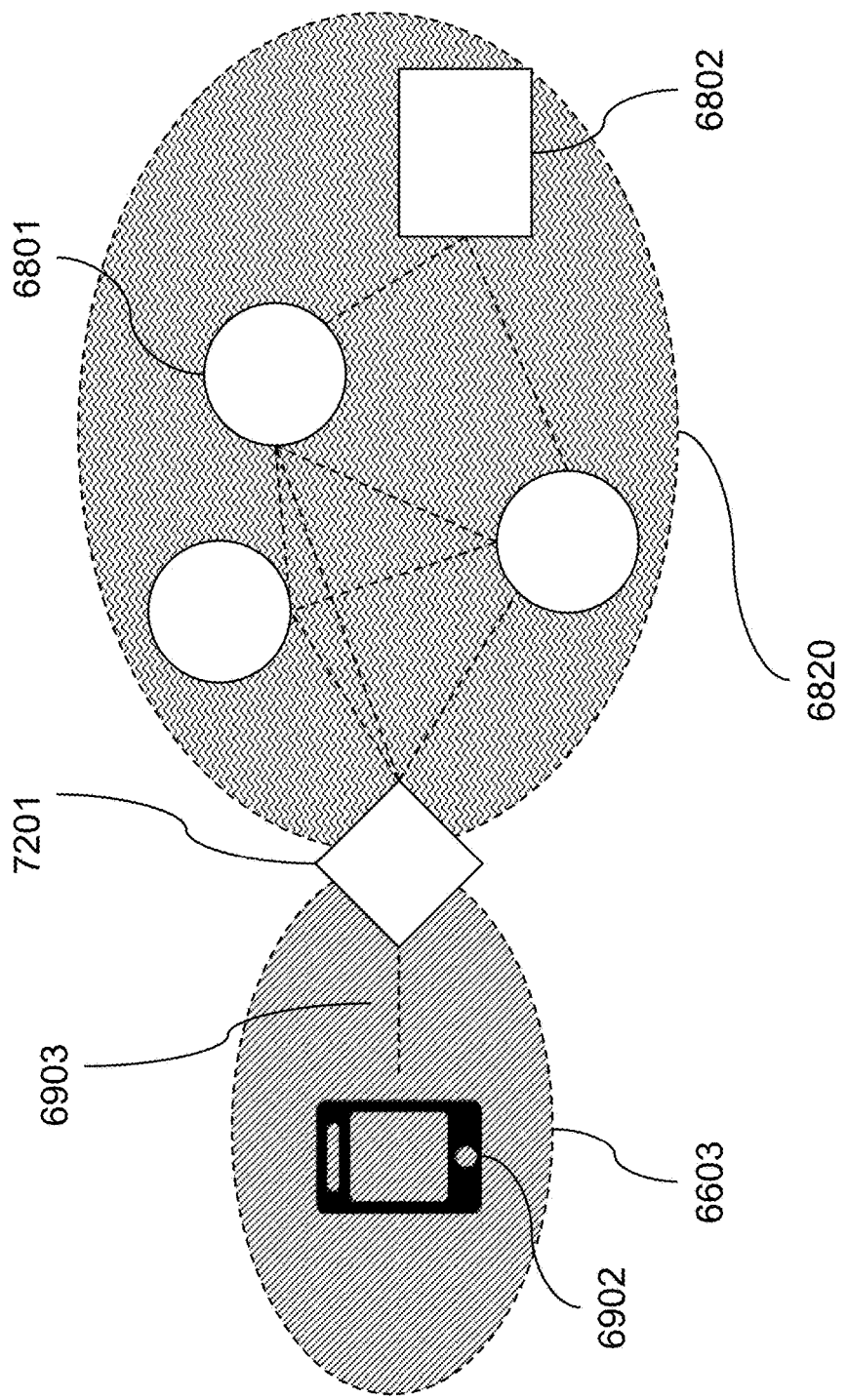
FIG. 72 shows a network configuration with a coordinator with two serial ports to serve as an intermediate between the Master and IOM nodes of the network according to embodiments of the invention.

In one embodiment, FIG. 72 illustrates a coordinator acting as a slave when interfacing to the Master and a coordinator when communicating to the IOMs 7201. This topology requires the coordinator to have two serial ports to serve as an interface. This example is termed a linear dynamic ZigBee DigiMesh.

Figure 73:
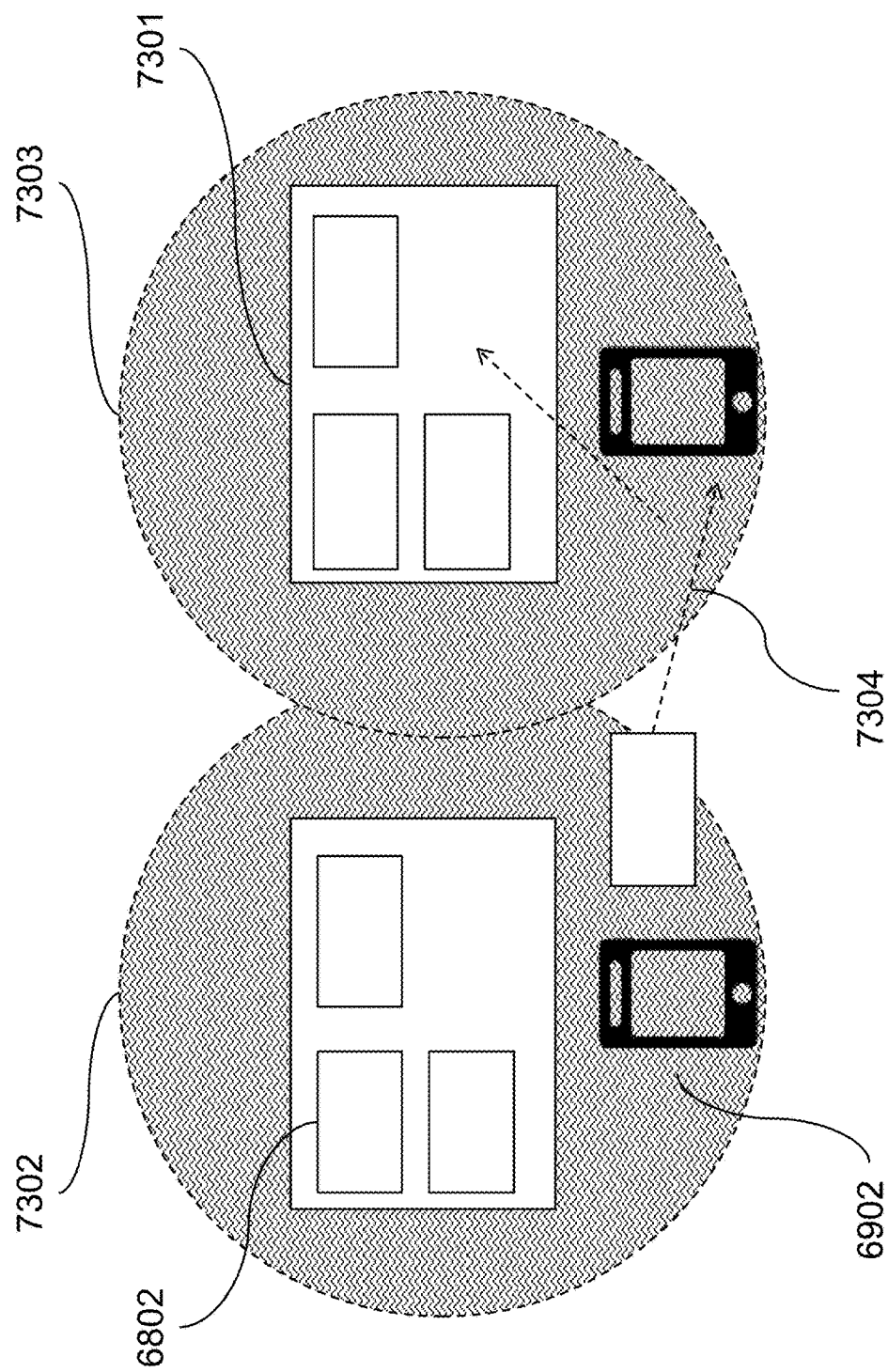
FIG. 73 shows ZigBee communications of IOMs in two different incubators with separate PAN IDs according to embodiments of the invention. This may introduce a switching problem when an IOM is moved from the first incubator into the second incubator.
Figure 74:
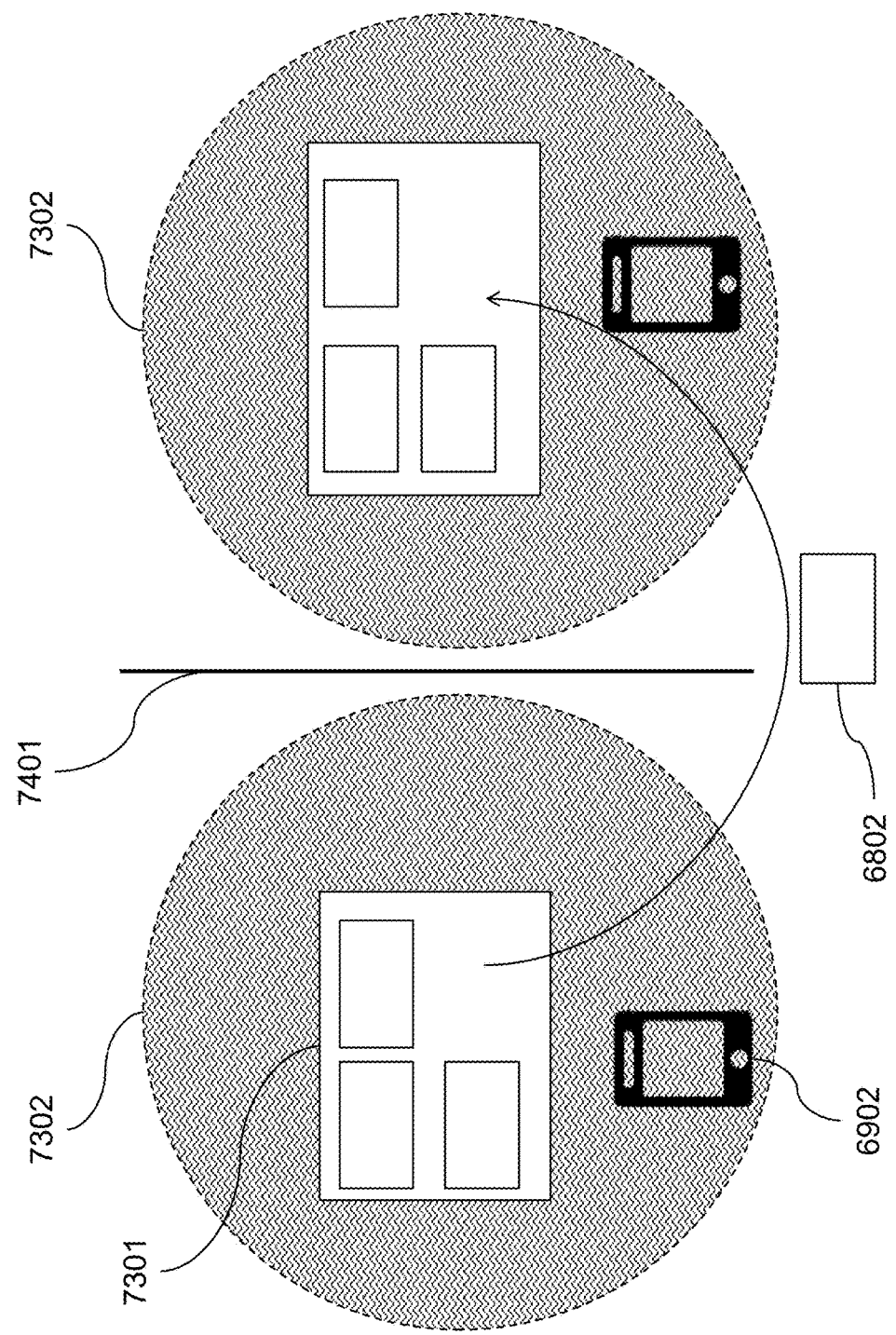
FIG. 74 shows ZigBee communications of IOMs in incubators with a shared PAN ID according to embodiments of the invention. This may introduce interference problems with coexisting networks.
Figure 75:
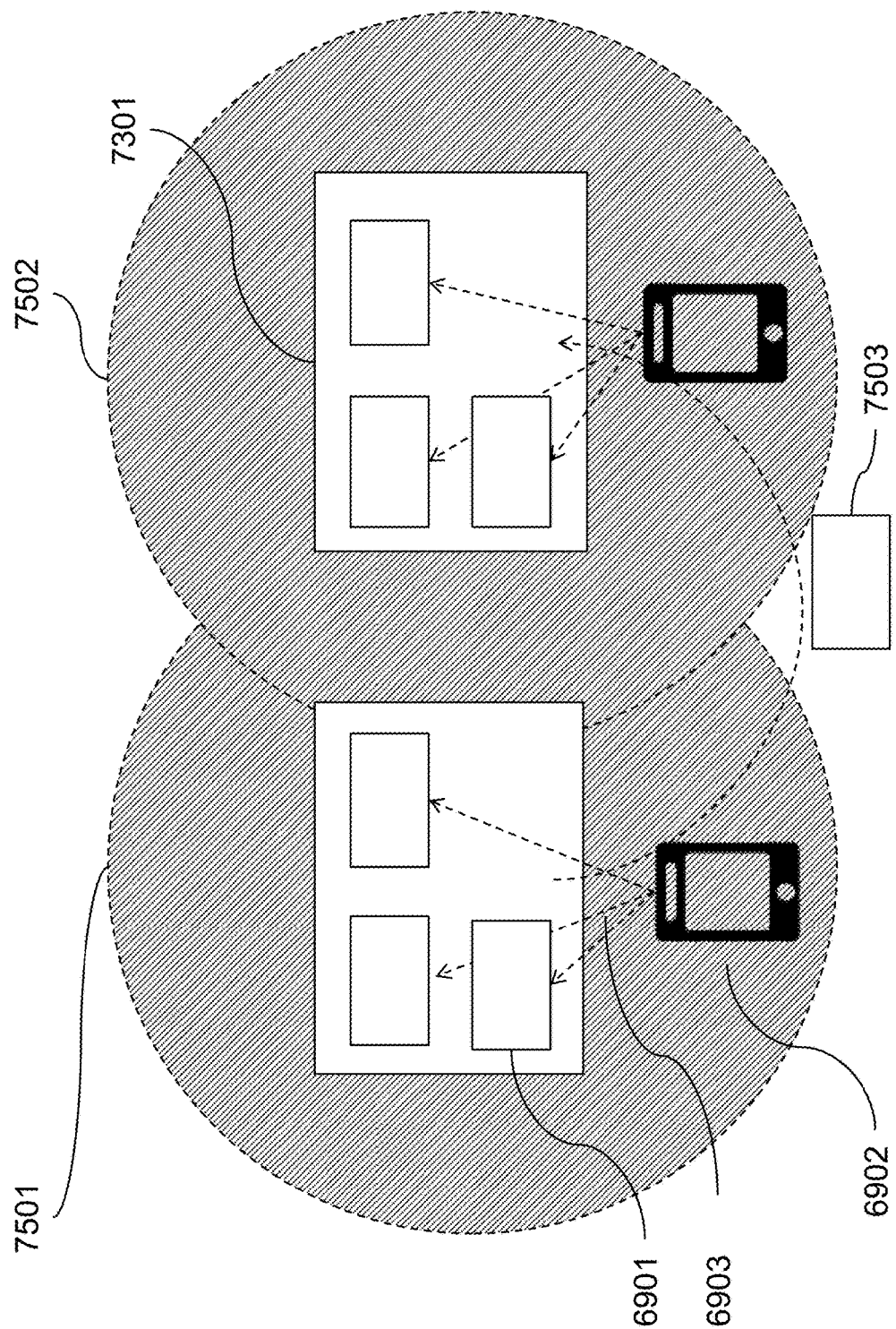
FIG. 75 shows Bluetooth communications of IOMs in incubators with separate PANs, as required for Bluetooth operation according to embodiments of the invention.

One of the challenges in any network architecture is providing for handoff of devices, i.e., when a device leaves one network coverage area and enters another network area, for example when being moved from one incubator to another. One embodiment is to utilize a ZigBee network with two differing PAN IDs (FIG. 73). This ensures that one knows the location of any IOM simply by examining the Coordinator Node 6801 of a PAN ID. When an IOM is moved from an incubator 7301 in one PAN ID 7303 to another PAN ID 7302, switching typically requires reprogramming the modem for several seconds, a task that can be accomplished through external input on the IOM or by a Master 7304. During this transition, the device is incommunicado. Another embodiment, which avoids these disadvantages, is to use a single PAN ID for all devices as shown in FIG. 74. If parent-child mesh types are used in this configuration, there must be physical separation of the wireless networks 7401, even though both networks operate on the same PAN ID. The theoretical limit of ZigBee devices on a single PAN ID using 16-bit addressing is approximately 64000, and networks of several hundred devices have been demonstrated. Alternatively, Bluetooth can support a limited number of devices on multiple co-existing PANs 7501 and 7502, with a successful exchange of PAN IDs occurring via automatic-repairing with a new master 7503, as shown in FIG. 75.

Figure 76:
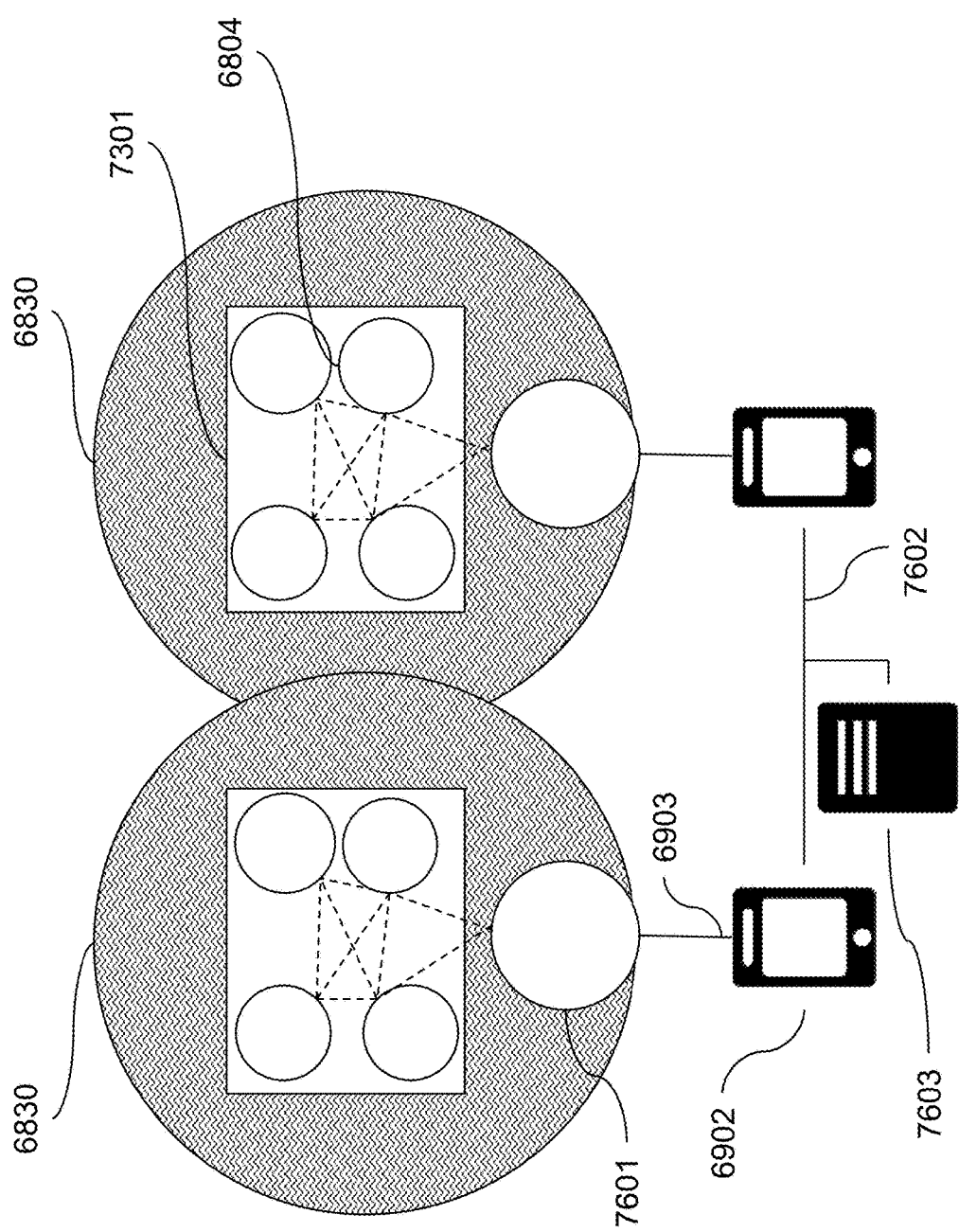
FIG. 76 shows a network configuration using a shared PAN with all IOMs operating as part of a ZigBee DigiMesh and communicating to the controlling Master tablet through a router as an intermediator, according to embodiments of the invention. The Master Control Computer has final authority over all devices in this network.

Another embodiment, as shown in FIG. 76, would take an integrative approach with a ZigBee DigiMesh 6830 network handling the IOM device-to-device communication, but with specified nodes designated as intermediate routers 7601. The DigiMesh is intrinsically self-healing, which will allow handoffs to take place seamlessly. In this embodiment, each incubator would contain a ZigBee antenna located within the incubator, as well as an antenna local to the lab to allow for optimal establishment of the mesh network. An intermediate router has an interface either over a wired or wireless connection 6903 to a tablet or smartphone acting as a surrogate for the Master Control Computer 7603. A Local Area Network 7602 allows tablets to communicate with each other and for a Master Control Computer for data storage and sharing. This topology allows for efficient, low-power communication between IOM modules, yet users have the greatest number of options to send instructions to the selected IOM.

Hence the digital communication networks shown for example in FIG. 76 enable the control and communication of a very large number of IOM modules used for the simultaneous, parallel, and asynchronous culture of organs-on-chips or other bio-objects without the bottlenecks that are present in the robotic systems shown in FIG. 2. This very same network architecture can be used to allow different modules to operate in consort on the same platform, as would be required when multiple organ-on-chip modules, MicroFormulator and MicroClinical Analyzers, and other analytic and control modules are required to function in a coordinated manner as shown in FIG. 4. The most important feature of this network design is that modules can be added to or removed from module arrays while maintaining full sensing and control of each module. While each module would undoubtedly have an optical barcode with a unique identifying number, the same modules would also have an electronic identifying number suitable for tracking within the entire network system.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A platform for cultivation, maintenance, and/or analysis of one or more bio-objects, each bio-object including an organ, a tissue construct, or a group of cells, comprising: one or more integrated bio-object microfluidics modules, each integrated bio-object microfluidics module configured to cultivate, maintain, analyze and/or mimic functionalities of a bio-object, comprising:

(a) one or more on-chip pumps;
(b) a plurality of fluidic switches;
(c) a microfluidic chip in fluid communication with the one or more on-chip pumps and the plurality of fluidic switches, comprising at least one chamber for accommodating the bio-object and a plurality of fluidic paths connecting the chamber, the one or more on-chip pumps and the plurality of fluidic switches; and
(d) a power and control unit programmed to selectively and individually controlling the one or more on-chip pumps and the plurality of fluidic switches for performing one or more bio-object microfluidics functions;

wherein the one or more on-chip pumps comprise a rotary planar peristaltic micropump (RPPM), wherein each of the plurality of fluidic switches comprises a rotary planar valve (RPV).

2. The platform of claim 1, wherein each integrated bio-object microfluidics module further comprises a reservoir having one or more ports for providing a plurality of solutions.

3. The platform of claim 2, wherein each integrated bio-object microfluidics module further comprises one imaging unit for operable evaluation of a respective bio-object.

4. The platform of claim 2, wherein each integrated bio-object microfluidics module further comprises at least one bubble trap coupled to at least one of the plurality of fluidic paths for removing bubbles therefrom.

5. The platform of claim 2, wherein the power and control unit comprises a microcontroller, a sensor array, and a power supply.

6. The platform of claim 1, wherein the one or more integrated bio-object microfluidics modules comprise a plurality of integrated bio-object microfluidics modules spatially arranged in an array.

7. The platform of claim 6, further comprising fluidic interconnects and nodes for connecting each of the plurality of integrated bio-object microfluidics modules to one another, wherein the plurality of integrated bio-object microfluidics modules is mechanically and fluidically interconnected to each other in series, in parallel, or in a combination of both in the array.

8. The platform of claim 7, wherein the array of the integrated bio-object microfluidics modules is movable as a unit by utilizing a transporting means.

9. The platform of claim 8, wherein the fluidic and mechanical connections between the integrated bio-object microfluidics modules are flexible, and wherein the array of the integrated bio-object microfluidics modules is aligned in a straight line or in a curved line.

10. The platform of claim 9, further comprising:

(a) a propulsion unit for applying a bidirectional traction force collinear with the array of the integrated bio-object microfluidics modules;
(b) a support module connected between the propulsion unit and the array of the integrated bio-object microfluidics modules; and
(c) a specialized module connected to the array of the integrated bio-object microfluidics modules to define a train-based interconnect platform that is movably disposed on the transporting means, wherein the train-based interconnect platform is configurable and interchangeable.

11. The platform of claim 10, further comprising a station having a base, and one or more subsystems fixed on the base at predetermined positions, wherein the station is placed in relation to the transporting means such that when the train-based interconnect platform is moved at the predetermined positions, the one or more subsystems perform desired operations on the linear array of the plurality of integrated bio-object microfluidics, wherein the desired operations on the array of the integrated bio-object microfluidics modules comprise performing at least one of analytical functions, mechanical functions, maintenance functions, fluid handling, microscopy, removal of one integrated bio-object microfluidics module, and replacement of one integrated bio-object microfluidics module with another on the array of the integrated bio-object microfluidics modules.

12. The platform of claim 11, wherein the transporting means on which the train-based interconnect platform moves comprises a guideway including a pair of parallel tracks, a central monorail, a lateral rail, a guiding channel, or an overhead conveyor system, for moving the array of the integrated bio-object microfluidics modules past the station or into or out of an incubator or container.

13. The platform of claim 12, wherein the guideway further comprises one or more branched tracks placed in relation to the pair of closed tracks, with switches placed between the pair of closed tracks and each branched track, for switching all or parts of the array of the integrated bio-object microfluidics modules to desired locations.

14. The platform of claim 13, wherein the transporting means further comprises a rotary turntable coupled between the pair of closed tracks and at least one of the one or more branched tracks for inserting propulsion units onto selected locations of the guideway, thereby allowing an automated assembly of module arrays of a desired configuration.

15. The platform of claim 8, wherein the transporting means comprises wheels, air bearings, roller bearings, low-friction pads, or desired mechanisms on each integrated bio-object microfluidics module to ensure the required linear displacement without undue stresses on the mechanical or fluidic connections.

16. The platform of claim 7, wherein the plurality of integrated bio-object microfluidics modules comprises at least one of an integrated brain module, an integrated lung module, an integrated heart module, an integrated liver module, an integrated stomach module, an integrated kidney module, an integrated gut module, an integrated testis module, and an integrated skin module.

17. The platform of claim 16, wherein the plurality of integrated bio-object microfluidics modules further comprises at least one of an integrated Perfusion Controller (PC) module for perfusing the bio-object maintained on the microfluidics chip, an integrated MicroClinical Analyzer ($\mu$CA) module for analyzing activities of the bio-object maintained on the microfluidics chip, and an integrated MicroFormulator ($\mu$F) module for providing desired substances to cultivate, maintain, and/or analyze the bio-object maintained on the microfluidics chip.

18. The platform of claim 7, wherein the microcontroller of each integrated bio-object microfluidics module is provided with at least one of a wireless communication protocol and a wired communication protocol, to form a network such that each integrated bio-object microfluidics module is capable of electronic communication with one another in the network and/or with a server that is in electronic communication with the network.

19. A system for cultivation, maintenance, and/or analysis of one or more bio-objects, each bio-object including an organ, a tissue construct, or a group of cells, comprising:
(a) at least one bio-object platform comprising one or more integrated bio-object microfluidics modules, each integrated bio-object microfluidics module configured to cultivate, maintain, analyze and/or mimic functionalities of a bio-object, comprising:
  (i) one or more on-chip pumps;
  (ii) a plurality of fluidic switches;
  (iii) a microfluidic chip in fluid communication with the one or more on-chip pumps and the plurality of fluidic switches, comprising at least one chamber for accommodating the bio-object and a plurality of fluidic paths connecting the chamber, the one or more on-chip pumps, and the plurality of fluidic switches; and
  (iv) a power and control unit programmed to selectively and individually controlling the one or more on-chip pumps and the plurality of fluidic switches for performing bio-object microfluidics functions; and
(b) a transporting means on which the at least one bio-object platform is movably disposed, for selectively moving at least one bio-object platform to desired locations; and
(c) at least one station having a base, and one or more subsystems fixed on the base at predetermined positions, wherein the at least one station is placed in relation to the transporting means such that when the at least one bio-object platform is moved at the predetermined positions, the one or more subsystems perform desired operations on the one or more integrated bio-object microfluidics.

* * * * *